(12) United States Patent
Iliff

(10) Patent No.: US 9,005,119 B2
(45) Date of Patent: *Apr. 14, 2015

(54) COMPUTERIZED MEDICAL DIAGNOSTIC AND TREATMENT ADVICE SYSTEM INCLUDING NETWORK ACCESS

(75) Inventor: Edwin C. Iliff, La Jolla, CA (US)

(73) Assignee: Clinical Decision Support, LLC, Nashville, TN (US)

( * ) Notice: Subject to any disclaimer, the term of this patent is extended or adjusted under 35 U.S.C. 154(b) by 461 days.

This patent is subject to a terminal disclaimer.

(21) Appl. No.: 11/932,784

(22) Filed: Oct. 31, 2007

(65) Prior Publication Data

US 2008/0051638 A1    Feb. 28, 2008

Related U.S. Application Data

(63) Continuation of application No. 11/045,676, filed on Jan. 28, 2005, now Pat. No. 7,306,560, which is a continuation of application No. 10/300,284, filed on Nov. 19, 2002, now Pat. No. 6,849,045, which is a
(Continued)

(51) Int. Cl.
*A61B 5/02* (2006.01)
*G06Q 10/00* (2012.01)
(Continued)

(52) U.S. Cl.
CPC .............. *A61B 5/0002* (2013.01); *A61B 5/411* (2013.01); *G06F 19/322* (2013.01);
(Continued)

(58) Field of Classification Search
CPC ... G06F 19/322; G06F 19/325; G06F 19/327; G06F 19/328; G06F 19/345; G06F 19/363; G06F 19/3418; G06F 19/3431; G06F 3/04847; G06Q 50/22; G06Q 50/24; A61B 5/0002; A61B 5/0871; A61B 5/0205; A61B 5/0452; A61B 5/412
USPC .................................... 600/300–301; 705/1–4
See application file for complete search history.

(56) References Cited

U.S. PATENT DOCUMENTS 3,970,996 A    7/1976    Yasaka et al.
4,041,522 A    8/1977    Healy
(Continued)

FOREIGN PATENT DOCUMENTS

CN    1291749 A    4/2001
CN    1477581 A    2/2004
(Continued)

OTHER PUBLICATIONS

The Alpha Media Catalog, Advertisement, Oct. 1993, "Physician's Database Manager" and "Iliad."
(Continued)

*Primary Examiner* — Gary Jackson
*Assistant Examiner* — Shirley Jian
(74) *Attorney, Agent, or Firm* — Suiter Swantz pc llo

(57) ABSTRACT

A system and method for providing computerized, knowledge-based medical diagnostic and treatment advice. The medical advice is provided to the general public over networks, such as a telephone network or a computer network. The invention also includes a stand-alone embodiment that may utilize occasional connectivity to a central computer by use of a network, such as the Internet. New authoring languages, interactive voice response and speech recognition are used to enable expert and general practitioner knowledge to be encoded for access by the public. "Meta" functions for time-density analysis of a number of factors regarding the number of medical complaints per unit of time are an integral part of the system. A re-enter feature monitors the user's changing condition over time. A symptom severity analysis helps to respond to the changing conditions. System sensitivity factors may be changed at a global level or other levels to adjust the system advice as necessary.

23 Claims, 49 Drawing Sheets

Related U.S. Application Data continuation of application No. 09/800,220, filed on Mar. 5, 2001, now Pat. No. 6,482,156, which is a continuation of application No. 09/376,185, filed on Aug. 17, 1999, now Pat. No. 6,206,829, which is a continuation of application No. 08/893,912, filed on Jul. 11, 1997, now Pat. No. 6,022,315, and a continuation-in-part of application No. 08/176,041, filed on Dec. 29, 1993, now Pat. No. 5,660,176.

(60) Provisional application No. 60/021,614, filed on Jul. 12, 1996, provisional application No. 60/021,615, filed on Jul. 12, 1996.

(51) Int. Cl.
 *A61B 5/00* (2006.01)
 *G06F 19/00* (2011.01)
 *G06Q 10/10* (2012.01)
 *G06Q 50/22* (2012.01)

(52) U.S. Cl.
 CPC ........... *G06F 19/324* (2013.01); *G06F 19/325* (2013.01); *G06F 19/3406* (2013.01); *G06F 19/3418* (2013.01); *G06F 19/345* (2013.01); *G06F 19/3456* (2013.01); *G06F 19/3487* (2013.01); *G06F 19/363* (2013.01); *G06Q 10/10* (2013.01); *G06Q 50/22* (2013.01); *A61B 2560/0271* (2013.01); *G06F 19/3481* (2013.01); *Y10S 128/92* (2013.01); *Y10S 128/904* (2013.01); *Y10S 128/925* (2013.01)

(56) References Cited

U.S. PATENT DOCUMENTS

| | | |
|---|---|---|
| 4,051,522 A | 9/1977 | Healy |
| 4,220,160 A | 9/1980 | Kimball et al. |
| 4,290,114 A | 9/1981 | Sinay |
| 4,315,309 A | 2/1982 | Coli |
| 4,337,377 A | 6/1982 | Van Riper et al. |
| 4,428,381 A | 1/1984 | Hepp |
| 4,458,693 A | 7/1984 | Badzinski et al. |
| 4,465,077 A | 8/1984 | Schneider |
| 4,531,527 A | 7/1985 | Reinhold, Jr. et al. |
| 4,606,352 A | 8/1986 | Geddes et al. |
| 4,712,562 A | 12/1987 | Ohayon et al. |
| 4,731,726 A * | 3/1988 | Allen, III ................ 600/300 |
| 4,733,354 A | 3/1988 | Potter et al. |
| 4,770,189 A | 9/1988 | Shyu |
| 4,803,625 A | 2/1989 | Fu et al. |
| 4,825,869 A | 5/1989 | Sasmor et al. |
| 4,838,275 A | 6/1989 | Lee |
| 4,839,822 A | 6/1989 | Dormond et al. |
| 4,858,121 A * | 8/1989 | Barber et al. ................ 705/2 |
| 4,866,772 A * | 9/1989 | Schroter ................ 713/151 |
| 4,868,763 A | 9/1989 | Masui et al. |
| 4,933,873 A | 6/1990 | Kaufman et al. |
| 4,945,476 A | 7/1990 | Bodick et al. |
| 4,962,491 A | 10/1990 | Schaeffer |
| 4,974,607 A | 12/1990 | Miwa |
| 4,975,840 A | 12/1990 | DeTore et al. |
| 5,012,411 A | 4/1991 | Policastro et al. |
| 5,012,815 A | 5/1991 | Bennett et al. |
| 5,023,785 A | 6/1991 | Adrion et al. |
| 5,030,948 A | 7/1991 | Rush |
| 5,054,493 A | 10/1991 | Cohn et al. |
| 5,084,819 A | 1/1992 | Dewey et al. |
| 5,099,424 A | 3/1992 | Schneiderman |
| 5,113,869 A | 5/1992 | Nappholz et al. |
| 5,193,541 A | 3/1993 | Hatsuwi |
| 5,196,682 A | 3/1993 | Englehardt |
| 5,200,993 A * | 4/1993 | Wheeler et al. ............ 379/93.02 |
| 5,228,449 A | 7/1993 | Christ et al. |
| 5,235,510 A | 8/1993 | Yamada et al. |
| 5,241,621 A | 8/1993 | Smart |
| 5,255,187 A | 10/1993 | Sorensen |
| 5,257,627 A | 11/1993 | Rapoport |
| 5,263,123 A | 11/1993 | Hayashi |
| 5,265,613 A | 11/1993 | Feldman et al. |
| 5,299,121 A | 3/1994 | Brill et al. |
| 5,307,263 A | 4/1994 | Brown |
| 5,337,752 A | 8/1994 | Reeves |
| 5,347,632 A | 9/1994 | Filepp et al. |
| 5,357,427 A | 10/1994 | Langen et al. |
| 5,377,258 A | 12/1994 | Bro |
| 5,390,238 A | 2/1995 | Kirk et al. |
| 5,404,292 A | 4/1995 | Hendrickson |
| 5,415,167 A | 5/1995 | Wilk |
| 5,418,888 A | 5/1995 | Alden |
| 5,421,343 A | 6/1995 | Feng |
| 5,435,324 A | 7/1995 | Brill |
| 5,437,278 A | 8/1995 | Wilk |
| 5,441,047 A | 8/1995 | David et al. |
| 5,442,728 A | 8/1995 | Kaufman et al. |
| 5,463,548 A | 10/1995 | Asada et al. |
| 5,471,382 A * | 11/1995 | Tallman et al. ............... 600/300 |
| 5,473,537 A | 12/1995 | Glazer et al. |
| 5,481,647 A | 1/1996 | Brody et al. |
| 5,486,999 A | 1/1996 | Mebane |
| 5,517,405 A | 5/1996 | McAndrew et al. |
| 5,519,433 A * | 5/1996 | Lappington et al. ............ 725/110 |
| 5,533,522 A | 7/1996 | Feng |
| 5,541,977 A | 7/1996 | Hodges et al. |
| 5,544,649 A | 8/1996 | David et al. |
| 5,551,436 A * | 9/1996 | Yago ................ 600/483 |
| 5,553,609 A | 9/1996 | Chen et al. |
| 5,555,169 A | 9/1996 | Namba et al. |
| 5,572,421 A | 11/1996 | Altman et al. |
| 5,583,758 A | 12/1996 | McIlroy et al. |
| 5,594,638 A | 1/1997 | Iliff |
| 5,596,994 A | 1/1997 | Bro |
| 5,601,435 A | 2/1997 | Quy |
| 5,619,991 A | 4/1997 | Sloane |
| 5,622,171 A | 4/1997 | Asada et al. |
| 5,626,144 A * | 5/1997 | Tacklind et al. ............... 600/538 |
| 5,633,910 A | 5/1997 | Cohen |
| 5,642,731 A * | 7/1997 | Kehr ................ 600/300 |
| 5,642,936 A | 7/1997 | Evans |
| 5,659,793 A | 8/1997 | Escobar et al. |
| 5,660,176 A | 8/1997 | Iliff |
| 5,672,154 A | 9/1997 | Sillén et al. |
| 5,672,501 A * | 9/1997 | Matulic-Adamic et al. .. 435/325 |
| 5,675,760 A | 10/1997 | Houwen et al. |
| 5,678,562 A | 10/1997 | Sellers |
| 5,692,220 A | 11/1997 | Diamond et al. |
| 5,692,501 A | 12/1997 | Minturn |
| 5,694,939 A | 12/1997 | Cowings |
| 5,703,786 A | 12/1997 | Conkright |
| 5,704,366 A * | 1/1998 | Tacklind et al. ............... 600/529 |
| 5,711,297 A | 1/1998 | Iliff |
| 5,722,418 A | 3/1998 | Bro |
| 5,724,968 A | 3/1998 | Iliff |
| 5,724,983 A * | 3/1998 | Selker et al. ................ 600/301 |
| 5,732,397 A | 3/1998 | DeTore et al. |
| 5,732,709 A * | 3/1998 | Tacklind et al. ............... 600/539 |
| 5,746,204 A | 5/1998 | Schauss |
| 5,764,923 A * | 6/1998 | Tallman et al. ................ 705/3 |
| 5,769,074 A | 6/1998 | Barnhill et al. |
| 5,772,585 A | 6/1998 | Lavin et al. |
| 5,778,882 A | 7/1998 | Raymond et al. |
| 5,788,640 A | 8/1998 | Peters |
| 5,794,208 A | 8/1998 | Goltra |
| 5,800,347 A | 9/1998 | Skates et al. |
| 5,801,755 A * | 9/1998 | Echerer ................ 348/14.01 |
| 5,802,495 A | 9/1998 | Goltra |
| 5,812,984 A | 9/1998 | Goltra |
| 5,822,715 A | 10/1998 | Worthington et al. |
| 5,823,949 A | 10/1998 | Goltra |
| 5,828,943 A | 10/1998 | Brown |
| 5,832,448 A | 11/1998 | Brown |
| 5,835,900 A | 11/1998 | Fagg, III et al. |
| 5,839,430 A | 11/1998 | Cama |
| 5,862,304 A | 1/1999 | Ravdin et al. |

(56) References Cited

U.S. PATENT DOCUMENTS

| | | | |
|---|---|---|---|
| 5,867,821 A * | 2/1999 | Ballantyne et al. | 705/2 |
| 5,868,669 A | 2/1999 | Iliff | |
| 5,879,163 A | 3/1999 | Brown et al. | |
| 5,887,133 A | 3/1999 | Brown et al. | |
| 5,897,493 A | 4/1999 | Brown | |
| 5,899,855 A | 5/1999 | Brown | |
| 5,908,383 A | 6/1999 | Brynjestad | |
| 5,909,679 A | 6/1999 | Hall | |
| 5,910,107 A | 6/1999 | Iliff | |
| 5,911,132 A | 6/1999 | Sloane | |
| 5,918,603 A | 7/1999 | Brown | |
| 5,933,136 A | 8/1999 | Brown | |
| 5,935,060 A | 8/1999 | Iliff | |
| 5,940,801 A | 8/1999 | Brown | |
| 5,951,300 A | 9/1999 | Brown | |
| 5,953,704 A | 9/1999 | McIlroy et al. | |
| 5,956,501 A | 9/1999 | Brown | |
| 5,960,403 A | 9/1999 | Brown | |
| 5,964,700 A * | 10/1999 | Tallman et al. | 600/300 |
| 5,974,389 A | 10/1999 | Clark et al. | |
| 5,976,082 A | 11/1999 | Wong et al. | |
| 5,987,519 A | 11/1999 | Peifer | |
| 5,997,476 A | 12/1999 | Brown | |
| 6,001,060 A | 12/1999 | Churchill et al. | |
| 6,022,315 A | 2/2000 | Iliff | |
| 6,032,119 A | 2/2000 | Brown et al. | |
| 6,032,678 A | 3/2000 | Rottem | |
| 6,071,236 A | 6/2000 | Iliff | |
| 6,081,786 A | 6/2000 | Barry et al. | |
| 6,101,478 A | 8/2000 | Brown | |
| 6,106,459 A | 8/2000 | Clawson | |
| 6,112,183 A * | 8/2000 | Swanson et al. | 705/2 |
| 6,113,540 A | 9/2000 | Iliff | |
| 6,117,073 A | 9/2000 | Jones et al. | |
| 6,144,837 A | 11/2000 | Quy | |
| 6,149,585 A | 11/2000 | Gray | |
| 6,151,586 A | 11/2000 | Brown | |
| 6,161,095 A | 12/2000 | Brown | |
| 6,167,362 A | 12/2000 | Brown | |
| 6,168,563 B1 | 1/2001 | Brown | |
| 6,177,940 B1 | 1/2001 | Bond et al. | |
| 6,186,145 B1 | 2/2001 | Brown | |
| 6,189,029 B1 | 2/2001 | Fuerst | |
| 6,196,970 B1 | 3/2001 | Brown | |
| 6,206,829 B1 | 3/2001 | Iliff | |
| 6,230,142 B1 | 5/2001 | Benigno et al. | |
| 6,233,539 B1 | 5/2001 | Brown | |
| 6,234,964 B1 | 5/2001 | Iliff | |
| 6,240,393 B1 | 5/2001 | Brown | |
| 6,246,975 B1 | 6/2001 | Rivonelli et al. | |
| 6,246,992 B1 | 6/2001 | Brown | |
| 6,247,002 B1 | 6/2001 | Steels | |
| 6,248,063 B1 | 6/2001 | Barnhill et al. | |
| 6,248,065 B1 | 6/2001 | Brown | |
| 6,260,022 B1 | 7/2001 | Brown | |
| 6,270,455 B1 | 8/2001 | Brown | |
| 6,270,456 B1 | 8/2001 | Iliff | |
| 6,330,426 B2 | 12/2001 | Brown et al. | |
| 6,334,778 B1 | 1/2002 | Brown | |
| 6,368,273 B1 | 4/2002 | Brown | |
| 6,375,469 B1 | 4/2002 | Brown | |
| 6,379,301 B1 | 4/2002 | Worthington et al. | |
| 6,381,577 B1 | 4/2002 | Brown | |
| 6,468,210 B1 | 10/2002 | Iliff | |
| 6,475,143 B2 | 11/2002 | Iliff | |
| 6,482,156 B2 | 11/2002 | Iliff | |
| 6,524,241 B2 | 2/2003 | Iliff | |
| 6,527,713 B2 | 3/2003 | Iliff | |
| 6,569,093 B2 | 5/2003 | Iliff | |
| 6,597,392 B1 | 7/2003 | Jenkins et al. | |
| 6,598,035 B2 | 7/2003 | Branson et al. | |
| 6,601,055 B1 | 7/2003 | Roberts | |
| 6,641,532 B2 | 11/2003 | Iliff | |
| 6,687,685 B1 | 2/2004 | Sadeghi et al. | |
| 6,725,209 B1 | 4/2004 | Iliff | |
| 6,730,027 B2 | 5/2004 | Iliff | |
| 6,746,399 B2 | 6/2004 | Iliff | |
| 6,748,353 B1 | 6/2004 | Iliff | |
| 6,764,447 B2 | 7/2004 | Iliff | |
| 6,767,325 B2 | 7/2004 | Iliff | |
| 6,770,029 B2 | 8/2004 | Iliff | |
| 6,817,980 B2 | 11/2004 | Iliff | |
| 6,849,045 B2 | 2/2005 | Iliff | |
| 6,900,807 B1 | 5/2005 | Liongosari et al. | |
| 6,903,657 B2 | 6/2005 | Kwoen | |
| 6,968,375 B1 | 11/2005 | Brown | |
| 7,076,437 B1 | 7/2006 | Levy | |
| 7,167,818 B2 | 1/2007 | Brown | |
| 7,223,235 B2 | 5/2007 | Brown | |
| 7,223,236 B2 | 5/2007 | Brown | |
| 7,252,636 B2 | 8/2007 | Brown | |
| 7,258,666 B2 | 8/2007 | Brown | |
| 7,259,681 B2 | 8/2007 | Kwoen | |
| 7,264,591 B2 | 9/2007 | Brown | |
| 7,297,108 B2 | 11/2007 | Iliff | |
| 7,297,109 B2 | 11/2007 | Brown | |
| 7,297,111 B2 | 11/2007 | Iliff | |
| 7,300,402 B2 | 11/2007 | Iliff | |
| 7,305,348 B1 | 12/2007 | Brown | |
| 7,306,560 B2 | 12/2007 | Iliff | |
| 7,310,668 B2 | 12/2007 | Brown | |
| 7,320,030 B2 | 1/2008 | Brown | |
| 7,344,496 B2 | 3/2008 | Iliff | |
| 7,392,167 B2 | 6/2008 | Brown | |
| 7,399,276 B1 | 7/2008 | Brown et al. | |
| 7,516,192 B2 | 4/2009 | Brown | |
| 7,769,600 B2 | 8/2010 | Iliff | |
| 7,780,595 B2 | 8/2010 | Iliff | |
| 2001/0012913 A1 | 8/2001 | Iliff | |
| 2001/0039503 A1 | 11/2001 | Chan et al. | |
| 2001/0053875 A1 | 12/2001 | Iliff | |
| 2002/0029157 A1 | 3/2002 | Marchosky | |
| 2002/0068857 A1 | 6/2002 | Iliff | |
| 2002/0148477 A1 | 10/2002 | Kwoen | |
| 2002/0186818 A1 | 12/2002 | Arnaud et al. | |
| 2003/0036686 A1 | 2/2003 | Iliff | |
| 2003/0069753 A1 | 4/2003 | Brown | |
| 2003/0078919 A1 * | 4/2003 | Suzuki et al. | 707/3 |
| 2003/0153819 A1 | 8/2003 | Iliff | |
| 2003/0163299 A1 | 8/2003 | Iliff | |
| 2003/0181790 A1 | 9/2003 | David et al. | |
| 2004/0017475 A1 | 1/2004 | Akers et al. | |
| 2004/0019259 A1 | 1/2004 | Brown | |
| 2004/0059200 A1 | 3/2004 | Iliff | |
| 2004/0107116 A1 | 6/2004 | Brown | |
| 2004/0116780 A1 | 6/2004 | Brown | |
| 2004/0117207 A1 | 6/2004 | Brown | |
| 2004/0117208 A1 | 6/2004 | Brown | |
| 2004/0117209 A1 | 6/2004 | Brown | |
| 2004/0117210 A1 | 6/2004 | Brown | |
| 2004/0193377 A1 | 9/2004 | Brown | |
| 2004/0199332 A1 | 10/2004 | Iliff | |
| 2004/0199409 A1 | 10/2004 | Brown | |
| 2004/0219500 A1 | 11/2004 | Brown | |
| 2004/0230511 A1 * | 11/2004 | Kannan et al. | 705/35 |
| 2004/0249778 A1 | 12/2004 | Iliff | |
| 2005/0010088 A1 | 1/2005 | Iliff | |
| 2005/0010444 A1 | 1/2005 | Iliff | |
| 2005/0027562 A1 | 2/2005 | Brown | |
| 2005/0060194 A1 | 3/2005 | Brown | |
| 2005/0080652 A1 | 4/2005 | Brown | |
| 2005/0086083 A1 | 4/2005 | Brown | |
| 2005/0177391 A1 | 8/2005 | Shimizu et al. | |
| 2005/0228883 A1 | 10/2005 | Brown | |
| 2005/0234306 A1 | 10/2005 | Schulte et al. | |
| 2005/0256739 A1 | 11/2005 | Brown | |
| 2005/0273359 A1 | 12/2005 | Young | |
| 2005/0273509 A1 | 12/2005 | Brown | |
| 2006/0004611 A1 | 1/2006 | Brown | |
| 2006/0010014 A1 | 1/2006 | Brown | |
| 2006/0089969 A1 | 4/2006 | Brown | |
| 2006/0100910 A1 | 5/2006 | Brown | |
| 2006/0135859 A1 | 6/2006 | Iliff | |
| 2006/0178914 A1 | 8/2006 | Brown | |

(56) References Cited

U.S. PATENT DOCUMENTS

| | | |
|---|---|---|
| 2006/0189853 A1 | 8/2006 | Brown |
| 2006/0234202 A1 | 10/2006 | Brown |
| 2006/0235722 A1 | 10/2006 | Brown |
| 2006/0241975 A1 | 10/2006 | Brown |
| 2006/0247951 A1 | 11/2006 | Brown |
| 2006/0247979 A1 | 11/2006 | Brown |
| 2006/0252089 A1 | 11/2006 | Brown |
| 2006/0253303 A1 | 11/2006 | Brown |
| 2006/0253574 A1 | 11/2006 | Brown |
| 2006/0253576 A1 | 11/2006 | Brown |
| 2006/0271404 A1 | 11/2006 | Brown |
| 2006/0285736 A1 | 12/2006 | Brown |
| 2006/0287889 A1 | 12/2006 | Brown |
| 2006/0287931 A1 | 12/2006 | Brown |
| 2006/0294233 A1 | 12/2006 | Brown |
| 2007/0016445 A1 | 1/2007 | Brown |
| 2007/0016446 A1 | 1/2007 | Brown |
| 2007/0016447 A1 | 1/2007 | Brown |
| 2007/0016448 A1 | 1/2007 | Brown |
| 2007/0021984 A1 | 1/2007 | Brown |
| 2007/0048691 A1 | 3/2007 | Brown |
| 2007/0055486 A1 | 3/2007 | Brown |
| 2007/0061167 A1 | 3/2007 | Brown |
| 2007/0067251 A1 | 3/2007 | Brown |
| 2007/0078681 A1 | 4/2007 | Brown |
| 2007/0094049 A1 | 4/2007 | Brown |
| 2007/0100665 A1 | 5/2007 | Brown |
| 2007/0100934 A1 | 5/2007 | Brown |
| 2007/0111176 A1 | 5/2007 | Brown |
| 2007/0118403 A1 | 5/2007 | Brown |
| 2007/0118404 A1 | 5/2007 | Brown |
| 2007/0124179 A1 | 5/2007 | Brown |
| 2007/0168226 A1 | 7/2007 | Brown |
| 2007/0168242 A1 | 7/2007 | Brown |
| 2007/0212671 A1 | 9/2007 | Brown |
| 2007/0213608 A1 | 9/2007 | Brown |
| 2007/0299321 A1 | 12/2007 | Brown |
| 2008/0004915 A1 | 1/2008 | Brown |
| 2008/0045811 A1 | 2/2008 | Iliff |
| 2008/0046268 A1 | 2/2008 | Brown |
| 2008/0051638 A1 | 2/2008 | Iliff |
| 2008/0051639 A1 | 2/2008 | Iliff |
| 2008/0051640 A1 | 2/2008 | Iliff |
| 2008/0051641 A1 | 2/2008 | Iliff |
| 2008/0052116 A1 | 2/2008 | Iliff |
| 2008/0052118 A1 | 2/2008 | Iliff |
| 2008/0052119 A1 | 2/2008 | Iliff |
| 2008/0052120 A1 | 2/2008 | Iliff |
| 2008/0052121 A1 | 2/2008 | Iliff |
| 2008/0052122 A1 | 2/2008 | Iliff |
| 2008/0052123 A1 | 2/2008 | Iliff |
| 2008/0052130 A1 | 2/2008 | Iliff |
| 2008/0052132 A1 | 2/2008 | Iliff |
| 2008/0052318 A1 | 2/2008 | Iliff |
| 2008/0059227 A1 | 3/2008 | Clapp |
| 2008/0059232 A1 | 3/2008 | Iliff |
| 2008/0059247 A1 | 3/2008 | Iliff |
| 2008/0072147 A1 | 3/2008 | Brown |
| 2008/0097180 A1 | 4/2008 | Brown |
| 2008/0097181 A1 | 4/2008 | Brown |
| 2008/0103377 A1 | 5/2008 | Brown |
| 2008/0108888 A1 | 5/2008 | Brown |
| 2008/0109172 A1 | 5/2008 | Brown |
| 2008/0162393 A1 | 7/2008 | Iliff |
| 2008/0262557 A1 | 10/2008 | Brown |
| 2008/0269571 A1 | 10/2008 | Brown et al. |
| 2009/0007924 A1 | 1/2009 | Iliff |

FOREIGN PATENT DOCUMENTS

| | | |
|---|---|---|
| DE | 4430184 C2 | 3/1995 |
| DE | 4430164 A1 | 2/1996 |
| EP | 0 320 749 A2 | 12/1988 |
| EP | 0447710 A1 | 9/1991 |
| EP | 0531889 A | 3/1993 |
| EP | 0 643 360 A2 | 3/1996 |
| EP | 0720336 A | 7/1996 |
| JP | 03191952 | 8/1991 |
| JP | 3202047 | 9/1991 |
| JP | 04015035 | 1/1992 |
| JP | 04015035 A | 1/1992 |
| JP | 4056561 | 2/1992 |
| JP | 06083847 | 3/1994 |
| JP | 06274472 | 9/1994 |
| JP | 08140944 | 4/1996 |
| JP | 08117210 A | 5/1996 |
| JP | 08164127 A | 6/1996 |
| JP | 08275927 | 10/1996 |
| WO | WO 93/23819 | 11/1993 |
| WO | WO 94/00817 | 1/1994 |
| WO | WO 94/06088 | 3/1994 |
| WO | WO 95/06296 | 3/1995 |
| WO | WO 95/06298 | 3/1995 |
| WO | WO 95/19604 | 7/1995 |
| WO | WO 96/22577 | 7/1996 |
| WO | WO 97/05553 | 2/1997 |
| WO | WO 98/02836 | 1/1998 |
| WO | WO 98/40835 | 9/1998 |
| WO | WO 99/52025 | 10/1999 |
| WO | WO 00/32088 | 6/2000 |
| WO | WO 01/61616 A2 | 8/2001 |
| WO | WO 01/85021 | 11/2001 |
| WO | WO 02/39250 A2 | 5/2002 |
| WO | WO 02/42876 A2 | 5/2002 |
| WO | WO 03/040879 A2 | 5/2003 |
| WO | WO 03/040964 A2 | 5/2003 |
| WO | WO 03/040965 A2 | 5/2003 |
| WO | WO 03/040989 A2 | 5/2003 |
| WO | WO 03/040990 A2 | 5/2003 |

OTHER PUBLICATIONS

Arthur D. Little, Inc., Acorn Park, Cambridge, MA, Jul. 1992, "Can Telecommunications Help Solve America's Health Care Problems?"

Becher, Ernst, "Fernmeldewesen für soziale Dienste in Entwicklungsländern," NTZ, 33:304, 1980.

Belzer et al., "Encyclopedia of Computer Science and Technology", Marcel Dekker, Inc., NY (US), 1978, pp. 78-79 and 114-115.

Bergman, "Computers make 'house calls' to patients; Harvard Community Health Plan offers computerized information service to patients," J American Hospital Association, 67(10): 52, May 20, 1993.

Bowden, K.F. et al., Information Processing, 71:1398-1406, 1972, "Data structures for general practice records."

Cimino, James J. et al., IEEE/Ninth Annual Conference of the Engineering in Medicine and Biology Society, 1987, "DXplain: An interactive knowledge base for assistance in medical diagnostic decisions."

Conrath, David W. et al., IEEE Transactions on Communications, COM-23(10):1119-1126, 1975, "A preliminary evaluation of alternative telecommunication systems for the delivery of primary health care to remote areas."

Currid, Cheryl, PC Week, Sep. 17, 1990, "Risky Business: doctors, lawyers shy away from computer technology."

Dahmer J., "Anamnese und Befund", Georg Thieme Verlag, 1981, pp. 22-25, 44-47, 292-295 and 371-375 (with English language translation of pp. 22-24, 44-45, 292, 295).

Dahmer J., Der Denkprozess "Vom Symptom zur Diagnose", Anamnese und Befund, Georg Thieme Verlag, 1981, pp. 3.

Doheny, Kathleen, LA Times Magazine, p. 8, Aug. 4, 1991, "Hack attack."

Fisher et al., "Great Expectations: Expectation-based reasoning in Medical Diagnosis," Proceedings of the 12th Annual Symposium on Computer Applications in Medical Care, Nov. 6, 1988, pp. 38-42.

Frenger, Paul, IEEE Frontiers of Computers in Medicine, 1982, "Details of a database management system for a telephone medical consultation service."

Frenger, Paul, ISA, pp. 103-107, 1983, "Advanced techniques used to create a telephone medical consultation service."

(56) References Cited

OTHER PUBLICATIONS

Freudenheim, Mill, The New York Times, Business and Health, p. D2, Jun. 25, 1991, "Computer says take 2 aspirin."
Gale et al., Medical Diagnosis From Student to Clinician, Oxford University Press, pp. 1-22 (1983).
Gini et al., "A Serial Model for Computer Assisted Medical Diagnosis," Int J Bio-Medical Comp., 11: 99-113 (1980).
Goldbard, Gary A, Class Notes, Tulane Medicine, Tulane University Medical Center, 1430 Tulane Avenue, New Orleans, LA 70112-2699, p. 26, Jun. 1991.
Gome, Amanda, Herald-Sun, p, 13, Nov. 19, 1991, "A picture of success."
Gorry, G. Anthony, Bulletin of the Operations Research Society of America, 19(2), 1971, "FA6.3 Automating Judgmental decision making in medicine."
"Harvard Community Health Plan Testing Computerized Service that Answers Health-Care Questions," Technical Computing, 6(9), Aug. 1991.
Hile, et al. "Reliability of an Automated Decision Support System for Behavioral Treatment Planning: Preliminary Results from the Mental Retardation-Expert", Computers in Human Services, 10(4): 19-29, 1994.
Hudson et al., "Human-Computer Interaction in a Medical Decision Support System." IEEE Computer Society Press, 2: 429-435, 1989.
Kerr, Jennifer, San Diego Union-Tribune, p. A3, Sunday, Jul. 18, 1993, "Phone is link to health-care information."
Larsson et al., "An Expert System Interface for an Identification Program," Automatica, Pergamon Press Ltd., Oxford, GB., 27(6): 919-930, 1991.
Laughlin, Michael L., ed., Computers in Health Care, pp. 32-37, Nov. 1992, "Telecommunications may offer poor a 'road' to healthcare."
Levin, Carol, PC Magazine, p. 32, Mar. 16, 1993, "Patient, heal thyself".
Mallory, Jim, Newsbytes, American Association for the Advancement of Science, Panel Discussion, Feb. 19, 1992, "Computers now giving medical advice."
McDonald et al., Environmental Science and Policy Institute, 1992, "Health in the Information Age: The Emergence of Health Oriented Telecommunication Applications."
"Netscape & Sun Announce Javascript The Open, Cross-Platform Object Scripting Language for Enterprise Networks and the Internet", Press Release, Dec. 4, 1995, web at http://java.sun.com/pr/1995/12/pr951204-03.html. (10 pages).
New York Times, p. 18, Jul. 13, 1991, "System helps doctors keep up to date."
O'Neil, et al., Conference Paper, IEEE Coll. On Computer Based Diagnosis, p. 8/1-4, 1989, "Diagnostic Support in the Oxford System of Medicine."
Rose, J, ed., "Progress of Cybernetics, vol. 2, Cybernetics and Industry, Social and Economic Consequences, Cybernetics and Artifacts," Proceedings of the First International Congress of Cybernetics, London, Gordon and Breach Science Publishers, pp. 803-811, 1969.
Rymon, et al., IEEE Transactions on Systems, Man, and Cybernetics, 23(6):1551-1560, Nov./Dec. 1993, "Progressive Horizon Planning—Planning Exploratory—Corrective Behavior."
Sacks, Terry, San Diego Union-Tribune, p. E-16, Mar. 24, 1992, "Pocket computer may cure technology-shy physicians."
Salvans, P. Ferrer and Alonso L. Vallès, Computer Biol. Med., 20(6):433-443, 1990, "An epidemiologic approach to computerized medical diagnosis—AEDMI program."
San Diego Emergency Physicians Society, Meeting Minutes, Regular Oct. 1991 Meeting, P.O. Box 16685, San Diego, CA 92176, first page.
Schild, W. et al., IBM J. Res. Develop., 22(5):518-532, 1978, "Computer-aided diagnosis with an application to endocrinology."
Shapiro, Encyclopedia of Artificial Intelligence, 2nd Edition, vol. 2, pp. 916-926, John Wiley & Sons, Inc., 1992.
Shortliffe, Edward H., Expert Systems and AI Applications, pp. 323-333, 1980, "Consultation system for physicians: the role of artificial intelligence techniques."
Sloane, L., New York Times, p. 16, Jul. 13, 1991, "For round-the-clock diagnosis, just pick up your telephone."
Smothers, R., New York Times, Sep. 16, 1992, "New video technology lets doctors examine patients many miles away."
Starr et al., "Gycon: A Microcomputer Based Gynecological Consultant," Proceed Inter Comp Symposium, Dec. 17-19, 1986, Tainan, Taiwan R.O.C. pp. 1678-1684.
Starr et al., "A microcomputer-based medical expert system shell using a weight/threshold decision mechanism," Proc. Of the 13th Annual Northeast Bioengineering Conference, Mar. 12-13, 1987, pp. 279-281.
Thorpe, C. William et al., "A microcomputer-based interactive cough sound analysis system", Computer Methods and Programs in Biomedicine, Section II, Systems and programs, 36:33-43, 1991.
Wagner, J at al., Conference Paper of Expert Systems and Decision Support in Medicine, 33rd Annual Meeting of the GMDS EFMI Special Topic Meeting, pp. 449-465, Sep. 1988, "A knowledge-based system for interactive medical diagnosis encoding."
Walz, Nancy, The Associated Press, Business News, Jun. 25, 1991, "Computer system aims to wipe out medical paperwork."
Waterman, A Guide to Expert Systems, Addison-Wesley Publishing Co., pp. 46-47 and 272-288, 1986.
Weinstock, Edward, Cover, Avant-Garde, 1984, "An Apple a Day™."
Werner, et al., Conference Paper, IEEE Engineering in Medicine and Biology, 3 pages, 1989, "Interlocutor: Conferring with an Expert Diagnostic Consultant in Geriatric Psychiatry."
JIPO Office Action dated Feb. 20, 2007 for Japanese Patent Application No. 506146/98 (and English language translation).
European Search Report dated Mar. 17, 2005 for Application No. EP 02075042.
Arthur D. Little, Inc., Acorn Park, Cambridge, MA, Jul. 1992, "Telecommunications: Can It Help Solve America's Health Care-Problems?" pp. 1-116.
Curtin et al. "Disease Management Information System: Design, Development, Testing, and Clinical Application for Cancer Management", Abstract http://ascobeta.infostreet.com/prof/me/html/abstracts/hre/m_1509.htm (1997).
Medical Computer Consultants' Consortium, Inc. "Disease State Management Software System *DMS2*—Product Description", http://www.mc3co.com/DMSS.htm (1997).
Memorial Sloan-Kettering Cancer Center "Center Develops New System for Disease Management" http://www.mskcc.org/document/cn950601.htm (1997).
Szolovits et al., Artificial Intelligence in Medical Diagnosis, Ann Intern Med., Jan. 1988, vol. 108, pp. 80-87 (1-13), 1.
International Search Report dated Dec. 3, 1997 in PCT/US97/12025, filed Jul. 11, 1997.
International Search Report dated Dec. 22, 1997 in PCT/US97/12162, filed Jul. 11, 1997.
International Written Opinion dated May 13, 1998 in PCT/US97/12025, filed Jul. 11, 1997.
International Preliminary Examination Report dated Oct. 22, 1998 in PCT/US97/12025, filed Jul. 11, 1997.
International Preliminary Examination Report dated Oct. 22, 1998 in PCT/US97/12162, filed Jul. 11, 1997.
EPO Examination Report dated May 6, 1999 in European Patent Application No. 97934919.8.
EPO Examination Report dated Jul. 1, 1999 for European Patent Application No. 97937972.5.
EPO Report re Interview-in-Person dated Dec. 22, 1999 for European Patent Application No. 97937972.4.
EPO 2nd Examination Report dated Dec. 22, 1999 in European Patent Application No. 97934919.8.
EPO Summons to Oral Proceedings dated Jul. 27, 2001 in European Patent Application No. 97937972.4.
EPO Summons to Oral Proceedings dated Jul. 27, 2001 in European Patent Application No. 97934919.8.
EPO Notice of Decision of Refusal dated Jun. 3, 2002 in European Patent Application No. 97934919.8.
EPO Minutes of Oral Proceedings dated Jun. 6, 2002 for European Patent Application No. 97937972.4.
EPO Minutes of Oral Proceedings dated Jun. 6, 2002 for European Patent Application No. 97934919.8.

(56) References Cited

OTHER PUBLICATIONS

International Search Report dated Jul. 29, 2002 in PCT/US01/04907, filed Feb. 14, 2001.
Written Opinion (Rule 66) dated Sep. 20, 2002 in PCT/US01/04907, filed Feb. 14, 2001.
International Preliminary Examination Report dated May 16, 2003 (Corrected) in PCT/US01/04907, filed Feb. 14, 2001.
SIPO Office Action dated Nov. 23, 2003 for Chinese Patent Application No. 97197873.5.
SIPO Office Action dated Dec. 19, 2003 in Chinese Patent Application No. 97197872.7.
EPO Notice of Grant dated Mar. 30, 2004 for European Patent Application No. 97937972.4.
CIPO 1st Examination Report dated Apr. 21, 2004 for Canadian Patent Application No. 2,260,836.
Ukrainian Office Action dated Feb. 14, 2005 in Ukrainian Application No. 2002086473, filed Feb. 14, 2003.
SIPO 2nd Office Action dated Mar. 11, 2005 for Chinese Patent Application No. 97197873.5.
SIPO 2nd Office Action dated Apr. 1, 2005 in Chinese Patent Application No. 97197872.7.
SIPIO Office Action dated Apr. 15, 2005 in Chinese Application No. 01808023.5, filed Feb. 14, 2001.
EPO Communication on Appeal dated Jul. 1, 2005 in European Patent Application No. 97934919.10.
SIPO Decision of Rejection dated Nov. 8, 2005 in Chinese Patent Application No. 97197872.7.
SIPO Decision of Rejection dated Dec. 23, 2005 for Chinese Patent Application No. 97197873.5.
CIPO 2nd Examination Report dated Jan. 19, 2006 for Canadian Patent Application No. 2,260,837.
SIPO 2nd Office Action dated Jan. 25, 2006 in Chinese Application No. 01808023.5, filed Feb. 14, 2001.
EPO Decision on Appeal dated Apr. 7, 2006 in European Patent Application No. 97934919.9.
EPO Office Action dated Nov. 23, 2006 in European Application No. 01910763.0, filed Feb. 14, 2003.
JIPO Rejection Notice dated Feb. 20, 2007 for Japanese Patent Application No. 506205/98.
International Search Report and Written Opinion dated Feb. 21, 2007 in PCT/US06/24090, filed Jun. 20, 2006.
INPI Office Action dated Jun. 28, 2007 for Brazilian Patent Application No. PI9712092-8.
INPI Office Action dated Aug. 27, 2007 for Brazilian Patent Application No. PI9712091-0.
JIPO Decision on Rejection dated Oct. 3, 2007 for Japanese Patent Application No. 506205/98.
SIPO Office Action dated Jan. 18, 2008 for Chinese Patent Application No. 200510128902.4.
SIPO 1st Office Action dated Jan. 18, 2008 in Chinese Patent Application No. 20050128901X.
JIPO Notice of Rejection dated Mar. 31, 2008 for Japanese Patent Application No. 506146/98.
EPO 2nd Examination Report dated Apr. 23, 2008 in European Patent Application No. 02075042.8, filed Jan. 7, 2002.
International Preliminary Report on Patentability dated Jul. 14, 2008 in PCT/US06/24090, filed Jun. 20, 2006.
International Search Report and Written Opinion dated Sep. 17, 2008 in PCT/US08/62112, filed Apr. 30, 2008.
INPI Technical Opinion dated Dec. 5, 2008 for Brazilian Patent Application No. PI9712091-0.
CIPO Office Action dated Dec. 5, 2008 in Canadian Application No. 2,398,823, filed Feb. 14, 2001.
SIPO 2nd Office Action dated Jan. 3, 2009 in Chinese Patent Application No. 200510128901X.
SIPO 2nd Office Action dated May 8, 2009 for Chinese Patent Application No. 200510128902.4.
SIPO 3rd Office Action dated Jun. 5, 2009 in Chinese Patent Application No. 200510128901.X.

Alexander G., Health Risk Appraisal, Intern Electro J Health Edu., 2000, 3(Special): 122-137.
Ellis et al., Health Education Using Microcomputers II: One year in the Clinic; Preventive Medicine, 1982, 11: 212-224.
Ellis et al., Health Education using Microcomputers: Initial Acceptability, Preventive Medicine, Jan. 1981, 10(1): 77-84.
Fielding J., Appraising the Health of Health Risk Appraisal, Am J Pub Health, Apr. 1982, 72(4): 337-340.
Goetz et al., Health Risk Appraisal: The Estimation of Risk, Health Promotion at the Worksite, Mar.-Apr. 1980, 95(2): 119-126.
Exhibit A, Part 1 to Second Revised Joint Claim Construction Statement, *Healthways, Inc. v. Alere, LLC*, U.S. District Court for the Northern District of Illinois, Case No. 08CV06337, Nov. 6, 2009, 15 pages.
Exhibit A, Part 2 to Second Revised Joint Claim Construction Statement, *Healthways, Inc. v. Alere, LLC*, U.S. District Court for the Northern District of Illinois, Case No. 08CV06337, Nov. 6, 2009, 15 pages.
Exhibit A, Part 3 to Second Revised Joint Claim Construction Statement, *Healthways, Inc. v. Alere, LLC*, U.S. District Court for the Northern District of Illinois, Case No. 08CV06337, Nov. 6, 2009, 17 pages.
Exhibit B to Second Revised Joint Claim Construction Statement, *Healthways, Inc. v. Alere, LLC*, U.S. District Court for the Northern District of Illinois, Case No. 08CV06337, Nov. 6, 2009, 24 pages.
Exhibit C to Second Revised Joint Claim Construction Statement, *Healthways, Inc. v. Alere, LLC*, U.S. District Court for the Northern District of Illinois, Case No. 08CV06337, Nov. 6, 2009, 8 pages.
Exhibit D to Second Revised Joint Claim Construction Statement, *Healthways, Inc. v. Alere, LLC*, U.S. District Court for the Northern District of Illinois, Case No. 08CV06337, Nov. 6, 2009, 8 pages.
Exhibit E to Second Revised Joint Claim Construction Statement, *Healthways, Inc. v. Alere, LLC*, U.S. District Court for the Northern District of Illinois, Case No. 08CV06337, Nov. 6, 2009, 8 pages.
Exhibit F to Second Revised Joint Claim Construction Statement, *Healthways, Inc. v. Alere, LLC*, U.S. District Court for the Northern District of Illinois, Case No. 08CV06337, Nov. 6, 2009, 7 pages.
Exhibit G to Second Revised Joint Claim Construction Statement, *Healthways, Inc. v. Alere, LLC*, U.S. District Court for the Northern District of Illinois, Case No. 08CV06337, Nov. 6, 2009, 7 pages.
Exhibit H to Second Revised Joint Claim Construction Statement, *Healthways, Inc. v. Alere, LLC*, U.S. District Court for the Northern District of Illinois, Case No. 08CV06337, Nov. 6, 2009, 9 pages.
Exhibit I to Second Revised Joint Claim Construction Statement, *Healthways, Inc. v. Alere, LLC*, U.S. District Court for the Northern District of Illinois, Case No. 08CV06337, Nov. 6, 2009, 9 pages.
Exhibit J to Second Revised Joint Claim Construction Statement, *Healthways, Inc. v. Alere, LLC*, U.S. District Court for the Northern District of Illinois, Case No. 08CV06337, Nov. 6, 2009, 9 pages.
Exhibit K to Second Revised Joint Claim Construction Statement, *Healthways, Inc. v. Alere, LLC*, U.S. District Court for the Northern District of Illinois, Case No. 08CV06337, Nov. 6, 2009, 6 pages.
Exhibit L to Second Revised Joint Claim Construction Statement, *Healthways, Inc. v. Alere, LLC*, U.S. District Court for the Northern District of Illinois, Case No. 08CV06337, Nov. 6, 2009, 5 pages.
Healthways, Inc.'s Third Supplemental Response to Defendant and Counterclaimant Alere, LLC's First Set of Interrogatories and Exhibit E, *Healthways, Inc. v. Alere, LLC*, U.S. District Court for the Northern District of Illinois, Case No. 08CV06337, Oct. 28, 2009, 14 pages.
Reply Memorandum in Support of Plaintiffs' Partial Motion for Judgment on the Pleadings Pursuant to Rule 12(C) and Rule 9(B), *Healthways, Inc. v. Alere, LLC*, U.S. District Court for the Northern District of Illinois, Case No. 08CV06337, Oct. 23, 2009, 9 pages.
Second Revised Joint Claim Construction Statement, *Healthways, Inc. v. Alere, LLC*, U.S. District Court for the Northern District of Illinois, Case No. 08CV06337, Nov. 6, 2009, 63 pages.
Replacement Statement and Explanation dated Nov. 21, 2009 from Request for Ex Parte Reexamination of U.S. Patent No. 6,116,540; U.S. Appl. No. 90/009,594, filed Nov. 21, 2009.
Brazilian Office Action dated Mar. 31, 2009 for Brazilian Patent Application No. PI 9712092, filed Jul. 11, 1997.

(56) References Cited

OTHER PUBLICATIONS

Canadian Office Action dated Jun. 5, 2006 for Canadian Patent Application No. 2,260,838, filed Jul. 11, 2007.
Gardner, Integrated Computer Systems for Monitoring of the Critically Ill, Proceedings of 1st Annual Symposium on Computer Application in Medical Care, Washington, D.C., IEEE Computer Society, 1977, pp. 301-302.
Koska, Mary T., Primary Care: Hospitals Begin to Target Community Needs, Hospitals, Apr. 5, 1990, 64(7): 24-28.
Plaintiff's Opening Brief on Claim Construction, *Healthways, Inc.* v. *Alere, LLC*, U.S. District Court for the Northern District of Illinois, Case No. 08CV06337, Apr. 20, 2010, 33 pages.
Exhibit 12 to Plaintiff's Opening Brief on Claim Construction, *Healthways, Inc.* v. *Alere, LLC*, U.S. District Court for the Northern District of Illinois, Case No. 08CV06337, Apr. 20, 2010, 14 pages.
Exhibit 13 to Plaintiff's Opening Brief on Claim Construction, *Healthways, Inc.* v. *Alere, LLC*, U.S. District Court for the Northern District of Illinois, Case No. 08CV06337, Apr. 20, 2010, 12 pages.
Exhibit 14 to Plaintiff's Opening Brief on Claim Construction, *Healthways, Inc.* v. *Alere, LLC*, U.S. District Court for the Northern District of Illinois, Case No. 08CV06337, Apr. 20, 2010, 6 pages.
Brazilian Examination Report dated Jan. 27, 2010 for Brazilian Patent Application No. PI19712092, filed Jul. 11, 1997.
Canadian Office Action dated Dec. 2, 2008 for Canadian Patent Application No. 2,260,838, filed Jul. 11, 1997.
Chinese Final Rejection dated Oct. 16, 2009 for Chinese Patent Application No. 200510128901.X, filed Jul. 11, 1997.
Chinese Office Action 3rd dated Feb. 12, 2010 for Chinese Patent Application 2005101289024, filed Jul. 11, 1997.
European Office Action dated Jul. 9, 2010 in European Application No. 02075042.8, filed Jul. 11, 1997.
Chinese Office Action dated Sep. 2, 2010 in Chinese Application No. 200510128902.4, filed Jul. 11, 1997.
Complaint, *Healthways, Inc.* v. *Alere, LLC*, U.S. District Court for the Northern District of Illinois, Case No. 08CV06337, Nov. 4, 2008, 14 pages.
Alere's Answer and Counterclaims, *Healthways, Inc.* v. *Alere, LLC*, U.S. District Court for the Northern District of Illinois, Case No. 08CV06337, Dec. 9, 2008, 29 pages.
Memorandum of Law in Support of Plaintiffs' Motion to Dismiss under Rule 12(b)(6) or Rule 9(b), *Healthways, Inc.* v. *Alere, LLC*, U.S. District Court for the Northern District of Illinois, Case No. 08CV06337, Dec. 29, 2008, 9 pages.
Plaintiffs' Reply to Alere's Counterclaims, *Healthways, Inc.* v. *Alere, LLC*, U.S. District Court for the Northern District of Illinois, Case No. 08CV06337, Dec. 29, 2008, 10 pages.
Alere's First Amended Answer and Counterclaims, *Healthways, Inc.* v. *Alere, LLC*, U.S. District Court for the Northern District of Illinois, Case No. 08CV06337, Jan. 6, 2009, 28 pages.
Alere's First Amended Answer and Counterclaims, *Healthways, Inc.* v. *Alere, LLC*, U.S. District Court for the Northern District of Illinois, Case No. 08CV06337, Jan. 8, 2009, 30 pages.
Plaintiffs' Reply to Alere's First Amended Counterclaims, *Healthways, Inc.* v. *Alere, LLC*, U.S. District Court for the Northern District of Illinois, Case No. 08CV06337, Jan. 9, 2009, 11 pages.
First Amended Complaint, *Healthways, Inc.* v. *Alere, LLC*, U.S. District Court for the Northern District of Illinois, Case No. 08CV06337, Jan. 15, 2009, 15 pages.
Alere's Answer to First Amended Complaint and Counterclaims, *Healthways, Inc.* v. *Alere, LLC*, U.S. District Court for the Northern District of Illinois, Case No. 08CV06337, Jan. 22, 2009, 32 pages.
Exhibit 1 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 2 pages.
Exhibit 2 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 5 pages.
Exhibit 3 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 6 pages.
Exhibit 4 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 2 pages.
Exhibit 5 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 3 pages.
Replacement Exhibit 1 to Alere's Answer to First Amended Complaint and Counterclaims, *Healthways, Inc.* v. *Alere, LLC*, U.S. District Court for the Northern District of Illinois, Case No. 08CV06337, Jan. 23, 2009, 4 pages.
Plaintiffs' Reply to Alere Medical, Inc.'s Counterclaims, *Healthways, Inc.* v. *Alere, LLC*, U.S. District Court for the Northern District of Illinois, Case No. 08CV06337, Feb. 10, 2009, 11 pages.
Plaintiffs' Amended Reply to Alere Medical, Inc.'s Counterclaims, *Healthways, Inc.* v. *Alere, LLC*, U.S. District Court for the Northern District of Illinois, Case No. 08CV06337, Feb. 10, 2009, 11 pages.
Alere, LLC's Objections and Answers to Plaintiffs First Set of Interrogatories (Nos. 1-8), *Healthways, Inc.* v. *Alere, LLC*, U.S. District Court for the Northern District of Illinois, Case No. 08CV06337, Feb. 11, 2009, 30 pages.
Alere, LLC's Objections and Answers to Plaintiffs' Second Set of Interrogatories (No. 9-10), *Healthways, Inc.* v. *Alere, LLC*, U.S. District Court for the Northern District of Illinois, Case No. 08CV06337, Mar. 2, 2009, 10 pages.
Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 23 pages.
Exhibit B to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 18 pages.
Exhibit C to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 5 pages.
Exhibit D to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case. No. 08CV06337, Mar. 3, 2009, 15 pages.
Exhibit E to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 12 pages.
Exhibit F to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 61 pages.
Exhibit G to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 31 pages.
Exhibit H to Alere, LLC's First Supplemental Objections and Responses to Plaintiffs First Set of Interrogatories (Nos. 1-8), *Healthways, Inc.v. Alere, LLC*, U.S. District Court for the Northern District of Illinois, Case No. 08CV06337, Mar. 3, 2009, 13 pages.
Exhibit I-1 to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 83 pages.
Exhibit I-2 to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 87 pages.
Exhibit J to Alere, LLC's First Supplemental Objections and Responses to Plaintiffs First Set of Interrogatories (Nos. 1-8),

(56) References Cited

OTHER PUBLICATIONS

*Healthways, Inc.* v. *Alere, LLC*, U.S. District Court for the Northern District of Illinois, Case No. 08CV06337, Mar. 3, 2009, 22 pages.
Exhibit K to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 41 pages.
Exhibit L to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 18 pages.
Alere LLC's Counterclaims, *Healthways, Inc.* v. *Alere, LLC*, U.S. District Court for the Northern District of Illinois, Case No. 08CV06337, Mar. 4, 2009, 10 pages.
Exhibit 12 to Alere LLC's Counterclaims, *Healthways, Inc.* v. *Alere, LLC*, U.S. District Court for the Northern District of Illinois, Case No. 08CV06337, Mar. 4, 2009, 2 pages.
Exhibit 13 to Alere LLC's Counterclaims, *Healthways, Inc.* v. *Alere, LLC*, U.S. District Court for the Northern District of Illinois, Case No. 08CV06337, Mar. 4, 2009, 5 pages.
Exhibit 14 to Alere LLC's Counterclaims, *Healthways, Inc.* v. *Alere, LLC*, U.S. District Court for the Northern District of Illinois, Case No. 08CV06337, Mar. 4, 2009, 6 pages.
Exhibit 15 to Alere LLC's Counterclaims, *Healthways, Inc.* v. *Alere, LLC*, U.S. District Court for the Northern District of Illinois, Case No. 08CV06337, Mar. 4, 2009, 2 pages.
Exhibit 16 to Alere LLC's Counterclaims, *Healthways, Inc.* v. *Alere, LLC*, U.S. District Court for the Northern District of Illinois, Case No. 08CV06337, Mar. 4, 2009, 3 pages.
Applied Medical Informatics, Inc., Medical House CallTM Interactive Home Medical Guide & Symptom Analysis, Applied Medical Informatics, 1995, p. 24, Salt Lake City, UT.
Barnett et al., A computer-based medical information system for ambulatory care, Proc. IEEE, 1979, Issue 67, pp. 1226-1237.
Bouhaddou et al., An interactive patient information and education system (Medical HouseCall) based on a physician expert system (Iliad), Medinfo, 1995, vol. Pt 2, Issue 8, pp. 1181-1185, Vancouver, Canada.
Bouhaddou et al., Iliad and Medical House Call: evaluating the impact of common sense knowledge on the diagnostic accuracy of a medical expert system, AMIA, Inc., 1995, pp. 742-746.
Collen, Machine diagnosis from a multiphasic screening program, Proceedings of $5^{th}$ IBM Medical Symposium at 131, 1963.
Cope, For well-connected in study, computer's diagnosis is just a phone call away, Minneappolis Star-Tribune, Mar. 1992, p. 03E.
Crossman, Confused? Take two aspirin and call up advisor, New Jersey Record, Apr. 1992, p. B02.
Dawson, Sun, Microsoft battle over Net computing, Multichannel News, Nov. 1996.
Gorry et al., Decision analysis as the basis for computer-aided management of acute renal failure, Am. J. Med., Oct. 1973, vol. 3, Issue 55, pp. 473-484.
Lai, Abstraction models at system level for interactive multimedia scripting, Master's Thesis, Massachusetts Institute of Technology, May 1995, Boston.
Magnet, Who's winning the information revolution, Fortune, Nov. 30, 1992, vol. 12, Issue 126, pp. 110-117.
Mallya et al., Correlation in rheumatoid arthritis of concentrations of plasma C3d, serum rheumatoid factor, immune complexes and C-reactive protein with each other and with clinical features of disease activity., Clin. Exp. Immunol., 1982, Issue 48, pp. 747-753.
Markoff, Making the PC come alive, New York Times, Sep. 1995.
Miller, Dial 1-900 for doctor, Newsweek, Oct. 1991.
Okada, Medical data base system with an ability of automated diagnosis, Computer Programs in Biomedicine, Sep. 1977, vol. 3, Issue 7, pp. 163-170.
Olson et al., $21^{st}$ century learning and health care in the home: creating a national telecommunications network, IAF/CRI, Jan. 1992.
Pauker et al., Towards the simulation of clinical cognition: taking a present illness by computer, Am. J. Med., Jun. 1976, vol. 7, Issue 60, pp. 981-996.
Riordan, Patents; Prodigy's patent is being debated as a possible threat to Sun Microsystems' Java language, New York Times, Feb. 1996.
Roberts, Dr. Schueler's home medical advisor 2.0, Compute!, Oct. 1992, Issue 145, p. 106.
Shannon, Peripherals; choosing a college, New York Times, Jan. 1989.
Shannon, Peripherals; advice on a disk: the doctor is really in, New York Times, Jul. 14, 1992 at C7.
Shannon, Peripherals; Doctor, I have this funny pain . . . , New York Times, Nov. 3, 1992.
Stearn et al., A statistical analysis of subjective and objective methods of evaluating fabric handle Part 2: Relationship between subjective and objective measurements, Journal of the Textile Machinery Society of Japan, 1988, vol. 2, Issue 34, pp. 39-46.
Szolovits et al., Categorical and probabilistic reasoning in medical diagnosis, Artificial Intelligence, Aug. 1978, vol. 1&2, Issue 11, pp. 115-144.
Tedesco, Microsoft, Intel and Sun advance NC visions, Broadcasting & Cable, Nov. 1996.
Templeton, Medical software that makes house calls, Business Week, Jun. 1992, Issue 3720.
Vaughn et al., Effective algorithm-based triage and self-care protocols: quality medicine at lower costs, Ann. Emerg. Med., Jan. 1980, vol. 1, Issue 9, pp. 31-36.
Warner, Knowledge sectors for logical processing of patient data in the help system, Proc. IEEE, 1978.
Wijkstra et al., Relation of lung function, maximal inspiratory pressure, dyspnoea, and quality of life with exercise capacity in patients with chronic obstructive pulmonary disease, Thorax, May 1994, vol. 5, Issue 49, pp. 468-472.
Zallen, Member-centered managed care and the new media, ed. Linda M. Harris, in Health and the New Media, 1995.
Ball et al. Eds. Computers in Health Care: Aspects of the Computer-based Patient Record, Springer Verlag, 1992, pp. 1-336.
Barr et al., (Eds.) The Handbook of Artificial Intelligence, HeurisTech Press, 1982, vol. II, Chapter VIII, pp. 175-222.
Bischoff, A Knowledge Based System for Assisting in Differential Diagnosis of Chemically Dependent/Mentally Ill Patients, Computers in Human Services, 1992, vol. 8, Nos. 3/4, pp. 143-151.
Bortolan et al., The role of patient history in a decision support system, IEEE, Computers in Cardiology, Sep. 1990, Proceedings, pp. 357-360.
Brown et al., Information Infrastructure Task Force, The National Information Infrastructure: Agenda for Action, Sep. 15, 1993, pp. 26.
Christine, The Future of Health Care Technologies, HighBeam Research, Risk Management, Nov. 1, 1992, 1-3.
Common Carrier Week 8, Home Education and Health Benefits said to be underestimated, Warren Publishing Inc., Jan. 20, 1992, 9(3): 1-3.
Creative Strategies International (CSI), The Emerging Self-Help Healthcare Market—Microcomputer Applications, 1984, pp. 130.
Evans, C. Edward, A Computer in the Waiting Room: Who Needs the Doctor?, Can Fam Phys., Apr. 1984, 30: 869-876.
Fallon et al., A Primer for Writing Medical Data Base for the Clinical Decision Support System, Computers and Brains, Progress in Brain Research, Eds. Schadé et al., vol. 33, pp. 155-175.
Federal Register, National Telecommunications and Information Administration, DOC—Administration Policy Statement, Notices, Sep. 21, 1993, Fed. Reg., 58(181): 49025-49036.
First Opinion Corporation, Canadian Trademark Application File History TMA447,669, registered Sep. 15, 1995 for the Trademark/ Servicemark: First Opinion, pp. 51.
Haug et al., Decision Support in Medicine: Examples from the Help System, Computers and Biomedical Research, 1994, 27: 396-418.
Henderson, A Trainable Pattern Classifier for Medical Questionnaires, Annals of Biomed Engin., Jan. 27, 1972, 1: 115-133.

(56) References Cited

OTHER PUBLICATIONS

Johnson et al., Psychological Systems Questionnaire: An Objective Personality Test designed for on-line computer Presentation, Scoring, and Interpretation, Behav Res Meth Instrument., 1979, 11(2): 257-260.

Lunin, Lois F., On Speaking Terms With the Computer, Information Today, Feb. 1992, 9(2): 19- 20.

Malcolm et al., Computer-Assisted Diagnosis of Alcoholism, Computers in Human Services, 1989, 5(3/4): 163-170.

McNish, David A., EMED Electronic Medical Database, DMC Software Packaging and Manual, DMC Software Company., 1987, 7 pages.

Miller et al., The Computerized Carroll Rating Scale, Indiana University School of Medicine, 1985, pp. 344-347.

Partin, A Preliminary Conceptual Framework for the Design, Development, and Use of Client-Oriented Information Systems in Health, J Med Sys. 1987, 11(2/3): 205-217.

Patel et al., A Computer-Based, Automated, Telephonic System to Monitor Patient Progress in the Home Setting, J Med Sys., 1992, 16(2/3): 101-112.

Shneiderman, Ben, Touch Screens now offer Compelling Uses, IEEE Software, 1991, pp. 93-94.

Shortliffe et al., A Model of Inexact Reasoning in Medicine, 1975, (shortened/editied version) Mathematical Biosciences, 11: 233-262.

Stead et al., Computer-Assisted Interview of Patients with Functional Headache, Arch Intern Med., 1972, 129: 950-955.

Szolovits et al., Guardian Angel: Patient-Centered Health Information Systems, May 1994, MIT Laboratory for Computer Science, TR-604, pp. 40.

The National Information Infrastructure: Agenda for Action, U.S. Government Paper, 1993, pp. 42.

Walmsley et al., Normal "Anion Gap" (Hyperchloremic) Acidosis, Case Reports, Clin Chem., 1985, 31(2): 309-313.

Weinstock, Edward, An Apple a Day . . . ™ , Computer Program Manual, Avant-Garde Publishing Corporation, 1984, pp. 47.

Weiss et al., Glaucoma Consultation by Computer, Comput Biol Med . . . , Pergamon Press, 1978, 8: 25-40.

Memorandum in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC* , U.S. District Court for the Northern District of Illinois, Case No. 08CV06337, Mar. 27, 2009, 20 pages.

Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 20 pages.

Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 4 pages.

Defendant-Counterclaimaint Alere LLC's Agreed Motion for Leave to Replace its Opposition to Plaintiffs' Partial Motion for Judgment on the Pleadings Pursuant to Rule 12(c) and Rule 9(b) and Exhibit 3 to its Opposition with Redacted Versions, *Healthways, Inc.* v. *Alere, LLC*, U.S. District Court for the Northern District of Illinois, Case No. 08CV06337, Sep. 30, 2009, 3 pages.

Defendant-Counterclaimant Alere, LLC's Alternative Motion for Leave to File First Amended Answer and Counterclaims, *Healthways, Inc.* v. *Alere, LLC*, U.S. District Court for the Northern District of Illinois, Case No. 08CV06337, Sep. 24, 2009, 3 pages.

Defendant-Counterclaimant Alere, LLC's Memorandum in Support of its Alternative Motion for Leave to File First Amended Answer and Counterclaims, *Healthways, Inc.* v. *Alere, LLC*, U.S. District Court for the Northern District of Illinois, Case No. 08CV06337, Sep. 24, 2009, 17 pages.

Defendant-Counterclaimant Alere, LLC's Unopposed Motion for Leave to Replace its Memorandum in Support of its Alternative Motion for Leave to File First Amended Answer and Counterclaims and First Amended Answer and Counterclaims with Redacted Versions, *Healthways, Inc.* v. *Alere, LLC*, U.S. District Court for the Northern District of Illinois, Case No. 08CV06337, Sep. 30, 2009, 3 pages.

Exhibit 1 to Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 2 pages.

Exhibit 1 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 2 pages.

Exhibit 10 to Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 5 pages.

Exhibit 2 to Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 4 pages.

Exhibit 2 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 5 pages.

Exhibit 3 to Alere LLC's Opposition to Plaintiffs' Partial Motion for Judgment on the Pleadings Pursuant to Rule 12(c) and Rule 9(b), Alere LLC's First Supplemental Objections and Responses to Plaintiffs' Second Set of Interrogatories (No. 9-10), *Healthways, Inc.* v. *Alere, LLC*, U.S. District Court for the Northern District of Illinois, Case No. 08CV06337, Sep. 24, 2009, 62 pages.

Exhibit 3 to Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 3 pages.

Exhibit 3 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 6 pages.

Exhibit 4 to Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 9 pages.

Exhibit 4 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 2 pages.

Exhibit 5 to Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 3 pages.

Exhibit 5 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 3 pages.

Exhibit 8 to Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 3 pages.

(56) References Cited

OTHER PUBLICATIONS

Exhibit 9 to Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 8 pages.
Exhibit A to Defendant-Counterclaimaint Alere LLC's Agreed Motion for Leave to Replace its Opposition to Plaintiffs' Partial Motion for Judgment on the Pleadings Pursuant to Rule 12(c) and Rule 9(b) and Exhibit 3 to its Opposition with Redacted Versions, Alere LLC's Opposition to Plaintiffs' Partial Motion for Judgment on the Pleadings Pursuant to Rule 12(c) and Rule 9(b), Redacted, *Healthways, Inc.* v. *Alere, LLC*, U.S. District Court for the Northern District of Illinois, Case No. 08CV06337, Sep. 24, 2009, 21 pages.
Exhibit A to Defendant-Counterclaimant Alere, LLC's Alternative Motion for Leave to File First Amended Answer and Counterclaims, Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 126 pages.
Exhibit A to Defendant-Counterclaimant Alere, LLC's Unopposed Motion for Leave to Replace its Memorandum in Support of its Alternative Motion for Leave to File First Amended Answer and Counterclaims and First Amended Answer and Counterclaims with Redacted Versions, Defendant-Counterclaimant Alere, LLC's Memorandum in Support of its Alternative Motion for Leave to File First Amended Answer and Counterclaims, Redacted, *Healthways, Inc.* v. *Alere, LLC*, U.S. District Court for the Northern District of Illinois, Case No. 08CV06337, Sep. 24, 2009, 18 pages.
Exhibit A, Part 1 to Joint Claim Construction Statement, *Healthways, Inc.* v. *Alere, LLC*, U.S. District Court for the Northern District of Illinois, Case No. 08CV06337, Aug. 10, 2009, 15 pages.
Exhibit A, Part 1 to Revised Joint Claim Construction Statement, *Healthways, Inc.* v. *Alere, LLC*, U.S. District Court for the Northern Distric of Illinois, Case No. 08CV06337, Sep. 4, 2009, 15 pages.
Exhibit A, Part 2 to Joint Claim Construction Statement, *Healthways, Inc.* v. *Alere, LLC*, U.S. District Court for the Northern District of Illinois, Case No. 08CV06337, Aug. 10, 2009, 15 pages.
Exhibit A, Part 2 to Revised Joint Claim Construction Statement, *Healthways, Inc.* v. *Alere, LLC*, U.S. District Court for the Northern District of Illinois, Case No. 08CV06337, Sep. 4, 2009, 15 pages.
Exhibit A, Part 3 to Joint Claim Construction Statement, *Healthways, Inc.* v. *Alere, LLC*, U.S. District Court for the Northern District of Illinois, Case No. 08CV06337, Aug. 10, 2009, 17 pages.
Exhibit A, Part 3 to Revised Joint Claim Construction Statement, *Healthways, Inc.* v. *Alere, LLC*, U.S. District Court for the Northern District of Illinois, Case No. 08CV06337, Sep. 4, 2009, 17 pages.
Exhibit B to Defendant-Counterclaimaint Alere LLC's Agreed Motion for Leave to Replace its Opposition to Plaintiffs' Partial Motion for Judgment on the Pleadings Pursuant to Rule 12(c) and Rule 9(b) and Exhibit 3 to its Opposition with Redacted Versions, Alere LLC's First Supplemental Objections and Responses to Plaintiffs' Second Set of Interrogatories (No. 9-10), Redacted, *Healthways, Inc.* v. *Alere, LLC*, U.S. District Court for the Northern District of Illinois, Case No. 08CV06337, Sep. 24, 2009, 63 pages.
Exhibit B to Defendant-Counterclaimant Alere, LLC's Unopposed Motion for Leave to Replace its Memorandum in Support of its Alternative Motion for Leave to File First Amended Answer and Counterclaims and First Amended Answer and Counterclaims with Redacted Versions, Defendant-Counterclaimant Alere, LLC's First Amended Answer and Counterclaims, Redacted, *Healthways, Inc.* v. *Alere, LLC*, U.S. District Court for the Northern District of Illinois, Case No. 08CV06337, Sep. 24, 2009, 127 pages.
Exhibit B to Joint Claim Construction Statement, *Healthways, Inc.* v. *Alere, LLC*, U.S. District Court for the Northern District of Illinois, Case No. 08CV06337, Aug. 10, 2009, 24 pages.
Exhibit B to Revised Joint Claim Construction Statement, *Healthways, Inc.* v. *Alere, LLC*, U.S. District Court for the Northern District of Illinois, Case No. 08CV06337, Sep. 4, 2009, 24 pages.
Exhibit C to Joint Claim Construction Statement, *Healthways, Inc.* v. *Alere, LLC*, U.S. District Court for the Northern District of Illinois, Case No. 08CV06337, Aug. 10, 2009, 8 pages.
Exhibit C to Revised Joint Claim Construction Statement, *Healthways, Inc.* v. *Alere, LLC*, U.S. District Court for the Northern District of Illinois, Case No. 08CV06337, Sep. 4, 2009, 7 pages.
Exhibit D to Joint Claim Construction Statement, *Healthways, Inc.* v. *Alere, LLC*, U.S. District Court for the Northern District of Illinois, Case No. 08CV06337, Aug. 10, 2009, 8 pages.
Exhibit D to Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 3 pages.
Exhibit D to Revised Joint Claim Construction Statement, *Healthways, Inc.* v. *Alere, LLC*, U.S. District Court for the Northern District of Illinois, Case No. 08CV06337, Sep. 4, 2009, 8 pages.
Exhibit E to Joint Claim Construction Statement, *Healthways, Inc.* v. *Alere, LLC*, U.S. District Court for the Northern District of Illinois, Case No. 08CV06337, Aug. 10, 2009, 8 pages.
Exhibit E to Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 3 pages.
Exhibit E to Revised Joint Claim Construction Statement, *Healthways, Inc.* v. *Alere, LLC*, U.S. District Court for the Northern District of Illinois, Case No. 08CV06337, Sep. 4, 2009, 8 pages.
Exhibit F to Joint Claim Construction Statement, *Healthways, Inc.* v. *Alere, LLC*, U.S. District Court for the Northern District of Illinois, Case No. 08CV06337, Aug. 10, 2009, 7 pages.
Exhibit F to Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 3 pages.
Exhibit F to Revised Joint Claim Construction Statement, *Healthways, Inc.* v. *Alere, LLC*, U.S. District Court for the Northern District of Illinois, Case No. 08CV06337, Sep. 4, 2009, 7 pages.
Exhibit G to Joint Claim Construction Statement, *Healthways, Inc.* v. *Alere, LLC*, U.S. District Court for the Northern District of Illinois, Case No. 08CV06337, Aug. 10, 2009, 7 pages.
Exhibit G to Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 2 pages.
Exhibit G to Revised Joint Claim Construction Statement, *Healthways, Inc.* v. *Alere, LLC*, U.S. District Court for the Northern District of Illinois, Case No. 08CV06337, Sep. 4, 2009, 7 pages.
Exhibit H to Joint Claim Construction Statement, *Healthways, Inc.* v. *Alere, LLC*, U.S. District Court for the Northern District of Illinois, Case No. 08CV06337, Aug. 10, 2009, 9 pages.
Exhibit H to Revised Joint Claim Construction Statement, *Healthways, Inc.* v. *Alere, LLC*, U.S. District Court for the Northern District of Illinois, Case No. 08CV06337, Sep. 4, 2009, 9 pages.
Joint Claim Construction Statement, *Healthways, Inc.* v. *Alere, LLC*, U.S. District Court for the Northern District of Illinois, Case No. 08CV06337, Aug. 10, 2009, 60 pages.
Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 12 pages.
Revised Joint Claim Construction Statement, *Healthways, Inc.* v. *Alere, LLC*, U.S. District Court for the Northern District of Illinois, Case No. 08CV06337, Sep. 4, 2009, 58 pages.
Request for Ex Parte Reexamination filed Oct. 8, 2009 of USP 6,113,540, issued Sep. 5, 2000.
CIPO Office Action dated Apr. 27, 2009 in Canadian Application No. 2,260,836, filed Jul. 11, 1997.

\* cited by examiner

Node Block

Node = 2205
Parent = 2200
Type = YesNo
Digits = 1
Help list → <empty list>
Play list → 2205
Next list → 1=2206, 2=2210
Work list → <empty list>

*226*

Symbol Table

Age = 45
Sex = Male
Real = True
Problem = CCHP

Node Block

Node = 2210
Parent = 2205
Type = YesNo
Digits = 1
Help list → <empty list>
Play list → 2210
Next list → 1=2211, 2=2215
Work list → <empty list>

*230*

Symbol Table

Age = 45
Sex = Male
Real = True
Problem = CCHP

The MDATA System Using the Internet

Malaria typically shows up as Chills, followed by Fever, and then followed by Sweats. Sometimes one has several such CFS bouts in a row, usually 2 or 3 days apart, each lasting several hours.

Did you experience something like that?

○ Yes, I have had Chills, Fever, and Sweats

○ Maybe – I am not sure if I did

○ No, this does not apply to me at all

SUBMIT   BACK   HELP

FIG. 33

COMPUTERIZED MEDICAL DIAGNOSTIC AND TREATMENT ADVICE SYSTEM INCLUDING NETWORK ACCESS

RELATED APPLICATIONS

This application is a continuation of application Ser. No. 11/045,676, filed Jan. 28, 2005, which is a continuation of application Ser. No. 10/300,284, filed Nov. 19, 2002, now U.S. Pat. No. 6,849,045, which is a continuation of application Ser. No. 09/800,220, filed Mar. 5, 2001, now U.S. Pat. No. 6,482,156, which is a continuation of application Ser. No. 09/376,185, filed Aug. 17, 1999, now U.S. Pat. No. 6,206,829, which is a continuation of application Ser. No. 08/893,912, filed Jul. 11, 1997, now U.S. Pat. No. 6,022,315, which claims the benefit of Provisional Applications Nos. 60/021,614 and 60/021,615, filed Jul. 12, 1996. Application Ser. No. 08/893,912, filed Jul. 11, 1997, now U.S. Pat. No. 6,022,315, is a continuation-in-part of application Ser. No. 08/176,041, filed on Dec. 29, 1993, now U.S. Pat. No. 5,660,176. The above referenced applications are hereby incorporated by reference in their entirety.

BACKGROUND OF THE INVENTION

1. Field of the Invention

The present invention relates to medical knowledge systems and, more particularly, to systems for giving medical advice to the general public over networks.

2. Description of the Related Technology

Health care costs currently represent 14% of the United States Gross National Product and are rising faster than any other component of the Consumer Price Index. Moreover, usually because of an inability to pay for medical services, many people are deprived of access to even the most basic medical care and information.

Many people delay in obtaining, or are prevented from seeking, medical attention because of cost, time constraints, or inconvenience. If the public had universal, unrestricted and easy access to medical information, many diseases could be prevented. Likewise, the early detection and treatment of numerous diseases could keep many patients from reaching the advanced stages of illness, the treatment of which is a significant part of the financial burden attributed to our nation's health care system. It is obvious that the United States is facing health-related issues of enormous proportions and that present solutions are not robust.

One prior attempt at a solution to the health care problem is called Ask-A-Nurse, wherein a group of nurses provide health information by telephone around-the-clock. A person with a medical problem calls an 800 number and describes the problem to the nurse. The nurse uses a computer for general or diagnostic information on the ailment or complaint mentioned by the caller. The nurse may then refer the caller to a doctor from a computerized referral list for a contracting hospital or group of hospitals. Client hospitals contract with Ask-A-Nurse to provide patient referrals. A managed care option called Personal Health Advisor is similar and adds the capability for the caller to hear prerecorded messages on health topics 24 hours a day. Several problems exist with these prior medical advice systems. First, these systems have high costs associated with having a nurse answer each telephone call. Second, the caller may have to belong to a participating health plan to utilize the service. Third, if for some reason all nurses on a particular shift happen to be busy and the caller has an emergency condition (that is not known by the caller to be an emergency), precious time in getting emergency services may be lost during the delay.

Another prior health system was developed by InterPractice Systems which provides a computerized service that answers health care questions and advises people in their homes. A health maintenance organization (HMO) may provide this service to its members in a particular geographic area. To get advice at home, an HMO member connects a toaster-sized box to a telephone and calls a toll-free 800 number. Using a keyboard that is part of the box, the user answers questions displayed on a screen of the box relating to the user's symptoms. Depending on the answers, the user might be told to try a home remedy, be called by a nurse or doctor, or be given an appointment to be examined. A limitation of this system is the additional expense of the electronics box, which could either be purchased by the user for approximately $300 or purchased by the health organization with the expense to be passed on to the users. Another limitation is that this service is directed to members of a particular contracting health organization, such as an HMO. What is desired is a system that does not require additional hardware for the basic service, but that utilizes the existing communication network. The desired system should be available for use by any person, not just members of a certain organization.

A prior attempt at a health care solution for a limited set of conditions is described in U.S. Pat. No. 4,712,562. A patient's blood pressure and heart rate are measured and the measurements are sent via telephone to a remote central computer for storage and analysis. Reports are generated for submission to a physician or the patient. U.S. Pat. No. 4,531,527 describes a similar system, wherein the receiving office unit automatically communicates with the physician under predetermined emergency circumstances.

U.S. Pat. No. 4,838,275 discloses a device for a patient to lay on or sit in having electronics to measure multiple parameters related to a patient's health. These parameters are electronically transmitted to a central surveillance and control office where a highly trained observer interacts with the patient. The observer conducts routine diagnostic sessions except when an emergency is noted or from a patient-initiated communication. The observer determines if a nonroutine therapeutic response is required, and if so facilitates such a response. As previously mentioned, highly trained people are needed by this system along with the special measurement apparatus (embedded in a bed or chair).

Other prior attempts at a health care solution are typified by U.S. Pat. No. 5,012,411 which describes a portable self-contained apparatus for measuring, storing and transmitting detected physiological information to a remote location over a communication system. The information is evaluated by a physician or other health professional. As before, highly trained people are necessary to utilize such an apparatus.

Several services to provide medical or pharmaceutical advice are now available via "1-900" telephone numbers, e.g., "Doctors by Phone." These services are available 24 hours a day and 7 days a week. A group of doctors, including some specialties, is available to answer questions about health care or medical conditions for people anywhere in the United States who call the "1-900" telephone of one of the services. A group of registered pharmacists answers questions about medications for the "1-900" pharmaceutical service.

SUMMARY OF THE INVENTION

The present solution to the health care problem is a computerized medical diagnostic and treatment advice (MDATA)

system that is a medical knowledge-based system designed to give medical advice to the general public over the telephone network. The goal of the MDATA system is to provide everyone with equal access to high quality, 100%-consistent medical advice at a reasonable cost. The MDATA system provides callers with extremely fast and virtually unlimited access to health care information, twenty-four hours a day, from any location around the world. Health care advice is made available to an entire spectrum of users, from elderly patients confined to their homes to travelers in a foreign country with telephones in their cars.

The central ideas leading to the development of the MDATA system are based on the following assumptions:

Nearly 90% of all patient complaints are confined to approximately 100 medical problems.

Almost all primary care decisions involved in these 100 problems can be made based upon information learned solely by obtaining a detailed medical history. The results of the physical examination, laboratory, and imaging studies only tend to confirm a diagnosis.

The minimal amount of information that many doctors believe can only be obtained from the physical examination can actually be directly acquired from the patient when given appropriate instructions.

In most cases, a face-to-face interaction between the doctor and patient is not necessary. A detailed and well-constructed history, along with physical findings elicited from the patient, can be obtained over the telephone.

Medicine is basically diagnosis and treatment. Although treatment recommendations change frequently, the fundamental principles of making the diagnosis do not.

There is a significant delay between the time a new therapy is recognized as safe and effective and the time physicians are able to provide it to their patients.

These central ideas are utilized in the implementation of the MDATA system.

A goal of the MDATA system is to give better medical advice than a family practitioner who is unfamiliar with a patient, e.g., an on-call physician. A person seeking medical advice frequently will not be able to see or speak with his or her personal physician in a timely manner. The MDATA system provides medical advice whenever desired by the caller—seven days a week/24 hours a day.

All previous medical algorithms, including those used in the military, are designed for face-to-face interactions. Self-help books generally do not consider age and sex in their algorithms. Furthermore, a book cannot take into account how many times a person has consulted the same algorithm within a short period of time for the same problem. The medical algorithms used by the MDATA system are designed for use in a telecommunications setting and overcome the deficiencies of self-help books.

Previous medical advice systems do not do a time-density analysis for a number of factors with regard to the number of complaints per unit of time. The MDATA system uses "meta" functions to perform these analyses.

Previous medical advice algorithms do not have a way of detecting the consciousness level of the person seeking consultation. The MDATA system invokes a "mental status examination" whenever a complaint or problem has the possibility of an altered level of consciousness. In addition, the MDATA system uses "semantic discrepancy evaluator loops" which allow the system to invoke the mental status exam if there are differences in answers to the parallel threads of thought that are woven or embedded into the system.

Other medical advice systems do not have a "re-enter" feature to monitor a patient's progress or worsening over time. The MDATA system checks for and responds to changing conditions over time.

Prior medical advice systems suffer from the inability to be nearly instantly up-dated as new medical information is made available. The MDATA system regularly and frequently updates the treatment aspect of the system.

The computerized medical diagnostic and treatment advice (MDATA) system is a medical knowledge-based system designed to give medical advice to the general public over the telephone network. Using a new authoring language, interactive voice response and speech recognition technology, the MDATA system encodes a highly useful core of expert and general practitioner diagnostic and treatment knowledge into a computerized system for access by non-medically trained personnel.

The MDATA system does not provide advice for every medical problem, nor does it make an exhaustive study of one vertical cross-section of medicine. Instead, the MDATA system provides up-to-date medical advice for approximately one hundred of the most commonly encountered problems in general practice and emergency medicine. It also provides valuable information to the public on any number of other medical topics.

As another embodiment of the MDATA system, a person desiring medical advice and having access to a personal computer (PC) loads a program into the PC to produce a stand-alone medical diagnostic and treatment advice (SA-MDATA) system. Rather than listening to questions and responding via touch tone keypresses or via voice, the user responds to questions and directions displayed on the computer screen via a computer input device, such as a keyboard or mouse. The diagnosis and/or treatment recommendations provided by the MDATA system are the same as that provided by the SA-MDATA system. The user of the SA-MDATA system can procure updates by contacting the MDATA system sponsor/administrator to obtain the most current treatment table information for a particular diagnosis.

Yet another embodiment of the MDATA system utilizes communication networks, such as the Internet, to connect a user or patient with the MDATA computer. The user utilizes a network access processor or computer to access the network. This embodiment utilizes medical diagnostic scripts executed on a script engine to generate medical advice or a diagnosis. The scripts and script engine may be executed on the MDATA computer in a manner similar to the telephonic embodiment above. Alternatively, selected portions of the MDATA software and one or more scripts may be downloaded to the user's computer for execution. The MDATA computer may download additional or newer scripts to the user's computer over the network as necessary.

In another embodiment, there is a medical diagnostic and treatment advice system for providing information to a patient, the system comprising a server connected to a public data network configured to a) receive patient information from a user over the public data network, b) selectively execute at least one diagnostic code portion based on at least a portion of the received information, and c) provide information indicative of a diagnosed condition to the user over the public data network.

In another embodiment, there is a method of providing a medical diagnosis, the method comprising receiving patient information from a user over a public data network, generating a medical diagnosis by selectively executing at least one diagnostic code portion based on at least a portion of the received information, and transmitting a medical diagnosis to the user over the public data network.

In yet another embodiment, there is a system for providing a medical diagnosis, the system comprising means for receiving patient information from a user over a public data network, means for generating a medical diagnosis by selectively executing at least one diagnostic code portion based on at least a portion of the received information, and means for transmitting a medical diagnosis to the user over the public data network.

BRIEF DESCRIPTION OF THE DRAWINGS

FIGS. 5b-5g are an exemplary sequence of data structures of the system shown in FIG. 1 at run time;

FIGS. 8a and 8b are a flow diagram of the patient login process 250 defined in FIG. 7a;

FIGS. 9a and 9b are a flow diagram of the patient registration process 252 defined in FIG. 7a;

FIG. 29 is a flow diagram showing the interaction of the MDATA computer with the patient's computer via the network of FIG. 25a;

FIG. 33 is an exemplary graphical user interface screen generated during a script that may diagnose Malaria.

DETAILED DESCRIPTION OF THE PREFERRED EMBODIMENT

The following detailed description of the preferred embodiments presents a description of certain specific embodiments to assist in understanding the claims. However, the present invention can be embodied in a multitude of different ways as defined and covered by the claims.

For convenience, the following description will be outlined into the following principal sections: Introduction, System Overview, Operating Features of the MDATA System, Authoring Language, Run-Time Operation, Software Structure, Top-Level Flow, Login Process, Registration Process, Evaluation Process, The Meta Function, Mental Status Examination, Semantic Discrepancy Evaluator Routine, Past Medical History Routine, Physical Self Examination, Symptom Severity Analysis, Treatment Table, The MDATA System Paradigm, Video Imaging, Benefits of the MDATA System, First Optional System Configuration, Summary of Advantages of the Present Invention, and Second Optional System Configuration.

I. Introduction

A consultation for a person seeking medical advice begins with a telephone call to the medical diagnostic and treatment advice (MDATA) system of the present invention. The MDATA system asks the caller specific questions and then analyzes each response.

Voice recognition and interactive voice response technology allow callers to respond to yes/no and multiple choice questions either by speaking directly into the telephone or by using the touch tone pad of their telephone.

Easy access to the information in the MDATA system is made possible by a natural user interface. The computer-driven dialogue consists of simple yes/no and multiple choice questions. The questions and treatment recommendations are very simply worded yet skillfully designed to reflect the accumulated experience of many physicians in conducting patient interviews.

Although all the MDATA system's questions are designed to be easily understood, unforeseen situations will inevitably arise. For this reason, hierarchical staffing is implemented. As an example, for every 10 telephone lines, one operator fully trained in triage and the MDATA system will be available. For every 10 operators there will be one registered nurse in attendance; and for every 10 registered nurses, there will be one physician in attendance. Staffing requirements are adjusted as the system is refined toward optimal efficiency. The MDATA system does not require the operator or the registered nurse to make any medical decisions.

II. System Overview

Figure 1:
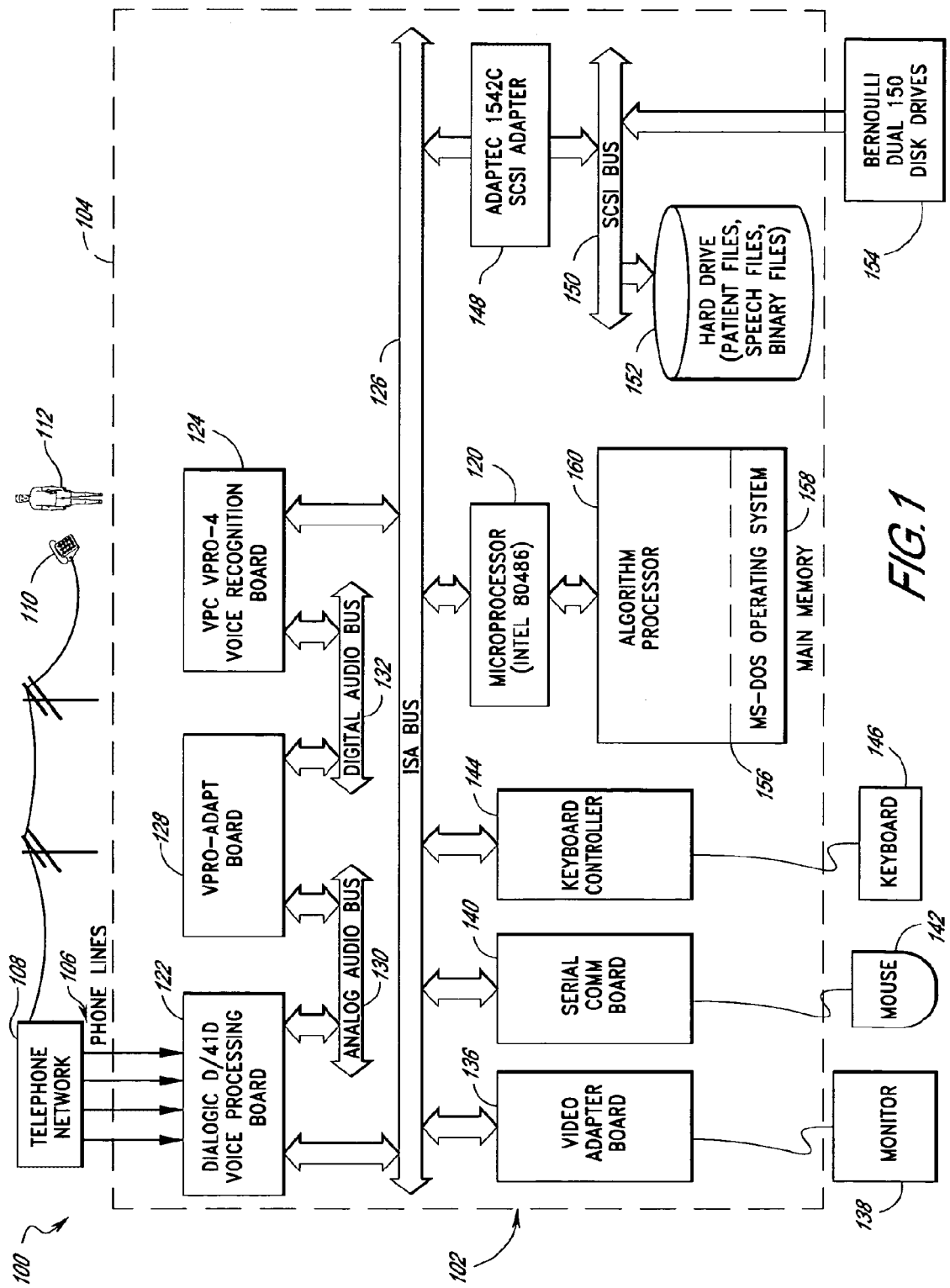
FIG. 1 is a block diagram illustrating the components of a presently preferred embodiment of the computerized medical diagnostic and treatment advice (MDATA) system of the present invention.

Referring to FIG. 1, the components of a presently preferred embodiment of the computerized medical diagnostic and treatment advice (MDATA) system 100 of the present invention are shown. A personal computer (PC) 102 includes a plurality of components within an enclosure 104. A plurality of telephone lines 106 interface the public telephone network 108 to the computer 102. As an example, one of telephone lines 106 is shown to be switched via network 108 to connect with a telephone 110 that is used by a person desiring medical advice (user) 112. Throughout this document, the words user, caller and patient are used interchangeably. However, it will be understood that the caller may be acting as a proxy for the patient. If this is the case, the caller will be registered as an assistant for the patient.

The hardware and system software were assembled with two basic concepts in mind: portability to other operating systems and the use of industry standard components. In this way, the system can be more flexible and will allow free market competition to continuously improve the product, while, at the same time, decrease costs. While specific hardware and software will be referenced, it will be understood that a panoply of different components could be used in the present system.

The system currently runs on the PC 102 with an Intel 80486 microprocessor. "Telephony" functions use Dialogic Corporation's D/41D voice processing board 122 based on a digital signal processor (DSP). The voice processing (VP) board 122 performs several functions including interfacing the telephone lines, decoding touch tone signals, speech recording and speech playback. Touch tone signals are also known as "dual tone multiple frequency" (DTMF) signals. A group of one to four telephone lines 106 connect to the VP board 122. The computer 102 may include a plurality of VP boards 122 based on how many phone line connections are desired for the system 100. Speech recognition is achieved using Voice Processing Corporation's speech recognition VPRO-4 board 124 (also DSP based). The voice recognition (VR) board 124 performs several functions including recognizing utterances and returning an index number of a recognition confidence level. The VR board 124 and the VP board 122 both connect to an industry standard architecture (ISA) bus 126. The ISA bus 126 interconnects the microprocessor 120 with a plurality of peripherals through controller circuits (chips or boards).

The VP board 122 also connects to a VPRO-Adapt board 128 via an analog audio bus 130 that is called Analog Extension Bus. Four simultaneous channels provide a 96 kbit/second data transfer rate. Each channel corresponds to a telephone line connected to the VP board 122 and is associated with a current patient consultation. The Adapt board 128 further connects to a digital audio bus 132. The VR board 124 also connects to the digital audio bus 132. The Adapt board 128 performs analog to digital signal conversion to a VPC-proprietary digital pulse code modulation (PCM) format. The digital bus 132 can accommodate 32 channels and has a data transfer rate of 2.048 Mbits/second.

The computer ISA bus 126 has a plurality of peripherals connected to it through adapters or controllers. A video adapter board 136, preferably at VGA or better resolution, interconnects to a video monitor 138. A serial communication circuit 140 interfaces a pointing device, such as a mouse 142. A parallel communication circuit may be used in place of circuit 140 in another embodiment. A keyboard controller circuit 144 interfaces a keyboard 146. A small computer systems interface (SCSI) adapter, such as model 1542C made by Adaptec, provides a SCSI bus 150 to which a 500 Mb or greater hard disk drive 152 and dual Bernoulli 150 Mb disk drives are preferably attached. The hard drive 152 stores database files such as the patient files, speech files, and binary support files.

A main memory 156 connects to the microprocessor 120. In the presently preferred embodiment, the MDATA system 100 operates under DOS version 5.0 operating system 158. The system software is written in Microsoft C\C++ version 7.0 using structured programming techniques. An algorithm processor 160 includes a parser and supporting functions that manipulate a memory variable symbol table and a run time stack, which will be described hereinbelow. Sequiter Software Inc. Codebase 5.0 allows access to X-base compatible database records stored on the hard drive 152. The MDATA system 100 also includes two new authoring languages (one each is used in two embodiments of the system), which will be discussed hereinbelow.

The system software includes the following code modules for which source code is included in the attached Microfiche Appendix:

A. main.c—a collection of functions that mostly deal with telephony functions, such as answering the phone line, speech file playback, and DTMF tone collection. Global data structures are defined here.

B. base.c—functions that invoke the CodeBase revision 5.0 library to perform xbase file manipulation.

C. pars.c—the parse function, and supporting functions that manipulate the memory variable symbol table and run time stack.

D. regi.c—an on-line patient registration module.

E. resp.c—gets the caller's responses, either DTMF or voice, and figures out what to do next by obeying a command (e.g., "repeat" or "backup"), or traversing through the algorithm node map.

F. term.c—a useful collection of text phrases for Dialogic and VPC board termination events and error codes.

G. user.c—"non-diagnostic" portions of the caller session: initial screening questions, caller login, and the next node playback initiator.

H. util.c—a collection of general purpose functions shared by a run time executable, a node editor and ASCII translator tools.

I. view.c—a module that controls the graphics system display.

J. x10.c—an X-10 computer interface routine for fault recovery.

K. xlat.c—a module linked with pars.c and util.c object modules to build xlat.exe, a stand-alone translation executable for offline ASCII text file translation.

The application is compiled with the Microsoft graphics, Dialogic board, VPC board and CodeBase database libraries.

The Voice Processing Corporation (VPC) VPro-4 VR board has eight voice recognition channels, which by default are associated one-to-one with the Dialogic D/41D channels. VPC's pioneering work in the voice processing field is in the area of continuous speech. This allows a person to speak a multiple digit number in a natural manner, without pausing after each digit. VPC supplies two continuous speech vocabularies: one vocabulary contains the digits 1 through 9, plus "zero" and "oh", and the other contains just the two words "yes" and "no". The vendor-supplied digits continuous speech vocabulary is used by the system 100. In the presently preferred embodiment, if the score is 75% or better, the response is unconditionally accepted. If the score is between 20% and 74%, the digits recognized are read back, and the caller is asked to accept or reject the digits. In another embodiment of the system 100, the above score thresholds are implemented as tunable parameters. The scoring parameters are stored in a configuration file that is manipulated off-line by a utility program and is read by the run-time system at initialization.

VPC also provides a few discrete vocabularies. Discrete vocabularies contain one or two word utterances. The vendor-supplied discrete speech vocabulary of the months of the year is used in the on-line patient registration process. A speaker-independent discrete speech vocabulary consisting of the words "yes" "no", "backup", "continue", "help", "operator", "pause", "quit" and "repeat" has been developed using a very powerful set of utilities supplied by VPC, Scripter and Trainer. These utilities are for collecting samples and training the vocabulary.

The VR board 124 has the minimum of two MB memory installed. The default memory configuration has a partition for both continuous vocabularies and a partition for one discrete vocabulary. Additional discrete vocabularies may be downloaded if the on-board memory is reconfigured.

The VR board 124 has four digital signal processors (DSP's) from which VPC derived eight voice recognition channels. Each of these eight recognition resources is referred to as a VPro Speech Processor (VSP). Discrete vocabulary recognition requires one VSP; continuous vocabulary recognition requires two adjacent VSP's. The MDATA system 100 has a VSP resource manager in the resp.c software module. This resource manager allocates VSP's in a dynamic manner to VP board 122 channels on a demand basis. As soon as the system receives a response, voice or DTMF, it releases the VSP's associated with the caller's VP board 122 channel.

The MDATA system 100 uses VPC's application programming interface (API) for the C programming language. This makes the application vendor specific to VPC, but also allows the system 100 to utilize all the powerful API features, e.g., on-line creation of discrete speaker dependent vocabularies used for voice pattern matching or voice printing.

The VPC API supports both continuous speech vocabulary (CSV) and discrete speech vocabulary (DSV) recognition.

The voice processing (VP) board 122 supports speech recording and playback, as well as touch tone (DTMF) signal detection and decoding. A device driver, associated with the VP board 122, is loaded into system memory during load operations. The device driver supports communications between the VP board 122 and the application code at run time (e.g., when a person is seeking medical advice). Through a shared memory segment, the device driver sends event and status data to the application code in real-time as events occur on the associated telephone line. These events include the ring of an incoming call, touch tone key pressed by the caller, and the hang-up signal. The VP board 122 plays back speech messages that are stored on the hard drive 152. The algorithm processor 160 sends a selected speech file having an encoded speech message that is retrieved from the hard drive 152 to the VP board 122 at the appropriate time for speech message playback. A speech message can be of variable length with a typical message about one to two minutes in length. Several speech messages may be chained together to produce an extended spoken message, e.g., giving instructions to the patient. During speech file playback, the VP board 122 is monitoring touch tone response from the caller. The VP board 122 may be configured to interrupt speech file playback when a touch tone signal is detected.

System Operating Contexts

The system has an activity flag in the port status block for each patient currently using the system to keep track of which state the associated VP board channel is in:

a. Idle Mode—an idle channel waiting for a telephone call;
b. Login Mode—a condition where a patient is in the login process;
c. Registration Mode—a condition where a patient is in the registration process;
d. Real Mode—a condition where a patient is consulting for an actual medical problem;
e. Info (Information) Mode—a condition where a patient is consulting for information or a hypothetical situation;
f. Pause Mode—a patient-initiated pause condition;
g. Pending Mode—similar to Real mode except that new medical information gathered for a patient is not automatically added to the patient's medical record, but rather written to a "Pending" file where it will be verified off-line by a staff person.

Voice Keywords and DTMF Command Keys

The system is responsive to the following voice keywords and DTMF keys when it is in a prompting state, i.e., not in response to a menu message:

| Voice | DTMF | |
|---|---|---|
| yes | 1 | Useful for answering yes/no questions. |
| no | 2 | |
| backup | # | Causes the system to back up to the "predecessor" message (see below), then resume playback. |
| help | * | Plays helpful information: either the node's help message list, or the DTMF command explanation message. |
| operator | 0 | Causes the system to transfer the caller to a live person. |
| pause | 7 | Transitions to pause mode. The system default pause period is 30 seconds. |
| quit | 9 | Quits the current algorithm, and takes the caller to node 110, which asks the caller if (s)he wishes to select another algorithm. |
| repeat | 3 | Repeats the current node's play message list. If this command is given in the middle of a long play list, then playback restarts with the first message in the list. |
| Pause Mode Commands | | |
| yes | 1 | Extends the pause period by one default pause interval (30 seconds). |
| continue | 2 | Ends pause mode. If this occurs at a Yes/No node, the system will repeat the question. If this occurs at a Link node, the system will resume playback with the "current" message. The system resolves the DTMF digit "2" ambiguity, "no" versus "continue", by examining the pause mode flag. |

Figure 2:
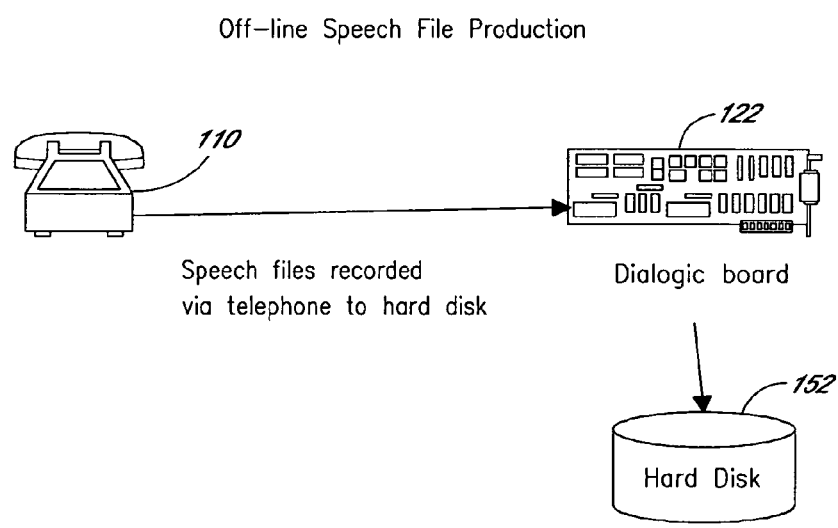
FIG. 2 is a diagram of the off-line process used in producing the speech files shown in FIG. 1.

FIG. 2 illustrates how speech files are created. A person programming medical algorithms uses speech messages to communicate with the person seeking medical advice. As previously mentioned, these speech messages are of variable length. The programmer typically writes a script for the speech message. Then using the handset of the telephone 110, a speakerphone feature, or other voice-input device, e.g., a microphone, the programmer reads the script into the voice-input device which is connected to the VP board 122. The VP board converts the speech into a digital format and records the digitized speech to a file that is stored on the hard drive 152. In the presently preferred embodiment, a subdirectory named vox contains the system speech files, and subdirectories for each medical algorithm. System speech files are of the form sysxxx, where xxx is some arbitrarily assigned number. The system messages are used by the "fixed" parts of the system, e.g., greeting, login process, registration process. There are a few speech files of the form msgxxx. These are the past medical history questionnaire messages, and response acknowledgements. There are additional speech files of the form msgxxxx in each of algorithm subdirectories, where xxxx generally matches the node number, which will be explained hereinbelow. Node messages include information, question, menu and help messages.

III. Operating Features of the MDATA System

One of the MDATA system's main objectives is to bring together highly-qualified medical experts, encode their knowledge in a central location, and make it available to everyone. A new and unique authoring language is used by the MDATA system to help accomplish this objective.

Each day, specialists perform the same tasks over and over. They enact the same diagnostic ritual of solving a familiar problem. At the same time, however, primary care physicians attempt to find the best path through the diagnostic maze of an unfamiliar problem. This process is inefficient and fraught with error.

In medicine, there is generally one best way to do things. Instead of physicians spending valuable time duplicating tasks, the MDATA system utilizes medical experts from each medical specialty who write detailed algorithms for the treatment of the 100 or so most commonly encountered complaints in family practice and emergency medicine. These algorithms are carefully and specifically designed to elicit historical data and physical findings over the telephone, rather than in face-to-face interactions.

Several experts could work together to thoroughly research one particular complaint as well as to anticipate the full spectrum of possible problems and patient responses. These experts could also provide and maintain the MDATA system treatment table as well as the imaging modality of choice and laboratory test of choice tables. These concepts will be described hereinbelow.

Carefully crafted questions, used in the taking of a medical history, are the main tools that the MDATA system uses to assess the problems of patients. The key to getting a good history is to ask the right questions. In a sense, in the diagnostic process questions are like tests. It is important to note that the right questions are basically always right; they don't change. Although they may be refined over time, in general, once excellent and well-crafted questions are developed they are good for a very long time. Of course, as new diseases are discovered, e.g., toxic shock syndrome and AIDS, new sets of diagnostic questions are developed that are disease specific.

The questions used by an earlier generation of physicians, who did not have any of the latest imaging modalities (types or methods), are far more sensitive and precise in diagnosing a patient's problem than the questions used by doctors today. The MDATA system makes use of fine nuances of language to diagnose patients as well as to determine when certain tests or imaging studies are necessary.

The MDATA system's statistic generating capabilities enable the system to analyze the effectiveness of the questions used in the diagnostic process. As a result, physicians benefit from the immense amount of statistical information that is gathered regarding the wording of questions asked in taking medical histories. For example, exactly what percentage of patients who answer "yes" to the question, "Is this the worst headache of your life?" actually have a subarachnoid hemorrhage? Although this is a classic description of this problem, the exact probability of having this kind of brain hemorrhage after answering "yes" to this question is not presently known.

Currently, doctors can only estimate the probability of certain conditions based on history. By applying the statistical information that is generated, the MDATA system not only provides the patient with advice that is continually improving, but it will also be able to pass along these probabilities to the entire medical community.

To function optimally, the MDATA system tries to gain as much medical information about its patients as possible. Although a first-time caller is given excellent advice, more specific advice can be given if the system has more information. Therefore, the MDATA system asks patients for their complete medical history. The MDATA system can either obtain the patient's medical record over the telephone or it can mail or fax a detailed questionnaire to each patient. The patient can then gather the necessary information at their convenience. The MDATA system will always be available by telephone to clarify any questions the patient may have.

The MDATA system uses the "International Classification of Diseases" (ICD-9-CM) codes to help summarize the information it has about a patient. This world standard is a comprehensive numerical system used to classify the entire spectrum of medical diseases. ICD-9-CM codes are also used to classify specific procedures performed (e.g., appendectomy) as well as the morphology of neoplasm (i.e., tissue diagnosis of a cancer).

In addition, the MDATA system 100 uses ICD-9-CM "E-Codes" to classify environmental events, circumstances, and conditions as the cause of injury, poisoning, and other adverse effects. These codes are particularly helpful for storing information about what drugs the patient has taken or is currently taking, as well as the context (e.g., therapeutic use, accident, poisoning, suicide attempt) in which they were or are being taken. For example, E942.1 is the code for the therapeutic use of digoxin. Medications are also cross-categorized according to the classification done by the American Hospital Formulary Service List (AHFS) Numbers. The MDATA system 100 also uses "V-Codes" to classify other types of circumstances or events such as vaccinations, potential health hazards related to personal and family history, and exposure to toxic chemicals.

It is estimated that the alphanumeric component of a patient's medical history will not exceed 1,000 atoms or pieces of information. An atom is considered herein to be a separate identifiable data item or point. With this assumption, the medical records of every person on the planet could currently be stored on approximately 1,000 optical disks.

While a patient interacts with the MDATA system, the system is constantly determining what questions to ask, based upon the information it has about the patient. Just as a physician gathers relevant pieces of information from his or her dialogue with a patient, the MDATA system flags and later stores all pertinent pieces of information that it learns from each interaction with its patient. Therefore, certain questions, because their answers remain the same, need not be repeated. For example, if the MDATA system learns that a patient's mother has suffered from migraine headaches, it will never have to ask for this information again.

Again, the more information the MDATA system has about a patient, the more specific is its advice. It is not uncommon for the MDATA system to give different advice to different patients calling for the same complaint. In other words, the advice given is patient-specific. Not only can the MDATA system's advice be different for different patients, but there are times when the advice given to the same patient (calling for the same complaint but at different times) is different. For example, one of a group of functions called "meta" keeps track of the number of times the MDATA system has been consulted for the same problem. Once a threshold is reached, the MDATA system advises the patient that the number of consultations alone, for the same complaint, may signify a problem. The system then makes an appropriate recommendation.

Before the MDATA system stores any information, the system verifies its accuracy. To accomplish this task, "confirmation loops" are used. Any piece of information that will become a part of the patient's medical record is sent through a confirmation loop where the system asks the patient to verify the accuracy of the information that the system has collected. The confirmation loop enables the system to verify new patient information and make corrections before it enters this information into the patient's medical record.

IV. Authoring Language

The MDATA system uses a new authoring language that is specifically designed to allow medical knowledge to be encoded into a usable computer program. The presently preferred voice response or telephony version of the MDATA system is written in object-oriented Microsoft C\C++ version 7.0. This allows the MDATA system to easily interface with industry-standard database programs, including those that are SQL-based, as well as to be portable to other operating systems. The operating system is transparent to the user.

Before the development of the MDATA system's authoring language, there was no practical way for medical experts to encode their knowledge into a meaningful, useful, and accessible structure. Although other computer languages have been used to build medical expert systems, they have almost always required a knowledge engineer and a programmer to be involved. Quite often, the knowledge encoded in these systems could only be accessed and fully understood by physicians. Typically, the programmer would try to translate the doctor's diagnostic skills and treatment rules into computer code. This separation of the physician's knowledge from the encoded treatment recommendations often engendered anxiety in the physician and has, at times, led to inaccurate treatment recommendations.

The MDATA system's authoring language, however, is designed to allow physicians to transfer their knowledge into a computer program that can be directly accessed by non-medically trained personnel. Recursive and iterative techniques are used to acquire the knowledge from the expert and assemble it in a way that allows it to be immediately transposed into the MDATA system's algorithms. Because of the simple interface of the language, and because a formula for writing the algorithms has already been developed, physicians who are not computer literate can encode their knowledge as well as understand exactly how that process takes place.

The MDATA system's authoring language allows flat information to be restructured into a hierarchical or layered format in which the arrangement of the knowledge conveys meaning. Thus, a textbook description of a disease can be transposed into a form that allows useful treatment recommendations to be made.

The new language also allows the formation of a structure in which multiple overlays of screening questions, combined with the application of recursive techniques, sequentially exclude some diagnoses while at the same time reaching treatment recommendations. The MDATA system's simplicity and elegance would not be possible without the new language.

The MDATA system's authoring language allows an algorithm programmer to retrieve information from a patient's medical record, request additional information from the patient, and guide the flow of algorithm execution based on medical history and the patient's responses. The language allows the programmer to implement an algorithm in a natural scripted style.

The course of an algorithm is determined by caller responses to questions that the MDATA system asks. For simple "yes/no" questions, the flow of interaction can be described by a binary tree. Multiple-choice questions (e.g., menus) provide multiple branches in the tree. Each question can be considered a node, and the acceptable responses to this question are branches leading to the next question (node). Using this abstraction of an algorithm, one can draw a directed graph (also known as a node map) of the nodes and branches of an algorithm, beginning with the initial question, and ending with all possible terminal points.

The node table is built in this manner:
1. An author develops an algorithm.
2. The algorithm is broken up into separate nodes.
3. A directed graph is drawn up, which is a flow chart of the algorithm's operation.
4. Each node's definition is entered into the MDATA system, either by:
   a. using an ednode utility to write each node's definition into the system's machine readable node table, or
   b. using an xlat utility to translate an ASCII file of human-readable node definitions into the system's machine readable node table.

Figure 3:
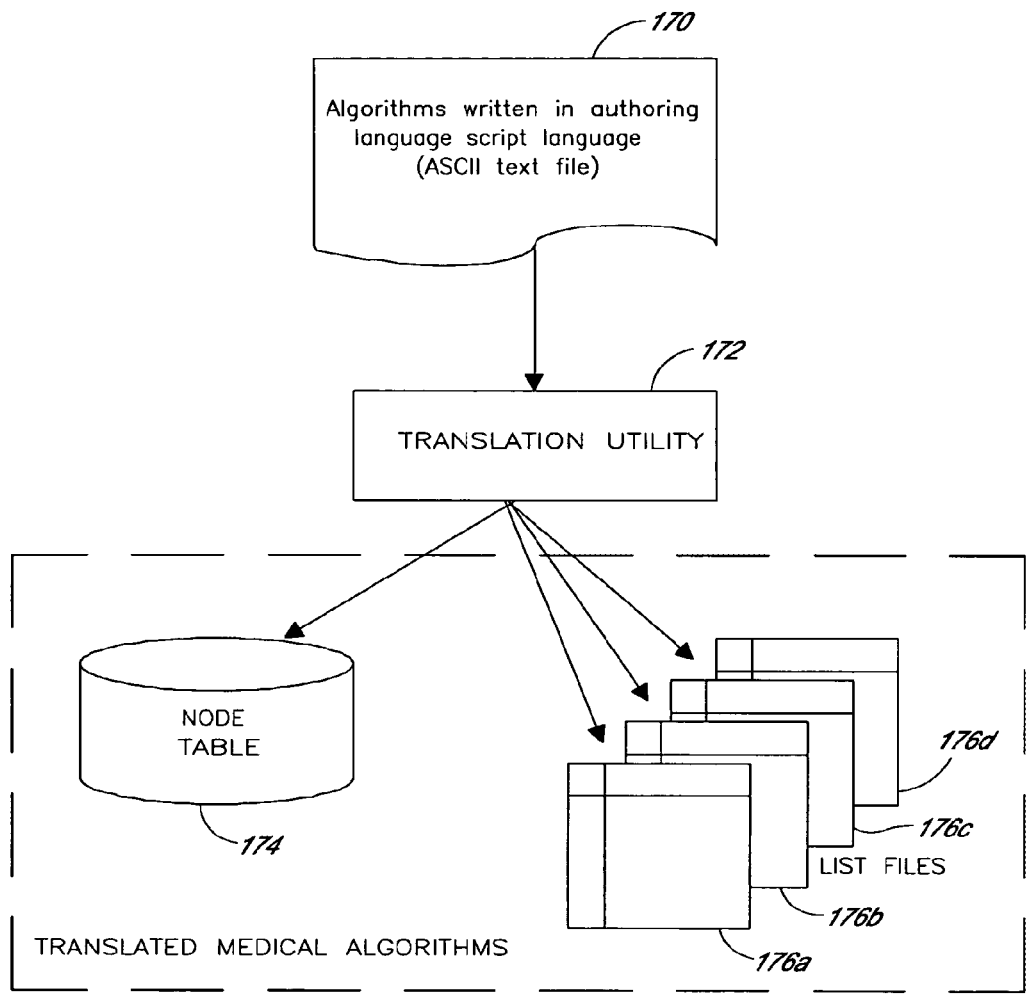
FIG. 3 is a diagram of the Node Translation process used in creating files for use by the system of FIG. 1.

Referring to FIG. 3, a process for translating a medical algorithm written in the authoring language will be described. FIG. 3 illustrates an ASCII (American Standard Code for Information Interchange) format text file 170 as an input to a translation utility 172. An ASCII file can be created by use of a text editor or a word processing program (may need to export to the ASCII format). The ASCII file 170 contains node definitions conforming to the syntax briefly described hereinbelow.

The purpose of the ASCII node definition translator utility 172 (xlat.exe, along with functions in pars.c and util.c) is to convert a human-readable document into a machine readable format that the MDATA system reads at run time to process an algorithm. This utility 172 may be considered to be a preprocessor; the translation must be accomplished prior to run time.

The output of the utility 172 is a set of binary (NOD_BLK) records written to a node table 174 (filename of node.fos), and a set of binary list files 176 (in a subdirectory \list\listxx\xxyy, where xx is the first two digits of the node number, and yy are the last two digits). Four list files 176a-176d are shown as an example. Each "list" file, e.g., 176a, contains a "next" table (i.e., the 'next node after this one'), a message play list for this node, and a "work" list (i.e., one or more "things to do" at this node before beginning speech playback). The binary record written to the node table 174 (node.fos) has fields containing the node number (which is redundant; the record's position in this file also indicates the node number), the node's "type" attribute (Menu, Link, Prompt, Yes/No, Return, Hangup) and a parent node number.

The node table 174 is a table of 10,000 NOD_BLK records. This table 174 is indexed by a node number, e.g., the fiftieth record corresponds to node 50. The contents of the individual node records may be viewed by selecting "Display Node" while running the ednode utility. The node records are modified by either using the ednode utility, or when translating node definitions from ASCII to the node file with the xlat utility.

One of the following keywords is necessary as the first item on each line, but only one keyword is accepted per line; any excess information will be discarded.

| | |
|---|---|
| Node | The Node keyword denotes the beginning of a new node and defines the node number. |
| Parent | The Parent keyword defines the parent of the node being defined. |
| Type | The Type keyword defines the class of the node being defined. Acceptable type names are: |
| Menu | This node presents a multiple choice question. |
| YesNo | This node presents a simple Yes/No type question. |
| Link | No caller response is required at this node, algorithm processing will continue at a predetermined node. |
| Prompt | This node requests some numeric information from the caller. The information is placed in a DTMF buffer which is then stored in the next node. |
| Return | Returns from a subroutine call (e.g., after configuring a past medical history object). |
| Hangup | The system will release this caller after it finishes speech file playback, or if the caller interrupts playback with a DTMF key press. |
| Wait nn | This node will play the message list, then pause for the specified nonzero number of seconds before continuing. |
| @ | The @ keyword defines the action to be taken for a response to either a Menu or YesNo type node. |
| Digits | The Digits keyword is used in conjunction with Type Prompt to indicate the maximum number of DTMF digits to collect from the caller. |
| Play | The Play keyword defines a play list of one or more messages to be played at this node. |
| Help | The Help keyword defines a play list of one or more messages containing useful hints for interacting with the system. These messages provide helpful instructions for a new or confused caller. |
| Next | The Next keyword defines the next node to jump to after the node being defined. It is used in conjunction with node types Link and Prompt. |
| Work | The Work keyword indicates a sequence of one or more operations to perform when arriving at the node being defined. This processing occurs before speech playback begins. |

A select set of math functions, relational operators, and nested if-then-else statements are supported. A pound sign ('#') or a hyphen ('-') in the first position on a new line will cause the translator to skip over the rest of the line. This is useful for inserting comments, or delimiting between individual node definitions. The translator also disregards blank lines.

In order for a node to be properly defined, a minimum number of keywords must be present for each node, and other keywords must be included depending on the node type. The minimum keyword set for a properly defined node is:
  Node, Parent, Type, and Play.
  Dependency Rules:
    (1) The Menu type requires at least an @ 1 line and an @ 2 line.
    (2) The YesNo type requires an @ 1 and an @ 2 line (@ 3, etc. are ignored).
    (3) The Link type requires a Next line.
    (4) The Prompt type requires a Digits line and a Next line.

The first keyword in a node definition must be Node. The other keywords may be given in any order. The next occurrence of the Node keyword will invoke a completeness test. If the completeness test is successful, then the node definition is saved in machine readable (binary) format, and translation continues with the new Node line. A set of reserved language keywords is listed in Table 1.

TABLE 1

Reserved language keywords (case insensitive):

@
and
digbuf
digits
else
essf
flush
hangup
help
if
keep
link
menu
meta
next
node
parent
play
pop
prompt
push
reenter
return
test
then
type
wait
write
work
xor
yesno

V. Run-Time Operation

Figure 4:
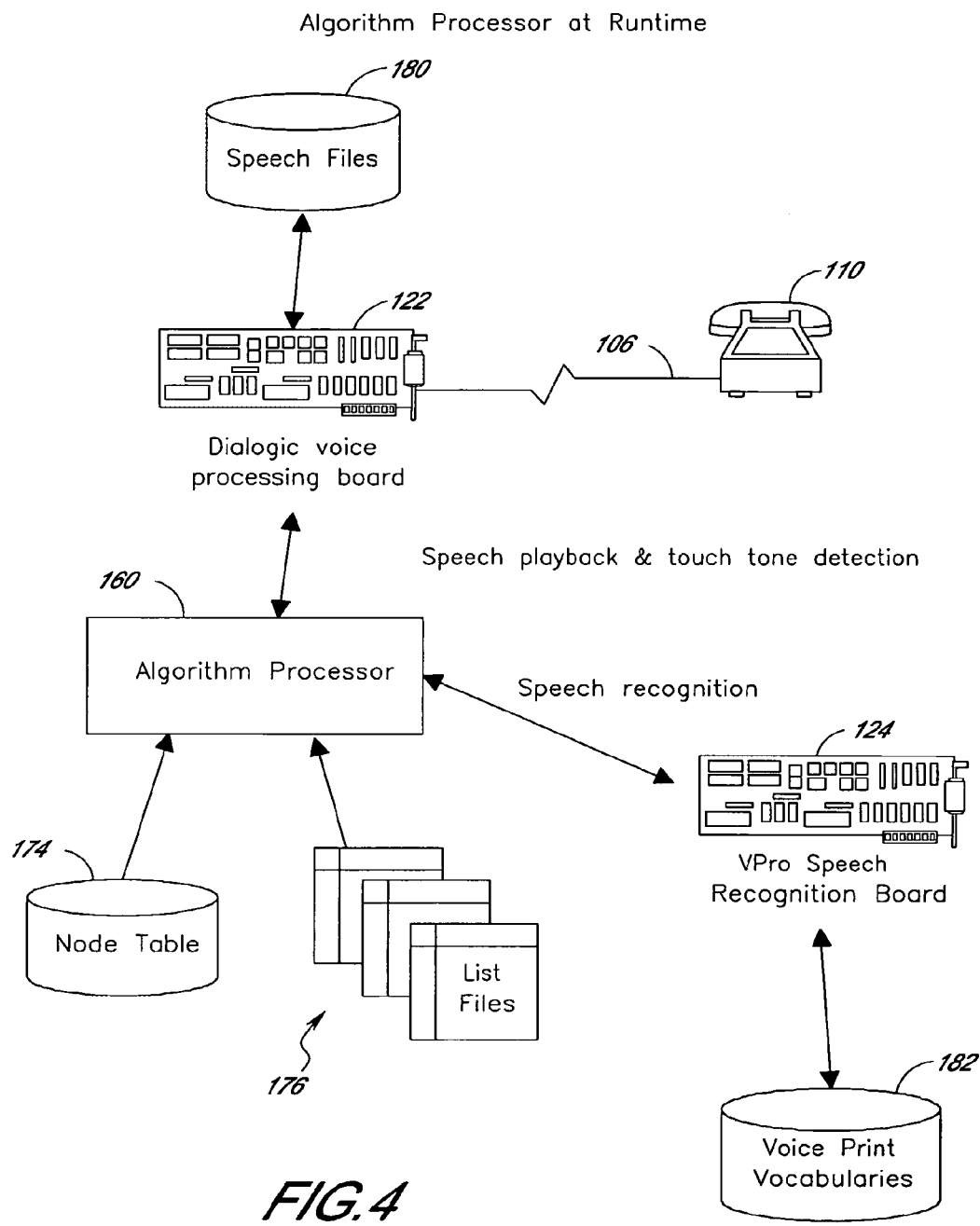
FIG. 4 is a diagram of some of the files and components of FIGS. 1 and 3 that are utilized at run time.

Referring to FIG. 4, the run time interaction among the hardware and software components of the MDATA system 100 will be described. As previously mentioned, algorithm processor 160 includes the parser and supporting functions that manipulate the memory variable symbol table and the run time stack. For a selected medical algorithm, a node record is read from the node table 174 and a list file is read from the plurality of list files 176. The algorithm processor also interacts with the Vpro voice recognition (VR) board 124 for speech recognition and with the Dialogic voice processing (VP) board 122 for speech playback and DTMF detection. The VP board 122 further is interconnected with a set of speech files 180 that are stored on a portion of hard disk 152 and with one of the telephone lines 106 that connects via the telephone network 108 (FIG. 1) to the patient's telephone 110. The VR board 124 further connects with the voice print vocabularies 182, previously described, also stored on a portion of hard disk 152. The algorithm processor 160 utilizes the speech recognition, speech playback, and DTMF detection resources as directed by the medical algorithm that is retrieved from the node table 174 and the list files 176.

Figure 5A:
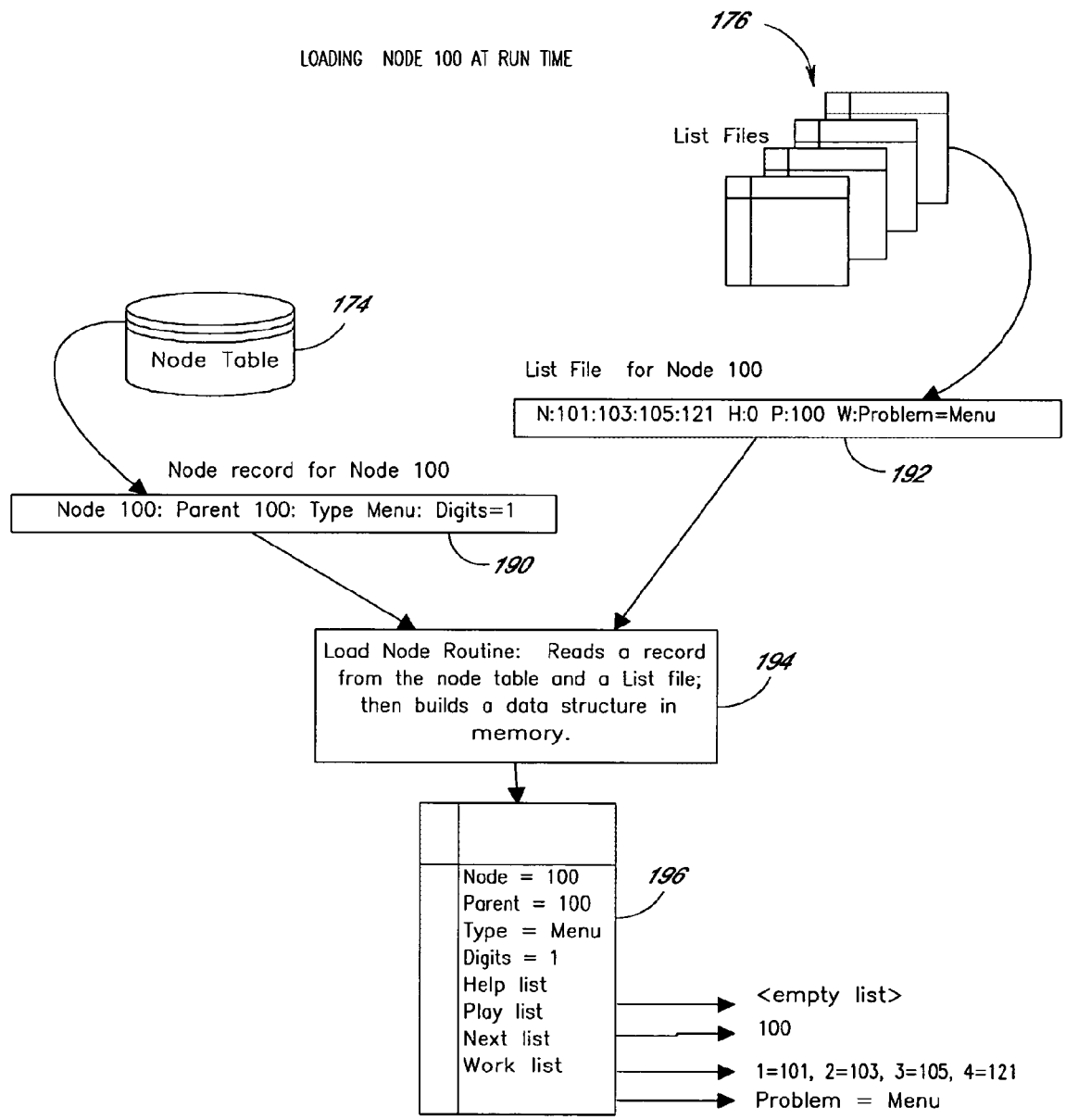
FIG. 5a is a diagram of the utilization of the files shown in FIG. 3 at run time.
Figure 5B:
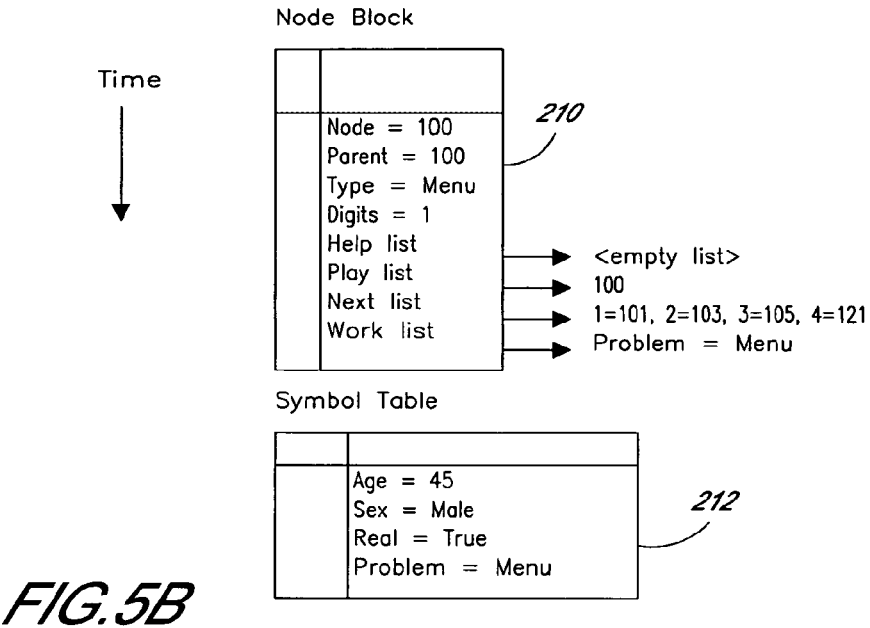

Referring to FIGS. 4, 5a and 5b, several data structures are utilized at run time. These data structures are described as follows:

A. Port Status Block (PSB). A port status block is created at run time for each VP board 122 channel. The PSB contains flags, buffers and tables that hold the state information of the channel, retain responses from the caller, and keep track of where to transfer control in response to voice recognition and telephony events. The PSB keeps track of whether the caller prefers to use spoken or touch tone responses, the caller's last response, the number of consecutive errors the caller has made, and other context sensitive parameters.

B. Node Block. This structure 196 contains the node number, the type attribute (link, menu, yes/no, hangup, prompt, wait, return) and pointers to:
  a. Help list—a Play list of help information;
  b. Play or Message list—a list of one or more messages or speech files to play in sequence at each node;
  c. Next table or list—contains entries for each possible response to a yes/no or menu node that are evaluated at run time to determine the next node to branch to; and
  d. Work list—things to do before message playback starts.

The load_node( ) routine 194 in util.c builds the node block structure 196 in memory by first reading in a node record 190 from the node table 174. Then linked lists are attached to the pointers help, play, next and work. These lists come from the list files 176, in subdirectory path \list\listxx\xxyy, where xxyy is the node number, wherein each list file 192 is associated with a unique node.

C. Symbol Table. Each patient has their own associated symbol table. A portion of a symbol table 212 is shown in FIG. 5b. The symbol table is loaded at run time with memory variables that hold patient specific data (age, sex, and items from medical history) and algorithm specific data. The items in the symbol table can be flagged for storage to the patient's medical history.

D. Run Time Stack (RTS). Each Dialogic VP board 122 channel has a RTS associated with it. The RTS is used by the parser. The algorithm programmer can push to and pop from the RTS, e.g. to temporarily store a value of a variable.

The work list has the non-playback tasks that are performed at each node. There is one work list for each node, and it is identified with the work keyword in the ASCII node definition file. The work list may be empty. Each time the system transits to a new node, it will execute the work list. If the patient repeats a node, the system will not execute the work list again; it will simply replay the message(s). If the patient requests the system 100 to back up the node map, the system will execute the work list of the node it backs up to. Typical tasks in the work list involve manipulating objects on the run time stack or in the symbol table, testing for the presence of memory variables, configuring past medical history or current medical condition objects, or writing database records. An example of a complex work list follows:

"Test OBJECT2; Phone=DIGBUF; Push Age"
  This example tests for the presence of a patient record object labelled "OBJECT2", loads the contents of the digit buffer into memory variable Phone, and pushes the value of memory variable Age onto the run time stack.

Each node has the "next" table or list. The next list indices range from 1 to 9, inclusive. The next list contains either a single node number, or an if expression. For all node types, except the Hangup node, there will be at least one next list:
  Link and Prompt nodes: the next node is stored at table index 1.
  Yes/No node: the next node for the Yes response is stored at table index 1, and the No response is stored at index 2. This corresponds to the prompt, "if the answer is yes, press 1; if no, press 2."
  Menu node: the response number and the table index are the same. Even though the actual data structure has a '0' index in the C programming language, this index is not used in the next table because a '0' response is reserved for operator assistance.
  Following is an example of a next list:
  "If Male and Age>55 then 100 else 200" is interpreted as:
    If the patient is both male and over 55 years old then go to node 100 else go to node 200.

Speech files 180 may be of an arbitrary length. A message may be informational, a list of menu options, or a yes/no question. A "two paragraph" or "under one minute" limit has been adopted as a style convention for the presently preferred embodiment. Typically, a node is programmed as a sequence of Yes/No nodes, with "informational" Link nodes interspersed as needed. When there is a lengthy discussion, the speech is recorded in multiple files. To simplify algorithm programming and enhance readability (viz., eliminate long chains of link nodes), the Link node's play list may contain up to ten message numbers.

Upon arrival at a Link node, the system positions a "current message" pointer at the beginning of the play list (trivial case: single message play list; interesting case: multiple message play list). As playback proceeds, the current message pointer moves down the play list. After the system plays the last message on the list, it moves on to the next node.

If the caller issues a "backup" command, the system will move the current message pointer back one message, and resume playback. If the pointer was at the beginning of the list (e.g., trivial case), the system backs up to the previous node and places the current message pointer at the beginning of the play list. If there is more than one message in the list, the system cues the pointer to the last message in the list. The system then resumes playback. In the "pause" mode, when the caller issues the "continue" command, the system will resume playback at the current message.

The MDATA system 100 uses three basic operating modes:
A. Real Mode—involves an actual medical problem. In this mode the system 100 loads the past medical history, saves new past medical history objects, and writes a meta record for each algorithm consulted. The medical algorithm programmer is responsible for providing code to jump past meta analysis in Information mode.
B. Information Mode—involves a "what if" scenario. In the Information mode the system 100 disregards past medical history, does not save newly configured past medical history objects, does not write a meta record for each algorithm consulted, and does not perform meta analysis. The patient has an option in Information mode to change the age and sex parameters to emulate a hypothetical patient.
C. Pending Mode—handles the situation when a patient's voice sample does not match the patient's reference sample. Pending mode is utilized also when an assistant is interacting with the MDATA system 100 on behalf of a patient and both the assistant's and the patient's voice samples fail the voice printing test. In the case where the assistant's voice sample fails the voice printing test but the patient's voice sample passes the test, Pending mode is not utilized. In Pending mode, the MDATA system 100 considers the patient's medical history and performs meta analysis during this consultation. However, a meta record is not written for this consultation and any new medical information gathered on this patient will not be written to the patient's medical record. The new medical information is written to a "Pending" file. The Pending file is verified off-line by a system administrator or staff person, and then is added to the patient's medical record only if the information can be verified.

One of the drawbacks of the traditional doctor-patient relationship is the short amount of time that physicians are able to spend with patients. The MDATA system 100, however, allows patients as much time as they wish to learn about their problem as well as to obtain information on any number of other medical topics.

Through the "Information mode" feature of the MDATA system 100, callers can learn about a disease process, an illness or the latest treatment for any disease, without adding any information to their personal medical record. Although the system 100 keeps track of the interaction, it is labeled as an "Information mode session." The record of the caller's path through the system is not used as the basis for any future advice, nor is it considered in generating system statistics.

The Information mode is not limited to complaints for which the MDATA system 100 offers medical advice. Information about early detection and treatment of many other diseases as well as the latest advances in medicine can be made available through the Information mode.

Referring to FIGS. 5b through 5g, as an example, a run time sequence of steps of how a patient may traverse a main menu node map several steps into a chest pain algorithm node map will be described. A portion of the main menu node map with associated script, and of the chest pain algorithm node map with associated script is included in the Microfiche Appendix. Six nodes with a portion of an associated symbol table will be discussed.

At FIG. 5b, the algorithm processor 160 loads the first node #100, represented by node block 210. The variables for Age, Sex, and Real mode were loaded into the symbol table 212 during the login process (which will be described hereinbelow). Throughout this example, the help list is empty, i.e., no help information is played for the patient. The work list sets the Problem variable of the symbol table 212 to be Menu. Then the system 100 begins playback of message#100. This message gives the patient a menu of choices to choose from. The Digits entry equal to one means that a one digit response is expected from the patient. The patient may respond by pressing a touch tone (DTMF) key on the telephone or speak the choice response into the telephone handset microphone. In this example, the patient selects menu option "1". The parser evaluates the Next list based on the patient selection and branches to node #101.

Figure 5C:
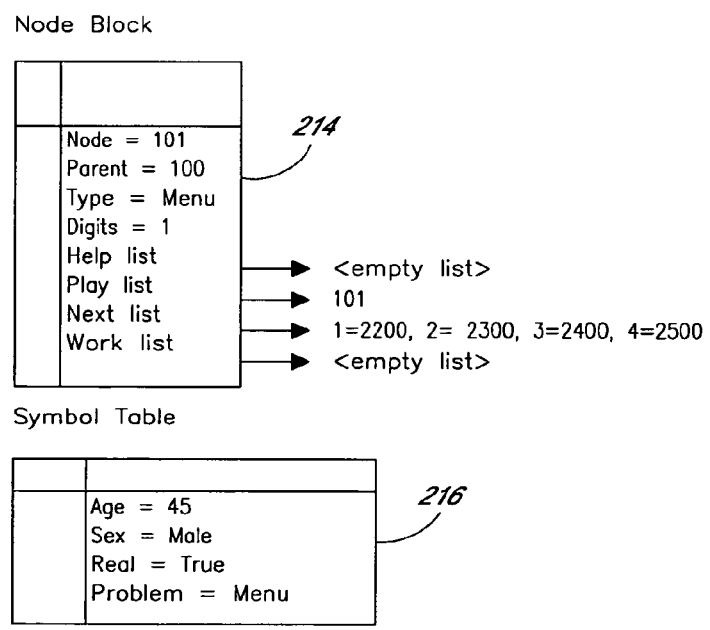

At FIG. 5c, the algorithm processor 160 loads node #101, represented by node block 214. The work list is empty, so the system 100 goes right to playing back message#101 which presents another menu of choices to the user. The Next list has four nodes for possible branch points. In this example, the patient selects menu option "1" for a chest pain complaint. The parser evaluates the Next list based on the patient selection and branches to node #2200.

Figure 5D:
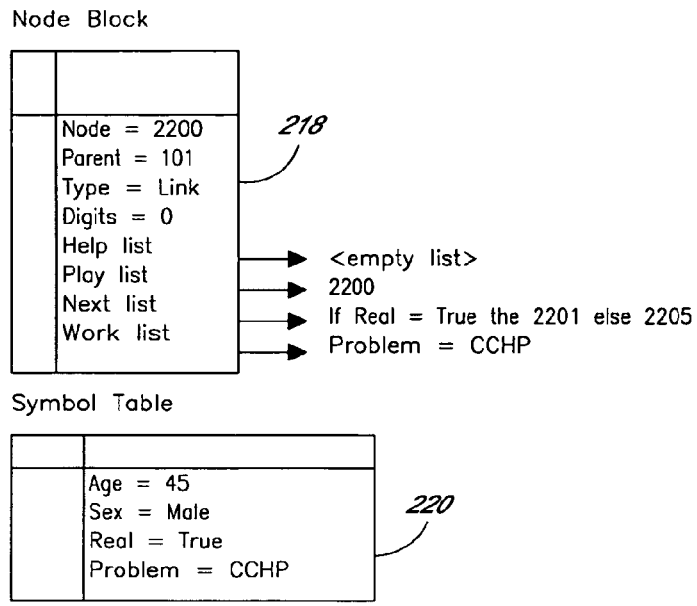

At FIG. 5d, the algorithm processor 160 loads node #2200, represented by node block 218. The work list command is to update the value of Problem in symbol table 220 to CCHP (chest pain). Then the system 100 begins playback of message#2200. No response is required from the patient for a Link type node. The Next list has two nodes for possible branch points depending on the value of symbol table variable Real. The parser evaluates the If expression in the Next list for the value of Real and, in this example, branches to node #2201.

Figure 5E:
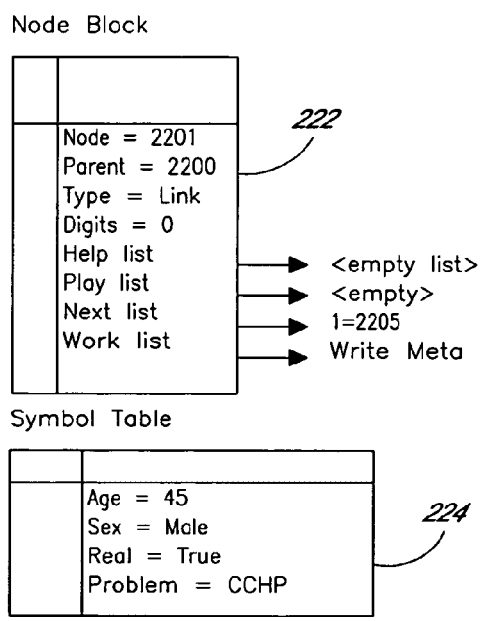

At FIG. 5e, the algorithm processor 160 loads node #2201, represented by node block 222. The work list command is to write a Meta consultation record for future use by a Meta function. The play list is empty so no message is played. No response is required from the patient for a Link type node. The main purpose of this node is to write the Meta consultation record (because the system is currently in Real mode for this patient). The Next list has only one node so no decisions are necessary by the parser which, in this example, branches to node #2205.

At FIG. 5f, the algorithm processor 160 loads node #2205, represented by node block 226. The work list is empty in this node so the system 100 goes right to playing back message#2205 which presents a yes/no type of question to the user. The Next list has two nodes for possible branch points depending on the response of the patient. In this example, the patient responds "no", and the parser evaluates the Next list based on the patient selection and branches to node #2210.

At FIG. 5g, the algorithm processor 160 loads node #2210, represented by node block 230. The work list is empty in this node so the system 100 goes right to playing back message#2210 which presents a yes/no type of question to the user. The Next list has two nodes for possible branch points depending on the response of the patient. If the patient answers "yes" to the question, the parser branches to node #2211, but if the patient answers "no" to the question, the parser branches to node #2215.

VI. Software Structure

Figure 6:
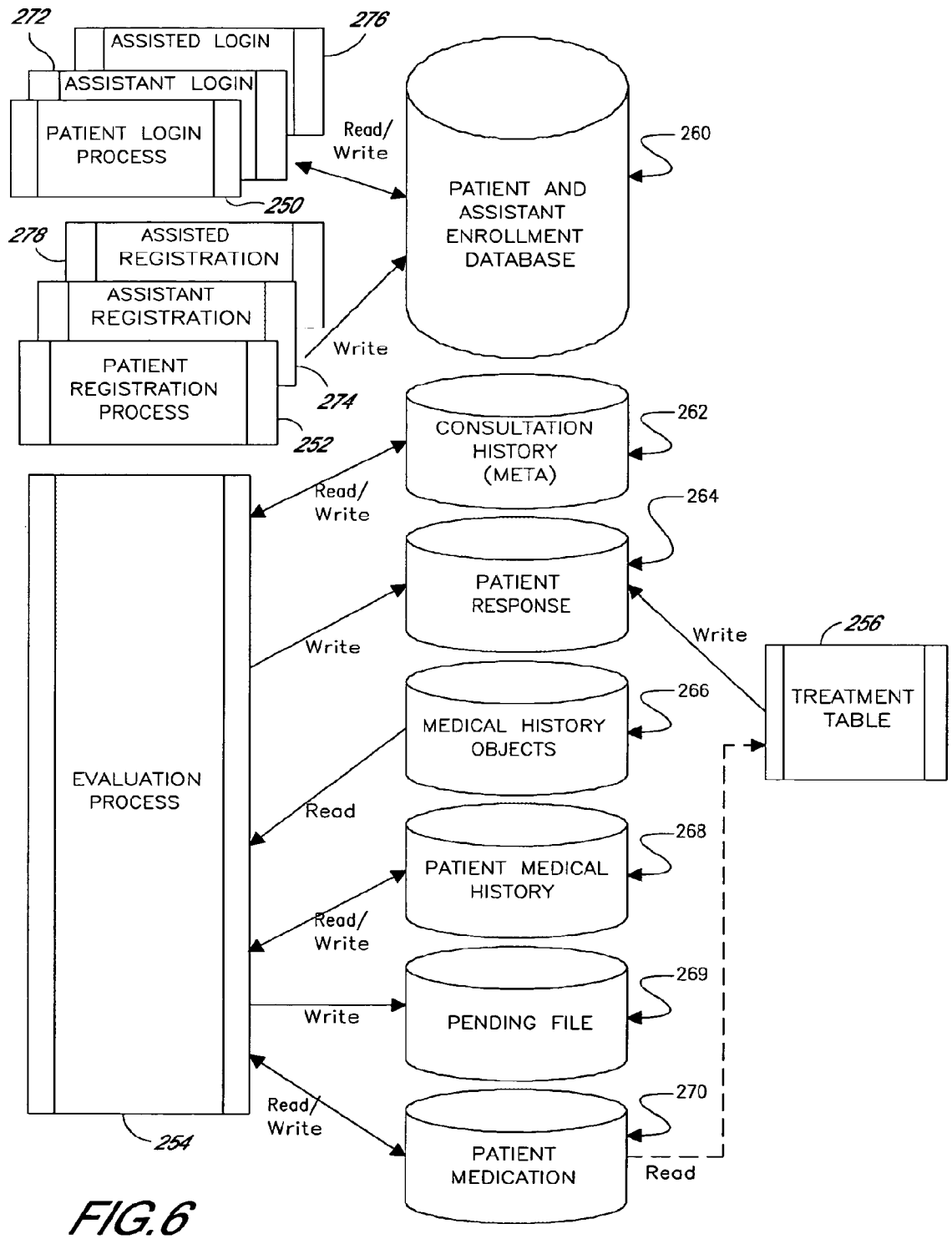
FIG. 6 is a block diagram illustrating a conceptual view of the database files and processes of the system of FIG. 1.

Referring to FIG. 6, the system utilizes eight principal, separate processes and seven related databases. A patient login process 250 is used by the system 100 to identify a patient who has previously registered into the system by prompting for a patient identification number (PIN). An assistant login process 272 is used by the system 100 to identify an assistant who has previously registered into the system by prompting for an assistant identification number (AIN). An assisted patient login process 276 is used by the system 100 to identify a patient who has previously registered into the system by prompting for the patient identification number. If the caller is the patient, a patient registration process 252 is used by the system to register new or first-time patients. If the caller is not the patient, an assistant registration process 274 is used by the system to register new or first-time assistants. Then, if the patient is not already registered, an assisted patient registration process 278 is used by the system to register the patient. These processes will be further described hereinbelow.

Once a caller has logged in or registered, the system provides a choice of two other processes in the current embodiment. The first of these processes is the evaluation process 254 that performs a patient diagnosis. The second of these is a treatment table process 256 to obtain current treatment information for a particular disease or diagnosis. In another embodiment, other choices are added to access other medical information processes.

Associated with these eight processes are a patient and assistant enrollment database 260, a consultation history database 262, a patient response database 264, a medical history objects database 266, a patient medical history database 268, a pending database 269, and a patient medication database 270 that are described as follows:

A. The master patient and assistant enrollment database 260 is created at run-time by one of the registration processes 252, 274, or 278. This database 260 is read by the patient login process 250 or the assisted patient login process 276 to validate a patient's identity at login time and by the assistant login process 272 to validate an assistant's identity at login time. The database 260 is essentially a master file of all registered patients and assistants indexed by their patient ID number or assistant ID number, respectively. The patient ID or assistant ID, date of birth and gender fields are entered by the on-line registration process; the system administrator manually enters the name of the patient or assistant in an off-line manner.

The patient and assistant database 260 contains one record for each patient or assistant. This database 260 is indexed by the identification number. The system appends the enrollment database 260 after a caller is successfully registered. The "next ID number" is stored in a binary file, config.fos, and is incremented after each successful registration. Each record has the following fields:

| Field Name | Data Type | Width | Usage |
| --- | --- | --- | --- |
| ID | Numeric | 10 | ID number |
| TYPE | Character | 1 | User type: "P"—patient, "A"—assistant |
| ASST_PERM | Boolean | 1 | Permanent assistant flag |
| ASST_EXP | Date | 8 | Expiration for permanent assistant |
| RELATIONS | Pointer | 20 | Pointers to related patients/assistants |
| ORGZTN | Character | 8 | Organization alphanumeric code |
| NAME | Character | 20 | Patient/Assistant name |
| SEX | Character | 1 | Gender |
| YEAR | Numeric | 4 | Year of birth |
| MONTH | Numeric | 2 | Month of birth |
| DAY | Numeric | 2 | Day of birth |
| ACCESS | Date | 8 | Last access |
| RV_PATH | Character | 20 | Path name of recorded voice file |

B. The consultation history or meta database 262 is created at run-time by the evaluation process 254. A consultation record contains alpha-numeric codes for the patient's complaint, the affected anatomic system and the diagnosed cause of the patient's complaint. When the meta function is invoked at run-time, it compares alphanumeric strings provided by the evaluation process with the fields of all the patient's meta records that fall within a time window specified by the evaluation process. The meta function returns the number of matches found, and an indication of the frequency of the patient's complaint.

Each patient has an individual meta file that is part of the consultation history database 262. At the conclusion of the evaluation process and dependent on the run-time operating mode flag, the system will create a new meta record, populate its fields with the information gathered during the evaluation process, and append this record to either the consultation history database 262 or the Pending file 269. For example, information used in the new meta record may come from a "Write Meta" command in a node Work list. Each record has the following fields:

| Field Name | Data Type | Width | Usage |
| --- | --- | --- | --- |
| DATE | Date | 8 | Date stamp |
| PROBLEM | Character | 5 | Patient complaint/symptom |
| SYSTEM | Character | 5 | Anatomical system affected |
| CAUSE | Character | 5 | Diagnosed cause of complaint |

C. The patient response database 264 is created at run-time by the evaluation process 254. The response database 264 is an audit trail: each record is time stamped and registers the patient's response to each question. This database 264 can later be analyzed off-line with a database program such as FoxPro/FoxBase to reveal how the patient responded to questions during the evaluation process 254, or a database program can be developed to gather response patterns and statistics and generate appropriate reports.

Each patient has a response trace file that is part of the patient response database 264. The system 100 appends this response trace file with a response record every time the patient answers a question or provides algorithm-requested data. For human readability, the system also inserts "Begin Call" and "End of Call" records in this file. Each record has the following fields:

| Field Name | Data Type | Width | Usage |
| --- | --- | --- | --- |
| DATE | Date | 8 | Date stamp MM/DD/YY |
| TIME | Character | 8 | Time stamp HH:MM:SS |
| NODE | Numeric | 6 | Current node number |
| TYPE | Character | 5 | Response type: DTMF or VOICE |
| RESP | Character | 5 | Response command or digit string |
| MODE | Character | 1 | Consultation operating context |
| VERSION | Character | 20 | Version or Begin/End call comment |
| SENS_FACT | Character | 20 | Current sensitivity factor settings |

D. The medical history objects database 266 is an auxiliary database that supports a key feature of the MDATA system 100: past medical history. The medical history objects database is a catalog of unique alphanumeric codes, each code corresponding to a medical condition or diagnosis that is not expected to change during the life of the patient (e.g., a diagnosis for asthma is coded as "RWHZAST").

In addition to the alphanumeric codes, the MDATA system 100 uses the "memo" field in a Foxpro database to store binary objects. Currently, these binary objects are clinical sounds obtained from the patient over the telephone.

It is anticipated, that as database technology gets more sophisticated (moving toward multi-media and so forth), it will allow storing of larger and more complicated binary files such as the following: a digitized x-ray, a digitized CAT scan, a digitized MRI scan. In addition, as video-telephone technology advances, it is anticipated that the system 100 will store video images or even holographic images of the patient.

For every past medical condition there is a record in the medical history objects database that contains the attributes of the medical condition, and contains a pointer into the past medical history questionnaire. The attributes of a medical condition include its data type (e.g., Boolean or numeric) and the number of digit positions needed to store the value of a numeric value associated with this condition (not applicable to Boolean type).

The pointer field is useful for obtaining medical history at run-time. If a patient has an incomplete medical history questionnaire on file with the MDATA system 100, then the pointer field allows the evaluation process to momentarily suspend the evaluation, go to the medical questionnaire and ask an individual question, collect and verify the patient's response, and then resume the evaluation process. This "ask-when-you-need-it" approach relieves the new patient of going through an exhaustive medical history questionnaire before the first consultation of the diagnostic process.

Each record of the medical history objects database has the following fields:

| Field Name | Data Type | Width | Usage |
|---|---|---|---|
| LABEL | Character | 8 | Object code name |
| TYPE | Character | 1 | Object data type |
| DIGITS | Numeric | 3 | Maximum number of digits in response |
| CALL | Pointer | 6 | Identifies question(s) to be asked to configure this object |
| AUDIO | Binary | N/A | Voice print |
| IMAGERY | Binary | N/A | Face print |
| RFU | Character | 20 | (For future use) |

E. The patient medical history (PMH) database 268 is created at run-time by the evaluation process 254 or by use of a past medical history questionnaire. The PMH database 268 is read by the evaluation process during run-time. This database 268 contains each patient's individual medical history. A new patient has an option to go through the entire medical questionnaire at one time, thereby configuring all the past medical history objects listed in the objects database 266. Alternately, the new patient can bypass the questionnaire and go right into the diagnosis of a medical complaint. Then, if a medical algorithm requires a past medical history object that has not yet been configured, the evaluation process 254 invokes a past medical history function before it continues with the algorithm.

Each patient has their own past medical history file, which is part of the PMH database 268, that contains records which describe medical events or conditions from the patient's life. The system 100 appends a record to this file each time a past medical history object is configured for the patient. The contents of this file are installed in the symbol table when the patient logs in to the system 100. The medical algorithm programmer is responsible for using a TEST command to verify that necessary items are present in the symbol table before algorithm execution. A side effect of a negative TEST result is that the system 100 prompts the patient to provide that information. The system 100 flags any new or modified items, and asks the patient to confirm these values during an Exit Confirmation Loop which will be described hereinbelow. Each record has the following fields:

| Field Name | Data Type | Width | Usage |
|---|---|---|---|
| LABEL | Character | 20 | The object's label |
| TYPE | Character | 1 | Object data type |
| VALUE | Character | 10 | Object's configured value |
| CERT | Numeric | 3 | Certainty of object's value |
| DATE | Date | 8 | Object configuration date |
| ICD9A | Float | 5 | First ICD-9 code |
| \| | \| | \| | \| |
| ICD9E | Float | 5 | Fifth ICD-9 code |

F. The "Pending" database file 269 holds medical information gathered during Pending mode for offline verification. The Pending database record structure is the same as that used for the past medical history (PMH) database 268. The evaluation process writes to the Pending database at run-time when it configures a new past medical history object for a patient during a Pending mode interaction. The contents of the Pending database are reviewed off-line by a staff person, and if the information is verified, the staff person appends the information to the patient's past medical history file.

G. An optional patient medication database 270 contains a file for each patient containing information about medication they are taking, or have taken in the past. The medication database 270 is created by the evaluation process 254 at run time. A "Write Drug" command builds a record and fills its fields with same-named memory variables from the symbol table. The evaluation process 254 may read the medication database 270 during run time as needed. The treatment table 256 optionally reads the medication database 270 to determine the medication(s) being used by the patient.

| Field Name | Data Type | Width |
|---|---|---|
| GENERIC_NAME | Character | 20 |
| TRADE_NAME1 | Character | 20 |
| TRADE_NAME2 | Character | 20 |
| TRADE_NAME3 | Character | 20 |
| ICD-9-CM_CODE | Character | 10 |
| ICD-9-CM_ECODE | Character | 10 |
| ICD-9-CM_VCODE | Character | 10 |
| OTHER | Character | 20 |
| DOSAGE | Character | 20 |
| ROUTE_OF_ADMINISTRATION | Character | 10 |
| FREQUENCY | Character | 10 |
| USE | Character | 20 |
| START_DATE | Date | 8 |
| STOP_DATE | Date | 8 |
| OTHER1 | Character | 20 |
| OTHER2 | Character | 20 |

VII. Top-Level Flow

Referring to FIGS. 7a, 7b, 7c and 7d, the top level flow 300 of the MDATA system 100 software will be described. The telephone number used to access the MDATA system 100 may vary in various embodiments of the system. If the sponsoring agency or hospital wishes to provide access to the MDATA system 100 at no cost to the caller, then a toll-free 800 service number can be used. If the sponsoring agency or hospital wishes to recover the costs of running the MDATA system 100 from the caller, it may use a pay-per-call or premium charge number (e.g., 900 service). "Current Procedural Terminology" (CPT-4) codes are available to describe and bill third party payers for telephone consultations. They are a listing of the descriptive terms and identifying codes for reporting medical services and procedures. CPT-4 codes are the most widely accepted nomenclature for reporting physician services to insurance companies.

Beginning at a start state 302, a person 112 (FIG. 1) desiring medical advice calls the telephone number for the MDATA system 100 on a telephone line 106. The caller may be the patient or may be an "assistant", e.g., parent, relative, or friend, that is helping the patient. Moving to state 304, the system 100 answers the call automatically and greets the caller 112 with an introductory greeting message by playing back a speech file stored on the hard drive 152 by use of the VP board 122. Proceeding at state 306, the MDATA system 100 asks each patient who calls the system a series of "initial screening questions." These questions are designed to identify patients who are critically ill; they are not designed to identify the patient's problem. The initial screening questions enable the system to filter out patients who require immediate medical attention.

Moving to decision state 308, any patient found to be critically ill is instructed to dial the emergency response telephone number "911" at state 309 or will be automatically connected to the nearest emergency medical services system in the patient's area. The telephone call is terminated by the computer 102 at state 310. The following are examples of initial screening questions:

IS THIS A MEDICAL EMERGENCY?
ARE YOU HAVING DIFFICULTY BREATHING?
ARE YOU EXPERIENCING SEVERE PAIN OR PRESSURE IN YOUR CHEST?

If the system determines that the patient is experiencing a medical emergency, it may provide the patient with a menu of emergency medical procedures at state 311. In situations where the patient or the caller for the patient is far from the nearest emergency help, e.g., a rural setting, the caller may need to initiate emergency procedures immediately. The menu of emergency medical procedures provides several choices to the caller. If the caller presses touch tone key "1" or speaks the word "one" into the telephone mouthpiece, the computer 102 branches to state 312 wherein well known CPR (cardiopulmonary resuscitation) information is recited. If the caller has a speakerphone capability associated with the telephone 110 being used, the caller may be able to listen to and perform the instructions given by the system 100 in a hands-free manner away from the telephone. If the caller presses touch tone key "2" or speaks the word "two" into the telephone mouthpiece, the computer 102 branches to state 313 wherein well known Heimlich Hug information for choking is recited. At the completion of either state 312 or state 313, the telephone call ends at state 314.

Figure 7A:
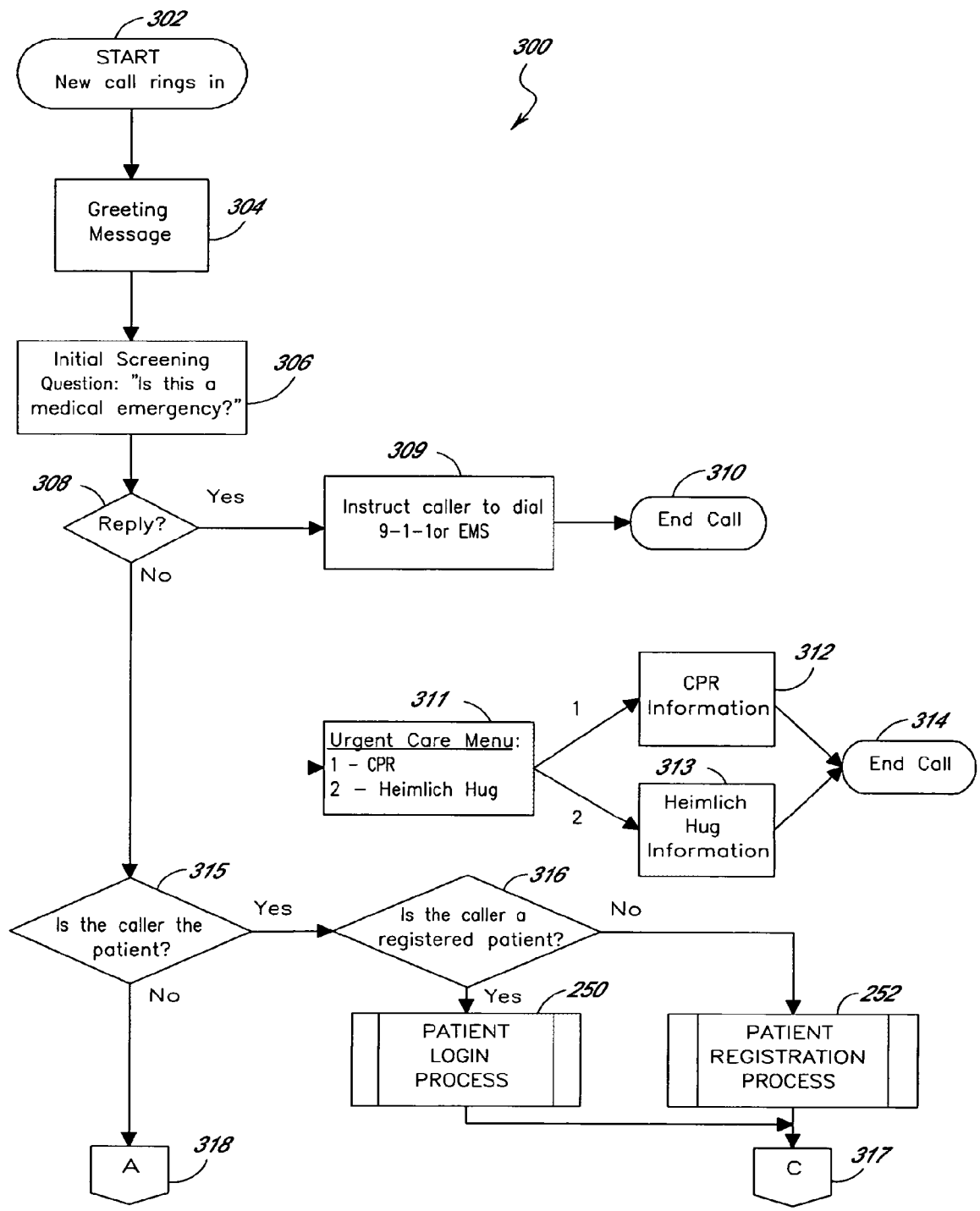
FIGS. 7a, 7b, 7c and 7d are a top-level flow diagram of the MDATA system of FIG. 1.

If the patient is determined at state 308 not to have a medical emergency, i.e., the MDATA system 100 is satisfied that no immediately life threatening condition is present, the computer 102 moves to a decision state 315 to determine if the caller is the actual patient. If so, the computer 102 proceeds to a decision state 316 to determine if the patient has previously registered or ever consulted with the system 100, i.e., is not a new or first-time caller. If so, the system 100 verifies the patient's identification and retrieves their medical record at the patient login process 250, which will be further described hereinbelow. At the completion of process 250, the computer 102 proceeds through off-page connector C 317 to state 344 (FIG. 7d). If the patient is not registered, the MDATA system 100 proceeds to the patient registration process 252 for a new patient, which will be described hereinbelow. At the completion of process 252, the computer 102 proceeds through off-page connector C 317 to state 344 on FIG. 7d.

Figure 7B:
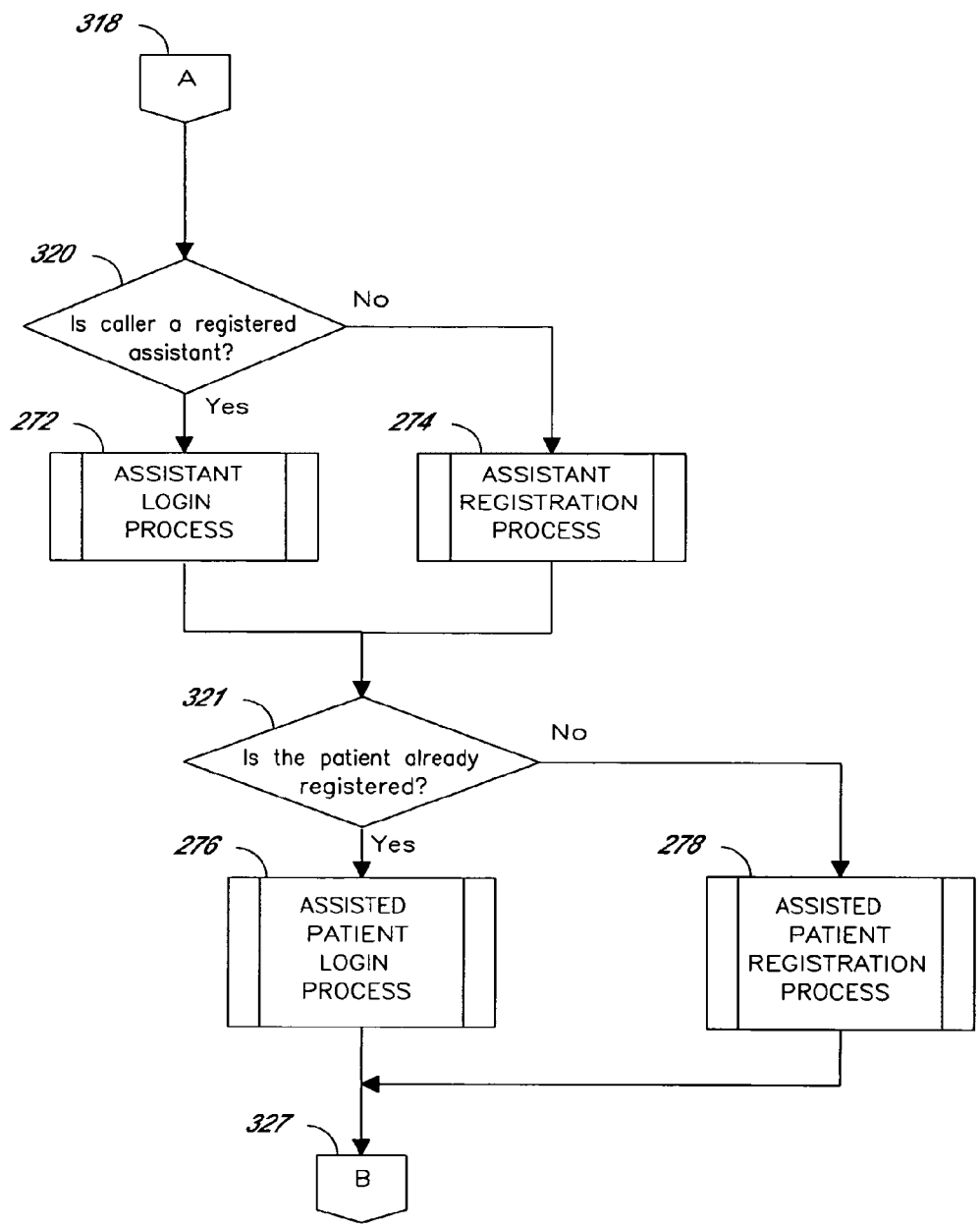
Figure 7C:
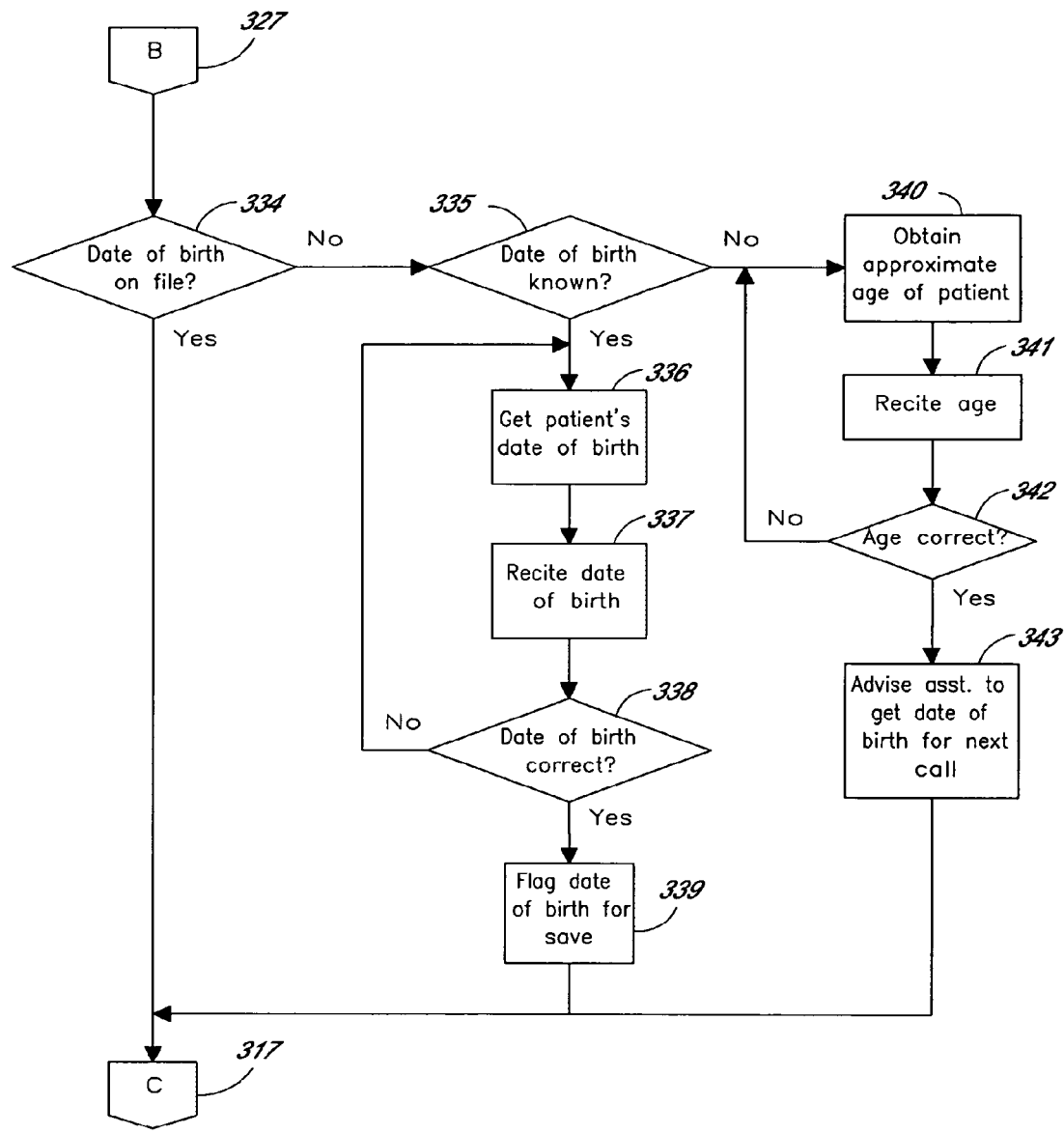
Figure 7D:
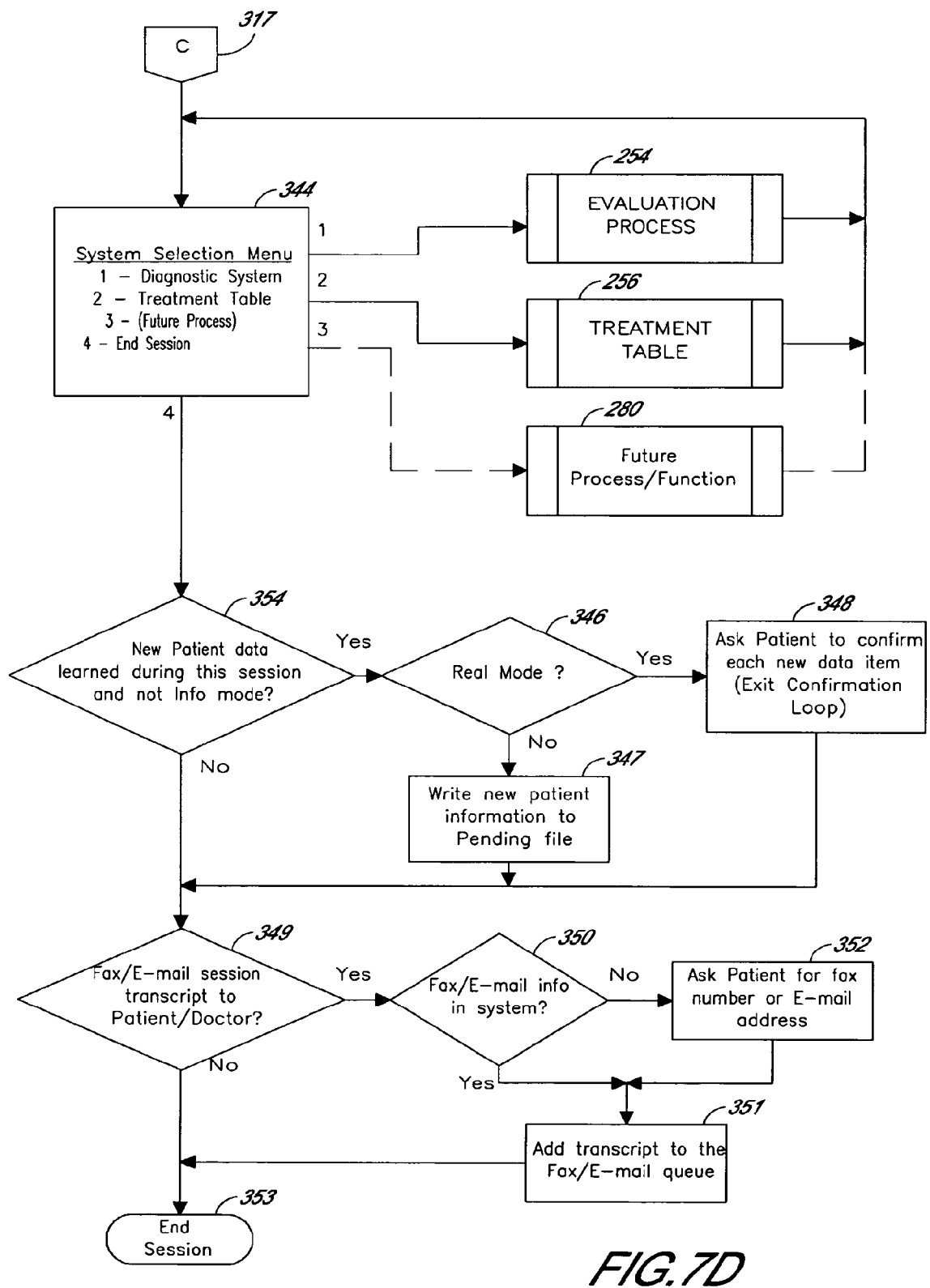

If the caller is not the patient, as determined at state 315, the computer 102 proceeds through off-page connector A 318 to state 320 on FIG. 7b. There will be times when the patient may not be able to use the MDATA system 100 directly, e.g., due to injury, weakness or altered level of consciousness. In these cases, an "assistant" may interact with the system on behalf of the patient.

An assistant registers with the system through the assistant registration process 274 which will be described hereinbelow. The assistant registration record is identical to the patient registration record in structure, but three fields have special significance for an assistant: ASST_PERM, ASST_EXP, and RELATIONS. The ASST_PERM field is a Boolean flag that can only be set true off-line by the system administrator who has verified, through separate means, that a relationship exists between a patient and an assistant. The relationships are one-to-many, i.e., a patient may have one or more assistants, and an assistant may be related to more than one patient. The ASST_PERM flag may also be constrained by the ASST_EXP field, which contains a timestamp for the expiration of the ASST_PERM attribute. If the ASST_PERM flag is true, then the RELATIONS pointers will point to one or more patient records for whom this assistant is a "permanent assistant;" otherwise the RELATIONS field will be empty.

The medical information gathered during an assisted consultation is written to the patient's medical record only if the following three conditions are met:

(a) the assistant's ASST_PERM flag is True
(b) the ASST_EXP timestamp has not been reached
(c) the assistant has a relationship pointer to the patient record If any of these conditions are not met, then any new medical information gathered on this patient will be saved to the Pending file 269 for off-line verification by the system administrator.

The system 100 establishes at state 315 whether the caller is the patient, or an assistant. If the caller is not the patient, then the system asserts that the caller is an assistant and, at a decision state 320, determines if the assistant is registered. If the assistant is not already registered with the system, the system enrolls the new assistant at the assistant registration process 274. If the assistant is already registered with the system 100, the computer 102 performs the assistant login process 272. At the completion of either process 272 or process 274, the computer 102 advances to a decision state 321.

If the patient is not already registered with the system 100, as determined at decision state 321, then the system allows the assistant to register a new patient at the assisted patient registration process 278. However, if the patient is already registered with the system 100, as determined at state 321, the computer 102 performs the assisted patient login process 276. At the completion of process 278 or process 276, the computer 102 proceeds through off-page connector B 327 to a decision state 334 on FIG. 7c.

At decision state 334, the computer 102 determines if the patient's date of birth is in the patient's medical record. If so, the computer proceeds through off-page connector C 317 to state 344 on FIG. 7d. If not, the system 100 attempts to get the patient's date of birth. Moving to state 335, the system 100 asks the assistant if the patient's date of birth is known. If so, the computer 102 advances to state 336 to request the patient's date of birth. At state 337, the system 100 recites the patient's date of birth obtained at state 336. At a decision state 338, the assistant determines if the date of birth is correct as recited by the system 100. If not, the computer 102 loops back to state 336 to request the patient's date of birth again. If the patient's date of birth is correct, as determined at state 338, the computer 102 flags the date of birth for saving in the patient's medical record at state 339, and proceeds to state 344 on FIG. 7d.

If the patient's date of birth is not known, as determined at state 335, the computer 102 proceeds to state 340 wherein the system requests the assistant to provide an approximate age of the patient. The age is an important parameter used in the evaluation process 254 and treatment table 256. At state 341, the system 100 recites the patient's approximate age obtained at state 340. At a decision state 342, the assistant determines if the age is correct as recited by the system 100. If not, the computer 102 loops back to state 340 to request the patient's approximate age again. If the patient's approximate age is correct, as determined at state 342, the system 100 advises the assistant at state 343 to get the patient's actual date of birth before the next consultation, and proceeds to state 344 on FIG. 7d. The system 100 uses the approximate age in the consultation during the evaluation process 254 and the treatment table 256.

At state 344 on FIG. 7d, the system 100 presents the caller with a system selection menu. Here, the caller is asked to select from among four choices: diagnostic system, treatment table, a future process/function, or end call as described below:
- A. Diagnostic System: The system starts the evaluation process 254 at a menu, where it asks the patient to begin identification of the complaint.
- B. Treatment Table: The system takes the patient to the treatment table process 256 at a menu, where it asks the patient to select a treatment selection method.
- C. Future Process/Function: A future process or function 280, undefined in the present embodiment, that reads and/or writes the databases shown in FIG. 6.
- D. End Call: The system performs several steps and then terminates the telephone call.

In either process 254 or 256, the computer 102 functions as an interpreter as performed by algorithm processor 160 in following the node map created by the algorithm programmer. At the exit point of the evaluation process 254, the system 100 gives the patient the option of selecting another complaint. At the end of the treatment table process 256, the system gives the patient the option of selecting another treatment.

At the completion of the evaluation process 254, treatment table process 256, or future process 280, the system 100 loops back to state 344 and recites the system selection menu to the caller. If the caller chooses the End Call selection at state 344, the MDATA system 100 moves to a decision state 345. At decision state 345, the system 100 determines if process 254, process 256, or process 280 did not occur in Information mode, i.e., did occur in either Real mode or Pending Mode, and examines the patient's symbol table to determine if any of the configured memory variables are past medical history conditions that need to be saved to the patient's medical history file. If both conditions are true at state 345, the system 100 advances to a decision state 346 to determine if the consultation is being performed in Real mode. If not, the consultation is being performed in Pending mode, and the system 100 then writes any new patient information obtained during the consultation to the Pending file 269. If state 346 proves to be true, i.e., Real mode, for each past medical condition that needs to be saved, the MDATA system 100 asks the patient at state 348 to grant permission to save the datum to the patient's medical history file and to confirm that the datum is correct. For example, during a consultation for cough, the MDATA system 100 learned that the patient has been diagnosed as being HIV positive. The system 100 will ask, "May I record the information about your HIV diagnosis in your medical record?" If the patient responds "yes", then the system 100 will ask, "Please verify that your diagnosis for HIV was positive, is this correct?" If the patient responds "yes", then the system 100 writes this fact to the patient's medical history file. After confirmation, each data item is stored in the patient's file in the patient medical history database 268 (FIG. 6).

At the completion of either updating the history database 268 at state 348, state 345 proves to be false, or at the completion of state 347, the system 100 moves to a decision state 349. Before the MDATA system 100 ends the consultation with the patient, it presents a summary of all the advice it has given. The patient is asked to write down and repeat back the key points. The MDATA system 100 then gives the patient the option of receiving a summary of the consultation session and specific recommendations provided by the system by facsimile, electronic mail (E-mail) or a mail service, such as first-class mail. If a fax or E-mail is desired, the system 100 moves to a decision state 350 to determine if information to send the summary and recommendations is available in the system. If not, the system 100 asks the patient for the information, e.g., a fax number, E-mail address or mail address, at state 352. The patient also has the option to send a summary of the consultation to his or her health care provider or specialist. Proceeding to state 351, the computer 102 adds the transcript of the current telephone session to a fax queue or an E-mail queue, as desired, for subsequent transmission. At the completion of state 351 or if the system 100 determined at state 349 that the session transcript was not to be sent, the telephone call is terminated at state 353.

VIII. Login Process

Figure 8A:
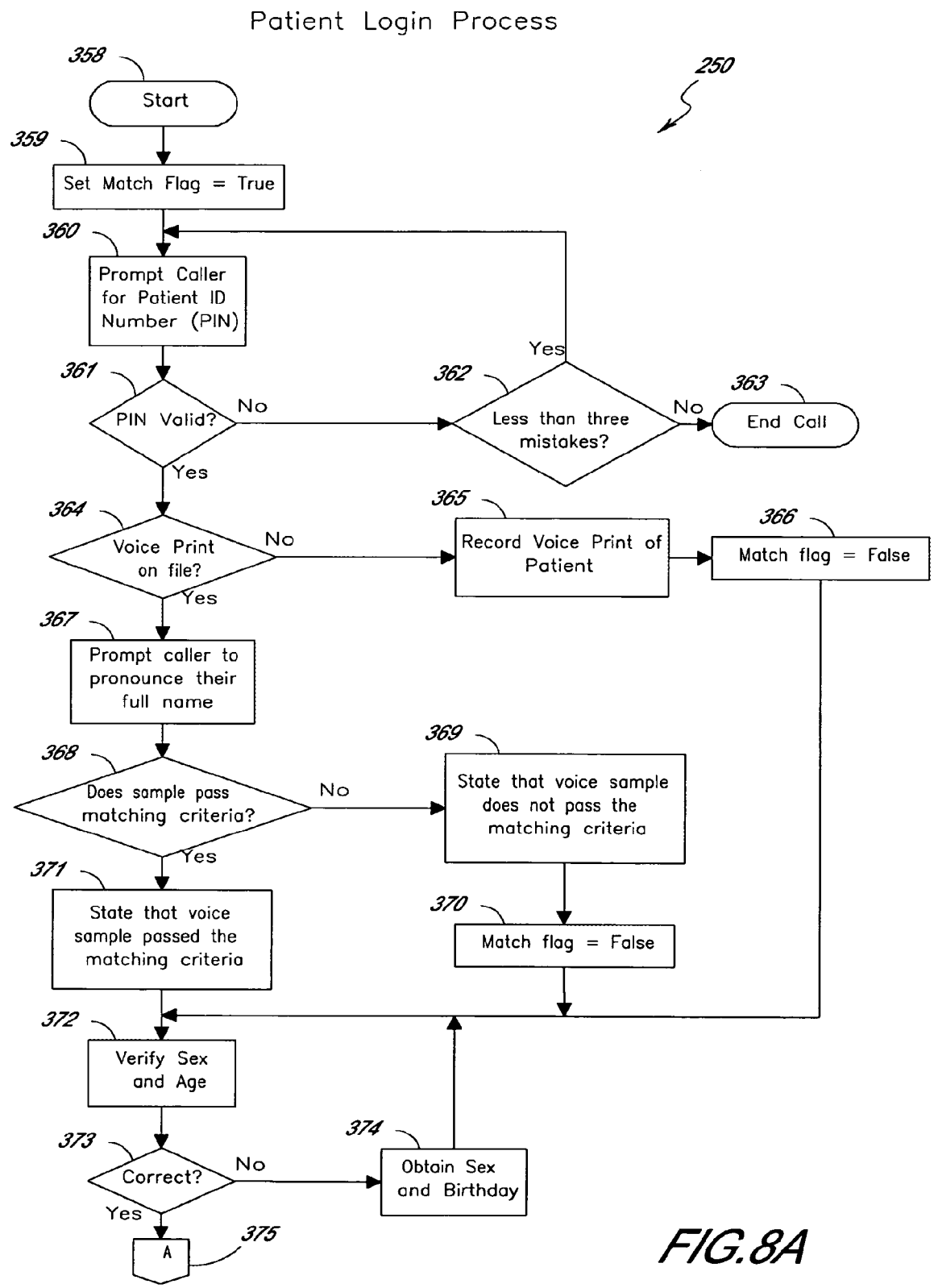
Figure 8B:
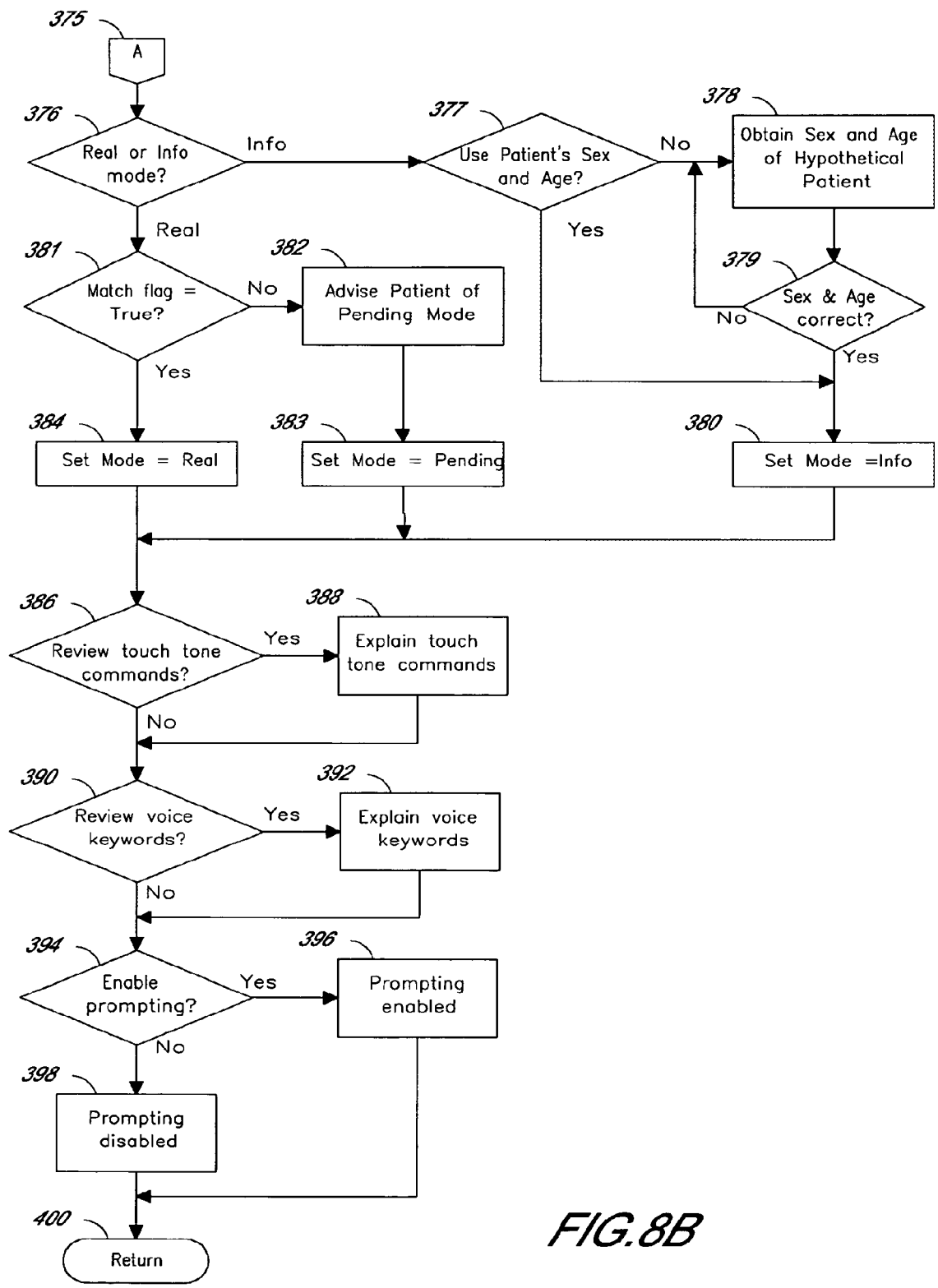

Referring now to FIGS. 8*a* and 8*b*, the patient login process 250 defined in FIG. 7*a* will be described. This process 250 is called if the patient has previously called and registered with the system 100. Beginning at a start state 358, the computer 102 moves to state 359 and initializes a match flag to true. The match flag is checked later in this process 250 in conjunction with setting the mode of the consultation. Proceeding to state 360, the computer 102 prompts the patient for the patient ID (identification) number (PIN) that is assigned during the registration process. The patient registration process 252 will be described in conjunction with FIGS. 9*a* and 9*b*. Proceeding to a decision state 361, the computer 102 determines whether the PIN is valid. If not, the computer 102 determines, at a decision state 362, if less than three tries at entering the PIN have been attempted. If so, the computer 102 loops back to state 360 to repeat the request for the PIN. However, if three attempts at entering the PIN have been made, as determined at state 362, the computer 102 plays a polite message that advises the patient that the login attempt failed and terminates the call at state 363. The computer 102 reports the failed login attempt to the system administrator at the sponsoring agency, hospital or other organization. The patient is allowed to reregister as a new patient, however, to permit access to the needed medical information. The system administrator resolves this type of situation off-line.

If the patient has correctly entered a valid PIN, as determined at state 361, the computer 102 moves to a decision state 364 to determine if the patient identified by the PIN has a voice print or sample voice waveform on file in the system 100. If not, the computer 102 proceeds to state 365 to record the voice print of the patient, e.g. the patient's pronunciation of his or her full name. The patient's voice print may not be on file, for example, if the patient could not provide a voice print during the assisted patient registration process 278 in a prior consultation. At the completion of recording the voice print at state 365, the computer 102 advances to state 366 wherein the match flag is set to false to indicate that the patient's voice print was recorded during the current login.

If the patient identified by the PIN has a voice print on file in the system 100, as determined at state 364, the computer 102 proceeds to state 367 and prompts the patient to pronounce his or her full name. Moving to a decision state 368, the computer 102 determines whether the voice sample obtained at state 367 passes the matching criteria. If not, the computer proceeds to state 369 and recites a message that the current voice sample does not pass the matching criteria. In the presently preferred embodiment, the current voice sample is compared to the reference voice sample recorded during the patient registration process 252 or the assisted patient registration process 278. Because the voice samples did not match, as determined at state 368, the computer 102 sets the match flag to false at state 370. In this case, the match flag is set to false to indicate that one of the security checking methods has failed. However, the process 250 continues at state 372 after the match flag is set to false at either state 366 or 370.

If the voice sample passed the matching criteria at state 368, the computer 102 advances to state 371 and recites a message that the current voice sample passed the matching criteria. This security check condition is now satisfied, and the match flag remains set to true. At the completion of state 371 the computer 102 moves to state 372. At state 372, the computer 102 verifies the sex and age of the patient by reciting the sex and age, as stored in the enrollment database 260 (obtained during the patient registration process 252), to the patient. At a decision state 373, the patient responds to the correctness of the recited information. If the sex or birth date information is not correct, the computer 102 moves to state 374 to request the correct information. The computer 102 then proceeds back to state 372 to verify the information received at state 374. If the result of the decision state 373 is true, i.e., the sex and age are correct, the computer moves through off-page connector A 375 to a decision state 376 on FIG. 8b to determine if the patient desires to conduct the telephone session in Real mode or Information mode. If Information mode is desired, the computer 102 moves to a decision state 377 to determine if the patient's sex and age are to be used during the Information mode consultation. If not, the computer 102 moves to state 378 to request an age and sex to use in a hypothetical situation during the Information mode session. Moving to a decision state 379, the computer 102 recites the sex and age obtained at state 378, and asks the patient to confirm that this information is correct. If not, the computer 102 moves back to state 378 to request the age and sex again. When decision state 379 is true or the patient's age and sex are to be used during this consultation, as determined at state 377, the computer 102 moves to state 380 and sets the operating mode to be Information mode.

If decision state 376 is determined to be Real mode, the computer 102 moves to a decision state 381 to check if the match flag is true. If not, the system 100 advises the patient, at state 382, that the current consultation is to be performed in Pending mode. The operating mode is set to be Pending mode at state 383. If the match flag is true, as determined at state 381, the computer 102 sets the operating mode to be Real mode at state 384.

At the completion of setting the operating mode at either state 380, state 383, or state 384, the computer moves to a decision state 386. At decision state 386, the computer 102 determines if the patient desires to review the touch tone commands described during the registration process. If so, the computer 102 advances to state 388 and recites the touch tone commands. At the completion of state 388 or if the patient did not wish to review the touch tone commands, the computer 102 proceeds to a decision state 390 wherein the computer 102 determines if the patient desires to review the voice keywords described during the registration process. If so, the computer 102 advances to state 392 and recites the voice keywords. At the completion of state 392 or if the patient did not wish to review the voice keywords, the computer 102 proceeds to a decision state 394 wherein the computer 102 determines if the patient desires to enable prompting. If so, the computer 102 advances to state 396 and enables prompting. If not, prompting is disabled at state 398. To "enable prompting" means that the patient would like to be prompted for responses. This is referred to as "hard" prompting, since this will remain in effect for the duration of the call. If hard prompting is off, and the system 100 has difficulty recognizing patient responses, the computer 102 turns on "soft" prompting. After the next successful recognition, the computer 102 turns off soft prompting. At the completion of state 396 or 398, the computer 102 returns at state 400 to the top level flow (FIG. 7).

Figure 12A:
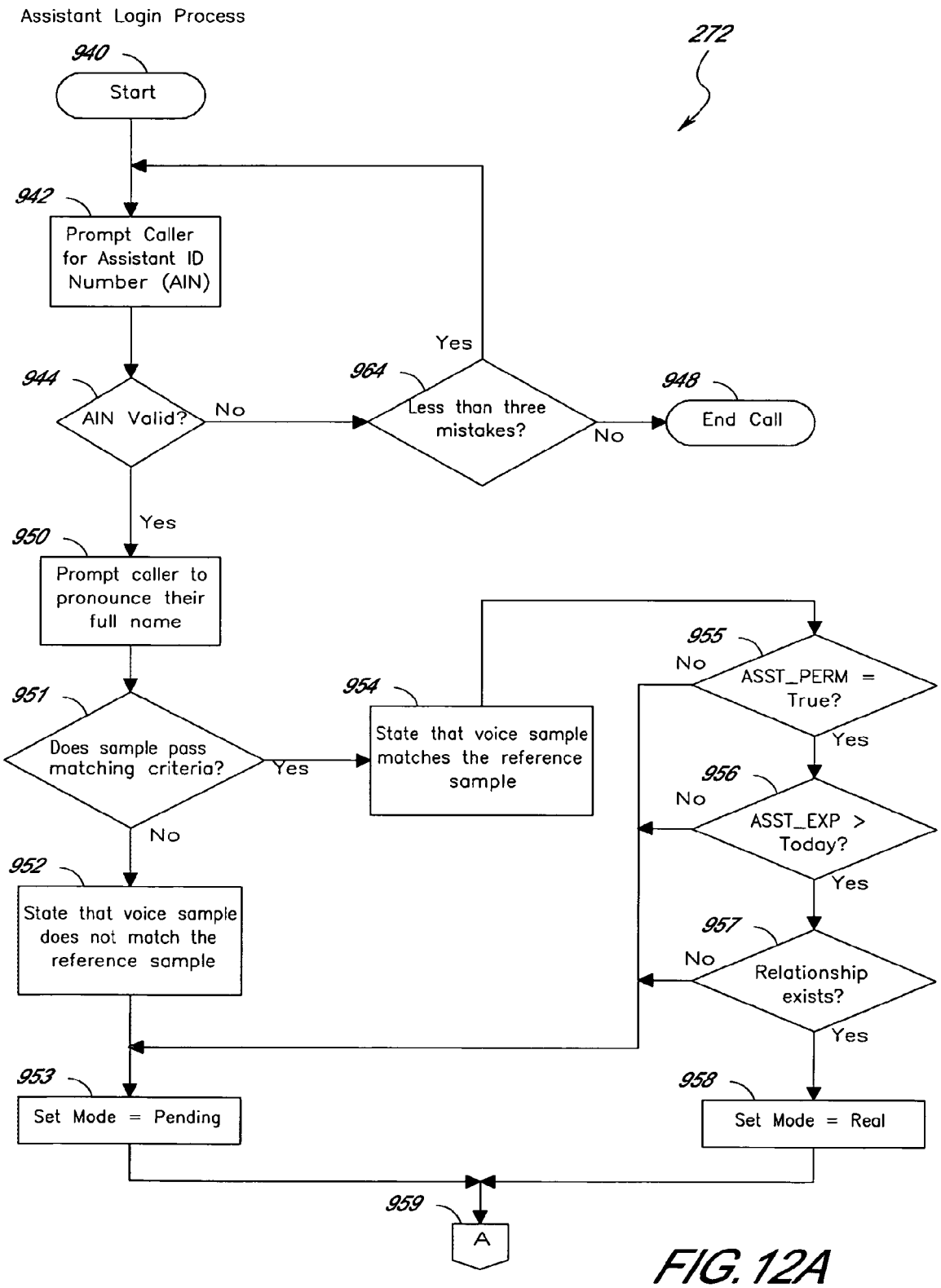
FIGS. 12a and 12b are a flow diagram of the assistant login process 272 defined in FIG. 7b.
Figure 12B:
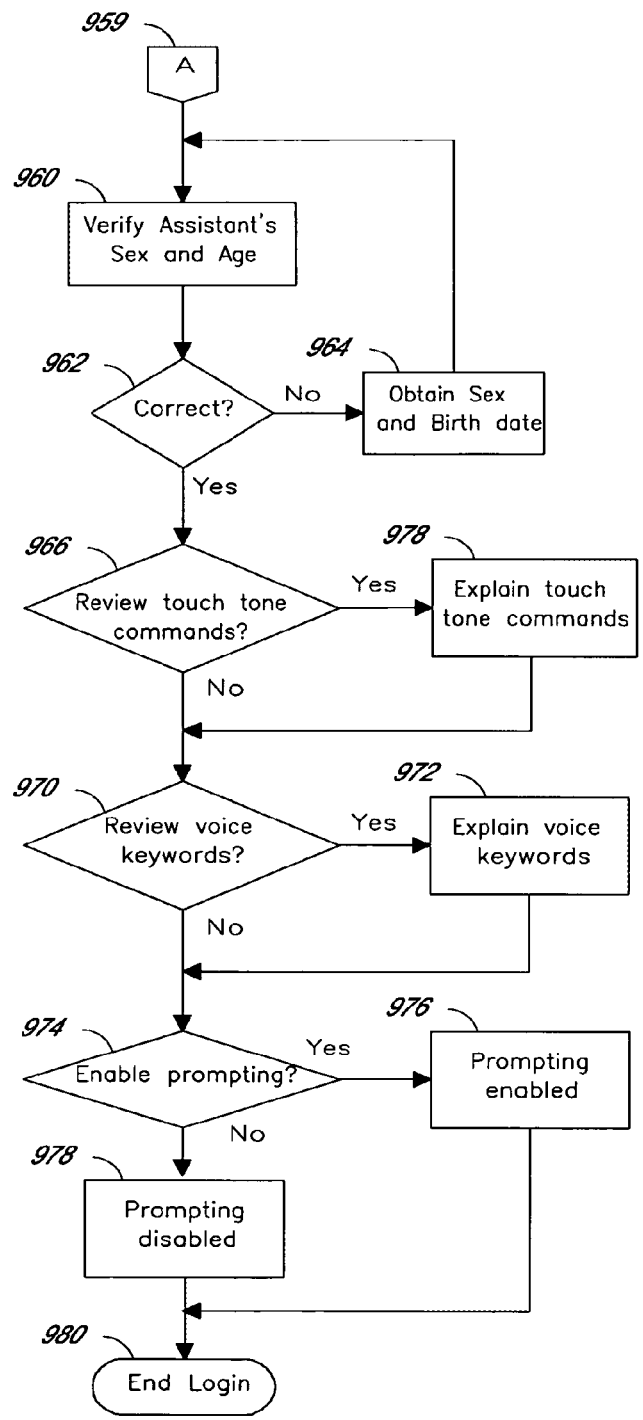

Referring now to FIGS. 12a and 12b, the assistant login process 272 defined in FIG. 7b will be described. This process 272 is called if the assistant has previously called and registered with the system 100. Beginning at a start state 940, the computer 102 moves to a state 942 and prompts the assistant for the assistant ID (identification) number (AIN) that is assigned during the registration process. The assistant registration process 274 will be described in conjunction with FIGS. 14a and 14b. Proceeding to a decision state 944, the computer 102 determines whether the AIN is valid. If not, the computer 102 determines, at a decision state 946, if less than three tries at entering the AIN have been attempted. If so, the computer 102 loops back to state 942 to repeat the request for the AIN. However, if three attempts at entering the AIN have been made, as determined at state 946, the computer 102 plays a polite message that advises the assistant that the login attempt failed and terminates the call at state 948. The computer 102 reports the failed login attempt to the system administrator at the sponsoring agency, hospital or other organization.

If the assistant has correctly entered a valid AIN, as determined at state 944, the computer 102 proceeds to state 950 and prompts the caller to pronounce his or her full name. Moving to a decision state 951, the computer 102 determines whether the voice sample obtained at state 950 passes the matching criteria. If not, the computer proceeds to state 952 and recites a message that the current voice sample does not pass the matching criteria. In the presently preferred embodiment, the current voice sample is compared to the reference voice sample recorded during the assistant registration process 274. Because the voice samples did not match, as determined at state 951, the computer 102 sets the operating mode to Pending at state 953. In this case, Pending mode is set to indicate that one of the security checking methods has failed. However, the process 272 continues at state 960 on FIG. 12b after Pending mode is set at state 953.

If the voice sample passed the matching criteria at state 951, the computer 102 advances to state 954 and recites a message that the current voice sample passed the matching criteria. This security check condition is now satisfied. Next, three additional checks are performed on the assistant identified by the AIN obtained at state 942. At a decision state 955, the computer 102 determines if the permanent assistant flag is true, as stored in the patient and assistant enrollment database 260. If so, the computer 102 advances to a decision state 956 to determine if the expiration date for the permanent assistant is in the future, i.e., the expiration date has not been reached yet. If so, the computer 102 advances to a decision state 957 to determine if a relationship exists between the assistant and a patient, i.e., the assistant has a relationship pointer to the patient record. If so, the operating mode is set to Real at state 958, and then the computer 102 advances through off-page connector A 959 to state 960 on FIG. 12b. However, if any of the decision states 955, 956, or 957 prove to be false, the computer 102 moves to state 953 wherein the operating mode is set to Pending.

States 960 through 964 are similar to states 372 through 374 of the patient login process 250 (FIG. 8). Because of this similarity, only significant differences are discussed in the interest of avoiding repetitiveness. States 960, 962 and 964 verify the assistant's age and sex, rather than the patient as in states 372, 373 and 374. States 966 through 980 are similar to states 386 through 400 of the patient login process 250 (FIG.

8b). The main distinction is that states 966-980 pertain to the assistant and states 386-400 pertain to the patient.

Figure 13A:
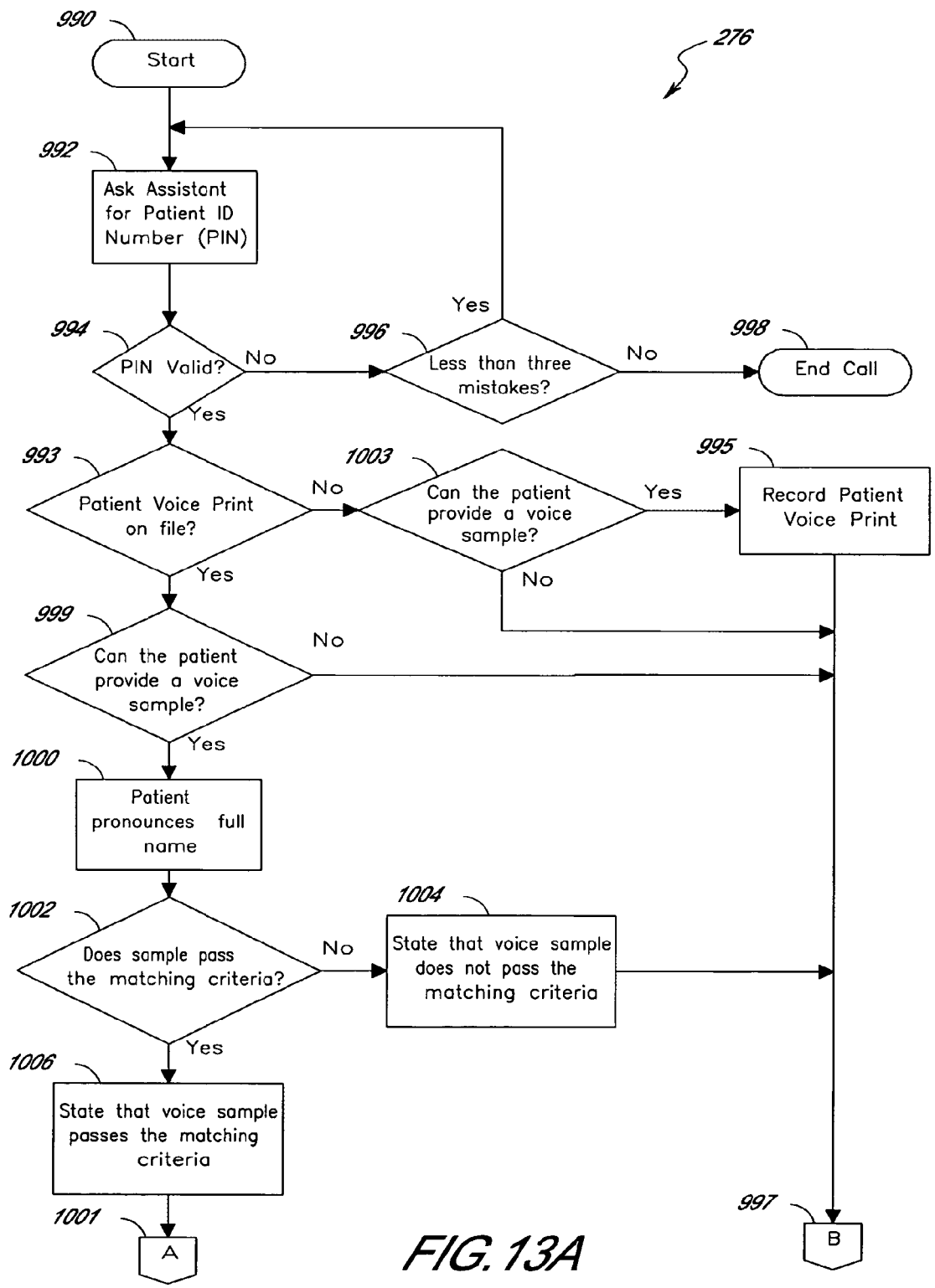
FIGS. 13a and 13b are a flow diagram of the assisted patient login process 276 defined in FIG. 7b.
Figure 13B:
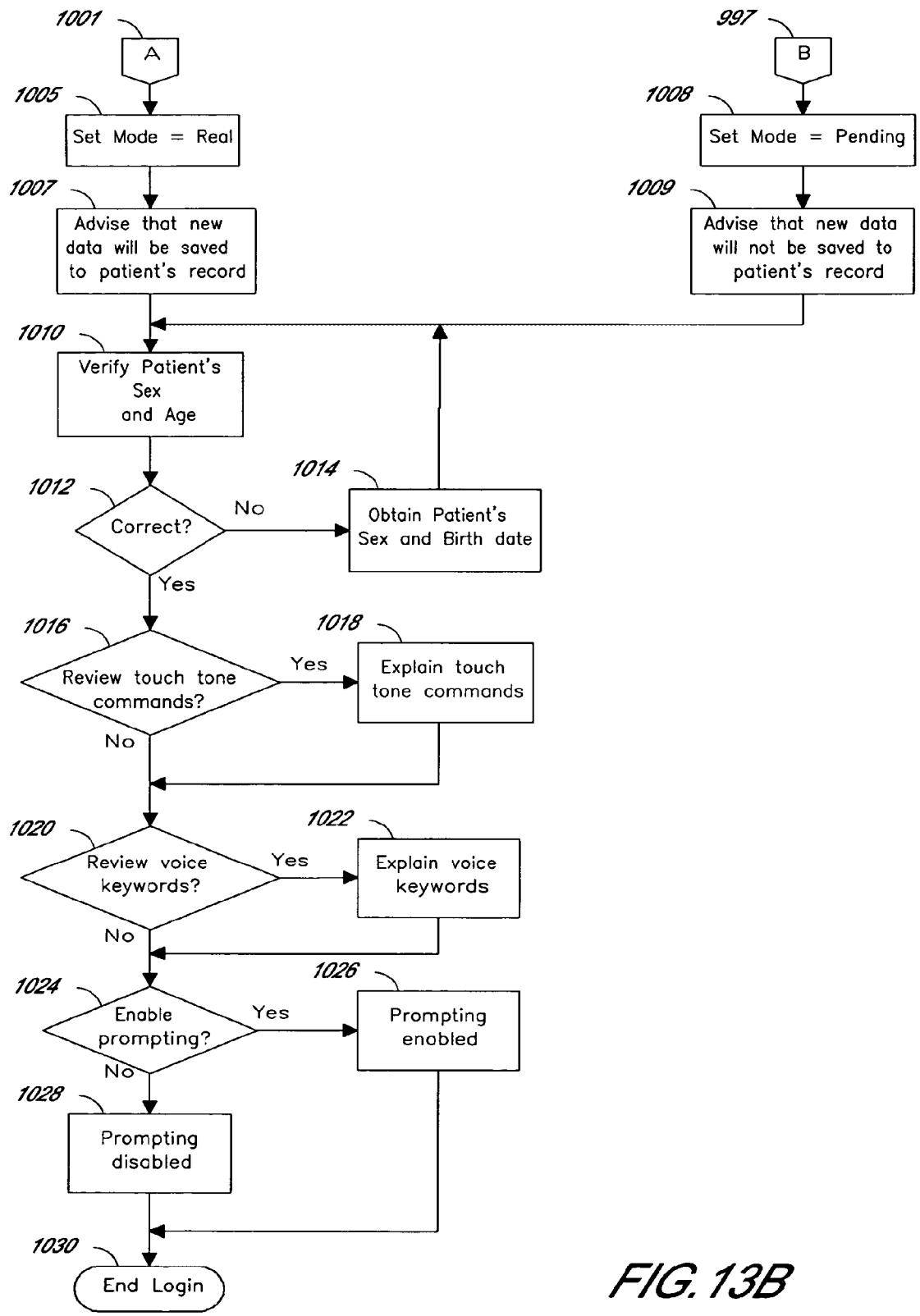

Referring now to FIGS. 13a and 13b, the assisted patient login process 276 defined in FIG. 7b will be described. This process 276 is called if both the patient and the assistant have previously called and registered with the system 100. This process allows the patient flexibility by permitting the assistant to provide help during the login and subsequent consultation. Beginning at a start state 990, the computer 102 moves a state 992 and prompts the assistant for the patient ID (identification) number (PIN) that is assigned during the registration process. As previously defined in FIG. 7, the assisted patient registration process 278 is called if the patient is not already registered. Process 278 will be described in conjunction with FIGS. 15a and 15b. Proceeding to a decision state 994, the computer 102 determines whether the PIN is valid. If not, the computer 102 determines, at a decision state 996, if less than three tries at entering the PIN have been attempted. If so, the computer 102 loops back to state 992 to repeat the request for the PIN. However, if three attempts at entering the PIN have been made, as determined at state 996, the computer 102 plays a polite message that advises the caller that the login attempt failed and terminates the call at state 998. The computer 102 reports the failed login attempt to the system administrator at the sponsoring agency, hospital or other organization. If the assistant doesn't know the PIN and the patient cannot provide it, the assistant is allowed to reregister the patient as a new patient at process 278 to permit access to the needed medical information. In this case, the assistant may have to estimate the age of the patient if the patient has, for example, an altered state of consciousness. The system administrator resolves the record-keeping in this situation off-line.

If the assistant has correctly provided a valid PIN to the system 100 at state 994, the computer 102 moves to a decision state 993 to determine if the patient identified by the PIN has a voice print or sample voice waveform on file in the system 100. If not, the computer 102 moves to a decision state 1003 to determine if the patient can provide a voice sample. If not, the computer 102 proceeds through off-page connector B 997 to state 1008 on FIG. 13b. If the patient can provide a voice sample, as determined at state 1003, the computer 102 moves to state 995 to record the voice print of the patient, e.g. the patient's pronunciation of his or her full name. The patient's voice print may not be on file, for example, if the patient could not provide a voice print during the assisted patient registration process 278 in a prior consultation. At the completion of recording the voice print at state 995, the computer proceeds through off-page connector B 997 to state 1008 on FIG. 13b.

If the patient identified by the PIN has a voice print on file in the system 100, as determined at state 993, the computer 102 proceeds to state 999 and asks whether the patient can provide a voice sample to the system. If not, the computer 102 proceeds through off-page connector B 997 to state 1008 on FIG. 13b. States 1000, 1002, 1004, 1006 are similar to states 367, 368, 369, 371, respectively, of the patient login process 250 (FIG. 8). Because of this similarity, only significant differences are discussed in the interest of avoiding repetitiveness. At the completion of state 1004, i.e., the patient's voice sample does not pass the matching criteria, the computer 102 proceeds through off-page connector B 997 to state 1008 on FIG. 13b. At the completion of state 1006, i.e., the patient's voice sample does pass the matching criteria, the computer 102 proceeds through off-page connector A 1001 to state 1005 on FIG. 13b.

At the completion of state 995, i.e., the patient's voice print is recorded, state 999 or state 1003, i.e., the patient cannot provide a voice sample, or state 1004, i.e., the voice sample match fails, the system continues process 276 at state 1008 on FIG. 13b. For the three situations just described in this process 276, the computer 102 sets the operating mode to Pending at state 1008. The system 100 then advises the caller at state 1009 that new patient information will not be saved to the patient's medical record because the consultation is in Pending mode until the information is verified off-line.

At the completion of state 1006, i.e., the voice sample passes, the computer 102 continues process 276 at state 1005 wherein the operating mode is set to Real. The system 100 then advises the caller at state 1007 that new patient information will be saved to the patient's medical record.

At the completion of state 1009 or state 1007, the computer 102 moves to state 1010. States 1010, 1012 and 1014 verify the patient's age and sex, similar to states 372, 373 and 374 (FIG. 8). States 1016 through 1030 are similar to states 386 through 400 of the patient login process 250 (FIG. 8). The main distinction is that states 1016-1030 are directed to the assistant and states 386-400 are directed to the patient.

IX. Registration Process

Figure 9A:
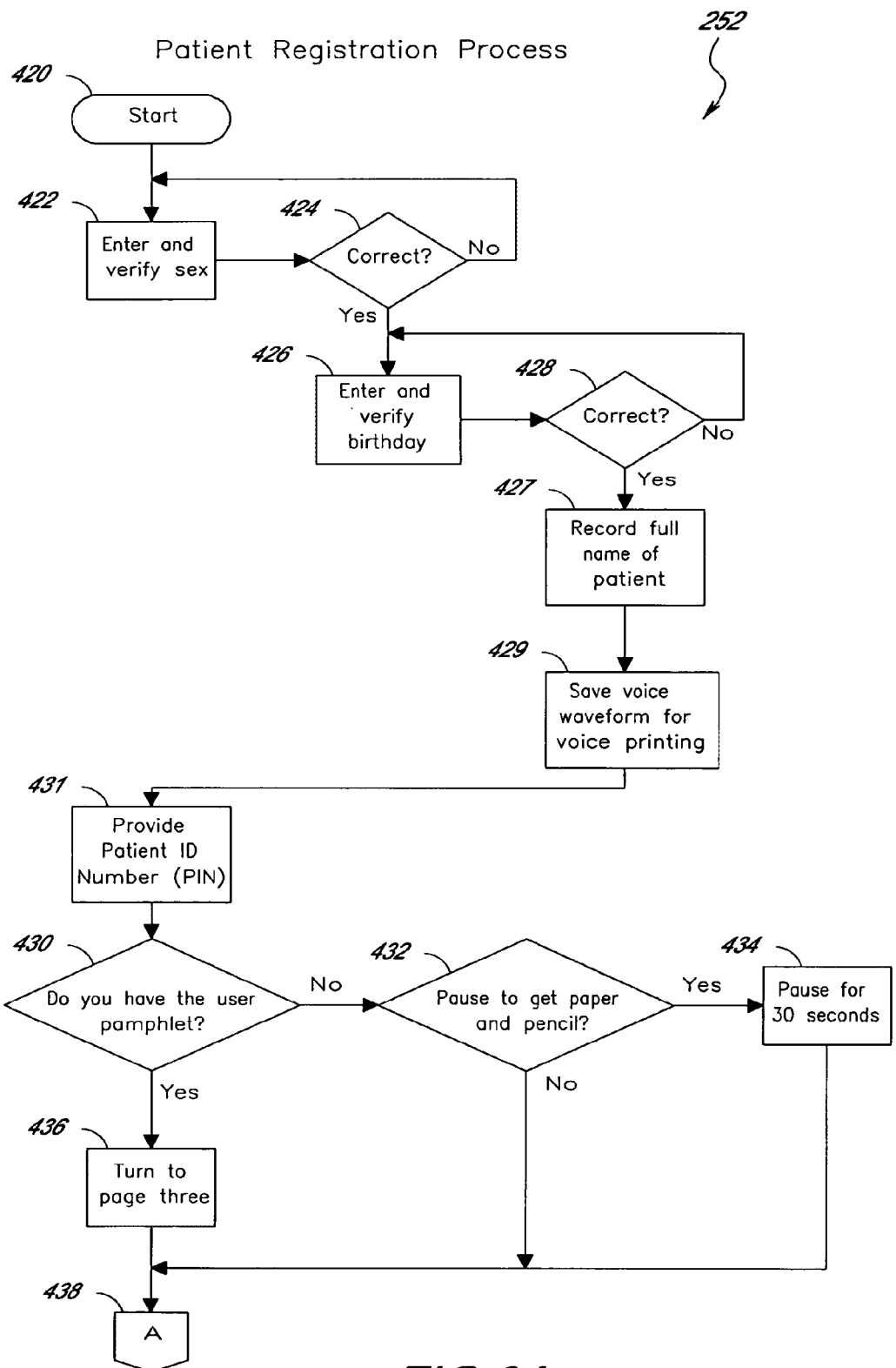
Figure 9B:
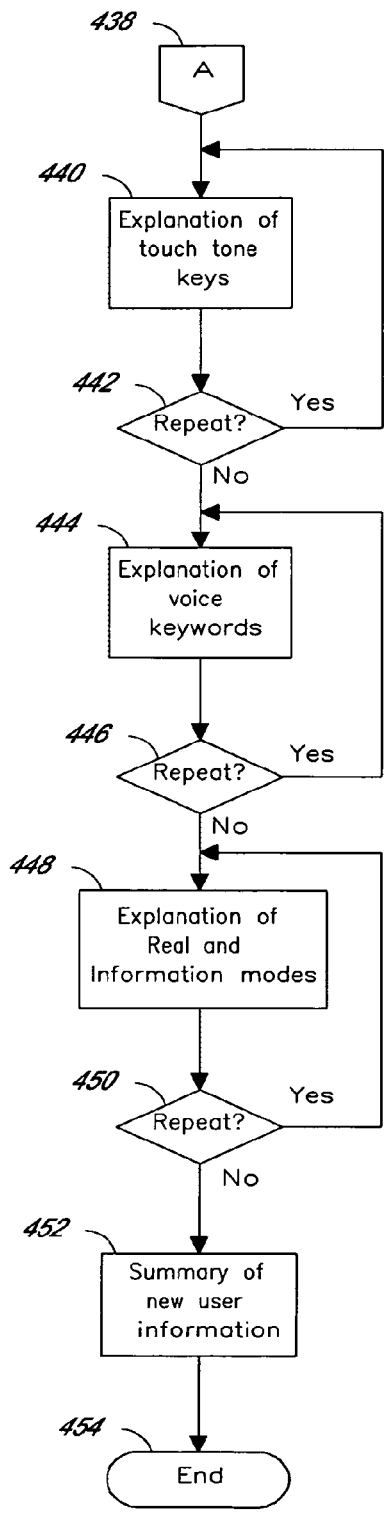

Referring now to FIGS. 9a and 9b, the patient registration process 252 defined in FIG. 7a will be described. This process 252 is called if the patient has not previously called and registered with the system 100. During the first consultation, the MDATA system 100 obtains the patient's age and sex. This is the minimum amount of information that the MDATA system requires in order to give medical advice. The more information the MDATA system has about a patient, however, the more specific is its advice.

The MDATA system 100 assigns each of its patients a unique patient identification number. In addition, when a patient initially registers, the patient's own pronunciation of his or her name is recorded, digitized and saved to their medical record. Then, when the patient calls back, the previous recording is retrieved and the patient is asked to repeat their name exactly as they did during registration. The two recordings are then compared to see if they match. This use of "voice printing" helps to further ensure the security and confidentiality of a patient's medical record.

Beginning at a start state 420, the computer 102 proceeds to state 422, requests the sex of the patient, and verifies by repeating the response given by the patient. Moving to a decision state 424, the patient responds by indicating to the system 100, via touch tone key or a voice response, whether the repeated information is correct. If not, the computer 102 loops back to state 422 to request the information again. When the information is correct at state 424, the computer 102 proceeds to states 426 and 428 to request and verify the birth date of the patient in a similar fashion to states 422 and 424.

When the decision state 428 is determined to be true, the computer 102 proceeds to state 427 and requests the patient to pronounce his or her full name. Moving to state 429, the full name is digitized and stored in a subdirectory on the hard drive 152 (FIG. 1) indexed by a Patient Identification Number (PIN). File names are of the form: <PIN>.vox. The computer 102 accesses a file to retrieve the next available PIN. The path name to the recorded voice file is saved in the patient's record in the enrollment database 260. In subsequent telephone sessions with the system 100, the patient's voice waveform will be compared to the recorded voice waveform for security and other optional purposes. When the voice waveform is stored, the computer 102 moves to state 431 and provides the PIN to the patient. The patient is informed of the importance to save the PIN for use in future consultations with the system 100.

At the completion of state 431, the computer 102 moves to a decision state 430 to determine if the patient has a MDATA system user pamphlet available. If so, the computer 102 moves to state 436 and requests the patient to turn to the pamphlet page that documents the touch tone keys, voice keywords, and modes. If not, the computer 102 moves to a decision state 432 to determine if the patient would like the system 100 to pause to enable the patient to get paper and a writing instrument for writing user instructions. If so, the computer 102 pauses at state 434 for 30 seconds. At the completion of the pause at state 434, if the user did not desire a pause at state 432, or after the patient is instructed to turn to the proper page of the pamphlet, the computer 102 proceeds to state 440 of FIG. 9b via the off-page connector A 438.

At state 440, the system 100 provides an explanation of the touch tone keys to the patient. These keys were described above in relation to the discussion on Voice Keywords and DTMF Command Keys. Moving to state 442, the computer 102 asks if the patient desires to hear the explanation of keys again. If so, the computer 102 repeats state 440. If not, the computer 102 advances to state 444 wherein an explanation of the voice keywords is provided to the patient. These keywords were previously described above. Moving to state 446, the computer 102 asks if the patient desires to hear the explanation of keywords again. If so, the computer 102 repeats state 444. If not, the computer 102 advances to state 448 wherein an explanation of Real and Information modes is provided to the patient. These modes were previously described above. Moving to state 450, the computer 102 asks if the patient desires to hear the explanation of the modes again. If so, the computer 102 repeats state 448. If not, the computer 102 advances to state 452 wherein a summary of new user information is recited to the patient. The summary includes a recap of the two methods of controlling the system: voice key words and DTMF, and the two interaction modes: Real and Info. The computer 102 returns at state 454 to the top level flow (FIG. 7).

Figure 14A:
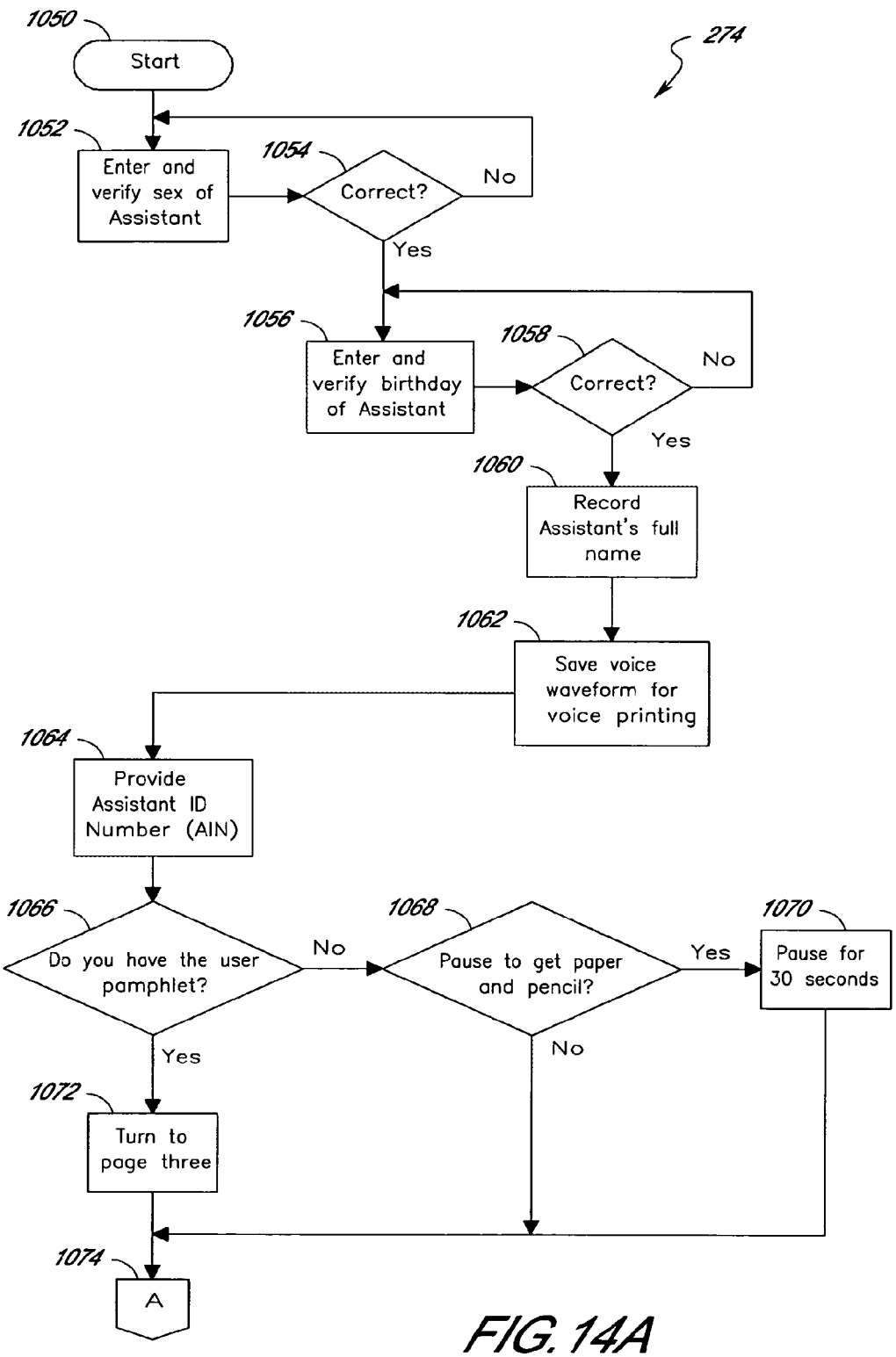
FIGS. 14a and 14b are a flow diagram of the assistant registration process 274 defined in FIG. 7b.
Figure 14B:
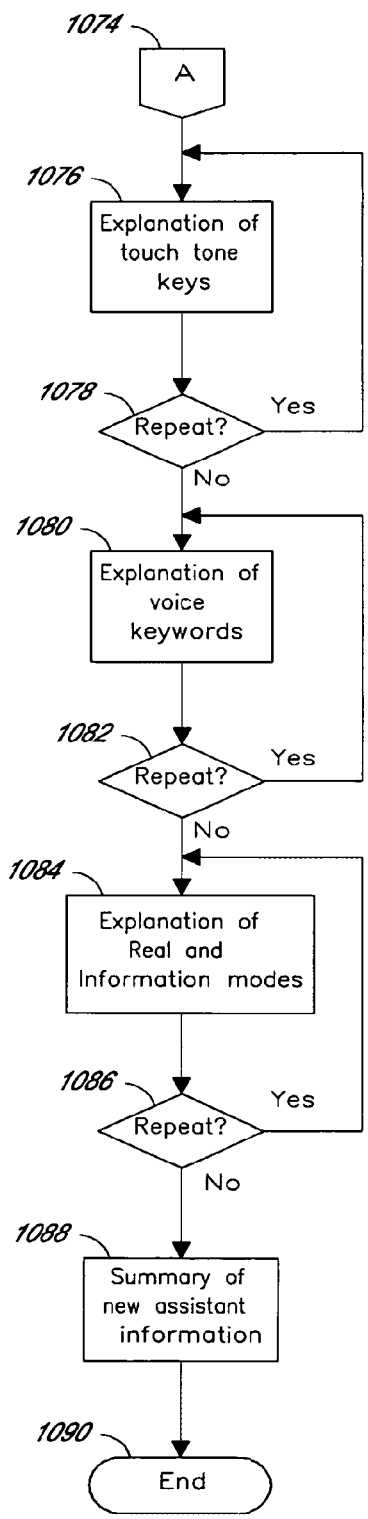

Referring now to FIGS. 14a and 14b, the assistant registration process 274 defined in FIG. 7b will be described. This process 274 is called if the caller is not a registered patient and has not previously called and registered as an assistant with the system 100. States 1050 through 1090 are similar to states 420 through 454 of the patient registration process 252 (FIG. 9). Because of this similarity, only significant differences are discussed in the interest of avoiding repetitiveness. States 1052, 1056, 1060, 1062 and 1064 pertain to the assistant rather than the patient as in states 422, 426, 427, 429 and 431 (FIG. 9a), respectively. State 1060 records the assistant's pronunciation of his or her full name and state 1062 saves it in the patient and assistant enrollment database 260. The system 100 provides an assistant identification number (AIN) at state 1064. The AIN is used similarly to the PIN in the access of files or records. The remaining states 1066-1090 are directed to the assistant also.

Figure 15A:
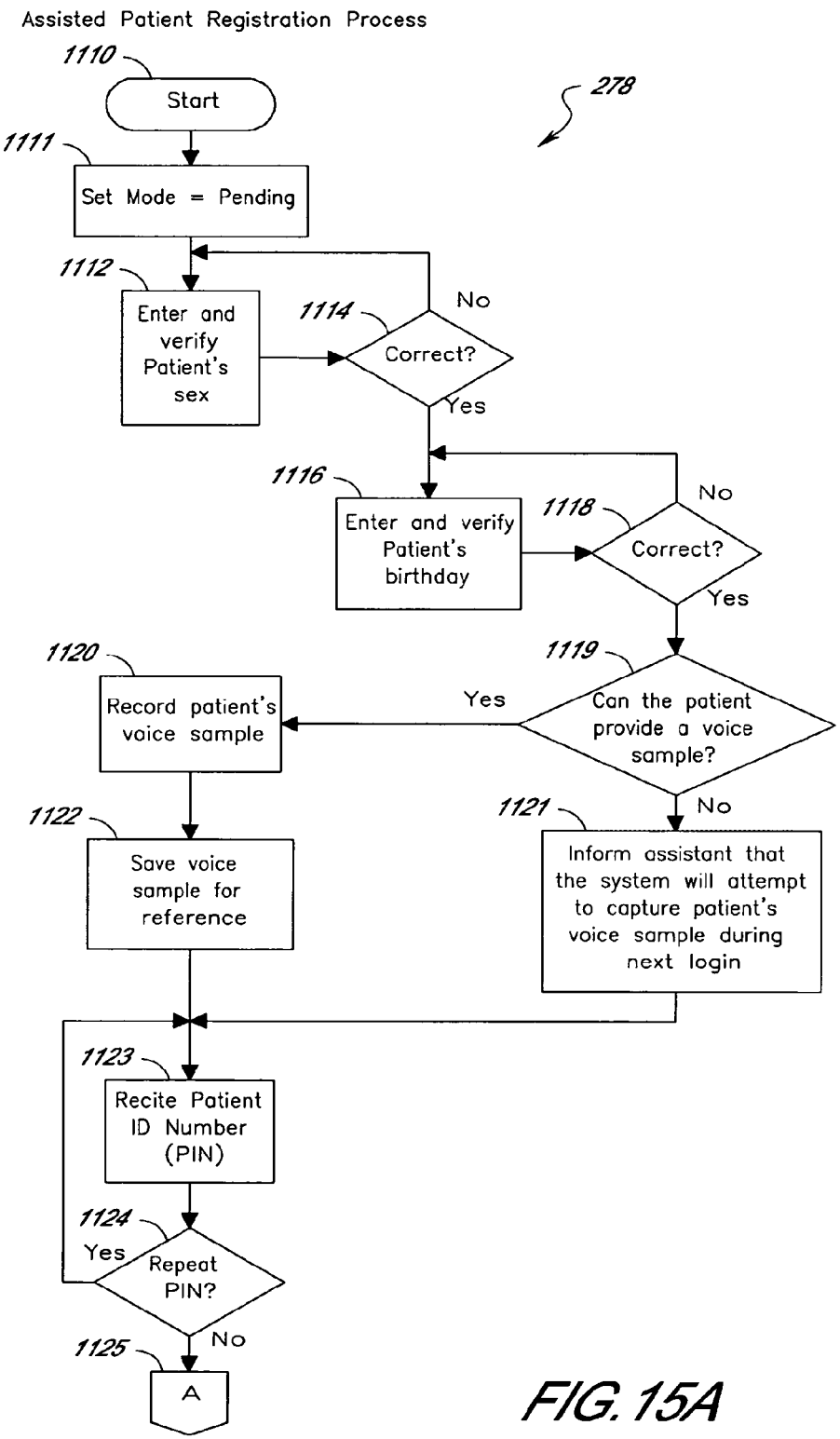
FIGS. 15a and 15b are a flow diagram of the assisted patient registration process 278 defined in FIG. 7b.
Figure 15B:
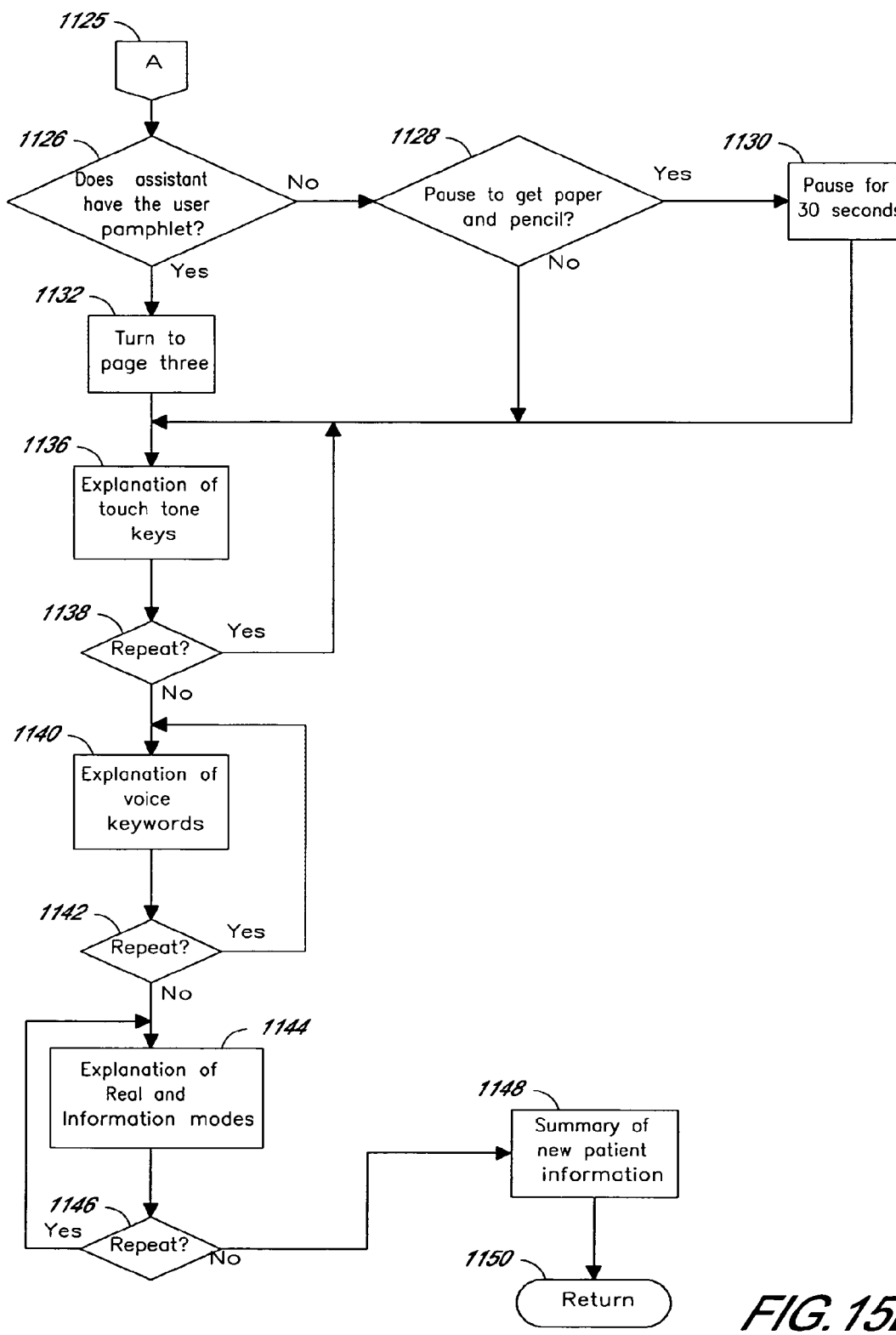

Referring now to FIGS. 15a and 15b, the assisted patient registration process 278 defined in FIG. 7b will be described. This process 278 is evoked if the caller is not the patient and the patient has not previously called and registered with the system 100. States 1110 through 1150 are similar to states 420 through 454 of the patient registration process 252 (FIG. 9). Because of this similarity, only significant differences are discussed in the interest of avoiding repetitiveness. The main difference is that the assistant is interacting with the system 100 on behalf of the patient during this process 278, and therefore, the operating mode is set to Pending at state 1111.

States 1112 and 1116 obtain the patient's sex and age, respectively. If the patient cannot provide the age to the assistant and the system, the assistant provides an estimated age. The estimated age can be corrected during a subsequent consultation with the system 100. At state 1119, the system 100 asks whether the patient can provide a voice sample of his or her full name. If so, the voice waveform is recorded and saved in enrollment database 260 (FIG. 6) at states 1120 and 1122. If the patient cannot provide a voice sample at state 1119, the system 100 informs the assistant, at state 1121, that the patient's voice sample will be requested during the subsequent consultation. Then, whether or not a voice sample is recorded, the system 100 provides a patient identification number (PIN) of the patient to the assistant and the patient (if coherent) at state 1123. The caller is instructed to safeguard the PIN for future consultations by either the patient or the assistant on behalf of the patient. If the assistant and/or patient desires to hear the PIN again, as determined at a decision state 1124, the computer 102 repeats the PIN at state 1123. The computer 102 proceeds through off-page connector A 1125 to a decision state 1126 on FIG. 15b. The remaining states 1126-1150 in process 278 are directed to the assistant rather than the patient, as in states 430-454 of process 252 (FIG. 9).

X. Evaluation Process

Figure 10A:
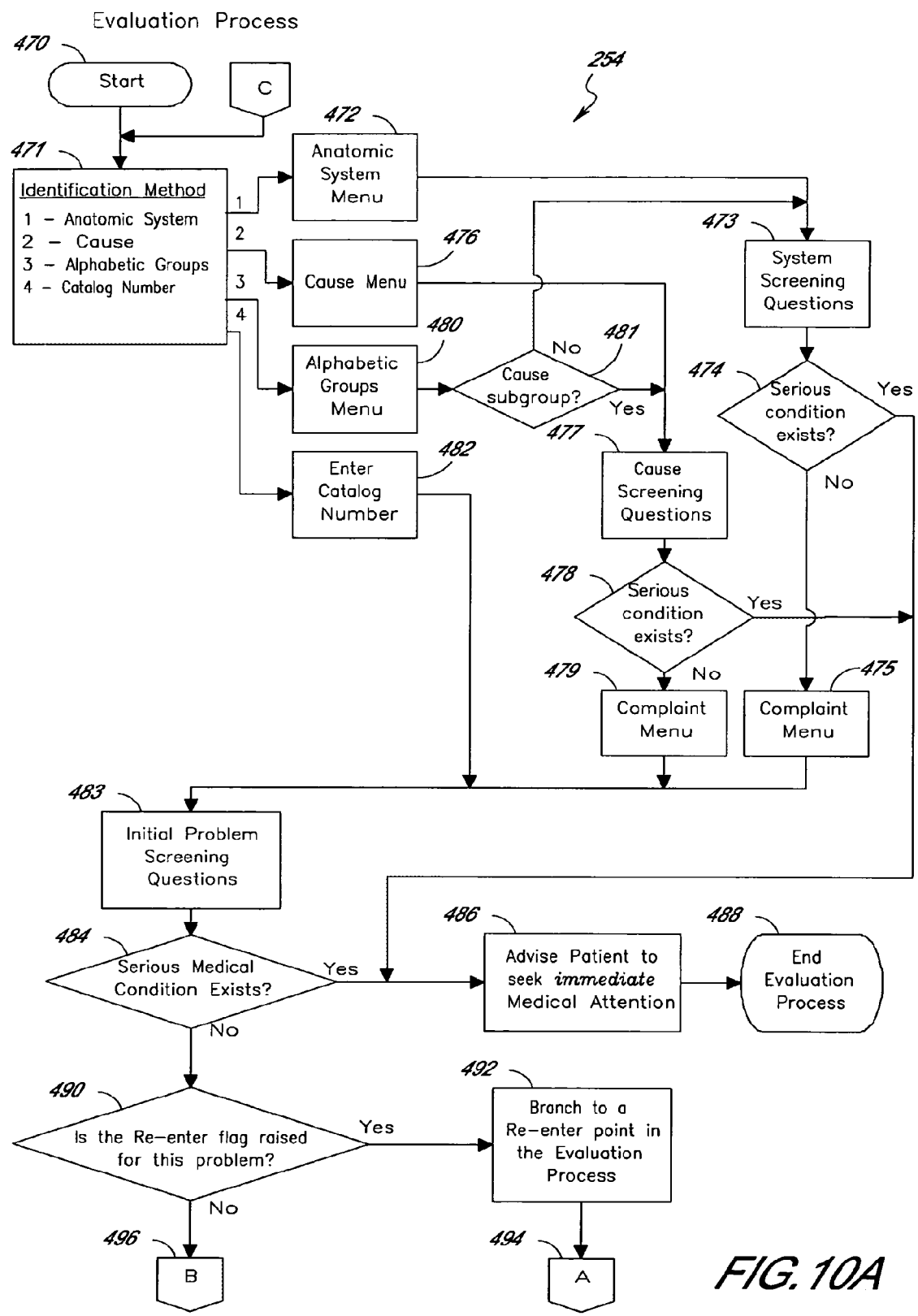
FIGS. 10a and 10b are a flow diagram of the evaluation process 254 defined in FIG. 7d.
Figure 10B:
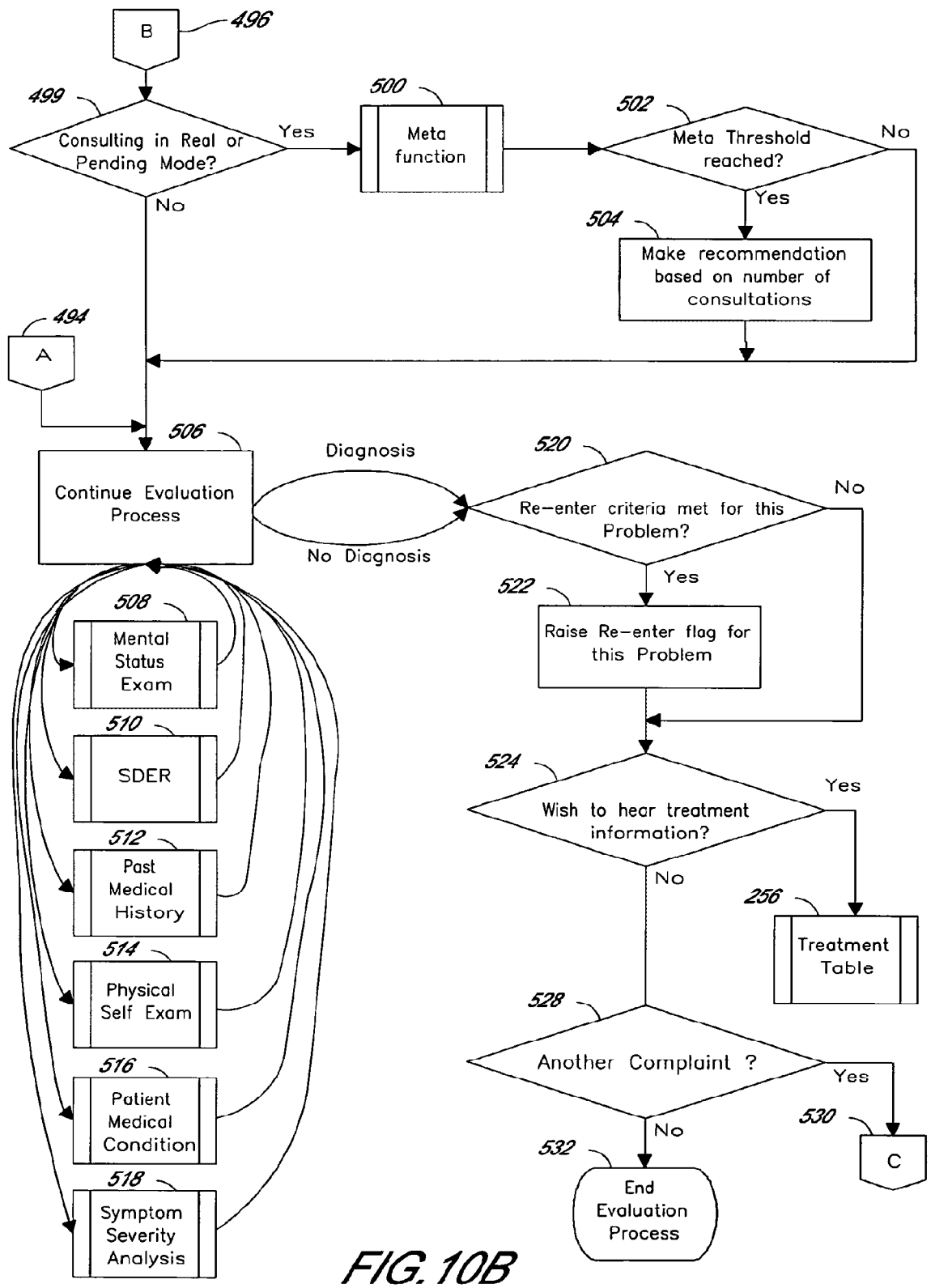

Referring now to FIGS. 10a and 10b, the evaluation process 254 defined in FIG. 7d will be described. This process 254 is called if the patient has selected the Diagnostic System choice in the system selection menu (FIG. 7d, state 344). Beginning at a start state 470, the computer moves to state 471 and recites a identification method menu to request complaint identification. After the initial screening questions (state 306, FIG. 7a) are completed and a medical record (registration function 252) has been opened, the MDATA system 100 asks the patient to describe the complaint. The identification of the patient's problem is one of the most important steps in the evaluation process. The system 100 has built-in safeguards to ensure that the patient understands the questions and that the MDATA system 100 understands the patient's complaint. For example, the system keeps tables of synonyms so that any problem regarding the semantics of a question or a response can be quickly resolved. The complaint may be identified in one of four ways: by anatomic system 472, by cause 476, by alphabetic groups 480 or by catalog number 482.

The easiest and most frequently used way to identify the complaint is by anatomic system, i.e., "what system is your problem in?". Anatomic system 472 refers to basic body systems such as cardiovascular, respiratory, nervous system, digestive, ear/nose/throat, opthalmology, gynecology/obstetrics, urology, blood/hematology, skin, and endocrine. After the patient has identified the anatomic system of their complaint, they are asked a series of "System Screening Questions" at state 473. For each anatomic system, there are some symptoms or combinations of symptoms that, if present, would mandate immediate intervention, such that any delay, even to go any further through the menuing process, could cause harm. For example, if the patient has identified the cardiovascular system as the anatomic system in which his or her complaint lies (i.e., chest pain), the MDATA system 100 will ask the cardiovascular system screening questions. For example, the patient would be asked, "Do you have both pressure in your chest and shortness of breath? If these symptoms are present together, immediate intervention is necessary. With the thrombolytic agents that are available today, time is critical in order to save myocardial cells. Just a few minutes can mean the difference between being able to resuscitate a patient or not.

Therefore, at state 474, the system 100 determines if a serious medical condition exists. If so, the system 100 moves to state 486, plays a message that advises the patient to seek immediate medical attention and ends the evaluation process 254 at a terminal state 488. If it is determined at state 474 that a serious medical condition does not exist, the system 100 proceeds to a complaint menu at state 475 and recites a list of algorithms dealing with the problem that corresponds to the anatomic system selected. The patient then selects an algorithm from the list.

If the patient is not sure of the anatomic system, the system 100 attempts to identify the problem by requesting the cause. Cause 476 refers to a cause for an illness or disease such as trauma, infection, allergy/immune, poisoning, environmental, vascular, mental, genetic, endocrine/metabolic, and tumor. Once the patient has identified what they think is the cause of their problem (e.g., trauma, infection), the MDATA system 100 asks the "Cause Screening Questions" at state 477. These questions are asked to make sure that the patient is not suffering from an immediate life-threatening problem. For example, if infection were chosen as the cause, the system would first rule out the possibility of epiglottitis or meningitis before proceeding. Therefore, at state 478, the system 100 determines if a serious medical condition exists. If so, the system 100 moves to state 486, plays a message that advises the patient to seek immediate medical attention and ends the evaluation process 254 at a terminal state 488. If it is determined at state 478 that a serious medical condition does not exist, the system 100 proceeds to a complaint menu at state 479 and recites a list of algorithms dealing with the problem that corresponds to the cause selected. The patient then selects an algorithm from the list.

Alphabetic groups 480 lists the items in the anatomic system group and the cause group together in alphabetic order. Moving to state 481, the system determines if the selected item is from the cause subgroup of the combined alphabetic groups. If so, the system 100 proceeds to the "Cause Screening Questions" at state 477. If not, the system moves to the "System Screening Questions" at state 473.

Enter Catalog number state 482 refers to the ability of the patient to select and enter an individual medical algorithm from a catalog of medical algorithms listed in the patient guide distributed to all patients. At the completion of state 475, 479, or 482, the complaint has been identified, and the computer 102 proceeds to state 483 wherein a series of "initial" problem screening questions are presented to the patient. There is a different set of problem screening questions for every complaint for which advice is offered.

For the purpose of this discussion, "Headache" will be used as an example to describe how the system approaches the diagnosis of a problem and provides treatment recommendations. As with many problems, there are some causes of headache that require immediate medical attention. Quite often, when a problem is very serious, any delay, even to discuss it further, can adversely affect the patient's outcome. The problem screening questions identify, at a decision state 484, the subset of patients whose headaches may require immediate medical care. If a serious medical condition exists, the patient is advised to seek immediate medical attention at state 486. The computer 102 then ends the evaluation process at state 488 and returns to state 344 in FIG. 7d.

The following is an example of a problem screening question for headache:
ARE YOU CONFUSED, LETHARGIC, OR LESS ORIENTED THAN USUAL?

By asking a question about the patient's level of consciousness, a dilemma has been confronted. What does the MDATA system 100 do about the patient whose problem itself prevents them from appropriately responding to questions or following advice?

There are some conditions that, by their very nature, may prevent patients from answering questions correctly. For this reason, the MDATA system 100 utilizes a "mental status examination" function 508. The mental status examination is a series of questions used to assess the patient's orientation. This function 508 allows the MDATA system 100 to assess the patent's ability to respond to questions and to follow advice. Although only shown in FIG. 10b, the mental status examination function 508 is incorporated into the dialogue of any problem whose presentation could include an altered level of consciousness. Function 508 will be further described in conjunction with FIG. 16.

The MDATA system 100 will, of course, be accessed by patients in whom an altered level of consciousness is not expected based on the problem that the patient has. The system 100 does anticipate the possibility of the patient having an altered level of consciousness in some problems, e.g., when a patient consults the system for striking his or her head, and invokes the mental status exam function 508. However, an intoxicated patient, calling for some other complaint, e.g., a sprained ankle, is one example where the patient may not be able to understand instructions from the system 100. For this reason, the MDATA system also utilizes a "semantic discrepancy evaluator routine" (SDER) function 510. The SDER function provides information to the patient and then, after a predetermined period of time, asks the patient to repeat or select the information. The patient's answer is then evaluated within system 100. If discrepancies are determined, the system automatically invokes the mental status examination function 508. In another embodiment, the system 100 asks the patient for some information in different ways at different times, and then compares the patient's responses to determine if they are consistent. If not, the system automatically invokes the mental status examination function 508. Although only shown in FIG. 10b, the SDER function 510 is embedded throughout system 100, and is randomly evoked by the computer 102. Function 510 will be further described in conjunction with FIG. 17.

Continuing with the headache example at state 483, the MDATA system 100 asks the next problem screening question in order to help exclude the possibility of meningitis, a very serious infection of the central nervous system.
IS BENDING YOUR NECK FORWARD SO THAT YOUR CHIN TOUCHES YOUR CHEST EITHER PAINFUL OR NOT POSSIBLE?

If the answer to this question is "yes", a serious medical condition exists at state 484 and the system 100 instructs the patient to seek immediate medical attention at state 486.

The initial screening questions (state 306, FIG. 7a) and the problem screening questions (state 483) can usually be completed within a minute or so. Once the MDATA system 100 has excluded the causes of headache that require immediate medical attention, the system becomes a little less formal and more conversational in the subsequent states. The examples given, of course, do not represent all the initial or problem screening questions.

If no serious medical condition exists, as determined at state 484, the computer 102 proceeds to a decision state 490 wherein the system 100 identifies those patients who are "re-entering" the system from an earlier consultation. This occurs most frequently when the system 100 needs to monitor a patient's symptom over time, or if the system is initially unable to make a specific diagnosis and would like the patient to re-enter the system again, typically within a few hours. The system sets an internal re-enter flag to identify the situation where a patient is calling again for the same complaint. If the flag is set at state 490, the computer 102 proceeds to state 492 and branches to a re-enter point in the evaluation process depending on which medical algorithm has been evoked. The computer 102 moves via off-page connector A 494 to state 506 (FIG. 10b) to the appropriate re-enter point.

If the re-enter flag is not set, as determined at state 490, the computer 102 moves via off-page connector B 496 to a decision state 499 to determine if the consultation is being performed in Real mode or Pending mode. If not (i.e., the consultation is in Information mode), the computer proceeds to state 506 to continue the evaluation process. If the consultation is in Real or Pending mode, the computer 102 calls a "meta" function 500 wherein patients are subjected to several "meta" analyses. This concept will be explained in conjunction with FIG. 11, but, in general, it refers to the system's ability to evaluate the patient's present problem in the context of their past use of the system. The Meta function 500 matches various parameters against a predetermined meta threshold. When the MDATA system 100 opens a patient's consultation history file in database 262 (FIG. 6), it calculates how many times the patient has consulted the system for the same complaint. For each problem, the MDATA system 100 allows a specified number of system consultations, per unit of time, before it takes action. If the meta threshold is reached, as determined at a decision state 502, the MDATA system 100 makes a recommendation based on this fact alone at state 504. For example, let us assume that the threshold was set at five headaches in two months. If the patient consulted the MDATA system 100 for headache more than four times in two months, the threshold would be reached and the system would make an appropriate recommendation. The threshold, of course, is different for each complaint, and may be modified by a set of sensitivity factors that will be described hereinbelow. Alternately, the system 100 uses a time density ratio (TDR) calculated by the meta function 500 to determine if a recommendation should be given to the patient.

At the completion of state 504, or if the meta threshold was not reached at state 502, the computer 102 proceeds to state 506 to continue the evaluation process. State 506 includes a medical algorithm as selected by the patient in states 475, 479, or 482. As a representative example, the Microfiche Appendix contains an algorithm for Headache and includes a Headache node map with the script or description of each node having a play list. A second example node map and associated script for Convulsion or Seizure, including meta and past medical history aspects, is also included in the Microfiche Appendix. Although not necessarily a complete list, other types of medical algorithms include: Chest Pain, Heatstroke, Altered Level of Consciousness, Tremor, Dizziness, Irregular Heartbeat, Fainting, Shortness of Breath, Chest Injury, Depression, Head Injury, Cough, Croup, High Blood Pressure, Hyperventilation, Numbness, Wheezing, Inhalation Injury, and Strokes. In addition to meta and past medical history functionality, at least some of the listed medical algorithms rely upon knowledge of age and/or sex of the patient as provided in the presently described system 100 at time of registration (see FIGS. 9a and 13a).

Depending on the medical algorithm and the exact patient condition, one or more auxiliary functions may be called by state 506 as follows: the mental status examination function 508, the SDER function 510, a past medical history function 512, a physical self examination function 514, a patient medical condition function 516, and a symptom severity analysis function 518. These functions will be described hereinbelow.

Returning to the headache example, after the meta analyses (function 500) are completed, the MDATA system 100 assesses the severity of the patient's headache on a one-to-ten scale. The importance of this purely subjective quantization of the symptom's severity will become apparent later in this description.

Although the MDATA system's paradigm is fundamentally an algorithmic one, the underlying logic of the diagnostic process for headache will be described. The MDATA system 100 begins the diagnostic process for headache by referring to three lists stored internally in the computer 102.

The first list is a ranking of the most common causes of headache in the general population. The most common cause is ranked first, the second most common is ranked second, and so on. In other words, the first list ranks all the causes of headache in the general population in decreasing frequency of occurrence.

The second list is a ranking of the various causes of headache according to the seriousness of the underlying cause. The more serious causes are positioned toward the top of the list, the less serious toward the bottom. For example, meningitis, brain tumor, and subarachnoid hemorrhage would be the top three causes on the second list.

The third list is quite similar to the second list. It ranks the causes of headache according to the rapidity with which intervention is necessary. The causes of headache that require immediate intervention, such as meningitis and subarachnoid hemorrhage, are toward the top. The problem screening questions (state 483) were developed from this list.

During the evaluation process 254, the MDATA system 100 asks the patient a series of "diagnostic screening questions." From the answers to these questions, along with any physical signs elicited from the patient (from function 514), under the direction of the MDATA system 100, the system establishes the most likely cause of the patient's headache.

The following are examples of diagnostic screening questions for headache:
  DO YOU EXPERIENCE MORE THAN ONE KIND OF HEADACHE?
  DO YOU, OR DOES ANYONE ELSE, KNOW THAT YOU ARE GOING TO GET A HEADACHE BEFORE THE ACTUAL PAIN BEGINS?
  DO YOUR HEADACHES FREQUENTLY WAKE YOU UP AT NIGHT?
  DO YOUR HEADACHES USUALLY BEGIN SUDDENLY?

Based upon the answers to the diagnostic screening questions, the MDATA system 100 reorders the first list. The first list then becomes a list of the possible causes of headache in decreasing levels of probability in the patient seeking consultation. The first list is now patient specific. If the MDATA system 100 concludes that migraine is the most likely cause of the patient's headache, then migraine will now be ranked at the top of the first list.

The MDATA system 100 is knowledgeable about the difference between classic, common, and all other variants of migraine, but for this discussion the general term "migraine" will be used. After reordering the first list and placing migraine at the top, the MDATA system 100 then asks several questions related specifically to migraine headaches. These are called the "migraine screening questions." The probability that the patient actually has a migraine headache is calculated from the answers to these questions. Each cause of headache has its own set of screening questions, physical examination signs, and, if the patient has the MDATA system's Home Diagnostic and Treatment Kit, appropriate laboratory tests.

The following are examples of migraine screening questions:

IS EITHER NAUSEA OR VOMITING ASSOCIATED WITH YOUR HEADACHE?
    ARE VISUAL DISTURBANCES ASSOCIATED WITH YOUR HEADACHE?

After obtaining the answers to the migraine screening questions, if the probability that the patient is suffering from a migraine headache does not reach an established threshold, the next cause of headache on the reordered first list is considered and pursued as a diagnosis.

If the probability of having a migraine headache does reach the threshold, the MDATA system 100 asks the patient several more questions designed to confirm the presence of migraine, given the fact that the system has already determined that it is the most likely diagnosis. These are called the "migraine confirmation questions." Just as each cause of headache has a set of screening questions, each cause of headache also has a set of confirmation questions.

The following are examples of migraine confirmation questions:

DOES ANYONE WHO IS RELATED TO YOU BY BLOOD HAVE MIGRAINE HEADACHES?
    WHEN YOU HAVE A HEADACHE DO YOU FEEL MORE LIKE LYING DOWN OR WALKING AROUND?

From the answers to the migraine confirmation questions, the MDATA system 100 calculates the probability of confirmation of migraine. In Bayes' terms (which refer to the probability of certainty of a diagnosis) this is called a "conditional probability."

If the probability of migraine headaches reaches threshold, but the probability of confirmation of migraine does not reach threshold, then, as mentioned, the system pursues the next diagnostic cause of headache on the patient specific list.

If the probability of the second cause of headache (say cluster) reaches threshold, then the "cluster confirmation questions" are asked. If they reach threshold, then again the serious causes of headache are excluded as a diagnosis.

The MDATA system 100 stores the scores of all the screening and confirmation questions in what are called "session memory variables" that are installed in the symbol table. It is, in part, these scores that are then used to determine the probability of one diagnosis versus another.

For example, if the answers to the cluster confirmation questions do not reach threshold, then the scores of the screening and confirmation questions of migraine and cluster are compared to see which cause is the more probable.

Whichever has the higher score, or exceeds the other by a predetermined threshold, is then assumed to be the more probable cause. The list is, if necessary, again reordered. This time it becomes the final diagnostic list which is a list of differential diagnoses in decreasing levels of probability for this patient.

All of the headache scoring thresholds are modified or modulated by a series of sensitivity factors as are all aspects of the system in which scalar thresholds are used. The sensitivity factors are discussed hereinbelow in section XVIII. For example, if it was found that a subset of patients in which the diagnosis of meningitis was not being made as early as it should be, then the sensitivity factor modifying the temperature threshold could be decreased so that now, a patient with a lower temperature would be instructed to seek an immediate evaluation.

Before discussing the results with the patient, however, the MDATA system 100 must again rule out the serious causes of headache. The problem screening questions have already filtered out those patients who have a serious cause of headache, such as meningitis, that requires immediate medical intervention.

The MDATA system 100 now proceeds to eliminate those causes of headache that, although serious, do not require immediate medical attention. For example, although a brain tumor is a serious cause of headache, it is not as immediately life threatening as meningitis or subarachnoid hemorrhage. To accomplish this task, the MDATA system 100 sequentially analyzes the serious causes of headache that are located at the top of the second list. The MDATA system 100 again asks the patient the set of screening questions associated with each of the serious causes of headache. This time, however, the MDATA system 100 makes sure that the probability of having any of the serious causes of headache is sufficiently low in order to exclude them from diagnostic consideration. Only after this is accomplished will the system discuss its conclusion and recommendations with the patient.

The discussion that the MDATA system would have with the migraine headache patient would include the following:

Its diagnostic impression, or its diagnostic impressions in decreasing levels of probability.
    Its estimate of the level of probability of migraine.
    Whether or not the system feels it has excluded the serious causes of headache to a level of certainty that satisfies the system.
    What tests, if any, should be obtained to confirm or exclude a diagnosis.
    How soon to see a physician.
    What kind of physician to see (e.g., family practitioner, internist, or neurologist).
    What kind of information to bring to the physician when a consultation is obtained.
    Questions to ask the physician.
    The latest treatment for migraine.

Even if the MDATA system 100 cannot determine with sufficient certainty what is causing the headache, it can still provide patients with valuable information and advice. For example, the patient may be told the following:

"At this time, the MDATA system is unable to pinpoint a particular cause of your headache with the degree of certainty required to make specific recommendations. The MDATA system, however, suggests a consultation with a neurologist. You can either call your family practitioner or internist and ask for a referral.

"While you are waiting to be seen by the neurologist, there are many things that you can do in order to help the physician diagnose your headache. Many headache experts have found that a record of when their patients' headaches occur and how bad they are is very helpful in finding both the cause of the headache as well as the best treatment.

"In order to assist you, the MDATA system will send you a blank calendar on which you can record the time and severity of your headaches. In addition, there is space for you to record what seems to bring on the headaches, makes them worse, or makes them better. The MDATA system will also send you a questionnaire to fill out and give to your doctor, containing a list of questions asked by some of the world's leading headache experts when they are trying to arrive at a diagnosis."

A full set of instructions will be provided.

The MDATA system is able to customize the information given to patients to accommodate the individual needs of a sponsoring agency or group such as a Health Maintenance Organization (HMO) or a Managed Care Plan. For example, if the system finds that the patient should see a physician, the MDATA system can determine from a patient's medical record whether they have an established relationship with an appropriate specialist. If they do, the specialist's name and phone number, or a list of participating specialists for their HMO or Managed Care Plan and any specific instructions, will be given to the patient with the recommendation to make an appointment within a specific time frame.

At the conclusion of state 506, the system may or may not have a reasonably certain diagnosis available. For example, the headache algorithm provides a diagnosis of migraine in response to a particular set of patient symptoms. In situations where the MDATA system 100 cannot determine with sufficient certainty what is causing a particular problem (no diagnosis) or in a situation where a diagnosis is available but additional information is desirable, e.g., to determine a trend, a re-enter flag may be set by the system 100. At a decision state 520, the computer 102 determines if re-enter criteria are met for the current algorithm and patient situation. If so, the computer sets the re-enter flag at state 522 for this problem so a subsequent telephone consultation by the patient will allow for additional information to be added to the patient record by the system in full knowledge of the previous call. This additional information may yield a better diagnosis.

If the re-enter criteria were not met, as determined at state 520, the computer 102 proceeds to a decision state 524 to determine if the patient desires to hear treatment information for the current problem. If so, the computer 102 calls the treatment table process 256, which will be described in conjunction with FIGS. 22 and 23. If the patient does not wish to hear treatment information at this time, the computer 102 advances to a decision state 528 to determine if the patient would like to investigate another complaint through the evaluation process 254. If so, the computer 102 moves via off-page connector C 530 to state 471 on FIG. 10a to repeat the process 254. However, if the patient does not wish to pursue another complaint, the computer returns at state 532 to the top level flow (FIG. 7d).

XI. The Meta Function

Figure 11A:
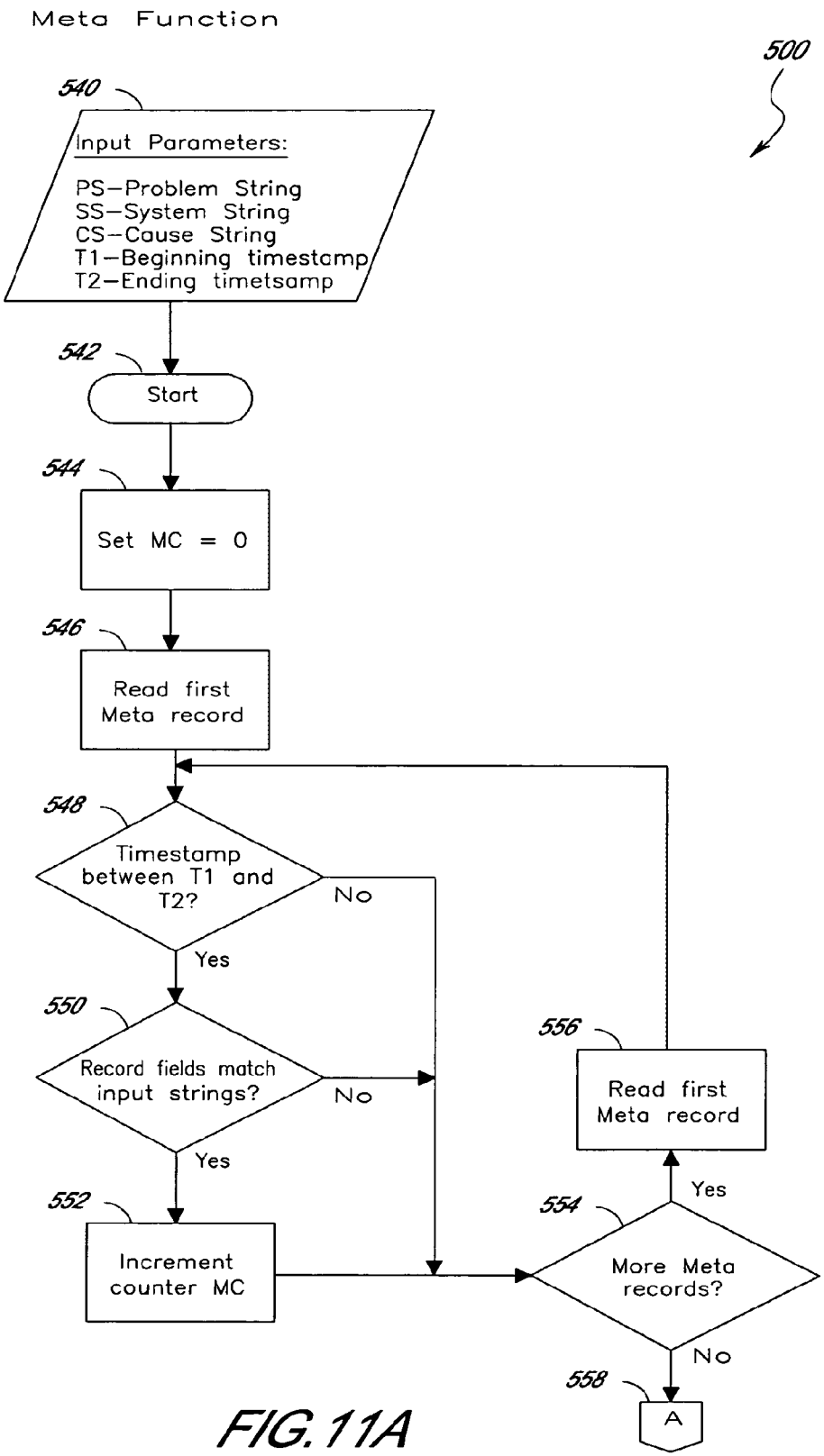
FIGS. 11a and 11b are a flow diagram of the meta function 500 defined in FIG. 10b.
Figure 11B:
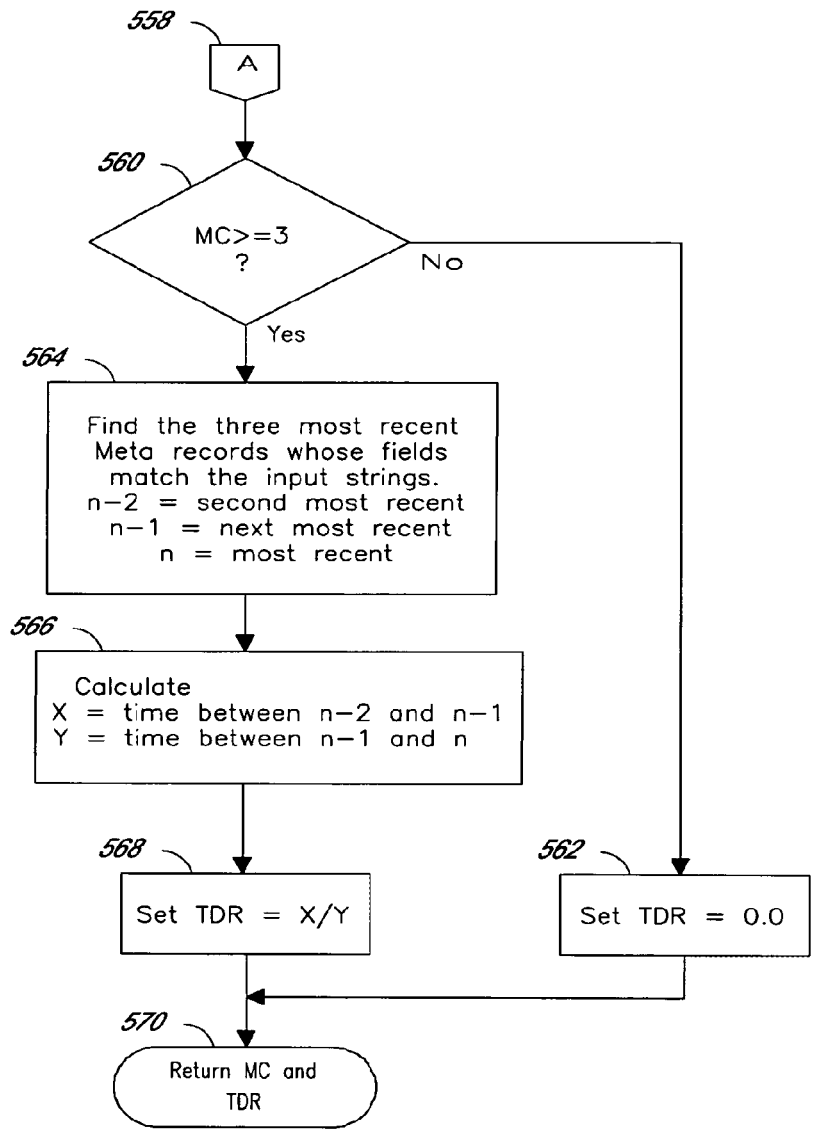

Referring now to FIGS. 11a and 11b, the meta function 500 defined in FIG. 10b will be described. One of the many ways the MDATA system 100 is qualitatively different from prior ways of providing medical advice is in its use of the "meta function." As mentioned earlier, "meta" refers to the system's ability to evaluate the patient's present problem in the context of his or her past use of the system. The meta function allows the system 100 to make an inference based upon the number and frequency of previous patient consultations (or, "medical complaints") and the system's previous diagnostic assessments. Every patient who has previously used the MDATA system 100 undergoes the meta analysis.

Input Parameters

The meta function 500 has five input parameters listed at state 540 as follows:

i. Problem String (PS)— a four character alphanumeric string indicating the patient's complaint. The first character of this string is taken from the Systems column of Table 2. For example, 'N' denotes the nervous system. The second through fourth characters identify an individual complaint, e.g., "NHDA" identifies headache. Other examples:

| CCHP | Chest Pain |
| NINJ | Head injury |
| RINH | Inhalation of toxic fumes | ii. System String (SS)— a four character alphanumeric string that indicates the affected anatomic system. The first character is taken from the Systems column of Table 2. The second through fourth characters are encoded with subsystem identification, or filled with the '*' wildcard character. For example, "N***" will match all cases that involve the nervous system.

iii. Cause String (CS)—a ten character alphanumeric string that indicates the cause of the patient's complaint. The first character is taken from the Causes column of Table 2. The second through tenth characters are filled in as needed to more closely specify the cause of interest. A very broad example is "I*********" which denotes any infection. Other examples which illustrate how the cause string can become very specific:

IV******** Viral infection

B********* Bacterial infection

IBN******* Gram negative bacterial infection

IBNM****** Meningococcal gram negative bacterial infection iv. Beginning Time ($T_1$)—a timestamp value which indicates the date and time to be used for the beginning of the time window under consideration.

v. Ending Time ($T_2$)—a timestamp value which indicates the date and time to be used for the end of the time window.

Table 2 lists code letters used as the first letter of the meta string parameter:

TABLE 2

| Causes | | Systems | |
|---|---|---|---|
| A | allergy | B | bones/orthopedics |
| E | environment | C | cardiology |
| I | infection | D | gastro-intestinal |
| M | mental | G | gynecology |
| P | poison | H | hematology (blood) |
| T | trauma | L | larynx (ENT) |
| V | vascular | N | nervous |
| X | genetic (chromosomal) | O | opthamology |
| Y | nutritional/metabolic/endocrine | R | respiratory |
| Z | tumor (cancer) | S | skin |
| | | U | urology |

A set of meta function analyses involves the identification of trends in the patient's medical history. For example, if a patient went to his or her doctor with a history of gradually worsening headaches (either more painful, more frequent, or both) the physician would consider this worsening trend in his or her management of the case. The MDATA system 100 also does this.

Meta Analysis

The algorithm author passes input parameters to the meta function by using the keyword Meta, followed by the input parameters enclosed in parentheses. The format for the meta function is:

Meta(PS, SS, CS, $T_1$, $T_2$)

Two types of analysis are performed by the meta function:
i. Pattern Matching
ii. Time density 1. Pattern Matching In pattern matching analysis, the meta function compares the input strings with the record fields in the patient's consultation history database 262. The use of the '*' wildcard character in the input string will cause the meta function to ignore the corresponding character position in the record field, thereby enabling the meta function to examine only the fields of interest. By providing input strings that are either general or specific, the fields of interest for analysis are selected. For example, Meta("NHDA", "**", "********", $T_1$, $T_2$)

will cause the meta function to only consider past consultations for the problem of headache, regardless of the anatomic system and cause involved.

Through the use of a common syntax, the meta process supports four types or modes of pattern matching analysis, shown here through examples:

(a) Problem analysis:
Meta("NHDA", "**", "********", 06/01/93, 12/31/93)

Here the meta function will find the number of complaints of headaches that occurred between Jun. 1, 1993 and Dec. 31, 1993.

(b) Anatomic System analysis:
Meta("**", "D*", "**********", 06/01/93, 12/31/93)

Here the meta function will find the number of complaints involving the gastrointestinal system between Jun. 1, 1993 and Dec. 31, 1993. For example, if a patient consulted the MDATA system 100 once for abdominal pain, once for vomiting, and once for diarrhea, but each on a different occasion, the system would recognize that these are all problems involving the gastrointestinal tract.

(c) Cause analysis:
Meta("**", "", "IB*******", 06/01/93, 12/31/93)

Here the meta function will find the number of complaints that were found to be caused by bacterial infection between Jun. 1, 1993 and Dec. 31, 1993. The problems (complaints) caused by bacterial infection could be in different parts of the body.

(d) Combination analysis:
Meta("NHDA", "**", "I*******", 06/01/93, 12/31/93)

Here the meta function will find the number of complaints of headache that were found to be caused by infection between Jun. 1, 1993 and Dec. 31, 1993.

2. Time Density

If the pattern matching analysis finds at least three matching records in the patient's consultation history database 262, then the meta function performs a time density analysis. Time density refers to the amount of time between each consultation. If the amount of time between consultations is getting shorter, then the frequency of consultation suggests that the nature of the complaint is getting worse. Time density analysis reveals when a problem is getting better, and when it is getting worse.

Time density analysis uses the meta records that matched the pattern matching criteria. The computer designates the most recent meta record 'n', the next most recent is record 'n−1', and the second most recent is record 'n−2'. The time stamp of each meta record is examined, and two time difference values, X and Y, are determined according to the formula:

$X$=time difference $(n-2, n-1)$ $Y$=time difference $(n-1, n)$

The ratio of these time differences produces the time density ratio (TDR):

Time Density Ratio=$X/Y$

The significance of the time density ratio value can be seen through the following examples:

Example 1

Time Between Consultations is the Same

| Consultation | Date of Consultation |
|---|---|
| n − 2 | Jun. 01, 1993 |
| n − 1 | Jun. 08, 1993 |
| n | Jun. 15, 1993 |

Calculate:

$X$=time difference (06/01/93,06/08/93)=7 days $Y$=time difference (06/29/93,06/15/93)=7 days Time Density Ratio=7 days/7 days=1.0

Example 2

Time Between Consultations is Getting Shorter

| Consultation | Date of Consultation |
|---|---|
| n − 2 | Jun. 01, 1993 |
| n − 1 | Jun. 22, 1993 |
| n | Jun. 29, 1993 |

Calculate:

$X$=time difference (06/01/93,06/22/93)=21 days $Y$=time difference (06/29/93,06/22/93)=7 days Time Density Ratio=21 days/7 days=3.0

When consultations are occurring at even intervals, then the TDR value is close to unity. If the frequency of consultations is decreasing, then the TDR value will be less than 1.0. This would be typical of a problem that is resolving itself. If the frequency of consultations increases, then the TDR value will be greater than one. In the second example, the TDR value of 3.0 indicates a consultation rate increase of three times during the analysis period. This would be typical of a problem that is rapidly getting worse.

Return Values

After the meta function returns, two local memory variables are installed in the symbol table and contain the results of the meta analysis:

i. Match Counter (MC)— an integer that contains the number of meta string matches found within the time window.

ii. Time Density Ratio (TDR)— a floating point value that expresses whether the frequency of meta string matches is increasing or decreasing.

After calling the meta function, the algorithm author can then make decisions based upon the values returned in these two memory variables.

For example:

Meta("NHDA", "**", "********", 06/01/93, 12/31/93)

If MC>=3 then 100 else 101

The meta function counts the number of complaints of headache between Jun. 1, 1993 and Dec. 31, 1993. If the number of complaints found (MC) is greater than or equal to 3, then the evaluation process branches to node 100; otherwise it branches to node 101.

Another example:

Meta("**", "", "I*******", 06/01/93, 12/31/93)

If TDR >=2.0 then 200 else 201

The meta function is invoked to count the number of diagnoses attributed to a cause of infection. If the infection caused diagnoses found have a time density ratio greater than or equal to 2.0, then the evaluation process branches to node 200; otherwise it branches to node 201.

Referring again to FIG. 11*a*, the meta function 500 initializes at state 540 by popping the input parameters off the run-time stack and storing them in local memory variables: PS for problem string, SS for anatomic system string, CS for cause string, $T_1$ for the beginning date and $T_2$ for the ending date. After the start state 542, the computer moves to state 544 and initializes the pattern match counter to zero.

The computer 102 then moves to state 546 wherein it begins the pattern matching analysis. The computer 102 reads the first meta record in the patient's consultation history database 262 and moves to a decision state 548 wherein it examines the record's timestamp. If the timestamp falls within the time window established by the input parameters $T_1$ and $T_2$, then the computer will move to state 550; otherwise it moves to state 554. At state 550, the computer 102 compares the contents of the meta record problem field with the input string PS, the meta record anatomic system field with the input string SS and the meta record cause field with the input string CS. If all these fields match the respective input strings, then the computer moves to state 552 wherein the match counter MC is incremented, and then the computer moves to state 554. If there is any mismatch between a meta record field and its respective input string, then the computer moves to state 554 and does not increment MC.

At decision state 554, the computer 102 determines if there are more meta records to process. If so, the computer 102 moves to state 556 wherein it reads the next record and then moves back to state 548 to perform the time window determination. The meta function iterates through this pattern matching until all of the meta records have been read. When there are no more meta records to be processed, the computer moves through off-page connector A 558 to a decision state 560 on FIG. 11*b* wherein a determination is made if the value of the match counter MC is greater than or equal to 3. If so, then the computer moves to state 564 wherein it begins the time density analysis.

At state 564, the computer 102 locates the three most recent meta records whose fields matched the input strings. The computer designates the most recent meta record 'n', the next most recent is record 'n−1', and the second most recent is record 'n−2'. The computer then moves to state 566 wherein it calculates X, the time difference between the timestamps of records n−2 and n−1, and Y, the time difference between records n−1 and n. The computer 102 then moves to state 568 wherein it calculates the time density ratio (TDR) as the time X divided by time Y.

If the computer 102 determined at state 560 that there were less than three matches, then it would move to state 562 wherein it sets the value of the time density ratio (TDR) to 0.0, which indicates that the time density analysis could not be performed. At the completion of establishing the value of TDR at either state 562 or 568, the computer 102 moves to terminal state 570 wherein the meta process terminates, returns the match counter MC and the time density ratio TDR, and returns control to the evaluation process 254 (FIG. 10).

The interaction of the meta analyses for cause and for anatomic system can be conceptualized by means of a simple geometric metaphor. Consider a two dimensional array in which the causes of disease (trauma, infection, allergy/immune, and so forth) are placed on the "Y" axis, or ordinate, and the anatomic systems of the body (cardiac, respiratory, nervous system, and so forth) are placed on the "X" axis or abscissa. Disease then can be represented by, or is produced at, the intersection of the lines drawn from the applicable cause and the anatomic system.

As a very simple illustration, consider the two-dimensional array shown in Table 3 below:

TABLE 3

| | Cardiac | Respiratory | Nervous | ... | Dermatologic |
|---|---|---|---|---|---|
| Trauma | | | | | |
| Infection | | | • | | |
| Allergy | | | | | |
| . | | | | | |
| . | | | | | |
| . | | | | | |
| Tumor | | | | | |

The array of Table 3 shows an infection in the central nervous system represented at the intersection of the cause of disease (infection) and the anatomic system involved (the nervous system).

Of course, each cause of disease can be further divided into subcauses. For example, infection would be broken down (or subdivided) into bacterial and viral, and bacterial would be further broken down into gram positive and gram negative, and gram positive would be further yet broken down into streptococcus, and so on. The anatomic systems could be broken down in a similar way.

As a patient uses the system 100, and as the meta analyses for cause and for anatomic system attribute causes to disease processes and record the anatomic systems involved, a three-dimensional cube (a "meta cube") is produced composed of these stacked two-dimensional arrays. The "Z" axis coordinate of each layer is the time of the patient's consultation obtained from the system clock (i.e., the moment that the actual intersection of the cause and anatomic system occurs indicating the diagnosis).

The "meta cube" then represents a summation of the patient's interaction with the system 100 through time. Although much of the patient's past history is stored using ICD-9-CM codes as well as conventional text strings in fields of the patient's medical record, the "meta cube" technique allows very useful analyses to be done.

Using the same modeling metaphor, the "Z" axis coordinate can be used to represent the practice of medicine. Here the "Z" coordinate is again time, but in this representation, time refers to a spectrum of ages from pediatrics to geriatrics. Thus, each coronal plane represents specialties by time, e.g., pediatrics, adolescent medicine, adult, geriatric. A vertical plane describes a specialty by anatomic site, such as neurology or cardiology, while a horizontal plane describes a specialty which practice is bounded (subsumed) by (on) cause, such as oncology or infectious disease. To further this metaphor, the rapidity with which intervention is necessary could be a fourth dimension of the model, and the frequency of an occurrence of a disease is the fifth dimension. Ethical and moral responsibility could be a sixth dimension of the model.

Node Map Traverse Analysis

The MDATA system 100 uses a "neural net emulator" program to determine if patterns produced by patients, as they traverse down the nodes (creating "node tracks" of the algorithms in the course of a consultation, may be early predictors of disease. Somewhat like the "meta cube," the "node tracks" can be superimposed, rather than stacked, upon one another to create a two-dimensional array. This time, however, the pattern produced represents the sum of the patient's previous consultations. In the MDATA system 100, this is called a "node track traverse analysis."

For example, the MDATA system 100 may discover that the pattern that is produced when a patient consults the system, at different times, for episodes of diarrhea, cough, and oral candidiasis may be predictive of AIDS. Or, that the pattern produced when a patient consults the system for increased frequency of urination and weight loss may be predictive of diabetes mellitus.

XII. Mental Status Examination

Figure 16A:
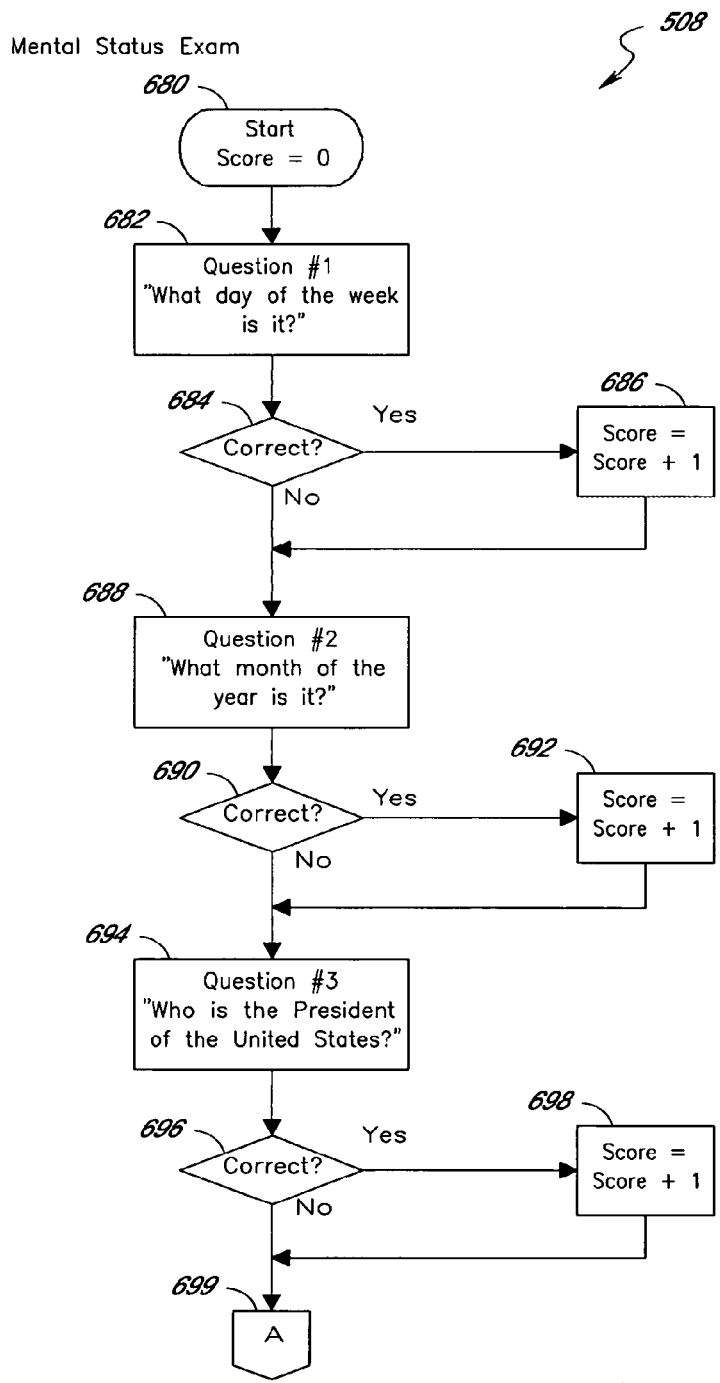
FIGS. 16a and 16b are a flow diagram of the mental status examination function 508 defined in FIG. 10b.
Figure 16B:
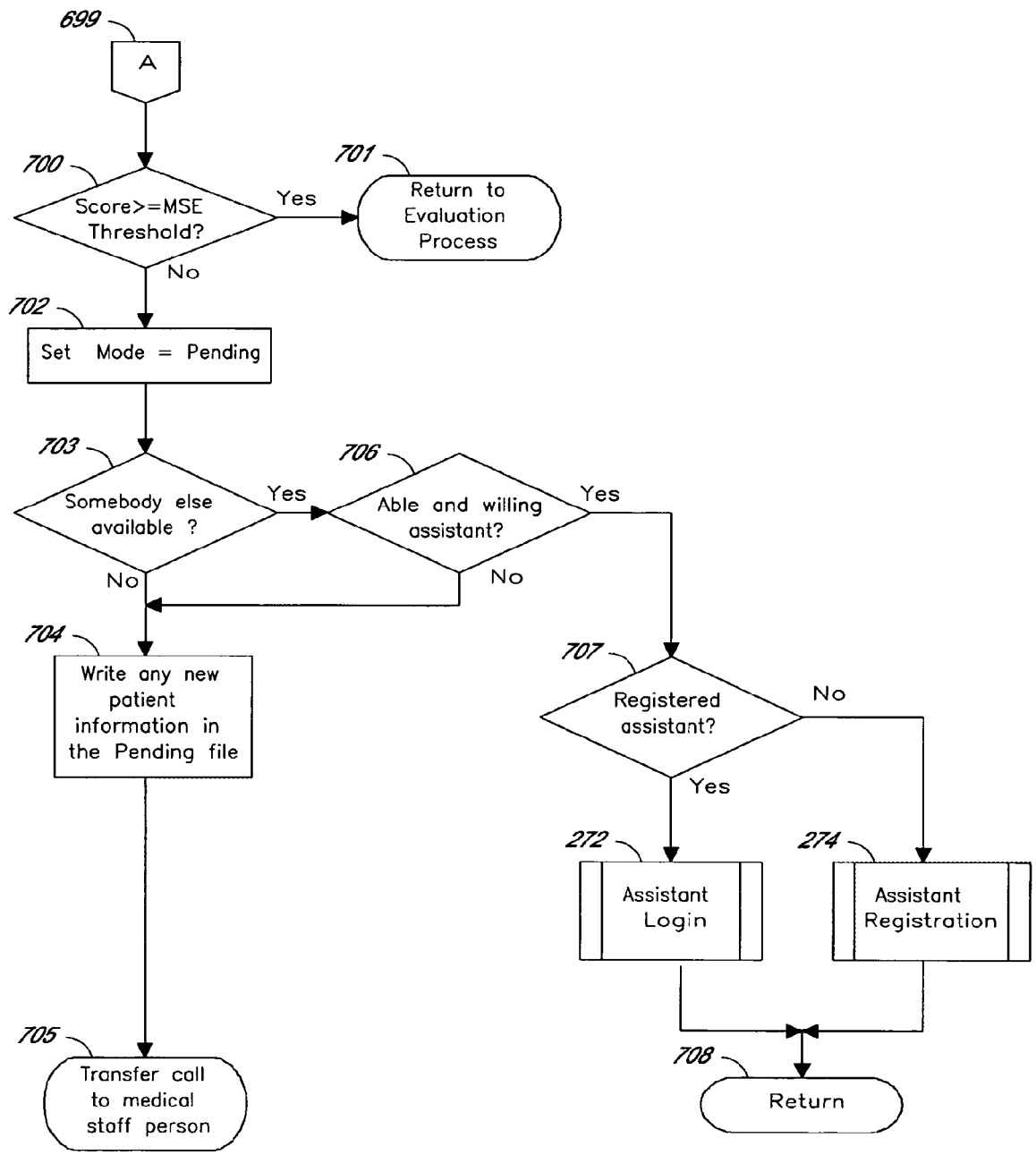

Referring to FIGS. 16a and 16b, the mental status examination function 508 defined in FIG. 10b will be described. The mental status examination is a series of questions used to assess the patient's orientation that allows the system 100 to determine the patent's ability to respond to questions and to follow advice. The examination is automatically incorporated into the dialogue of any problem whose presentation could include an altered level of consciousness. If an operator or nurse monitoring a telephone consultation at any time feels there may be a problem with the caller's ability to understand or respond to questions, the mental status examination may also be manually invoked.

If the MDATA system 100 determines that the patient is not sufficiently oriented based on the results of the mental status examination, the system 100 will ask to speak to someone other than the patient. If no one else is available, the MDATA system 100 can contact the emergency medical services system in the patient's area if the system knows the patient's present geographic position.

Beginning at a start state 680 of FIG. 16a, the computer 102 initializes the value of a variable Score to be zero. Moving to state 682, the computer asks the patient Question #1. In the presently preferred embodiment, the question is "what day of the week is it?" If the person answers the question correctly, as determined by a decision state 684, the computer 102 increments the value of Score by one. After Score is incremented or if the patient did not answer the first question correctly, the computer 102 moves to state 688 wherein the computer 102 asks the patient Question #2. In the presently preferred embodiment, the question is "what month of the year is it?" If the person answers the question correctly, as determined by a decision state 690, the computer 102 increments the value of Score by one. After Score is incremented or if the patient did not answer the second question correctly, the computer 102 moves to state 694 wherein the computer 102 asks the patient Question #3. In the presently preferred embodiment, the question is "who is the President of the United States?" If the person answers the question correctly, as determined by a decision state 696, the computer increments the value of Score by one. After Score is incremented at state 698 or if the patient did not answer the third question correctly, the computer 102 moves through off-page connector A 699 to a decision state 700 on FIG. 16b.

At decision state 700, the computer 102 compares the score to the mental status exam threshold at a decision state 700. If the score meets or exceeds the threshold, then the mental status exam returns to the evaluation process at state 701 and the diagnostic evaluation continues. If the score does not reach or exceed the threshold value, the computer 102 moves to state 702 wherein the operating mode flag is set to Pending. The MDATA system 100 will then ask, at a decision state 703, if someone else is available to continue the consultation. If no one else is available, any new information gathered up to this point in the session is saved to Pending file 269 at state 704 and then, at state 705, the telephone call with the patient is transferred to a medical staff person. If someone else is available, as determined at state 703, and is able and willing to continue the evaluation process of the patient, as determined at state 706, the computer 102 asks the person if he or she is a registered assistant at state 707. If the person responds "yes", the computer 102 invokes the assistant login process 272 at start state 940 on FIG. 12a. If the person is not a registered assistant, the computer 102 invokes the assistant registration process 274 at start state 1050 on FIG. 14a. After assistant registration or login, the computer 102 moves to terminal state 708 wherein the mental status examination process terminates and the evaluation process 254 resumes. At the end of the evaluation process 254, any new information gathered during the session will be written to the patient's past medical history file at state 348 or to pending file 269 at state 347 on FIG. 7d, depending on whether the session continued in real or pending mode. In the presently preferred embodiment, the value of Score could be zero, one, two, or three. Of course, in other embodiments, different questions to be asked of the patient may be utilized in the mental status exam function 508.

XIII. Semantic Discrepancy Evaluator Routine

Figure 17:
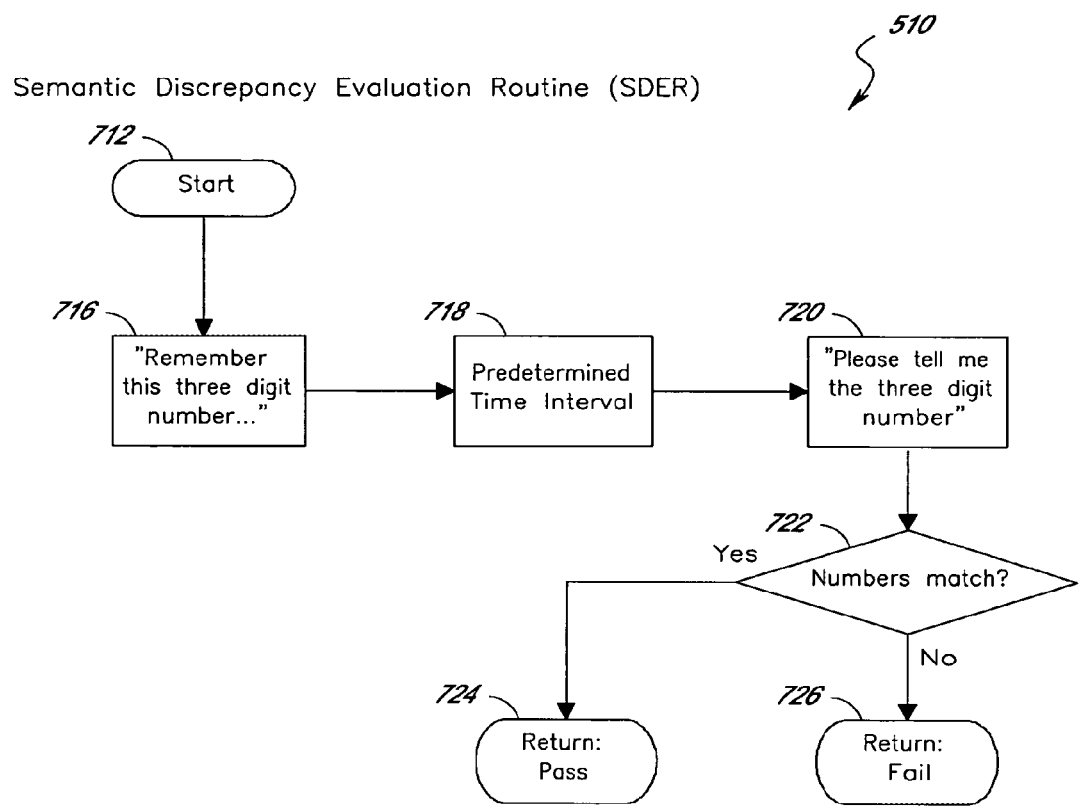
FIG. 17 is a flow diagram of the semantic discrepancy evaluator routine (SDER) 510 defined in FIG. 10b.

Referring to FIG. 17, the semantic discrepancy evaluator routine (SDER) 510 defined in FIG. 10b will be described. The SDER 510 uses one or more questions that ask for the same information at different times, and in other embodiments, in different ways. The answers given by the patient are then compared within the system 100 to help determine the mental status of the patient.

Beginning at a start state 712, the computer 102 moves to state 716 and recites a message to the patient. In the presently preferred embodiment, the message is "remember this three digit number . . . NUMBER", where the computer generates a random three digit number (i.e., in the range 100 to 999 inclusive) as NUMBER which is kept in a session memory variable.

Then, after a predetermined time interval at state 718, the computer 102 moves to state 720 and recites a request of the patient. In the presently preferred embodiment, the request is "please tell me the three digit number." The computer 102 then compares the number given by the patient in response to state 720 against the NUMBER kept in the memory variable at a decision state 722. If the numbers match, the computer 102 returns at state 724 with a status of pass to the evaluation process (FIG. 10b). If the numbers do not match, the computer 102 returns at state 726 with a status of fail to the evaluation process. In the presently preferred embodiment, if the return status of the SDER 510 is "fail", the evaluation process 254 automatically invokes the mental status examination function 508.

XIV. Past Medical History Routine

Figure 18:
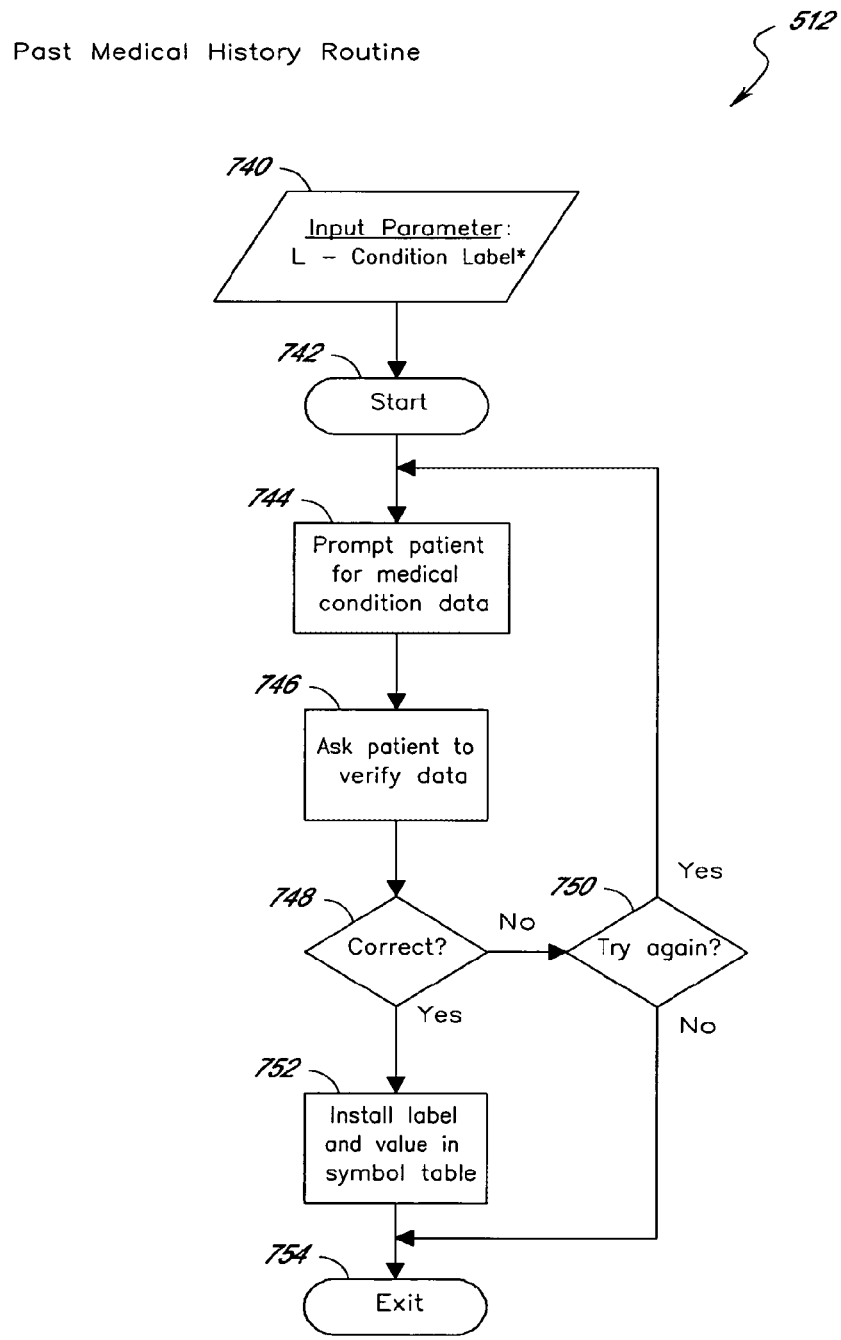
FIG. 18 is a flow diagram of the past medical history routine 512 defined in FIG. 10b.

Referring to FIG. 18, the Past Medical History Routine (PMHR) 512 defined in FIG. 10b will be described. The contents of a patient's past medical history file, which is part of the PMH database 268, are loaded to the symbol table when the patient logs in to the system 100. During the evaluation process 254, a TEST is performed by the computer 102 before a particular medical algorithm is initiated to verify that necessary items are present in the symbol table. The effect of a negative TEST result is that the system 100 prompts the patient to provide the missing past medical history information via the PMHR 512.

The PMHR 512 uses an input parameter "condition label" (L) as indicated at State 740. The "Condition label" is unique, e.g., PMHRLTB1 corresponds to the first PMH object tested in the croup (RLTB) algorithm: diagnosis for croup in children. The label is passed so that PMHR 512 knows what questions to ask. The ability of the system 100 to ask a past medical history question in the middle of the evaluation process 254 is a feature that saves the patient from having to answer the entire PMH questionnaire during the registration process. The Boolean result, or scalar value, is stored in the symbol table under this label (PMHRLTB1), and the algorithm can use it in decision making, e.g., If PMHRLTB1=True Then 4310 Else 4320.

Beginning at a start state 742, the computer 102 moves to state 744 and prompts the patient for the missing medical condition data. Moving to state 746, the computer 102 repeats the information provided at state 744 and asks the patient if the repeated information is correct. Moving to a decision state 748, the patient responds by indicating whether the repeated information is correct. If the data is not correct, the computer 102 proceeds to state 750 to determine if the patient would like to attempt the data entry step again. If so, the computer 102 loops back to state 744 and prompts the patient for the data again. If not, the computer 102 returns at state 754 to the evaluation process (FIG. 10b).

If the newly-entered data is correct, as determined at state 748, the computer 102 advances to state 752 and installs the condition label (L) and the data value in the symbol table for the patient. The computer 102 then returns at state 754 to the evaluation process 254.

XV. Physical Self Examination

Figure 19:
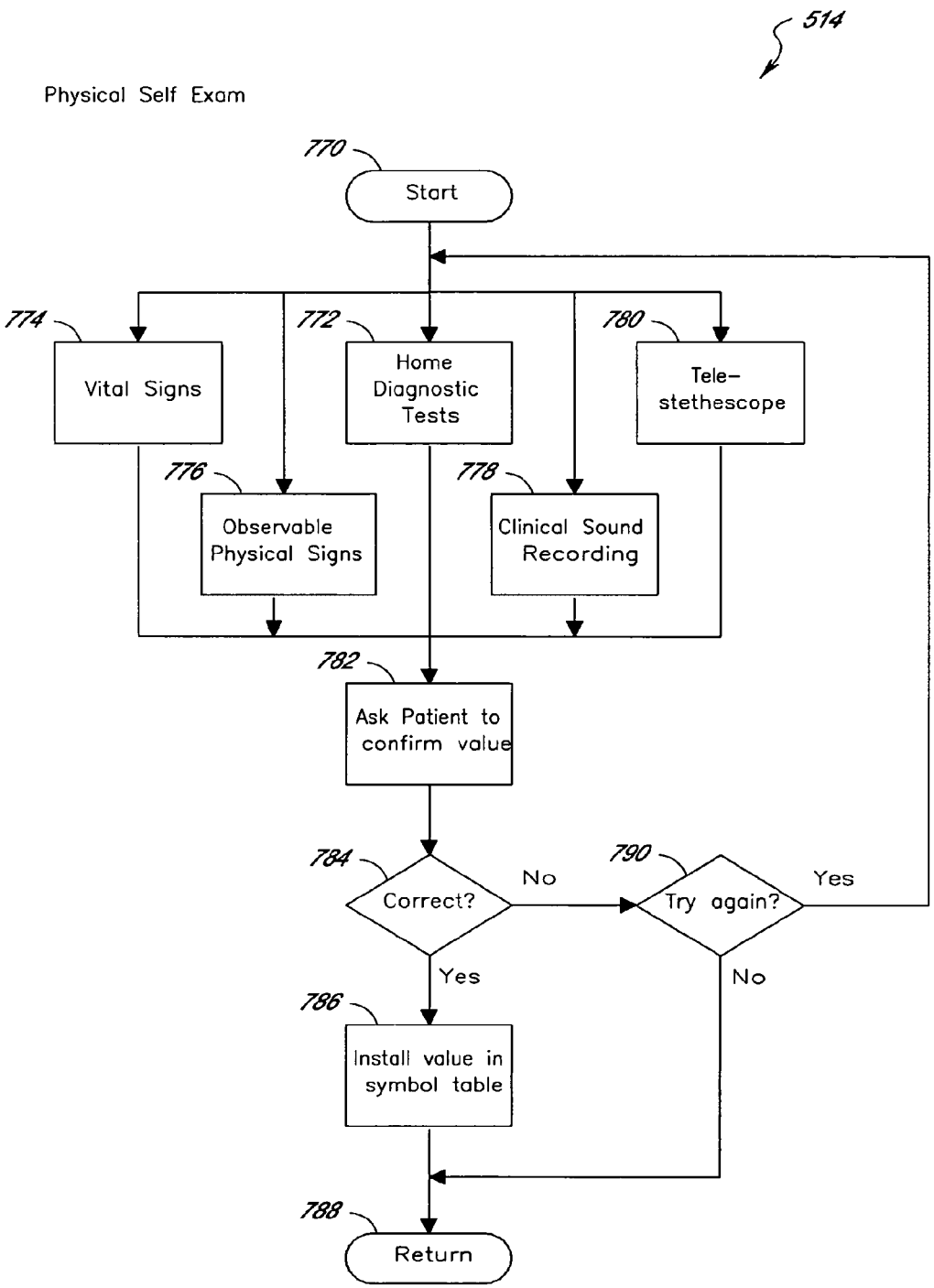
FIG. 19 is a flow diagram of the physical self examination function 514 defined in FIG. 10b.

Referring to FIG. 19, the Physical Self Examination function 514 defined in FIG. 10b will be described. A physical examination can actually be done by the patient under the direction of the MDATA system 100. The MDATA system 100 is designed to function primarily based upon responses to carefully crafted questions, i.e., history, and physical findings elicited from the patient. There are times, however, when the addition of certain laboratory tests can increase the accuracy of the diagnosis as well as help determine the appropriate treatment recommendations. For this reason, a MDATA system Home Diagnostic and Treatment Kit is available for use by patients. If the patient has the Home Diagnostic and Treatment Kit, including visual field cards, Snelling chart, and possibly the MDATA system's "tele-stethoscope" to assess intracranial or carotid bruits, this information will be used in the diagnostic process as well.

The MDATA system 100 is also able to play tones of different frequencies and intensities to emulate audiometric testing for hearing acuity. This allows, for example, the MDATA system 100 to detect the unilateral decrease in hearing caused by an acoustic neuroma.

Beginning at a start state 770, the computer 102 branches to one or more physical self examination procedures depending on the current problem and what equipment if any is available for use by the patient. These procedures include: home diagnostic tests 772, vital signs 774, observable physical signs 776, clinical sound recording 778, and tele-stethoscope 780.

A variety of home diagnostic tests 772 are available for use by the patient. New advances in biotechnology, including a new generation of urine dipsticks such as a "Multistix 8 SG" produced by Ames and monoclonal antibody tests such as "ICON® STREP B" produced by Hybritech®, allow an entire spectrum of laboratory tests to be performed at home by the patient under the direction of the MDATA system. For example, urine dipsticks can be used to check for blood, nitrites, leukocytes, or leukocyte esterase indicating cystitis or a bladder infection.

In order to use much of the monoclonal antibody technology, however, a small amount of blood must be obtained by using a fingertip lancet. This is already successfully being done by diabetics at home who use a glucometer to measure their blood sugar after pricking their finger to get a small sample of blood.

The MDATA system Home Diagnostic and Treatment Kit also contains equipment to allow the patient, or someone else, to measure the patient's vital signs 774. A blood pressure cuff and thermometer are included with instructions for their use as well as instructions to measure pulse and respiratory rate.

The patient may be directed by the system 100 to observe various physical signs 776. For example, a headache patient will be asked to palpate their temporal artery area, and to look at themselves in the mirror to identify the ptosis and tearing of a cluster headache or to identify the steamy cornea that may occur with acute narrow angle glaucoma.

As an example of how the MDATA system Home diagnostic and Treatment Kit could be helpful, consider a woman who (using the MDATA system's urine pregnancy test based on ICON® II HCG ImmunoConcentration™ Assay, produced by Hybritech®) finds out that she is pregnant. This is her first pregnancy. Later, when consulting the system for headache, a urine dipstick indicates protein in her urine and the measurement of her vital signs shows a significant rise in her blood pressure. This is a classic presentation of preeclampsia.

Instead of going to a doctor's office, patients could also use the MDATA system's Home Diagnostic and Treatment Kit to collect samples at home and then send them to a designated lab for analysis as needed. This saves time for the patient and is especially useful if the patient has difficulty in traveling. Costs should also be minimized in this type of laboratory analysis.

The MDATA system 100 records clinically relevant sounds 778 of a patient such as the cough of bronchitis, the seal bark cough of croup or the inspiratory stridor of epiglottitis. These sounds are digitized and stored in the patient's medical record. Then, using the re-enter feature of the system 100, the system can monitor, for example, a patient's cough over time to be sure that the cough is resolving as it should.

The general concept of recording and analyzing a cough is disclosed in the article *A microcomputer-based interactive cough sound analysis system*, C. William Thorpe, et al., published in *Computer Methods and Programs in Biomedicine*, 1991. The cough sound analysis system describes the filtering, amplification, recording, and software processing of a cough sound. The MDATA system 100 uses the telephone handset microphone in conjunction with an amplifier to procure the clinical sounds. These sounds are then transmitted to the system 100 where they are filtered, digitized using VP board 122 and recorded to a file in the patient medical history database 268 on the hard drive 152 (FIG. 1).

The MDATA system 100 is building a library of clinical sounds that allows patterns or profiles to be developed that relate the wave form of the clinical sound to the probability of a particular diagnosis. For example, the MDATA system 100 could compare the cough of a patient to the sound library to see if the cough of the patient is similar to those that eventually have been diagnosed as lung cancer.

In addition, the patient's record of the pronunciation of his or her name may be periodically recorded and compared to previous recordings. This allows the MDATA system 100 to potentially detect and evaluate the hoarseness that could be produced by a nodule on the patient's vocal cords.

A "tele-stethoscope" 780 is a device that allows the sounds a physician would hear through a stethoscope to be transmitted over the telephone. The tele-stethoscope 780 is functionally similar to that described in the 1992 Arthur D. Little report entitled "Telecommunications: Can It Help Solve America's Health Care Problems?". The tele-stethoscope 780 permits the MDATA system 100 to greatly expand the spectrum of its sound analyses to include heart murmurs, the bruits of intracranial aneurysms, breathing sounds like the wheezes of asthma and the rales of congestive heart failure, or even the bowel sounds of an intestinal obstruction.

There is more information in clinical sounds than can be represented by a two-dimensional pattern matching model. Transforms, e.g., Fourier, are used to shift different aspects of sounds into domains that can be quantified. The sounds are then pattern matched using an n-dimensional array. Consider a simple two dimensional array where time is represented on the X coordinate and amplitude is measured on the Y coordinate. For example, a cough may be recorded at two times several days apart. In this example, the computer 102 superimposes the waveform from one cough upon the other cough. The non-overlapping parts of the pattern both above and below represent the difference in the domain being measured between the two sounds. The area under these two curves is integrated to obtain the area. The sum of the areas of the two curves represents the difference between the two sounds in the domain being measured. The resultant area is then subjected to one or more sensitivity factors which are discussed hereinbelow. Hence, the more sensitive the system, the sooner it makes a match.

In a similar way, a sound pattern may be considered with time on the X coordinate and frequency on the Y coordinate. The same methodology is used to quantify the differences between the two curves. Thus, in a similar way, all aspects of sound can be measured.

In this pattern matching scheme, different weights are given to the different aspects of the sound depending upon which clinical sound is measured. In most sounds, the amplitude and frequency are the most important aspects. The weight or the relative importance of an aspect is different for each of various clinical sounds, such as heart murmurs, bruits, wheezes, coughs, stridor and so forth.

When value(s) from any of the procedures 772-780 are procured by the system 100, the computer 102 moves to state 782, recites the value and requests the patient to confirm the value. If the patient indicates that the value is correct, as determined at a decision state 784, the computer 102 proceeds to state 786 and installs the value into the symbol table associated with the current patient. If the value is not correct, as determined at decision state 784, the computer 102 proceeds to state 790 to determine if the patient would like to try providing the value again. If so, the computer 102 loops back to the beginning of the function 514. If the patient does not wish to try again, as determined at state 790, or if state 786 is completed, the computer 102 returns at state 788 to the evaluation process (FIG. 10b).

Figure 20:
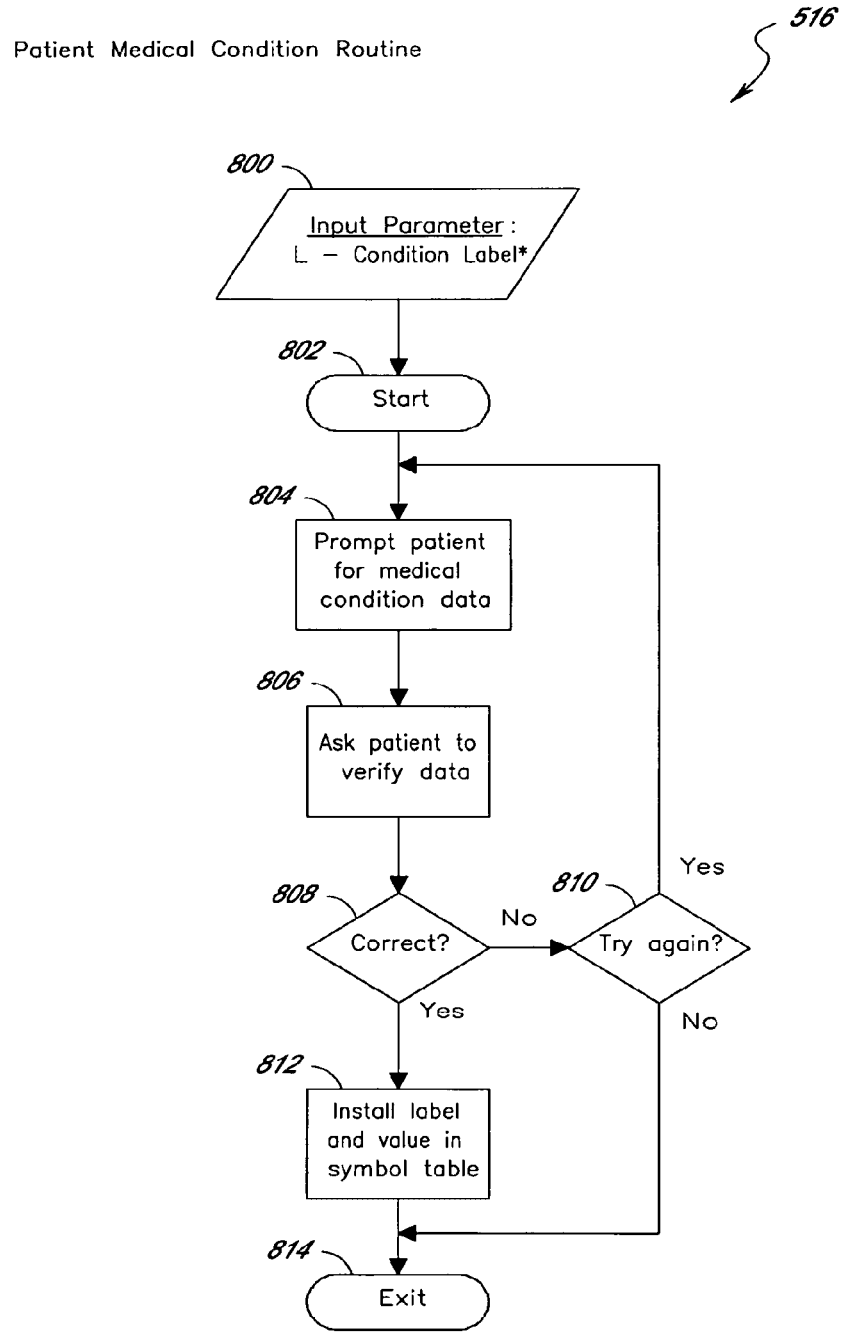
FIG. 20 is a flow diagram of the patient medical condition routine 516 defined in FIG. 10b.

Referring to FIG. 20, the Patient Medical Condition Routine 516 defined in FIG. 10b will be described. In the course of executing a particular medical algorithm in the evaluation process 254 (as shown at state 506), the computer 102 may request additional medical condition information of the patient. This information reflects the current condition of the patient, which is in contrast to the information requested by the past medical history routine 512 (FIG. 18) for past history information. The states 800 through 814 of the routine 516 are essentially the same as states 740 through 754 of routine 512, except that in routine 512 the condition label (L) denotes a value for which a past medical history question is to be asked during the evaluation process, while in routine 516 the condition label denotes a new value desired by the algorithm. Therefore, states 800-814 are not further described herein.

XVI. Symptom Severity Analysis

Figure 21:
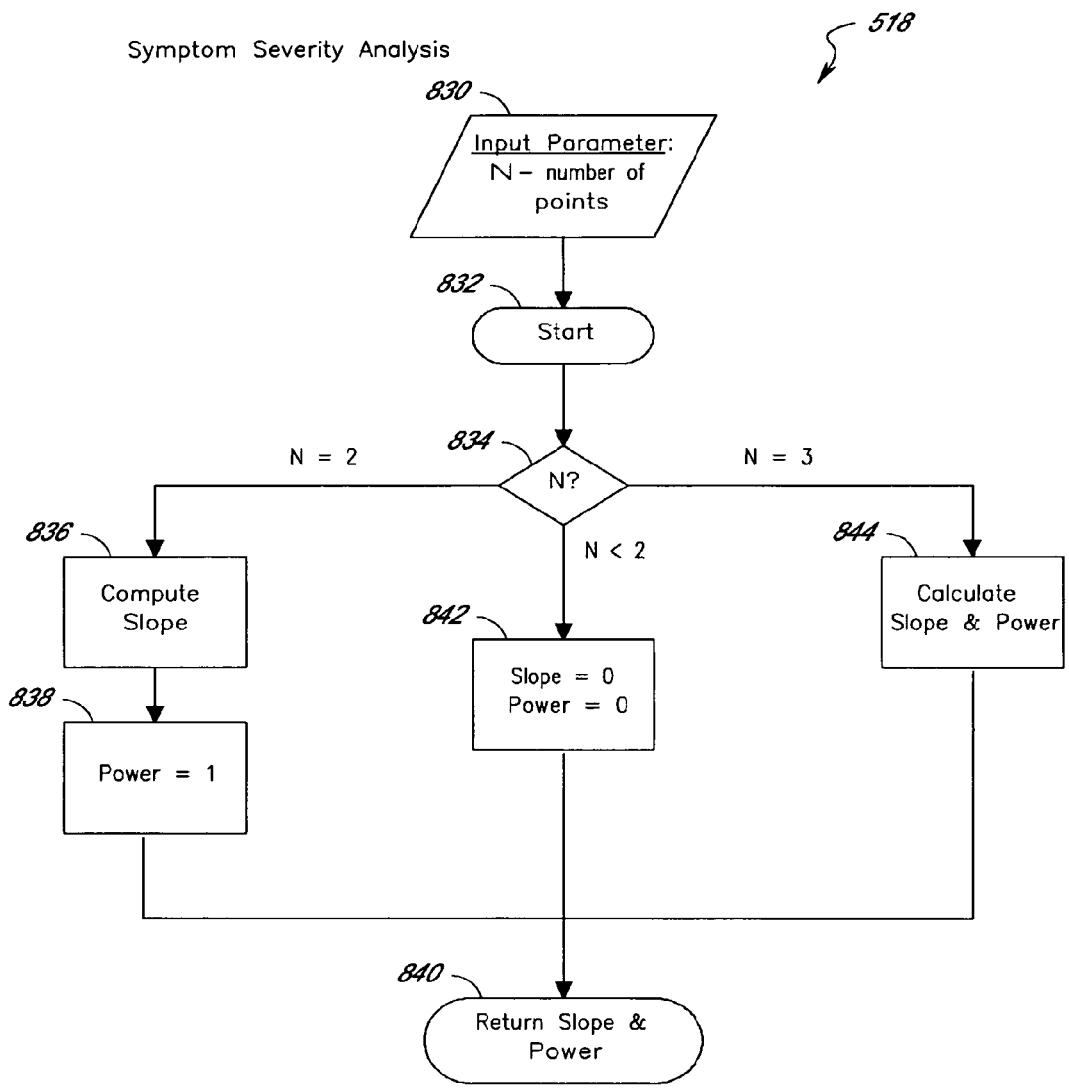
FIG. 21 is a flow diagram of the symptom severity analysis function 518 defined in FIG. 10b.

Referring now to FIGS. 10a, 10b, and 21, the symptom severity analysis function 518 defined in FIG. 10b will be described. A review and further description of the re-enter feature, which is associated with symptom severity analysis, is also provided here.

An important feature of the MDATA system 100 is its ability to follow or monitor a patient over time. If the MDATA system 100 is in the process of diagnosing a patient's complaint but is not certain what action should be taken (states 520-522 of FIG. 10b), system 100 may ask the patient to re-enter the system at a designated time, usually within a few hours.

When the patient calls the MDATA system at the designated time, the system takes the patient through the initial problem screening questions (state 483 of FIG. 10a) in order to exclude those problems that require immediate medical attention. The system detects that the patient is a re-enter case (state 490 of FIG. 10a), and then determines the re-entry point in the evaluation process based upon the patient's previous interaction with the system (state 492 of FIG. 10a). For example, if the MDATA system established a diagnosis of migraine, that is, if both the probability of migraine and the probability of confirmation of migraine reached threshold values, the patient would not repeat the diagnostic process, which is the usual case.

Occasionally, however, a patient for whom a diagnosis has not been established will be asked to re-enter the system 100. This patient is again asked the diagnostic screening questions, in addition to the initial screening questions (state 306 of FIG. 7a) and problem screening questions (state 483 of FIG. 10a). If the MDATA system 100 is not able to establish a diagnosis for a re-enter patient, he or she is referred to a physician for further evaluation.

In addition to the re-enter feature, the MDATA system 100 has the capability to call patients back in order to monitor their progress. The same trending methodologies are used regardless of who initiates the call, i.e., the system or the patient. Using this capability, the MDATA system 100 can provide regular or periodic monitoring of elderly patients in their homes as well as inform patients when a new therapy becomes available.

Many problems for which the MDATA system 100 offers advice have absolute thresholds for the initial quantization of the severity of a symptom. For example, chest pain that is described by a patient as being 10 on a 10-scale of severity, would reach the problem-specific initial symptom-severity threshold and would mandate a consultation with a physician.

Interestingly, with headache, an initial severity characterized by the patient as 10 on a 10-scale would not, in itself, necessarily require an immediate consultation with a physician. If, in addition, the headache came on suddenly and, as was mentioned earlier, was described as the worst headache of the patient's life, the MDATA system 100 would consider this to be suggestive enough of a subarachnoid hemorrhage to advise an immediate consultation with a physician.

Continuing in the headache example, after a re-enter patient with an established diagnosis is asked the initial and problem screening questions, the MDATA system 100 again assesses the severity of the patient's headache. Reassessing the severity of the headache, by having the patient re-enter the system, establishes two points of reference. The system 100 is now able to analyze any changes in the level of severity as well as calculate the rate of change in severity over time.

The symptom severity analysis function 518 has a Number of Points (N) as an input parameter as indicated at state 830. Number of Points refers to the points of reference established during the initial consultation for a particular problem and during subsequent re-enter consultation(s). Beginning at a start state 832, the computer determines the value of (N), i.e., the number of reference points, at a decision state 834. If it is determined that N=2, the computer 102 moves to state 836 to compute the slope of a line connecting the two reference points using standard mathematical techniques. Proceeding to state 838, a variable named Power is set to be one because only two reference points are used at state 836. The computer 102 returns at state 840, with output parameters Slope and Power as determined by function 518, to the evaluation process (FIG. 10b).

Using the returned Slope and Power parameters in the evaluation process 254, if the MDATA system 100 determines that the severity of the headache, for example, is increasing too rapidly, that is, if a slope of the line connecting two points on a graph of the severity reaches a set threshold, system 100 will make an appropriate recommendation.

If the MDATA system 100 finds that the severity of the headache is staying the same or is getting worse but is doing so at a relatively slow rate, it may ask the patient to re-enter the system a second time (i.e., for a third consultation), usually within a shorter period of time. The third consultation gives the MDATA system 100 three points of reference from which to trend the severity of the headache. Thus, when the function 518 is called by the evaluation process, the value of (N) is three, as determined at state 834, and the computer 102 branches to state 844. At state 844, the computer 102 determines the slope and power of a line connecting the three reference points. The presently preferred embodiment uses the well-known Runge-Kutta method, which is a numerical approximation technique for solving differential equations. Other embodiments may use other well-known, standard curve fitting functions at state 844.

If the system 100 determines that yet one or more additional consultations, i.e., beyond three consultations, are desired, e.g., to establish a trend with certainty, it will again request the patient to re-enter the system at a later time. In this situation, the three most recent reference points are used in the calculation at state 844.

The system 100 then performs a "sequential symptom-severity slope analysis" to determine if the symptom is getting worse too rapidly as follows. The slopes of the lines connecting the first and second point, the second and third point, and then the first and third point are calculated. If any of these reach a problem-specific threshold, the appropriate recommendation is given.

If the sequential symptom-severity slope analysis does not reveal the need to seek medical attention, then the MDATA system 100, in addition to calculating the rate of change in the severity of the symptom with respect to time (the slope analysis), now calculates the rate of change of the rapidity with which the headache is getting worse. This is the first derivative.

Table 4 illustrates this relationship below. Time maps onto the "X" axis and the symptom's severity maps onto the "Y" axis.

TABLE 4

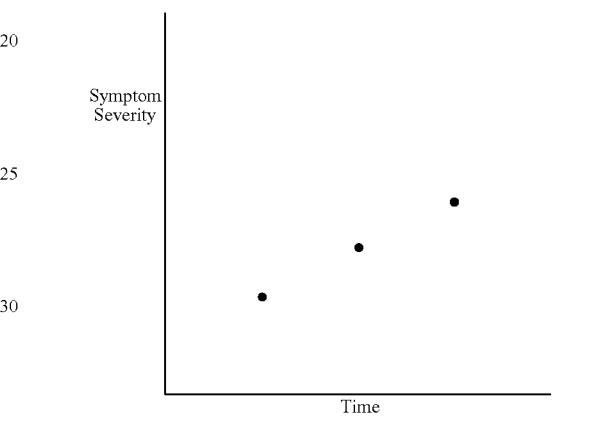

Note that a line connecting these three points forms a gently sloping straight line. The MDATA system 100 using this data determines that, although the symptom is getting worse, it is doing so in an arithmetical or linear way. That is, although the severity of the symptom is increasing, the symptom's rate of change is not increasing.

In contrast, a line connecting the three points on the graph of Table 5 forms a sharply upturned curve.

TABLE 5

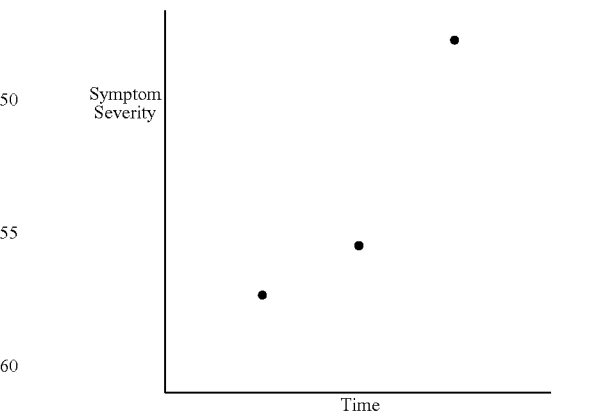

The MDATA system 100 using the data of Table 5 determines that, not only is the symptom rapidly getting worse, but more significantly, the rate at which the symptom is getting worse is also increasing. In the MDATA system 100, this analysis is termed an "exponential symptom-severity filter." All patients who re-enter the system a second time are subjected to this analysis.

It is important to note that the severity of a problem, e.g., a headache, is not necessarily related to the seriousness of the underlying cause. The MDATA system 100 is programmed such that when any symptom gets rapidly worse, medical intervention is frequently advised as necessary. This concept is valid for many symptoms.

Returning to the symptom severity analysis function 518 (FIG. 21), if the function 518 is called with N=0, or N=1, the computer branches to state 842. At state 842, the Slope and Power parameters are set to zero, and the computer 102 returns these parameters at state 840 to the evaluation process (FIG. 10b). The values set at state 842 essentially flag an error condition that is acted on by the evaluation process 254.

XVII. Treatment Table

Figure 22:
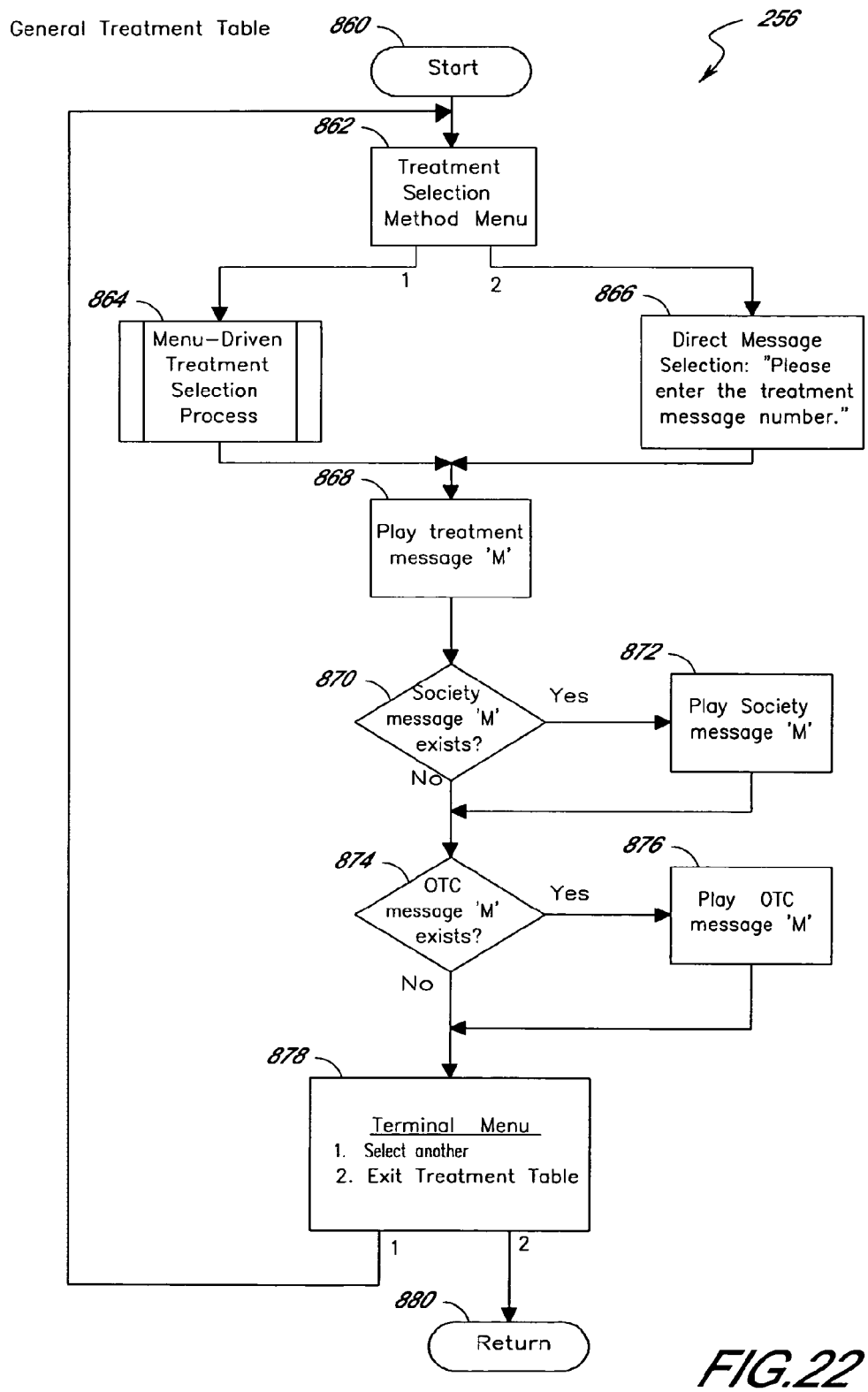
FIG. 22 is a flow diagram of the treatment table process 256 defined in FIG. 7d.

Referring to FIG. 22, the Treatment Table process 256 defined in FIG. 7d will be described. The MDATA system 100 is modularized in its approach to diagnosis and treatment. In medicine, diagnosis simply means figuring out what is causing the problem, and treatment refers to what action should be taken once the cause of the problem is known.

Diagnosis is composed of history, physical examination, imaging studies, and laboratory tests. Again, history is by far the most important factor in making the diagnosis. In fact, in medical school, students are taught that if they don't have a good idea of the diagnosis by the end of the history, they are doing something wrong.

The treatment side of medicine is conceptually different from diagnosis in that, while the basic principles of making the diagnosis remain the same, treatment is continually changing. Treatment is fundamentally a "look-up" table with the diagnosis, age and sex on the left and the most current treatment on the right as shown in Table 6. Or, treatment can be thought of like the cubbyholes or boxes of a post office. Each individual box holds the treatment for a given disease. The information given is age and sex specific. The contents of the box are constantly changing, but the location of the box does not. For example, what is thought to be the best antibiotic to treat meningitis in a two-year-old child could literally change from week to week as more antibiotics are developed and approved or more controlled studies are published.

TABLE 6

Simplified TREATMENT TABLE Example

| Diagnosis | Treatment |
| --- | --- |
| meningitis in a two-year old child | antibiotic of choice as of current date |

The MDATA system 100 maintains a treatment table that can be updated instantaneously to provide the most current treatment recommendations.

The treatment table can be directly accessed by patients who already know their diagnosis. For example, asthma patients can consult the system as often as they wish to see what the absolute latest treatment is for their condition. In fact, links are maintained between the treatment table and the patient medical history files 268. In this way, when a new treatment is introduced for any of the ICD□C□9□CM codes listed in the MDATA system 100, patients can be contacted and asked to either call the system 100 back at their convenience or have the MDATA system 100 fax or mail the information to them. The MDATA system 100 can also notify patients' doctors when a new treatment is identified.

The concept of using a table is also helpful with regard to two aspects of the diagnostic process that often do change: the imaging modality of choice (like X-ray, Computerized Tomography (CT), Magnetic Resonance Imaging (MRI)), and the laboratory test(s) of choice. Therefore, the MDATA system 100 also maintains a table for imaging modality of choice as well as laboratory test(s) of choice in the work-up or diagnosis of a particular complaint. By modularizing these aspects of the diagnosis, as new imaging techniques, like Positron Emission Tomography (PET) scanning, and new laboratory tests, like recombinant DNA technology, are discovered, only the tables have to be altered, not the medical algorithms themselves.

The treatment table will be further described in a general way as process 256 in FIG. 22. The treatment table process 256 begins at start state 860 and proceeds to state 862 wherein the computer prompts the caller to choose a treatment selection method:

i. Treatment selected from layered menus, or
ii. Treatment selected via direct entry of a catalog number.

The first selection method entails the use of the menu-driven treatment selection process 864 which will be described hereinbelow in conjunction with FIG. 23. The second selection method at state 866 uses a treatment table catalog message number. This catalog is part of the patient information package, a section of which appears in Table 7. The treatment table catalog is organized by anatomic area and diagnosis, and when applicable, by age and gender. After the patient selects a catalog number, the computer 102 stores the selection in a memory variable 'M'. As an alternate selection method, the system 100 allows the patient to directly enter the ICD□9□CM code for their problem. In this case, the computer 102 will look-up the ICD□9□CM code in an internal cross-reference table to identify the catalog number, and set the memory variable 'M' to this catalog number.

TABLE 7

Portion of Treatment Table Catalog
NEUROLOGY

| Diagnosis | Message |
| --- | --- |
| Epilepsy | 1101 |
| Meningitis | |
| 2 years old & younger | 1201 |
| over 2 years old | 1202 |
| Depression | |
| Male | |
| Under age 50 | 1301 |
| 50 years and older | 1303 |
| Female | |
| Under age 50 | 1302 |
| 50 years and older | 1304 |

Once the value of the memory variable 'M' is established by process 864 or state 866, the computer 102 moves to state 868 and plays treatment message 'M' to the patient. At the conclusion of treatment message playback, the computer 102 moves to a decision state 870.

At state 870 the computer 102 checks for existence of society message 'M'. The society message category contains information about organizations that assist patients with a particular disease. If the society message 'M' does not exist, the computer 102 moves to a decision state 874. Otherwise, the computer 102 will move to state 872 wherein it plays society message 'M' to the patient. At the end of the society message 'M', the computer moves to state 874.

At state 874, the computer 102 checks for the existence of an over-the-counter (OTC) message 'M'. The OTC message category contains information about generally available over-the-counter medications and home treatment for a particular diagnosis. If the OTC message 'M' does not exist, the computer moves to state 878. Otherwise, the computer 102 moves to state 876 wherein it play OTC message 'M' to the patient. At the end of the OTC message 'M', the computer 102 moves to state 878.

At state 878 the computer 102 plays a terminal menu to the patient which allows the patient to either select another treatment, or to exit from the treatment table process 256. If the patient wishes to hear another treatment message, the computer 102 moves back to the treatment selection method menu state 862. If the patient wishes to exit the treatment table process 256, the system moves to state 880, wherein the treatment table process 256 terminates and returns to the top level flow (FIG. 7*d*) at state 344.

An example of the treatment, society and OTC messages for epilepsy are given in Table 8. Note that since the OTC message is empty, the computer 102 would skip over the OTC message playback and proceed directly to the terminal menu.

TABLE 8

Treatment Table Messages for Epilepsy

Treatment Message
As of Dec. 20, 1993, according to Emergency Medicine: Concepts and Clinical Practice, Third Edition, by Drs. Rosen, Barkin, et. al., pages 1800 and 1801, the initial treatment of generalized tonic-clonic seizures, i.e., grand mal seizures, is as follows:
    After efforts to discover and treat acutely correctable causes like hypoglycemia, the following pharmacologic agents are indicated:
    1.    Intravenous administration of lorazepam, with a loading dose of 0.1 mg/kg
        and an infusion rate not to exceed 2 mg/min.
Which is usually followed by:
    2.    Intravenous administration of phenytoin, with a loading dose of 15 to 18 mg/kg
        and an infusion rate not to exceed 0.75 mg/kg per minute.
If lorazepam is not effective, and in those individuals allergic to phenytoin:
    3.    Intravenous administration of phenobarbital, with a loading dose of 8 to 20 mg/kg
        and an infusion rate not to exceed 0.75 mg/kg per minute.
If the above is not successful:
    4.    A neuromuscular blocking agent like pancuronium, with an intravenous
        dose of 0.03 to 0.1 mg/kg.
    5.    Intravenous administration of paraldehyde, with a loading dose of 0.1 to
        0.15 ml/kg, diluted with saline to a 4% to 6% solution and slowly infused
        over 1 hour.
Society Message
"For further information on epilepsy, contact:
    Epilepsy Foundation of America
    1828 L Street, N.W., Suite 406
    Washington, D.C. 20036
    (202) 293-2930
    In addition to the national headquarters, there are 100 local chapters. The San Diego chapter can be contacted at (619) 296-0161."
OTC Message
None.

Figure 23:
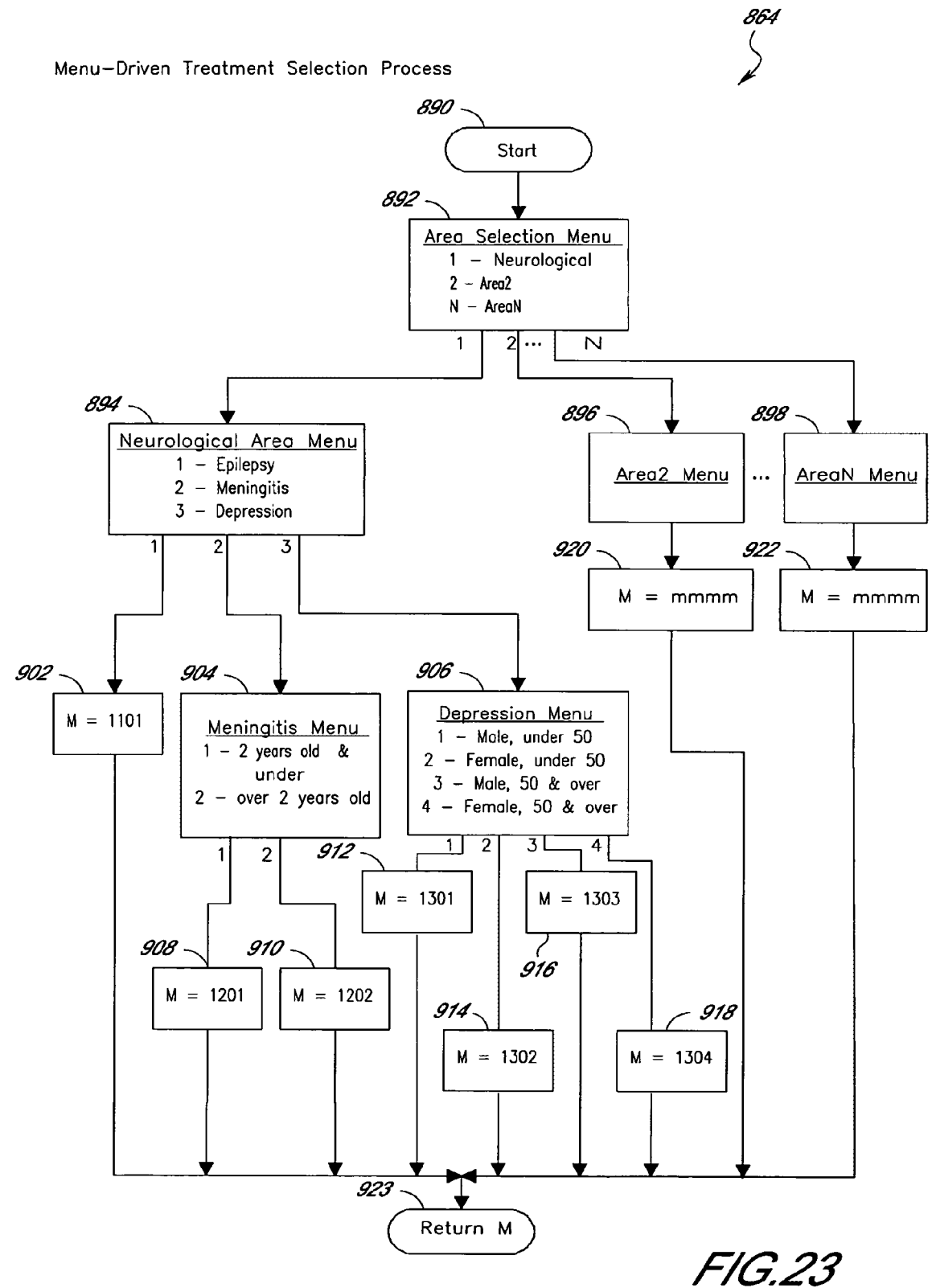
FIG. 23 is a flow diagram of the menu-driven treatment selection process 864 defined in FIG. 22.

Referring now to FIG. 23, the menu-drive treatment selection process 864 defined in FIG. 22 will be described. The menu-driven treatment selection process 864 begins with start state 890 and proceeds to state 892 wherein the computer 102 recites an area menu to the patient and requests selection of one area. The complete menu is not shown in state 892. The areas are arranged by anatomic system. For example, if a patient has epilepsy, the patient can simply select this from the anatomic system menu for the neurological system.

Based on the patient's selection, the computer 102 branches to a selection area menu state, such as neurological area menu state 894, wherein the computer 102 recites a list of diagnoses to the patient and requests selection of a diagnosis. In some cases the diagnosis is further subdivided by gender, age or both gender and age. At state 904, for example, for a diagnosis of meningitis, the computer 102 would prompt the patient to select from a secondary menu between a treatment for a child two years old or younger and a treatment for somebody over two years old. Then, based on the patient's selection, the computer 102 sets a memory variable 'M' to the value of the selected diagnosis message number at state 908 or 910. State 906 is another example secondary level menu which has four choices based on gender and age. These four choices are associated with four states, 912, 914, 916, 918, wherein the computer 102 sets the memory variable 'M' to the value of the diagnosis message number that was selected at state 906. After the catalog number has been stored in memory variable 'M', the computer 102 moves to return state 923 wherein the menu-driven treatment selection process terminates and returns control to the treatment table process 256.

Area2 menu 896 and AreaN menu 898 are indicative of menus similar to menu 894 but for different anatomic systems. Menu 896 and 898 may have secondary menus, similar to menus 904 and 906 under menu 894. Then, states 920 and 922 are indicative of the computer 102 setting memory variable 'M' to the value of the diagnosis message number selected from the parent menu 896 or 898, respectively.

XVIII. The MDATA System Paradigm

The MDATA system paradigm is based on several fundamental principles. They are as follows:
    Centralization of medical information
    Accessibility of medical information
    Modularity of medical information
    Modifiability of the system.

As mentioned earlier, one of the purposes of the MDATA system 100 is to bring together highly qualified medical experts, encode their knowledge in a central location, and make this information available to everyone.

Although the issue of accessibility has been discussed several times, it is important to understand its significance. Accessibility in the MDATA system 100 refers both to the way in which the medical information can be retrieved from the system 100 by non-medically trained personnel as well as to the need for people everywhere to easily and promptly obtain medical information. By using the already established worldwide telecommunications network, the MDATA system 100 can provide universal and nearly instantaneous access to high quality, 100%-consistent medical advice.

In the MDATA system 100, the concepts of modularity and modifiability are inextricably intertwined. Modularity is the key to the MDATA system's ability to provide patients with the most current medical information available. The MDATA system's modular design and object oriented techniques allow the individual components of the system to be modified or updated without generating a ripple effect on other information in the system 100.

In contrast, the print media suffers from an inability to quickly adapt to changing information. Once a book or journal is published, it cannot be modified until its next publishing date. The MDATA system 100, however, can be modified within hours of a new discovery in medicine. Easy modifiability is another way in which the MDATA system 100 is qualitatively different from previously published algorithms.

Once the medical algorithms for the MDATA system 100 are written and programmed, they can then be continuously updated and refined as advances in medicine are made. Unfortunately, physicians today are simply not able to keep up with the explosion of new medical information and technology. This ability to nearly instantaneously modify the MDATA system 100 is a powerful feature of the system.

It is presently possible for a computer to search the world's medical literature daily. Any articles pertaining to a particular topic can automatically be requested and the information used to update the system.

In addition, the MDATA system 100 is currently using optical character recognition technology to digitize its medical database. Then, using indexing techniques, the MDATA system 100 is able to search for and retrieve any information desired. For example, the system can search for the character string "headache" and retrieve any amount of surrounding text or graphic information. This information is then collected, collated, printed and referred to the physician(s) maintaining the headache algorithm. This process will become easier as more of the world's medical literature is digitized.

Global Factors—Sensitivity and Selectivity

Another way in which the MDATA system is modifiable is in its use of global sensitivity/selectivity factors. As with every decision, there is always a balance to be achieved between risk and benefit, and so with the MDATA system 100. One of the questions the MDATA system 100 tries to answer is whether the patient needs to be seen immediately by a physician. This leads to this discussion about sensitivity and selectivity.

Sensitivity and selectivity are statistical terms that refer to how accurately a decision can be made. In this case, sensitivity refers to the number of patients which the MDATA system 100 did not think needed to be seen by a physician but that actually did.

If the program were to be so sensitive that no disease process that eventually required meaningful physician intervention would be treated at home (no false negatives), then every single complaint would necessitate a visit to the doctor, which is a useless system. On the other hand, too selective a system (no false positives) i.e., no unnecessary visits to the doctor's office, would necessitate that an attempt be made at home treatment for every complaint, which is a useless and dangerous system.

So again, a balance must be reached between these two ends of the spectrum. To achieve this, the sensitivity/selectivity ratio of the entire MDATA system 100 can be changed by setting or tuning a plurality of sensitivity factors. These sensitivity factors affect the following functions: meta thresholds, re-enter horizon threshold, frequency of call back, symptom-severity filters, sequential slope filters, exponential symptom-severity filters, and probabilities of diagnoses in the treatment table. In addition, as in the headache example, the scoring of the screening questions already weighted is modulated or modified by the sensitivity factors.

Experience from the regionalization of trauma centers in this country shows an interesting trend over time with respect to sensitivity and selectivity. It has been shown that the inverse relationship between sensitivity and selectivity, when plotted over time, yields a sinusoidal wave form in which the amplitude of the wave form gradually decreases with time as the system is "fined tuned" as shown below in Table 9.

TABLE 9

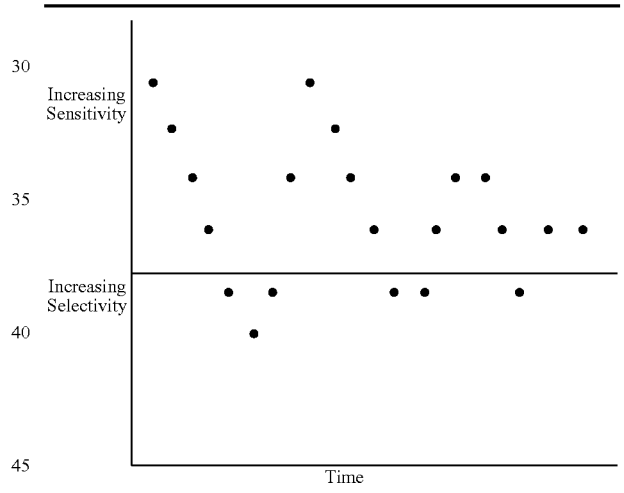

The MDATA system's sensitivity factors are designed to do just that, i.e., fine tune the system over time to find the right balance between sensitivity and selectivity.

In addition to the use of global factors, the MDATA system 100 maintains what are termed "emergency filter response sets." When a patient replies "yes" to any of the problem screening questions, the recommendation or message that follows is called an emergency filter response or "EFR." The EFR sets are modularized so that the system can customize the message that the patient hears. This allows the system 100 to match the EFR sets to the desired level of sensitivity or selectivity as well as provide information specific to an HMO or Managed Care Plan.

System Sensitivity Factors

There are ten sensitivity factors that affect threshold determination in the MDATA system 100:

S1=system-wide (usually established by the system administrator and affects the entire MDATA system)

S2=the anatomic system of the body involved (e.g., nervous system in headache example)

S3=cause (e.g., infection causes meningitis)
S4=problem specific (established by the algorithm author at the beginning of an algorithm)
S5=question specific (within a particular algorithm)
S6=organizational specific (e.g., HMO, hospital)
S7=patient specific
S8=a reserved sensitivity factor for later use
S9=a reserved sensitivity factor for later use
S10=a reserved sensitivity factor for later use Initially, the sensitivity factors have a value of 1.0. The sensitivity factor's value is usually inversely proportional to sensitivity; i.e., if the value is decreased, sensitivity increases.

The sensitivity factors are applied to the threshold constant value in the relational expression component of an IF-Then or If-Then-Else statement of a medical algorithm. For example, let's assume that the system 100 is in the meningitis algorithm and that a temperature greater than 102 degrees will trigger a recommendation to go to a hospital. An example of a threshold calculation without sensitivity factors follows:

If temp>102 then X else Y where X denotes the recommendation to go to the hospital and Y denotes a different branch point. Following is the same example, but including sensitivity factors:

If temp>(102*S1*S2*S3*S4*S5*S6*S7*S8*S9*S10) then X else Y

The use of the sensitivity factors permits anticipation of change. Tuning the initial product of the sensitivity factors from "1.00" to "0.95" would decrease the temperature at which the system recommends a trip to the hospital. Each threshold calculation or other use of the sensitivity factors may use any number of (e.g., two factors) and any combination of the factors. Additionally, any combination of factors may be modified from the initial 1.0 value in any particular threshold calculation.

Age criteria is also modified by use of the sensitivity factors. For example: If Age>45*S1*S4 then X else Y.

Examples of areas the system 100 could be tuned follow:
Anatomic system (e.g., cardiovascular)—the system is missing too many heart attacks;
Cause (infection)—the system is missing too many injuries (trauma);
Problem specific (e.g., headache)—the headache algorithm is missing too many cases of meningitis or subarachnoid bleeds;
Question specific (each question in an algorithm can be modified)—this would change the "weight" of a question in a series of weighted questions like the migraine screening questions;
Patient specific—one patient might want to be VERY careful while another might say, "in general I don't go to the doctor until I'm really sure something is wrong with me";
Organizational (e.g., Kaiser patients)—Kaiser hospital management may say that the system is missing too many cases of meningitis and may request to be more careful with their patients (send them in with a lower temperature).

The sensitivity factors affect the following system 100 functions:
(a) Re-enter Feature—the sensitivity factors affect the re-enter horizon, i.e., the amount of time after which the system 100 considers a repetition of the same complaint to be a new problem. If sensitivity increases, the re-enter horizon becomes sooner.
(b) Meta Function—the sensitivity factors affect the matching and time density ratio thresholds. By reducing the values of the system-wide and problem sensitivity factors, e.g., from 1.0 to 0.9, the matching threshold and the time density ratio are decreased:

Example 1

Without Sensitivity Factors

Meta("NHDA", "**", "********", 06/01/93, 12/31/93)
If MC>=3 then 100 else 101

Example 1

With Sensitivity Factors

Meta("NHDA", "**","********", 06/01/93, 12/31/93)
If MC>=(3*S1*S4) then 100 else 101

Example 2

Without Sensitivity Factors

Meta("**", "", "I*******", 06/01/93, 12/31/93)
If TDR >=2.0 then 200 else 201

Example 2

With Sensitivity Factors

Meta("**", "", "I*******", 06/01/93, 12/31/93)
If TDR >=(2.0*S1*S4) then 200 else 201

Thus, there is no necessity to change the algorithms themselves. In other words, the factors can be modified rather than changing the algorithms.

(c) Problem Questions—To take the headache example previously used, the sum of the scores of the screening and confirmation questions (and sometimes the questions themselves) is multiplied by the sensitivity factors. The questions are also weighted, of course, depending upon how important each question is to the diagnosis. The sum of the weighted scores is compared against the threshold value that will result in either making the diagnosis of say migraine (in response to the migraine screening questions) or confirming the diagnosis of migraine in response to the migraine confirmation questions.

Thus, if we wanted to increase the sensitivity of diagnosing subarachnoid hemorrhage, we would not have to write another algorithm, but rather, simply multiply the screening and confirmation scores by the sensitivity factors.

For example, if the threshold for the MDATA system 100 to make a diagnosis of subarachnoid hemorrhage based on the sum of the weighted subarachnoid screening questions threshold is set at, say 75%, then that percentage of the sensitivity variable would make this diagnosis with a smaller score and, thus, pick up more cases. Thus, individual diagnoses within an algorithm can be "tuned" independently, and in some cases, this even applies to the individual questions themselves.

(d) Symptom Severity and Symptom Severity Trend Analysis—the sensitivity factors alter the absolute value, the first, second and third slope thresholds. With increased sensitivity, a more gently sloping line triggers an earlier medical evaluation. In the algorithm, when the system 100 makes use of any quantitatable parameter to make a decision, all of these are joined, influenced or multiplied by the sensitivity factors. As a very simple example, if the MDATA system 100 would normally make a recommendation, partly based on the age of the patient (e.g., if you are male and you are over 50 and . . . ), the decision can be triggered if the patient is 49 or 48 and so on.

(e) Home Diagnostic and Treatment Kit—if the patient has a MDATA system treatment kit or a blood pressure cuff, the level at which a fever or blood pressure effects a decision can be changed.

(f) Mental Status Examination—the mental status examination can be modified at a system, or problem (algorithm) level.

(g) Clinical Sound Library—the pattern matching process (as in the clinical sound library) is quantifiable by modifying the sensitivity factors.

XIX. Video Imaging of the Patient

There are four main types of video imaging: static black and white, static color, video black and white and video color. Each of these main types is now discussed.

Images as basic as static black and white images can provide useful information to the system 100. Static black and white imaging is used with neural net pattern matching. This process permits analyzing for example, facial features to aid in the detection of certain diseases, such as the characteristic facies of Cushing's syndrome or the exopthalmos of Graves disease.

Color static imaging allows color frequency analysis to detect diseases that are not as readily detected with static black and white imaging, such as cyanosis of respiratory failure or the scleral icterus of hepatitis. Color thus provides an incremental benefit in the level of disease detection.

Real time black and white video imaging allows for the evaluation of physical signs such as pupillary responses, extra ocular muscle function, lid lag, and nystagmus. Cranial nerve function can be remotely evaluated, along with, for example, the distinction between central and peripheral VII nerve function.

Color video imaging, especially using fiber optics, adds much more capability in the evaluation of a patient's condition. For example, color video imaging is very useful in evaluating capillary refill or monitoring the response of a patient with cyanosis to supplemental oxygen. Another embodiment of the system 100 may employ inexpensive laser sources to perform real time holographic imaging.

XX. Benefits of the MDATA System

It is rare when the humanitarian and entrepreneurial interests of a venture overlap. The confluence of purpose that exists in the MDATA system is striking. It is a "win-win" proposition from every perspective.

Not only will the MDATA system 100 substantially reduce the overwhelming costs of our current health care system, but for the first time in history, every person can have access to high quality, 100%-consistent and affordable medical advice and information. No matter from what perspective one views the MDATA system 100, its benefits are substantial.

The health care consumer obviously gains the most. Now, whenever he or she has a medical problem, or any member of their family, an immediate consultation can be obtained. The knowledge that the best health care information and medical advice is only a telephone call away can assuage the anxiety of everyone from new mothers to elderly patients confined to their homes.

By endorsing the MDATA system 100, federal, state and local governments could discharge their obligation to provide a universal and affordable level of health care for all of their citizens. In addition, the MDATA system 100 helps care for patients who cannot pay, thus relieving primary care physicians of the necessity to provide care without reimbursement. For the first time, Health Maintenance Organizations and Managed Care Plans will be able to effectively screen patients by telephone in order to ensure that patients are best matched with the services they need.

Specialists can use their talents, not on the repetition of familiar rituals, but will be free to concentrate on those more challenging problems that cannot easily be resolved by the MDATA system 100. They will also benefit from an increased number of patient referrals as well as having a well-constructed patient history when a consultation is sought.

Physicians themselves can access the MDATA system 100 in order to stay informed about new information and technological advances in the medical field. This is particularly true with the treatment, imaging, and laboratory test databases.

Medical information is a continually renewable resource because it is not consumed in its dissemination. The opportunity exists, through the MDATA system 100, for the United States to provide much needed medical information to the world and, at the same time, bring capital into this country. In the process, this country could maintain its leadership in innovation, technology, and software development.

The United States and the world are facing a health care crisis so monumental that it is difficult to comprehend. There are diseases that threaten our very survival as a species. All of us know the apprehension and bewilderment we feel when an illness strikes. When this occurs, we need answers to specific medical questions, answers that are absolutely up-to-date, instantly available, and affordable.

The key is information: information about prevention, early detection of disease, and about its most efficient treatment. The MDATA system 100 can provide this information through the simple use of the telephone, to nearly every inhabitant of the planet. In addition, the MDATA system 100 converts and explains complicated medical terminology and concepts into language easily understood by everyone.

People do not have to be ill to consult the MDATA system 100, just curious. Patients do not have to schedule appointments, they can simply pick up the telephone. Although many patients will later be seen by a physician, the MDATA system 100 can provide immediate help for everyone. The MDATA system 100 at once establishes egalitarian access to health care information. Although many patients in this country receive state-of-the art medical care, there is a large segment of the population that is deprived of one the most basic health care and medical information. The MDATA system 100 begins to close this enormous gap.

The MDATA system 100 begins to effect a restructuring of the health care delivery system in which both health care consumers and providers participate in the improvement of the system itself. The MDATA system 100 and its patients will be in partnership to provide the most current, economical, and concise treatment available. The upside potential is unlimited. Whether one believes health care is a right or a privilege, there can be no doubt that it is fundamentally necessary. Whether one believes we have a civic responsibility or a moral obligation to care for one another, it must be done. The fundamental simplicity of the structure of the MDATA system 100 belies its power as a highly useful tool in the delivery of health care.

XXI. First Optional System Configuration

A second embodiment of the MDATA system entails a major shift of how the questions and responses are delivered to the patient. Rather than the use of a telephone, the voice processing and voice response technology, the system software is published via media such as floppy disks, CD ROM, or PCMCIA cards for use on a patient's personal computer. This second embodiment is referred to as the screen version or the (Stand-Alone) SA-MDATA system. The computer could be, for example, a desktop computer, a laptop or notebook computer, or a handheld, pen-driven computer. The system questions are displayed on a display screen that is part of the computer or is connected to the computer. The patient uses a keyboard or a pointing/writing device connected to the computer to respond to the questions. The patient files are maintained and updated within the computer or on removable storage devices. The diagnosis, advice, and treatments can be displayed on the screen and also printed in hardcopy form on a printer (if available). New versions of the SA-MDATA system are either mailed to subscribers are available via modem. These new versions may include updates of the treatment table for new treatments. Another embodiment of the SA-MDATA system may include using specialized receiver devices that receive encoded FM signals on a demand basis when an event (a new treatment) triggers the device, such as described in U.S. Pat. No. 5,030,948.

A unique and separate authoring language (called File Output or FO) was used to develop the medical algorithms used in the screen version embodiment of the system 100. Through the use of FO, the contents of text files are presented online to users, and then the users respond to questions and directions issued by the text files.

FO is designed as a typical, generalized authoring language, in which commands are embedded into text files (herein called FO files) to perform specific screen and keyboard functions. FO files are in effect programs written in the FO "language" that communicate (via FO) with the user online.

FO adds no text of its own. In fact, FO does not need to know what text file content it is executing. The programmer or author of a FO file is in complete control of the text content and the sequence in which it is presented. Using the various commands described in the Authoring Language Syntax document listed in the Microfiche Appendix, the author can display text, format the screen, ask the user questions, input responses from the user, select different text files for execution, and generally control and direct the entire session.

This version of FO is intended as a development version that gives the user much freedom at the keyboard. The user can interrupt a presentation and edit the FO file being presented. The assumption here is that the user is in fact the author or an alpha tester charged with verifying and correcting file content.

A FO file is any standard sequential ASCII text file with variable-length lines terminating with a Carriage Return (ASCII 13). Any line with a period in column one is treated as a command. A line without a leading period is treated as a print command.

The FO program processes a FO file by reading it one line at a time into memory. If the line is a text line, it is printed and the next line is loaded. If the line is a command line, the command is executed. If the command involves a wait on the user (such as a .M command), FO continues loading the FO file behind the scenes until it has been completely loaded. In this manner, FO executes the FO file as it is loading it. Once loaded, the FO file remains entirely in memory.

The system software for the screen version embodiment is written in Borland Turbo Pascal version 3.0. A second version of the system software for the screen version embodiment of the system 100 is written in Microsoft G.W. Basic and is run in interpretive mode. The Microfiche Appendix contains the following for the screen version:
 Authoring Language Syntax Document;
 Pascal Source Code;
 System Functions; and
 An Exemplary Medical Algorithm (Headache).

In yet other embodiments, other databases/files or algorithms can be used. The general system, method and procedures would remain the same. For example, a specialty field such as sports medicine could be added to the system.

The MDATA system 100 described herein finds application in many environments, and is readily adaptable for use therein. For example, the system finds use in any application that is step-oriented and can be algorithmically described. For example, the system could give car diagnostic services over the phone to a caller. Then, when the car is brought to a service facility for repairs (treatment), the caller will be informed and have a good idea of what the problem is and probable repairs will be. Accordingly, the claims are to be interpreted to encompass these and other applications of the invention within their scope and are not to be limited to the embodiments described herein.

XXII. Summary of Advantages of the Invention

One of the main problems of the health care crisis is the limited access to health care information when it is needed. The MDATA system provides up-to-date medical information and advice that is instantly available twenty-four hours a day. The advice that is given is 100% consistent.

The quality of the advice is much better if a physician can stop, research, and anticipate all possible causes of a problem and then systematically go about dealing with all of these possible causes. In medical practice, a physician just does this from memory.

No humans are necessary to actually give the medical advice. The MDATA system is automated which helps to bring down the cost of health care.

An exact record of the questions asked and the answers given is stored in the patient's database. The MDATA system time-and-date stamps the responses to the questions (as transaction records) so that an exact reconstruction of the patient's interview(s) can be generated for use by a physician or other health care professional. The system also keeps a record of what version of an algorithm has been consulted as well as the sensitivity factor set for that consultation. At the conclusion of the interaction, the MDATA system can tell the patient how long the consultation has taken and what charges have been incurred, if any.

When possible, the MDATA system 100 takes into account the past medical history of the patient, especially those pieces of information learned from past consultations with the MDATA system 100, before advice is given. In addition, the advice given is different depending upon the age and sex of the patient. The "meta" functions provide another advantage by allowing the MDATA system 100 to evaluate a problem in the context of the patient's prior consultations with the system.

XXIII. Second Optional System Configuration

Background

The Medical Diagnostic and Treatment Advice (MDATA) system is a computer system that conducts automated interviews of patients for the purpose of establishing a medical diagnosis. The MDATA system consists of a number of databases of medical information and programs (e.g. diseases, symptoms, treatments, medications, scripts) as well as supporting software to provide services to its user community (patients, doctors, nurses, laboratories, health management organizations (HMOs)).

To conduct the interviews, MDATA uses "scripts", which are, essentially, program modules that know how to interview a patient about a given complaint, access patient medical records, and use the supporting databases to diagnose and advise patients.

Figure 24:
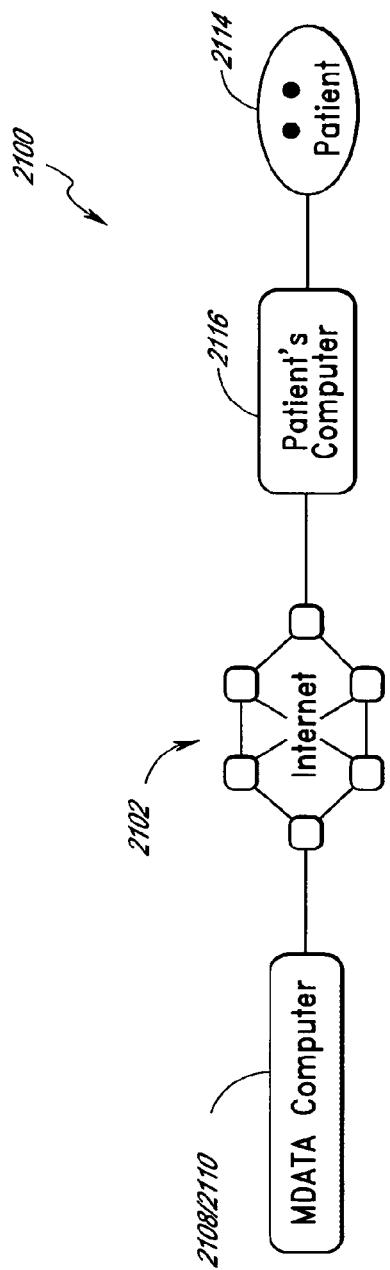
FIG. 24 is a high-level block diagram of a network-based embodiment of the MDATA system that utilizes communication networks.

The MDATA system has been previously described as using the telephone network to connect patients to a MDATA computer on which the MDATA system runs. Referring to FIG. 24, this portion of the patent application describes a networked embodiment 2100 of the MDATA system that uses communications networks 2102, such as the Internet to connect the MDATA computer(s) 2108/2110 to an on-line patient 2114 using a network access processor or patient computer 2116.

The MDATA Computer

Figure 25A:
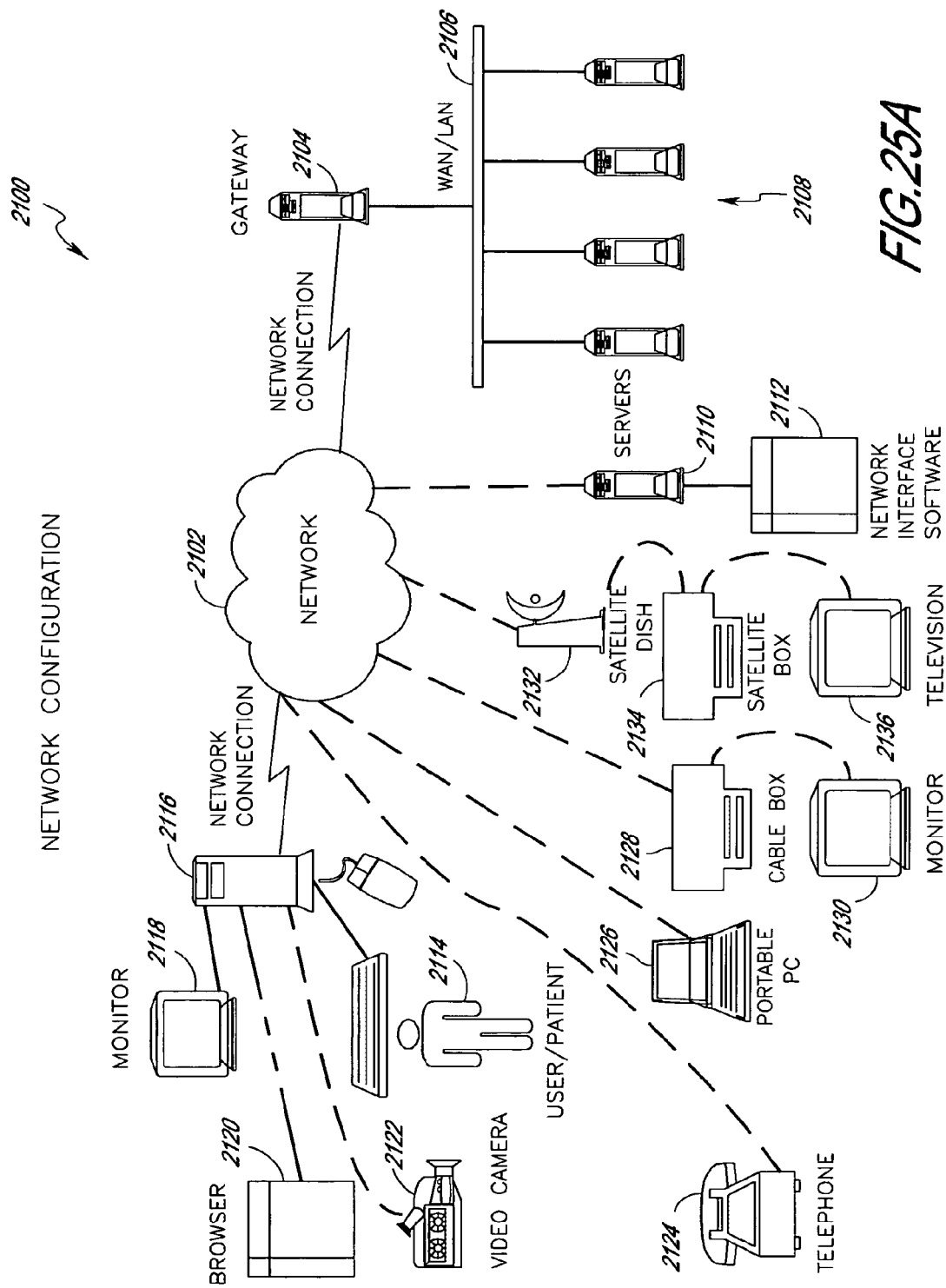
FIG. 25a is a block diagram illustrating the components of a presently preferred network-based embodiment of the computerized MDATA system of the present invention.
Figure 30:
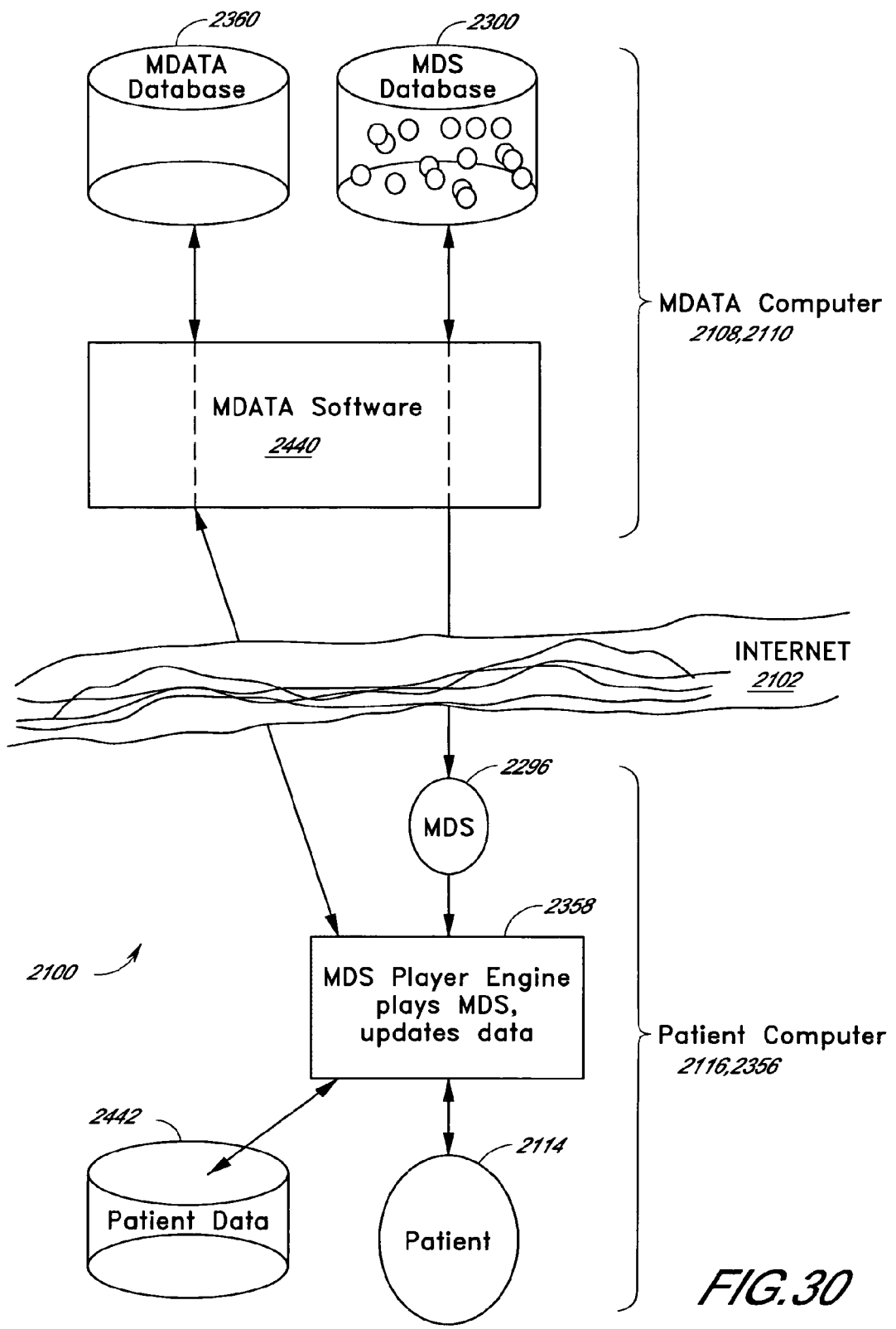
FIG. 30 is a block diagram showing the interaction of the MDATA computer with the patient's computer via the Internet.

The MDATA computer (on which the MDATA system resides and runs) can be a single computer such as a server 2110 (FIG. 25a) or the MDATA computer 2110 of FIG. 30. However, it can also be configured as several servers 2108 (FIG. 25a) connected by a Local Area Network (LAN) or a Wide-Area Network (WAN), in several LANs or WANs that are distributed around the country, or as some combination of these methods, such as shown at 2106 (FIG. 25a). Whichever configuration is used, the MDATA computer is the central corporate tool to:

develop, install, maintain, update MDATA software,
store and maintain all MDATA system support databases,
support medical software research and development,
verify, validate, and test the MDATA system,
document the use of MDATA programs and data,
support access by patients for diagnosis and advice,
generally manage and control MDATA system operation.

The MDATA Software

The MDATA software, previously described above, is modified or extended to accommodate the Internet's communication protocols and the patient computer's storage, processing, and display capabilities. These changes to the MDATA system consist of changes in its input/output subsystem, which is modified to communicate with the Internet and (via the Internet) with the computer of the on-line patient. These changes are described in this document in a section that describes how the MDATA system uses networks, such as the Internet, to perform its functions, and in a section that describes the impact of having a computer available at the patient's location.

The Internet

The Internet connects about 50,000 computer networks, which in turn connect about 5 million computers, which serve an estimated 50 million users. The Internet connects many diverse networks of many different computer hardware/software makes, versions, formats, codes, and protocols. There is no single "operating system" for the Internet, but there are various widely used file formatting, site locating, message routing, and display encoding standards. To participate on the Internet, a host computer's operating system must acquire and uses such Internet-smart software, which is widely available commercially.

The Internet solves the problem of incompatible hardware and software mix by extending the file name with prefixes that identify the protocol (and other things) that apply to the file. For example, many Internet filenames begin with "http://", which indicates that this file should be handled by software that understands the Hyper Text Transfer Protocol (HTTP), a program that knows how to follow embedded pointers or "links" to files on other Internet computers.

The Remote Login Concept

One way to use the Internet is as an access mechanism for running programs on a remote host computer. Instead of dialing in from a telephone, the user dials in via the Internet. All of the application data and processes are stored and manipulated on the host computer. The Internet serves only to transmit the user keystrokes and mouse clicks to the host, and to return the host computer output to the user computer. On the Internet, remote login is supported by Telnet and rlogin protocols. These use a simple command line protocol familiar to those who have ever used DOS on a PC. They are available in UNIX versions as well as for GUI-oriented systems like Windows.

Remote login represents a way for the MDATA system to use the Internet as an I/O device for patients, doctors, laboratories, HMOs, and so on to gain access to the central MDATA computer. That is, patients log in to and are diagnosed by MDATA software running on the MDATA computer.

The HTML Concept

To transmit text in readable form, the Internet software begins with ASCII code and "marks it up" with special codes to indicate special text handling such as bold, underlining, colors and fonts, and so on. The ASCII (American Standard Code for Information Interchange) code assigns a unique number to every letter, digit, punctuation mark, as well as some control actions such as new-line, tab, and end-of-text. The HTML (Hyper Text Markup Language) adds text treatment instructions. For example, to display a word in some emphasized manner, HTML may encode it as follows:

The quick <EM> brown </EM> fox jumps over the lazy dog

The local display software detects the <EM> tags and substitutes some emphasizing action so that on the local screen the text may appears as The quick brown fox jumps over the lazy dog HTML provides a way for a sender to convey commands to the receiver. For example, the tag <EM> above really commands the receiving software to emphasize a portion of the text. In other uses, other tags could command the receiving software to do special MDATA-oriented functions such as table lookup, access to patient medical data, or display of special graphics. In this manner, HTML (or some modified version of it) can be used as a batch language to transmit commands from the central MDATA computer to the remote patient's computer.

The CGI Concept

After a sending computer transmits a page over the Internet to a receiving computer, no further interaction is normally required or expected between the two computers. After loading the page, the sending software can go on to handle other requests.

However, to engage in a two-way conversation with the remote user, the user's response must be handled. This is done by Internet software using a special protocol called CGI (Common Gateway Interface). Using CGI, when the user clicks a hypertext field in an HTML file, or fills in a HTML "form", the Internet software sends a "reply" back to the original sender, where it is intercepted and handled by a CGI program. The CGI concept is to insert a software step that "catches" user responses and processes them. The CGI protocol supports two-way communication between the remote computers via the Internet, and supports the storing of session-specific data between sessions. This preserves the "state" of the communication, so that a continuous dialog can be generated.

The features and advantages that CGI-invoked programs offer to the MDATA system are that they:
- run on the central MDATA computer,
- are part of the diagnostic program library,
- can access central MDATA databases,
- can accept and process patient inputs from the current HTML file,
- can calculate values based on patient data and inputs,
- can interpret mouse clicks on active screen images, so that the patient can respond by clicking on anatomical and medical charts, drawings, and photos,
- can appear to react to patient responses much like a GUI-based program,
- can be maintained and updated by MDATA staff as needed.

The Java Concept

The Java concept is an example of a software mechanism for attaching executable processes to the HTML page, transmitting them, and then running them on the receiving computer. Whereas CGI-invoked programs run on the sender's computer and are "blind" to the capabilities of the remote receiver's machine, the Java approach essentially permits both data and programs to be transmitted across the Internet. The HTML programmer basically writes application source code in Java and appends it to the HTML page. When the user's browser displays the HTML page on the user's computer, it executes (actually "interprets") the Java code and handles the input/output to the user. Since the browser is written for the user's computer, it "knows" the user's system, and can take full advantage of this fact.

The Java concept is merely an illustration of the concept of transmitting programs to the receiver. In fact, any executable software can be appended to the HTML page, provided the receiver knows how to read and interpret or execute it. Any number of other codes and languages can be used to do this for the MDATA system. Ultimately, the MDATA system can transmit the necessary MDATA support software to its subscribers.

Advantages of MDATA on a Network

Using the Internet and its software mechanisms such as HTML, CGI, and Java permits the MDATA system to:
- support Internet communication protocols and formats;
- store charts, tables, graphs, images, photos, video, audio files;
- store Internet pages and scripts (HTML, CGI, Java);
- stage scripts and other files for transmission;
- transmit pages and scripts as requested via the Internet;
- upload medical data collected by MDATA scripts from patients;
- download medical data to patients, physicians, labs, and HMOs;
- download MDATA scripts, programs, and data to patient computers;
- monitor and manage patient traffic, demand, and queuing;
- transmit medical data in color, graphics, and sound formats;
- transmit executable code to user computers;
- use the users' Graphic User Interface (screen, mouse, dialogs);
- distribute its computational load to user computers;
- extend its diagnostic tools to include visual analysis;
- access other sites via the Internet, such as:
  - HMOs, insurance carriers, credit agency, bank;
  - attending and referred physicians, hospitals, clinics, recovery homes;
  - laboratories, pharmacies, health supply stores;
  - nurses, health practitioners, aides;
  - emergency rooms, paramedics, ambulance services.

Network Configuration

Referring to FIG. 25a, the user/patient 2114 communicates with a computing environment. The computing environment may include a single computer utilizing MDATA software or the computing environment may include multiple computers in a client/server relationship on a computer network. In a client/server environment, the server includes the MDATA system which communicates with a client that may include a network terminal equipped with a video display, keyboard and pointing device. The network terminal is connected to a wide area network via a network connection, which may be either a dial-up connection using a modem and the public switched telephone network (PSTN) or via a dedicated data circuit. The wide area network can be a public network, like the Internet, or a closed, private data network, like a corporate network or an intranet. There is an array of servers which host the medical advice and treatment applications and the patient databases at a central MDATA location. These servers are connected via a local area network to a network gateway, which provides access to the wide area network via a high-speed, dedicated data circuit. Alternatively, a single server may host the medical advice and treatment applications and the patient databases.

The Patient's Computer

A significant advantage of using the Internet to run the MDATA system is the fact that, at the patient's location, there is now a computer 2116 (FIG. 25a) or other network access device instead of just a telephone (as in FIG. 1). This means that the MDATA system can use the patient computer's processing and storage capabilities to handle at least some part of the MDATA storage and processing load. The patient's computer can be used to:
- download HTML pages from the MDATA computer;
- execute program code (e.g. Java) embedded in the HTML;
- respond to questions posed on the page;
- upload responses via the Internet to the MDATA computer;
- store MDATA-related scripts, programs and utilities;
- print patient-oriented materials and reports;
- store MDATA system data;
- store patient medical data;
- run scripts locally, off-line;
- save session data to continue later (re-enter);
- offload or distribute the processing load from the MDATA computer.

The Graphic User Interface (GUI)

A "graphic user interface" (GUI) is low-level computer software that exploits the display properties of a CRT as an output device for human users and combines it with a pointing device such as a mouse or joystick to handle graphical input. Color monitors and operating systems that support GUI software have been in use for some 15 years now and are well-documented. Three good examples are: Apple's Macintosh System, Microsoft's Windows, and IBM's OS/2.

Given that there is a computer to handle graphic input/output at the patient's end, the MDATA system encodes the medical script operations into some Internet-compatible protocol, such as HTML. That is, to move the MDATA system from a telephone-based system to the Internet, the MDATA software responsible for input/output is swapped out for a module that handles the Internet protocol.

In addition to redirecting the input/output traffic, given the flexibility of a GUI-based operating system, the MDATA system can be enhanced in numerous ways. For example, using a GUI, MDATA diagnostic scripts can:

use various fonts and colors to highlight and emphasize output text;

display graphic drawings and images to illustrate anatomical features;

instruct, illustrate, and exemplify meanings of words and phrases;

display photographic images as samples of lesions;

display medical charts to compare the patient's health status to population averages;

use multiple, overlapping or tiled screen displays to present data;

display moving images to inquire about motion ranges;

input one-digit or one-letter answers by pressing a key on the keyboard;

present graphs, sketches, diagrams, images, photos, videos;

present color, sound, and audio;

input responses by way of edit boxes, checkboxes, and buttons;

let the patient select and refine responses with mouse, joystick, keyboard;

let the patient identify problems by selecting from pictures presented by MDATA;

enter textual data into fields displayed on the screen by MDATA;

enter lengthy textual descriptions using the keyboard;

use labeled fields to let the patient "fill in a form" to be submitted to MDATA;

select responses from a list of choices presented on the screen;

point to a selected area of an anatomical drawing or image;

click the mouse to indicate intensities on a chart that shows a range of intensities;

use hypertext and hypergraphics "links" to control the diagnostic sequence;

provide various levels of "help" text tied to specific parts of the screen display.

User Configuration

Referring again to FIG. 25a, the networked MDATA system 2100 includes a network "cloud" 2102, which may represent a local area network (LAN), a wide area network (WAN), the Internet, or another connection service.

The MDATA programs and databases preferably reside on a group of servers 2108 that are preferably interconnected by a LAN 2106 and a gateway 2104 to the network 2102. Alternatively, the MDATA programs and databases reside on a single server 2110 that utilizes network interface hardware and software 2112. The MDATA servers 2108/2110 store the diagnostic scripts used by the script engine, described hereinbelow.

The network 2102 may connect to a user computer 2116, for example, by use of a modem or by use of a network interface card. The user 2114 at computer 2116 may utilize a browser 2120 to remotely access the MDATA programs using a keyboard and/or pointing device and a visual display, such as monitor 2118. Alternatively, the browser 2120 is not utilized when the MDATA programs are executed in a local mode on computer 2116. A video camera 2122 may be optionally connected to the computer 2116 to provide visual input, such as visual symptoms.

Various other devices may be used to communicate with the MDATA servers 2108/2110. If the servers are equipped with voice recognition or DTMF hardware, the user can communicate with the MDATA program by use of a telephone 2124, as described in the telephonic embodiment above. Other connection devices for communicating with the MDATA servers 2108/2110 include a portable personal computer 2126 with a modem or wireless connection interface, a cable interface device 2128 connected to a visual display 2130, or a satellite dish 2132 connected to a satellite receiver 2134 and a television 2136. Other ways of allowing communication between the user 2114 and the MDATA servers 2108/2110 are envisioned.

Figure 25B:
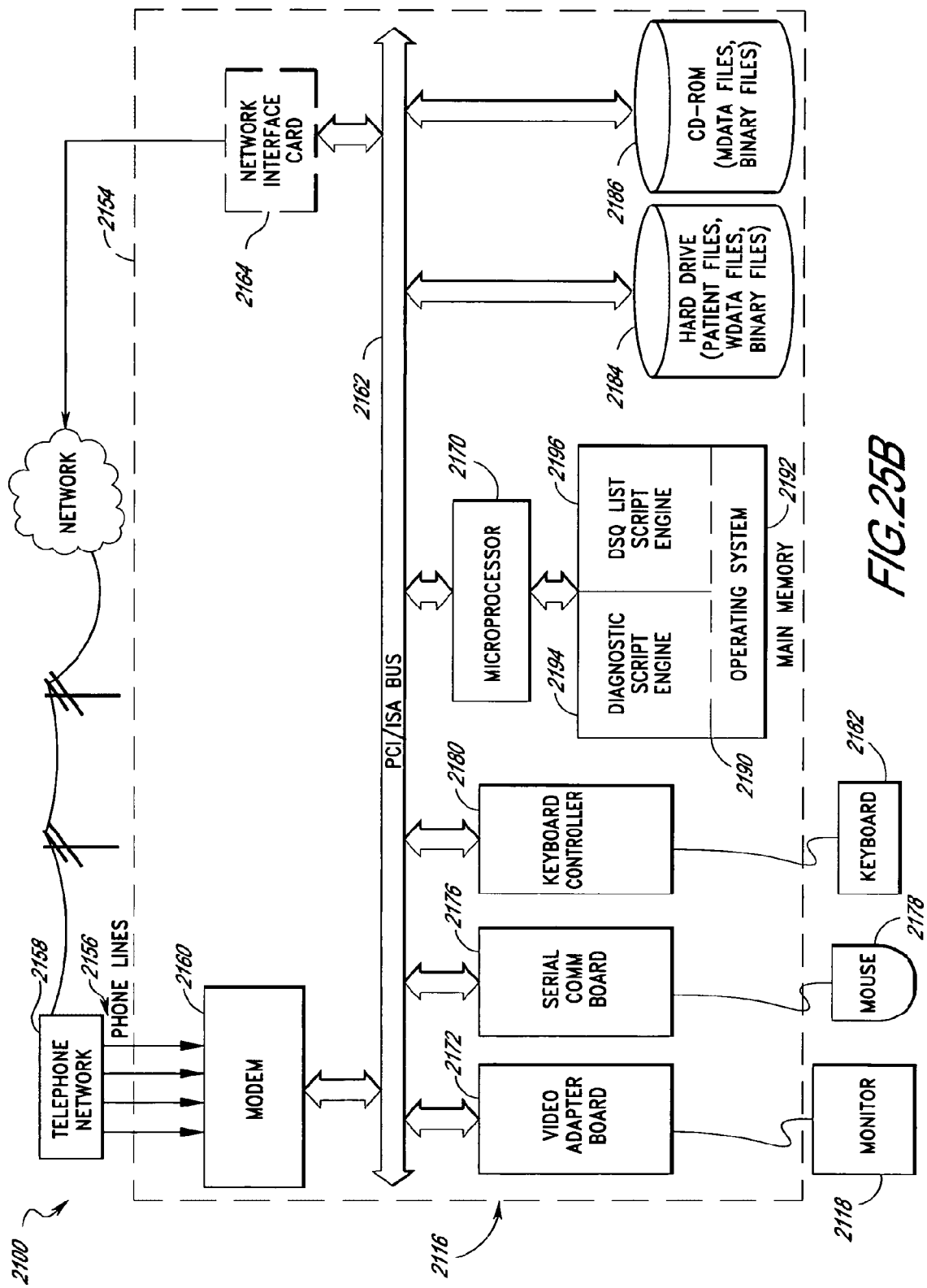
FIG. 25b is a block diagram illustrating the components of a user computer in the network-based embodiment of the computerized MDATA system.

Referring to FIG. 25b, a diagram of a presently preferred user/patient computer shows several possible interconnections to the network. FIG. 25b, 2194 and 2196 show the major software used to "play" a script, a special program called a Script Engine is used, which reads a MDS file and uses its codes to perform interview actions, such as outputting a question to a patient and inputting an answer. The script engine also collect the answers from the patient, evaluate the answers, issue a diagnosis, and update the patient's medical record. The script engine preferably resides in the user computer. The script engine may be stored on the hard drive or CD-ROM, and is loaded into the main memory for execution.

The components of a presently preferred computer 2116, utilized by a user 2114 of the computerized MDATA system 2100 of the present invention, are shown in FIG. 25b. Alternatively, other devices for conducting a medical interview, such as those shown in FIG. 25a, can be utilized in place of the computer 2116.

The computer 2102 includes a plurality of components within an enclosure 2116. A telephone line 2106 interfaces the public telephone network 2158 to the computer 2116 via a modem 2160. The telephone network 2158 may connect to the network 2102, which has connections with the MDATA system server(s) 2108/2110. Alternatively, the user may connect to the network 2102 by use of a network interface card 2164.

Throughout this document, the words user and patient are used interchangeably. However, it will be understood that the user may be acting as a proxy for the patient. If this is the case, the user is registered as an assistant for the patient.

The hardware and system software are assembled with two basic concepts in mind: portability to other operating systems and the use of industry standard components. In this way, the system can be more flexible and will allow free market competition to continually improve the product, while, at the same time, decreasing costs. While specific hardware and software may be referenced, it will be understood that a panoply of different components could be used in the present system.

The computer 2116 preferably is a personal computer with an Intel Pentium microprocessor 2170. Other computers, such as an Apple Macintosh, an Amiga, a Digital Equipment Corporation VAX, or an IBM mainframe, could also be utilized. The modem 2160 or the network interface card 2164 connect to an industry standard architecture (ISA) or a peripheral component interconnect (PCI) bus 2162. The bus 2162 interconnects the microprocessor 2170 with a plurality of peripherals through controller circuits (chips or boards).

The computer bus 2162 has a plurality of peripherals connected to it through adapters or controllers. A video adapter board 2172, preferably at SVGA or better resolution, interconnects to a video monitor 2118. A serial communication circuit 2176 interfaces with a pointing device, such as a mouse 2178. A parallel communication circuit may be used in place of circuit 2176 in another embodiment. A keyboard controller circuit 2180 interfaces with a keyboard 2182. A 500 Mb or greater hard disk drive 2184 and an optional CD-ROM drive 2186 are preferably attached to the bus 2162. The hard disk 2184 stores database files such as the patient files, other MDATA files, and binary support files. The CD-ROM drive 2186 also stores database files, such as files for the patients using the computer 2116, and binary support files.

A main memory 2190 connects to the microprocessor 2170. In the presently preferred embodiment, the computer 2116 preferably operates under the Windows 95 operating system 2192. The memory 2190 contains a diagnostic script engine 2194 that preferably utilizes a disease/symptom/question (DSQ) list script engine 2196. In one embodiment, the script engine software is written in Borland Delphi Pascal, version II. Of course, any other computer language could be used.

Referring to both FIGS. 25a and 25b, the user interface includes a graphical network browser client, such as Netscape or Mosaic, which interacts with the MDATA server. An enhanced user interface may incorporate small graphical applications, e.g., Java applets, downloaded from the server and executed on the user's network terminal. Java is a new language developed by Sun Microsystems, Inc. for programming applications on the Internet.

As the user proceeds through a diagnostic process, information on the user's medical condition is communicated to the MDATA system by completing or answering screen-displayed forms or by pointing at an item on the display and clicking with a mouse. The diagnostic process retrieves data from the patient and other MDATA databases and stores the users responses via common gateway interface (CGI) script language utilities or by use of a Web server application programming interface (API), such as a Netscape Applications Programming Interface (NSAPI) or the Microsoft Internet Server Applications Programming Interface (ISAPI).

If the user's network terminal is equipped with a camera, such as a digital still camera or a video camera, then the MDATA system is capable of capturing imagery of the patient over time. For medical conditions that require treatment by a health care provider, a chronological sequence of images allows the health care professional to make an assessment of the patient's condition by analyzing visual manifestations of an infection or disease.

Likewise, if the user's network terminal is equipped with a microphone, then the MDATA system is capable of capturing clinical sounds provided by the patient (e.g., a cough or the wheezing of asthma). The MDATA system can assist a health care professional in the assessment of a patient's medial condition by playing back the clinical sounds it captured.

MDATA System Structures

Figure 26:
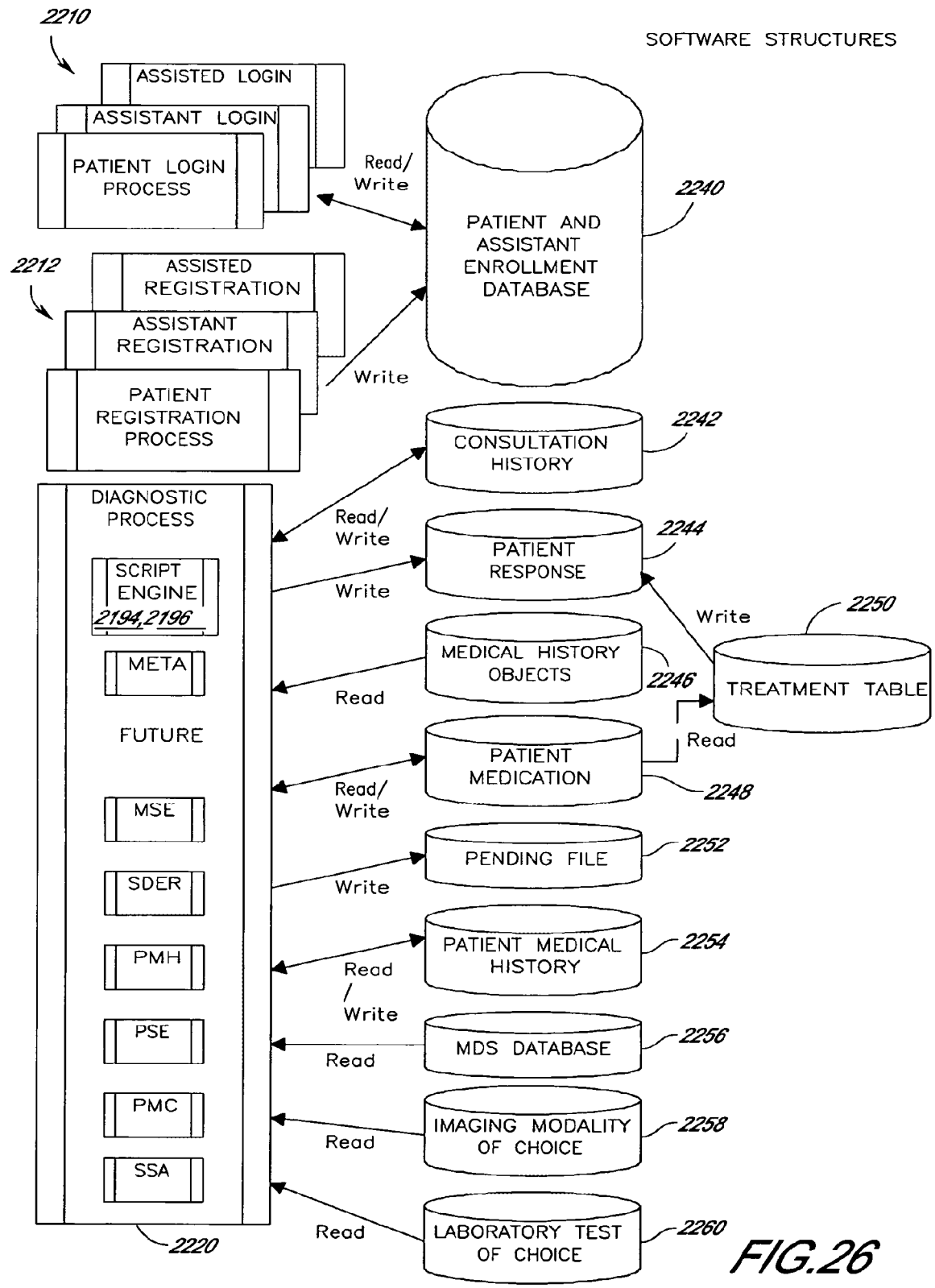
FIG. 26 is a block diagram illustrating a conceptual view of the database files and processes of the system of FIGS. 25a and 25b.

Referring to FIG. 26, a set of processes, files, and databases utilized by the networked MDATA system 2100 will be described. Except for the script engine process, the MDS database, the Imaging Modality database, and the Laboratory Test database, which are described hereinbelow, these processes, files, and databases were previously described above.

The MDATA system 2100 utilizes several principal processes and related databases. A set of patient login processes 2210 is used by the system 2100 to identify a patient who has previously registered into the system in one of three ways: 1) by prompting for a patient identification number (PIN); 2) identify an assistant who has previously registered into the system by prompting for an assistant identification number (AIN); 3) identify a patient, having an assistant, who has previously registered into the system by prompting for the patient identification number. A set of processes 2212 are used to register a patient or assistant. If the user is the patient, a patient registration process is used by the system to register new or first-time patients. If the user is not the patient, an assistant registration process is used by the system to register new or first-time assistants. Then, if the patient is not already registered, an assisted patient registration process is used by the system to register the patient.

Once a user has logged in or registered, the system provides a choice of processes. The primary process of concern in the current embodiment is the Diagnostic process 2220 that performs a patient diagnosis. The evaluation process 2220 accesses a laboratory test of choice and imaging modality of choice database to recommend the appropriate tests in this patient at this point in time and a treatment table 2250 to obtain current treatment information for a particular disease or diagnosis. In another embodiment, other choices are added to access other medical information processes.

Associated with these processes are a patient and assistant enrollment database 2240, a consultation history database 2242, a patient response database 2244, a medical history objects database 2246, a patient medication database 2248, a pending database 2252, a patient medical history database 2254, a medical diagnostic scripts (MDS) database 2256, an imaging modality database 2258, and a laboratory test database 2260.

Script Generation

Figure 27:
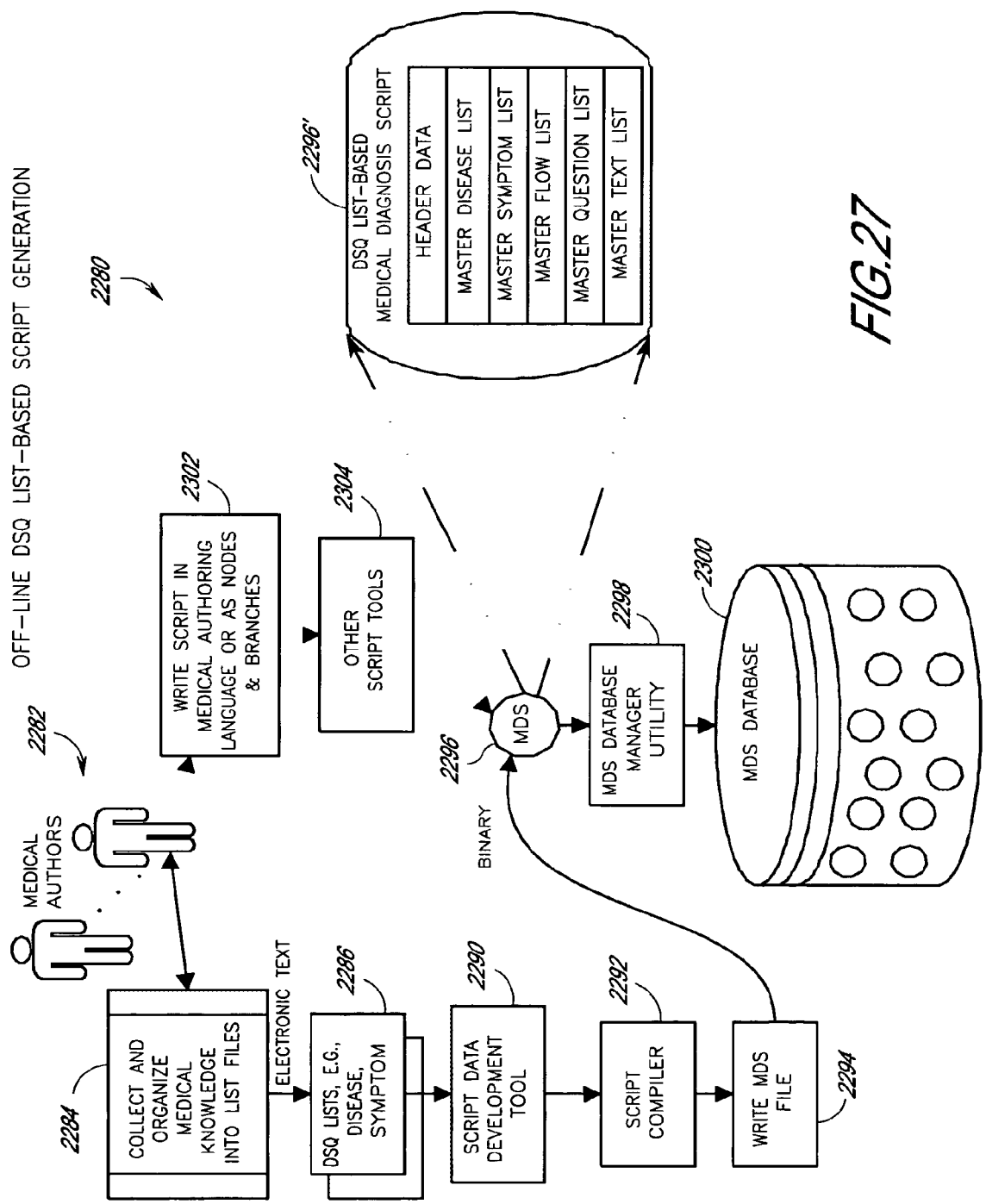
FIG. 27 is a diagram of an off-line process used in producing the medical diagnosis script (MDS) files used by the system of FIGS. 25a and 25b.

Referring to FIG. 27, an off-line process 2280 for generating a DSQ script will now be described. Beginning at a process 2284, medical knowledge is collected and organized into list files. The data for the list files is collected for one or more medical authors 2282. Process 2284 has two portions. A first portion typically performed by a script coordinator or supervising author for assigning diseases and a second portion for capturing the disease knowledge for each disease in the script. The portion for capturing the disease knowledge is typically performed by a plurality of medical experts in their respective fields. The output of process 2284 is electronic text, such as an ASCII file. This electronic text is in the form of DSQ lists such as disease, symptom, and question lists 2286.

Process 280 moves to state 2290 which takes the DSQ lists in electronic text format and processes them by use of a script data development tool. A script compiler 2292 works closely with the script data development tool to generate an MDS file. The process 2280 may utilize the script data development tool and the script compiler in an iterative fashion to generate a final MDS file. At state 2294, the MDS file is written to an MDS database 2300 by an MDS database manager utility 2298. The MDS file 2296 is preferably in a binary format. In an exemplary representation of the MDS file shown in FIG. 27 at 2296', the MDS preferably includes a header data section, a master disease list section, a master symptom list section, a master flows section, a master question list section and a master text list section. In another embodiment, the medical authors may write the scripts in a medical authoring language or as nodes and branches as shown at state 2302. Other script tools, which may include compilers, are shown at state 2304 to generate an MDS 2296.

Run-Time Structures

Figure 28:
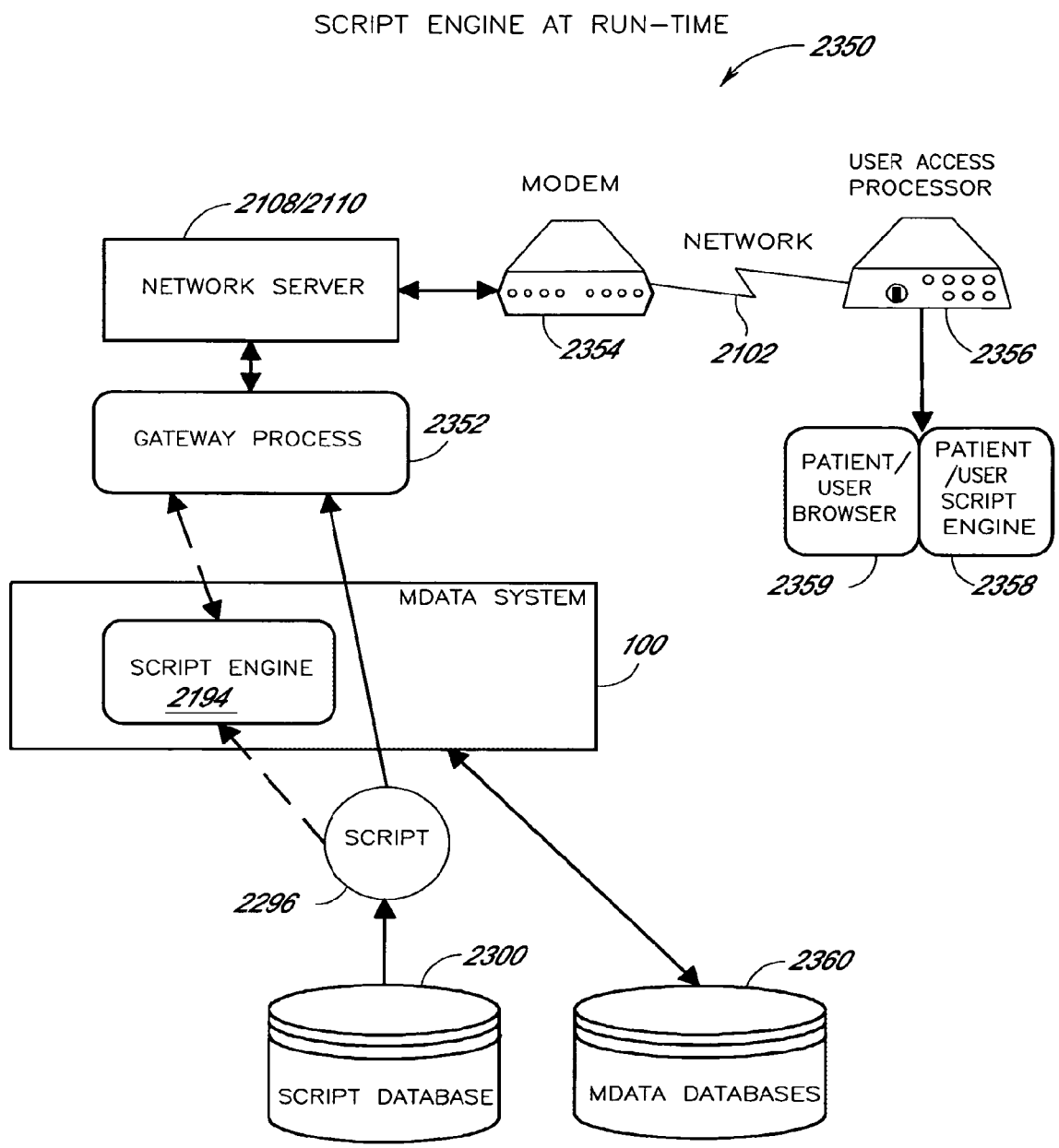
FIG. 28 is a diagram of some of the files and components of FIGS. 25a, 25b, 26, and 27 that are utilized at run-time.

Referring to FIG. 28, some of the files and components of FIGS. 25a, 25b, 26, and 27 that are utilized at run-time will now be described. The MDATA databases symbol 2360 shown in FIG. 28 represents the databases and files of FIG. 26 other than the MDS database 2256. If the script engine 2358 executes the script 2296 at the patient/user access processor 2356, the network-based MDATA system 2100 passes the script 2296 to the gateway process 2352, that is part of the MDATA network server 2108/2110, for transfer to the user processor 2356. The gateway process is also known as a CGI program, which was previously described above, and is more fully explained in conjunction with FIG. 32 below. Alternatively, a script engine 2194 at the MDATA system 100 may utilize the script to provide questions to the user, respond to user input, and generate results across the network 2102.

The patient/user access processor 2356 may utilize, in one embodiment, a Java virtual machine, licensed by Sun Microsystems, which may or may not execute within the context of a browser 2359. Another embodiment may utilize a plug-in script engine for the browser 2359. The user access processor 2356 may be a Network PC (NetPC) such as defined by a collaboration of Intel, Microsoft, Compaq, Dell and Hewlett-Packard, or a Net Computer (NC), such as available from Oracle Corporation or Sun Microsystems Inc. The input devices utilized in conjunction with computer 2116 may be also with the user access processor 2356.

Initial Script and Evaluation Process

See FIGS. 7a, 7b, 7c and 7d for a flow diagram of a process similar to a process of an Initial script used by the MDATA system 2100 of FIG. 25a. FIGS. 10a and 10b are a flow diagram of the Evaluation process 254 defined in FIG. 7d, which is also called the Diagnostic process 254 shown in FIG. 26. FIG. 19 is a flow diagram of the physical self examination function 514 defined in FIG. 10b. This function, for example, may request that a clinical sound recording be performed, or a still or video image be captured.

On-Line Interaction with the Patient

Figure 29:
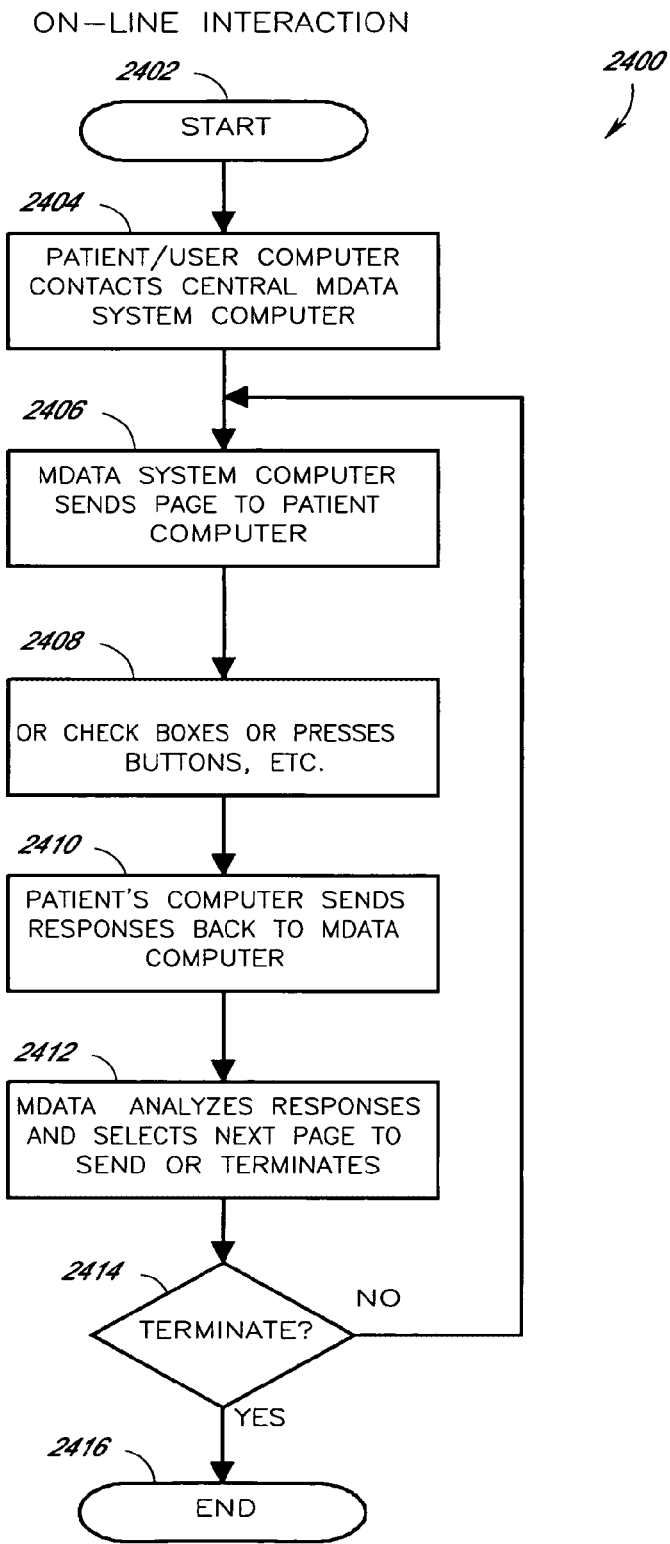

Referring to FIG. 29, a process 2400 of how the MDATA system 2100 (FIG. 25a) interacts on-line with the patient's computer 2116 via the network 2102 will now be described. One major variant of process 2400 is the ability for (Java-enabled) pages to perform some calculations on the patient computer 2116, instead of having to send the page to the MDATA computer 2108/2110.

Beginning at a start state 2402, process 2400 moves to state 2404 wherein the patient's computer 2116 contacts the central MDATA computer 2108/2110. Proceeding to state 2406, the central MDATA computer 2108/2110 electronically sends a "page" or screen of electronic information to the patient computer 2116 for display on the visual display 2118 to the user 2114. Continuing at state 2408, the patient 2114 fills in form fields, check boxes, buttons, or other similar response mechanisms that are on the page. Advancing to state 2410, the patient's computer 2410 sends the responses on the page back to the MDATA computer 2108/2110. Moving to state 2412, the MDATA computer 2108/2110 analyzes the received responses and selects the next page to send to the patient computer 2116 or determines, at state 2414, if the user or the MDATA software desires to terminate the communication between the patient computer and the MDATA computer 2108/2110. If so, the process 2400 completes at an end state 2416. However, if process 2400 determines not to terminate, execution continues back at state 2406 wherein the MDATA computer 2108/2110 sends the next selected page to the patient's computer 2116.

Referring to FIG. 30, a preferred high-level interaction between the MDATA computer 2108/2110 and the patient's computer 2116 or access processor 2356 via the Internet 2102 will be described. A MDS 2296 is passed from the MDS database 2300 by the MDATA software 2440 to a MDS player (script) engine 2358 at the patient computer 2116/2356. The player or script engine 2358 executes the script 2296 and updates the local patient database 2442. Periodically, if desired by the MDATA system 2100, the script result data is transferred to the central MDATA databases 2360 (FIG. 28). Alternatively, the local patient database 2442 is either not used at all, or is only used for certain data items, such that all or most of the medical data is sent across the network 2102 for storage in the MDATA databases 2360.

Network Program and Data Transfer

Figure 31:
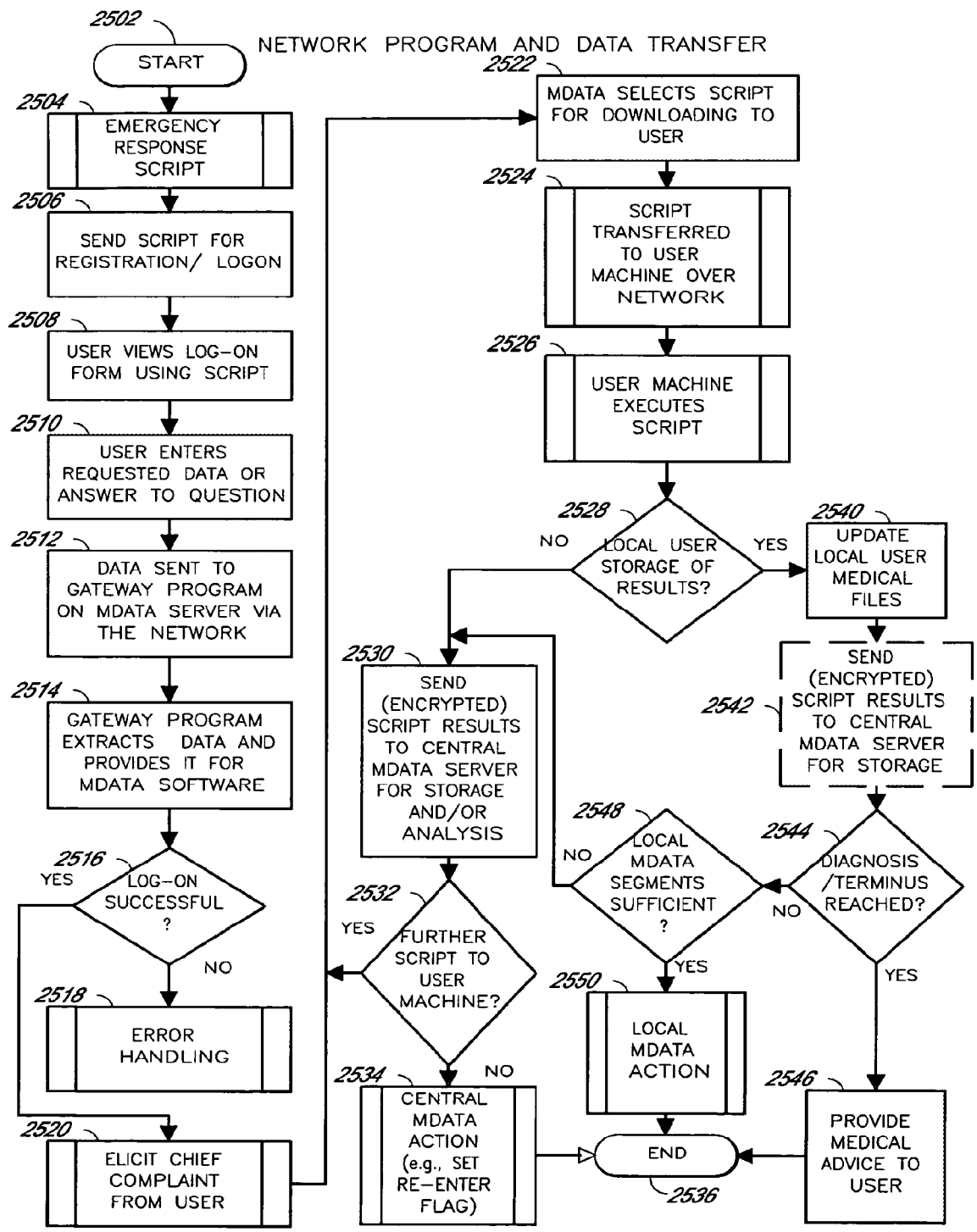
FIG. 31 is a flow diagram of a network program and data transfer process that is used during execution of the Initial script (similar to the process shown in FIGS. 7a-7d) and the Evaluation process shown in FIGS. 10a-10b.

Referring to FIG. 31, a network program and data transfer process 2500 that is used during execution of the Initial script and the Evaluation process will now be described. The transfer process 2500 shows portions of the Initial script (similar to the process of FIGS. 7a-7d) and the Diagnostic process 2220 (FIG. 26) as functions. This process can be executed on the system 2100 shown in FIG. 30. A decision block 2528 in the process 2500 determines if there is to be local storage of patient data and results at the patient/user computer 2116. Even if there is local storage of the patient data, the process may optionally send the data to the MDATA server at state 2542 in a parallel operation. Processing continues at the user computer 2116 until either a diagnosis or a terminal node is reached in the current script or help is needed from the MDATA server. Some of the actions performed by the MDATA server include sending a different script to the user computer for further diagnostic processing or performing analysis, such as meta analysis, determining if re-enter criteria are matched, checking for symptom severity patterns and so forth, as previously described in conjunction with the telephonic embodiment above.

In one embodiment of the on-line network system 2100, the user computer 2116 may have MDATA code segments, which are portions of code of the overall MDATA software in addition to the downloaded script to use in diagnosis of the problem. In this embodiment, if a diagnosis or a terminus has not been reached, the process determines if the local code segments can continue in the diagnostic process. If not, the user computer sends the results back to the central MDATA server for further help. However, if the local code segments are sufficient to carry on the process, the local user computer uses the MDATA code segments for further action, such as setting an indicator and asking the patient to consult the system at a later time or other actions that are performed by the MDATA software.

Beginning at a start state 2502, process 2500 moves to a function 2504 to execute an emergency response script. The emergency response script determines if the patient has a life-threatening emergency that needs immediate response. If an emergency does exist, the patient is referred to an emergency medical provider, such as an ambulance service or they are requested to call "911". If there is no medical emergency, process 2500 proceeds to state 2506 and sends a script for patient registration or log-on. If the user has previously registered, the log-on process will be executed, but if the user has not registered previously, the registration process will be executed. Assuming the user has previously registered, process 2500 proceeds to state 2508 wherein the user views a log-on form using a script. Advancing to state 2510, the user enters any requested data or answers to questions on the log-on form. Moving to state 2512, the response data from the form is sent to the gateway program 2352 (FIG. 28) on the MDATA server 2108/2110 via the network 2102. Continuing at state 2514, the gateway program extracts the response data from the form and provides it for the MDATA software. Continuing at a decision state 2516, process 2500 determines if the log-on is successful. If not, process 2500 proceeds to an error handling function 2518 to determine why the log-on was not successful and to deal with the log-on problem accordingly.

If the log-on is successful, as determined at decision state 2516, as determined at decision state 2516, process 2500 proceeds to a function 2520 to elicit the chief complaint from user. Proceeding to state 2522, the MDATA software selects a script for downloading to the user based on the chief complaint from the user, the amount of time since the beginning of the symptoms for the patient, any previous script results, the patient's past medical history, and so forth. After the script has been selected, process 2500 proceeds to a function 2524 wherein the script is transferred to the user machine over the network 2102. Continuing to a function 2526, the script engine 2358 at the user machine 2116 executes the script received over the network. Script processing is described in applicant's U.S. Pat. No. 5,935,060, filed Jul. 11, 1997, for "COMPUTERIZED MEDICAL DIAGNOSTIC SYSTEM UTILIZING LIST-BASED PROCESSING,", which is hereby incorporated by reference.

After execution of the script, process 2500 moves to a decision state 2528 to determine if there will be local user storage of the script results. If not, process 2500 moves to state 2530 to send the script results to the central MDATA server 2108/2110 for storage and/or analysis of the script results. The script results may be sent over the internet in an encrypted state to protect the medical data. Proceeding to a decision state 2532, process 2500 determines if a further script needs to be sent to the user machine to further help diagnose the chief complaint of the user. If so, process 2500 moves back to state 2522 wherein the next script for downloading to the user is selected. However, if no further scripts need to be sent to the user machine, as determined at decision state 2532, process 2500 moves to a function 2534. At function 2534, the central MDATA computer takes some action, such as performing a meta analysis, determining if re-enter criteria are matched, checking for system severity patterns or other similar actions. The MDATA computer may provide a diagnosis to the patient or may provide medical advice, such as requesting that the patient contact the system at a predetermined future time. At the completion of the actions by the MDATA computer, process 2500 completes at an end state 2536.

Returning to decision state 2528, if process 2500 determines that local user storage of results is desired, processing continues at state 2540 wherein the local user medical files are updated at database 2442 (FIG. 30). The decision of where to store script results may be made by various entities. For example, the laws of the country where the program is executed may determine if medical results can be stored locally or not, the MDATA system administrator may determine where the results may be stored, a medical health organization may make that decision, or the patient may be allowed to choose where the script results are to be stored. Moving to an optional state 2542, the MDATA administrator may require that the script results be sent to the central MDATA server for storage concurrently with the local storage of the medical data. The script results may be sent in an encrypted format to the central MDATA server.

Proceeding to a decision state 2544, process 2500 determines if the script reached a diagnosis or terminus point in the script. If a diagnosis was reached by the script, process 2500 proceeds to state 2546 to provide the diagnosis or medical advice to the user. Process 2500 then completes at the end state 2536. However, if a diagnosis was not reached, as determined at decision state 2544, process 2500 proceeds to a decision state 2548. At decision state 2548, process 2500 determines if any local MDATA software code segments are available on the user machine, and if so, whether they are sufficient to take further action based on the script results. If not, process 2500 moves to a decision state 2530 to send the script results to the MDATA server, if not already done, such that the MDATA server can take additional steps or further analyze the patient's problem. However, if local MDATA segments on the user machine are sufficient to take further action, process 2500 proceeds to function 2550 to take further local action based on the software code segments. After the local MDATA action is performed, which may include requesting the patient to consult the system at a later time, process 2500 completes at the end state 2536.

Network Data Transfer

Figure 32:
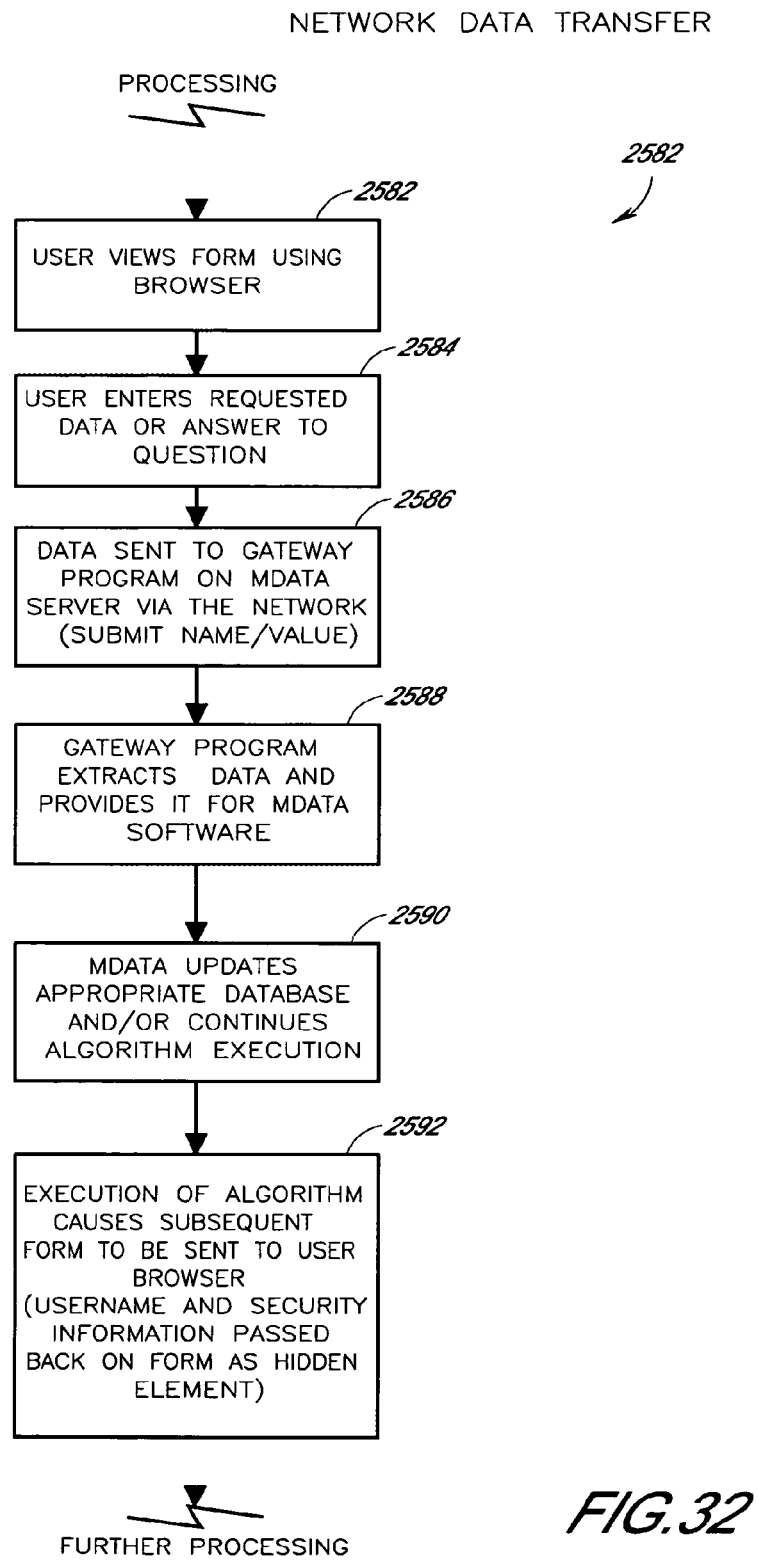
FIG. 32 is a flow diagram showing an excerpt of a network data transfer process performed during execution of the Initial script (similar to the process shown in FIGS. 7a-7d) and the Evaluation process shown in FIGS. 10a-10b.

Referring to FIG. 32, an excerpt of a network data transfer process 2580 performed during execution of the Initial script and the Evaluation process will now be described. This process 2580 uses a CGI form that is viewed by the user 2114 at state 2582 and is completed by the user at state 2584 for responding with data and/or answers to MDATA questions or prompts. Advancing to state 2586, the responses are sent to a gateway program 2352 (FIG. 28) on the MDATA server 2108/2110 via the network 2102 to extract the responses at state 2588 and forward the responses to the MDATA software. Moving to state 2590, the MDATA system 2100 continues execution of the script and/or performs a database update using the newly received data. Proceeding to state 2592, the script execution may cause a subsequent form to be sent to the user for further responses, and so forth. The username and security information, such as a password, for the user are passed back on the form as a "hidden element" to preserve the state of the client/server transaction.

Typical Script Window

FIG. 33 shows a sample of a typical GUI screen, generated by MDATA software, from an exemplary script that may diagnose Malaria. The user selects one of the radio buttons 2612 and then presses the SUBMIT button 2614 to forward the responses to the script engine. If the user presses the BACK button 2616, the script engine goes back to a previous screen. The HELP button 2618 displays a screen that discusses the concept and diagnostic meaning of malarial paroxysms in detail.

Summary of the Second Optional System Configuration

Running the MDATA system on a network such as the Internet is a significant extension of the previously described telephony-based MDATA system as well as the Stand-Alone (SA-MDATA) system. By replacing the telephone network with the Internet, the MDATA system extends its power to communicate with the patient as well as with other persons and agencies involved in the medical care of the patient. By replacing a purely sound-based system with a GUI, the MDATA system has a richer set of input/output choices to perform its diagnostic functions. By inserting the patient's computer into the communications path, the MDATA system has many more options of storing data running programs on the patient's computer. Here are three examples of uses of the Internet embodiment:

1. To extend the scope of the telephone-based MDATA system:

Use Internet HTML pages to advertise, announce, instruct, and guide patients to the availability and features of the telephony MDATA system.

Use Internet HTML pages as an extension to the telephony MDATA system, for purposes requiring visual data input/output such as for registering patients, taking a medical history, distributing free health advice and instructions, E-mailing physician's reports, handling HMO paperwork.

For the CD-ROM version of MDATA, let patients conduct diagnostic sessions solely on their own computer. Use the Internet administratively to communicate with patients for updates, questions, special consultations, HMO administration, and so on.

2. Use the Internet to run MDATA on a central computer:

Augment access to MDATA by telephone with access by remote login.

Provide an alternate I/O front-end to MDATA for Internet login.

Maintain the medical databases and scripts on a central machine.

Run diagnostic sessions on a central machine.

Use Internet to send scripts, data, advice, reports selectively to patient computers.

3. Use the Internet to run MDATA scripts on the patient's computer:

Replace the telephone as I/O device with a combination of HTML, CGI, and Java software.

Reshape the I/O portion of the MDATA system to focus on the Internet as the I/O device. Convert diagnostic scripts into HTML text and images, then use text and image links to select next pages from a diagnostic page database.

Same as above plus expand the MDATA system computer to a WAN to distribute the computing load and provide R&D support to physicians, hospitals, and HMOs.

Same as above and also let patients download all or part of the MDATA system to conduct diagnostic or disease management sessions on their own computer.

Various mixes of the above, such as putting Disease Management scripts for Diabetes on a CD-ROM, and allowing diabetic patients to run the scripts to monitor their health on their computer, then using the Internet to check periodically with the central MDATA computer or when needed.

While the above detailed description has shown, described and pointed out the fundamental novel features of the invention as applied to various embodiments, it will be understood that various omissions and substitutions and changes in the form and details of the device illustrated may be made by those skilled in the art, without departing from the spirit of the invention.

What is claimed is:

1. A medical diagnostic and treatment advice system for providing information to a patient, the system comprising:
   a server connected to a public data network and having a storage with a plurality of medical algorithms, wherein the server:
   a) conducts periodic direct interactive dialogues between the server and a user to receive patient information from the user over the public data network, the periodic direct interactive dialogues including multiple choice questions and user answers, the patient information including at least a subjective user input, the subjective user input factored by a patient specific sensitivity factor, wherein the patient specific sensitivity factor is tuned by the user based on its application to the patient;
   b) selectively executes at least one of the medical algorithms based on at least a portion of the received information;
   c) encrypts at least a portion of the patient information and diagnosis information indicative of a diagnosed condition;
   d) transmits the encrypted diagnosis information to the user over the public data network; and
   e) transmits the encrypted patient information to a health maintenance organization or an insurance carrier over the public data network.

2. The system of claim 1, wherein the public data network is the Internet.

3. The system of claim 1, wherein the user associated with the interactive dialogue is a patient or a proxy or assistant thereto.

4. The system of claim 1, wherein the user associated with the interactive dialogue is a medical professional.

5. The system of claim 1, further comprising a medical history database in data communications with the server configured to store medical data.

6. The system of claim 5, wherein the medical data is securely stored.

7. The system of claim 1, wherein the at least one medical algorithm scores at least a portion of the received information and diagnoses a medical condition associated with the executed medical algorithm if the score reaches or passes a threshold.

8. The system of claim 1, wherein the server monitors and manages patient traffic, demand, and queuing.

9. The system of claim 1, wherein the server communicates with a credit agency or a bank over the public data network.

10. The system of claim 1, wherein the server communicates with a laboratory, pharmacy, or health supply store over the public data network.

11. The system of claim 1, wherein the diagnosis information comprises scripts, data, advice, or reports.

12. The system of claim 1, wherein the patient information further comprises an objective measurement, a subjective user input and a combination of the objective measurement and subjective user input, the objective measurement and subjective user input factored by a patient specific sensitivity factor and a time density ratio, wherein the patient specific sensitivity factor is tuned by the system based on its application to the patient.

13. A method of providing a medical diagnosis using a medical diagnosis system having a server, the method comprising:
   storing a plurality of medical algorithms;
   conducting periodic direct interactive dialogues between a user and the server;
   receiving, at the server over a public data network via the direct interactive dialogues, patient information from the user, the periodic direct interactive dialogues including multiple choice questions and user answers, the patient information including at least a subjective user input, the subjective user input factored by both a patient specific sensitivity factor, wherein the patient specific sensitivity factor is tuned by the user based on its application to the patient;
   generating a medical diagnosis by selectively executing at least one of the medical algorithms at the server based on at least a portion of the received patient information;
   encrypting at least a portion of the patient information and diagnosis information indicative of the medical diagnosis;
   transmitting the encrypted diagnosis information to the user over the public data network;
   transmitting the encrypted patient information to a health maintenance organization or an insurance carrier over the public data network.

14. The method of claim 13, wherein the public data network is the Internet.

15. The method of claim 13, wherein the user associated with the interactive dialogue is a patient or a proxy or assistant thereto.

16. The method of claim 13, wherein the user associated with the interactive dialogue is a medical professional.

17. The method of claim 13, further comprising storing the received patient information in a medical history database.

18. The method of claim 13, wherein the at least one medical algorithm scores at least a portion of the received patient information and generates the medical diagnosis based on whether the score reaches or passes a threshold.

19. The method of claim 13, wherein the diagnosis comprises at least one of: a single medical condition, and a differential diagnosis list.

20. The method of claim 13, wherein the patient information further comprises an objective measurement, a subjective user input and a combination of the objective measurement and subjective user input, the objective measurement and subjective user input factored by a patient specific sensitivity factor and a time density ratio, wherein the patient specific sensitivity factor is tuned by the system based on its application to the patient.

21. A system for providing a medical diagnosis, the system comprising:
   means for receiving, via direct interactive dialogue between a server and a user over a public data network, patient information from the user, the periodic direct interactive dialogues including multiple choice questions and user answers, the patient information including at least a subjective user input, the subjective user input factored by a patient specific sensitivity factor, wherein the patient specific sensitivity factor is tuned by the user based on its application to the patient;
   means for generating a medical diagnosis by selectively executing at least one of a plurality of stored medical algorithms based on at least a portion of the received patient information;
   means for encrypting at least a portion of the patient information and diagnosis information indicative of the medical diagnosis;
   means for transmitting the encrypted diagnosis information to the user over the public data network; and
   means for transmitting the encrypted patient information to a health maintenance organization or an insurance carrier over the public data network.

22. The method of claim 13, wherein the patient information is representative of at least one of: a medical history, a medical record, a family history, an international classification of diseases (ICD) code, an environmental event, a cause of injury, a drug use, a vaccination, a symptom, a syndrome, or a disease.

23. The system of claim 21, wherein the patient information further comprises an objective measurement, a subjective user input and a combination of the objective measurement and subjective user input, the objective measurement and subjective user input factored by a patient specific sensitivity factor and a time density ratio, wherein the patient specific sensitivity factor is tuned by the system based on its application to the patient.

* * * * *